(12) United States Patent
Fyfe et al.

(10) Patent No.: US 9,676,701 B2
(45) Date of Patent: Jun. 13, 2017

(54) CYCLOPROPYLAMINE DERIVATIVES USEFUL AS LSD1 INHIBITORS

(71) Applicant: Oryzon Genomics, S.A., Cornellá de Llobregat, Barcelona (ES)

(72) Inventors: Matthew Colin Thor Fyfe, Chipping Norton (GB); Alberto Ortega Muñoz, Barcelona (ES); Julio Castro-Palomino Laria, Premia de Mar (ES); Marc Martinell Pedemonte, Barcelona (ES); Maria de los Angeles Estiarte-Martinez, Barcelona (ES); Nuria Valls Vidal, Barcelona (ES)

(73) Assignee: ORYZON GENOMICS, S.A., Cornella de Llobregat, Barcelona (ES)

( * ) Notice: Subject to any disclaimer, the term of this patent is extended or adjusted under 35 U.S.C. 154(b) by 0 days.

(21) Appl. No.: 14/640,395

(22) Filed: Mar. 6, 2015

(65) Prior Publication Data
US 2016/0052865 A1   Feb. 25, 2016

Related U.S. Application Data

(62) Division of application No. 13/812,386, filed as application No. PCT/EP2011/062947 on Jul. 27, 2011, now Pat. No. 9,006,449.

(30) Foreign Application Priority Data

Jul. 29, 2010 (EP) .................... 10171345

(51) Int. Cl.
| | |
|---|---|
| C07C 211/40 | (2006.01) |
| C07C 215/64 | (2006.01) |
| C07C 217/64 | (2006.01) |
| C07C 217/74 | (2006.01) |
| C07C 255/53 | (2006.01) |
| C07C 255/54 | (2006.01) |
| C07C 311/08 | (2006.01) |
| C07C 311/09 | (2006.01) |
| C07C 311/21 | (2006.01) |
| C07D 213/38 | (2006.01) |
| C07D 213/40 | (2006.01) |
| C07D 213/42 | (2006.01) |
| C07D 213/56 | (2006.01) |
| C07D 213/57 | (2006.01) |
| C07D 239/26 | (2006.01) |
| C07D 277/28 | (2006.01) |
| C07D 333/20 | (2006.01) |
| C07D 401/04 | (2006.01) |
| C07D 405/04 | (2006.01) |
| C07D 409/04 | (2006.01) |
| C07C 255/59 | (2006.01) |
| C07D 213/64 | (2006.01) |
| C07D 401/10 | (2006.01) |

(Continued)

(52) U.S. Cl.
CPC .......... *C07C 211/40* (2013.01); *C07C 215/64* (2013.01); *C07C 217/74* (2013.01); *C07C 255/53* (2013.01); *C07C 255/54* (2013.01); *C07C 255/59* (2013.01); *C07C 311/08* (2013.01); *C07C 311/09* (2013.01); *C07C 311/21* (2013.01); *C07D 213/38* (2013.01); *C07D 213/40* (2013.01); *C07D 213/42* (2013.01); *C07D 213/56* (2013.01); *C07D 213/57* (2013.01); *C07D 213/64* (2013.01); *C07D 239/26* (2013.01); *C07D 277/28* (2013.01); *C07D 333/20* (2013.01); *C07D 401/04* (2013.01); *C07D 401/10* (2013.01); *C07D 405/04* (2013.01); *C07D 405/10* (2013.01); *C07D 409/04* (2013.01); *C07D 409/10* (2013.01); *C07B 2200/07* (2013.01); *C07C 2101/02* (2013.01)

(58) Field of Classification Search
None
See application file for complete search history.

(56) References Cited

U.S. PATENT DOCUMENTS

| | | |
|---|---|---|
| 3,106,578 A | 10/1963 | Kaiser et al. |
| 3,365,458 A | 1/1968 | Biel et al. |

(Continued)

FOREIGN PATENT DOCUMENTS

| | | |
|---|---|---|
| EP | 1193268 | 4/2002 |
| EP | 1704859 | 9/2006 |

(Continued)

OTHER PUBLICATIONS

Ahmed et al, "Ticagrelor: a new reversible oral antiplatelet agent" Int Research Journal of Pharmacy, 2010, 1(1), 62-69.

(Continued)

*Primary Examiner* — Zinna Northington Davis
(74) *Attorney, Agent, or Firm* — Finnegan, Henderson, Farabow, Garrett & Dunner, LLP

(57) ABSTRACT

The invention relates to cyclopropylamine compounds, in particular the compounds of Formula (I), and their use in therapy, including e.g. in the treatment or prevention of cancer, a neurological disease or condition, or viral infection.

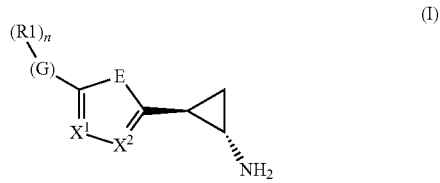

20 Claims, No Drawings

Related U.S. Application Data

(60) Provisional application No. 61/460,992, filed on Jan. 10, 2011.

(51) Int. Cl.
    *C07D 405/10*     (2006.01)
    *C07D 409/10*     (2006.01)

(56) References Cited

U.S. PATENT DOCUMENTS

| | | |
|---|---|---|
| 3,471,522 A | 10/1969 | Biel et al. |
| 3,532,712 A | 10/1970 | Biel et al. |
| 3,532,749 A | 10/1970 | Biel et al. |
| 3,758,684 A | 9/1973 | Elion et al. |
| 4,409,243 A | 10/1983 | Lieb |
| 4,522,811 A | 6/1985 | Eppstein et al. |
| 4,530,901 A | 7/1985 | Weissmann |
| 6,043,393 A | 3/2000 | de Meijere et al. |
| 6,211,244 B1 | 4/2001 | Van Wagenen et al. |
| 6,337,074 B1 | 1/2002 | Marsden et al. |
| 6,809,120 B1 | 10/2004 | Warrington et al. |
| 7,399,825 B2 | 7/2008 | Lipps et al. |
| 7,611,704 B2 | 11/2009 | Thorpe et al. |
| 7,628,993 B2 | 12/2009 | Vilalta et al. |
| 7,799,782 B2 | 9/2010 | Munson et al. |
| 8,524,717 B2 | 9/2013 | Guibourt et al. |
| 8,722,743 B2 | 5/2014 | Ortega-Munoz et al. |
| 8,859,555 B2 | 10/2014 | Ortega-Muñoz et al. |
| 8,946,296 B2 | 2/2015 | Ortega Muñoz et al. |
| 8,993,808 B2 | 3/2015 | Guibourt et al. |
| 9,006,449 B2 | 4/2015 | Fyfe et al. |
| 9,061,966 B2 | 6/2015 | Laria et al. |
| 9,149,447 B2 | 10/2015 | Ortega-Muñoz et al. |
| 9,181,198 B2 | 11/2015 | Ortega-Muñoz et al. |
| 9,186,337 B2 | 11/2015 | Baker et al. |
| 2003/0008844 A1 | 1/2003 | Spero et al. |
| 2003/0236225 A1 | 12/2003 | Protopopova et al. |
| 2004/0019117 A1 | 1/2004 | Protopopova et al. |
| 2004/0033986 A1 | 2/2004 | Protopopova et al. |
| 2004/0048802 A1 | 3/2004 | Ripka et al. |
| 2004/0132820 A1 | 7/2004 | Gosselin et al. |
| 2004/0147741 A1 | 7/2004 | Sundermann et al. |
| 2004/0162287 A1 | 8/2004 | Sundermann et al. |
| 2004/0176469 A1 | 9/2004 | Thomas |
| 2004/0229872 A1 | 11/2004 | Friderichs et al. |
| 2004/0254158 A1 | 12/2004 | Qiao et al. |
| 2005/0009832 A1 | 1/2005 | Sun et al. |
| 2005/0154056 A1 | 7/2005 | Yang et al. |
| 2006/0116370 A1 | 6/2006 | Dollinger et al. |
| 2006/0148904 A1 | 7/2006 | Protopopova et al. |
| 2006/0211709 A1 | 9/2006 | Buhr et al. |
| 2006/0270673 A1 | 11/2006 | Duggan et al. |
| 2006/0275366 A1 | 12/2006 | Malcolm et al. |
| 2006/0287287 A1 | 12/2006 | Gerritz et al. |
| 2007/0213338 A1 | 9/2007 | Lebsack et al. |
| 2008/0139665 A1 | 6/2008 | Schuele et al. |
| 2008/0242698 A1 | 10/2008 | Flor et al. |
| 2008/0269228 A1 | 10/2008 | Moore et al. |
| 2009/0203750 A1 | 8/2009 | Kozikowski et al. |
| 2009/0247530 A1 | 10/2009 | Nolte et al. |
| 2010/0016262 A1 | 1/2010 | Mehal et al. |
| 2010/0240649 A1 | 9/2010 | Zhang |
| 2010/0292225 A1 | 11/2010 | Chamoin et al. |
| 2010/0324147 A1 | 12/2010 | McCafferty et al. |
| 2012/0202810 A1 | 8/2012 | Nolte et al. |
| 2013/0197095 A1 | 8/2013 | Nolte et al. |
| 2013/0274267 A1 | 10/2013 | Cesar Castro Palomino Laria et al. |
| 2014/0163041 A1 | 6/2014 | Fyfe et al. |
| 2014/0256742 A1 | 9/2014 | Baker et al. |
| 2014/0296255 A1 | 10/2014 | Maes et al. |
| 2014/0329833 A1 | 11/2014 | Maes et al. |
| 2015/0025054 A1 | 1/2015 | Ortega Muñoz et al. |
| 2015/0119396 A9 | 4/2015 | Ortega Muñoz et al. |
| 2015/0232436 A1 | 8/2015 | Baker et al. |
| 2015/0368186 A1 | 12/2015 | Ortega Muñoz et al. |
| 2015/0376177 A1 | 12/2015 | Ortega Muñoz et al. |
| 2016/0000768 A1 | 1/2016 | Castro-Palomino Laria et al. |
| 2016/0045456 A1 | 2/2016 | Guibourt et al. |
| 2016/0081947 A1 | 3/2016 | Maes et al. |

FOREIGN PATENT DOCUMENTS

| | | |
|---|---|---|
| EP | 1741708 | 1/2007 |
| EP | 2233495 | 9/2010 |
| GB | 1307341 | 2/1973 |
| JP | 2001354563 | 12/2001 |
| SU | 230169 | 10/1968 |
| WO | WO94/27947 | 12/1994 |
| WO | WO96/38141 | 12/1996 |
| WO | WO98/18459 | 5/1998 |
| WO | WO99/05142 | 2/1999 |
| WO | WO99/05143 | 2/1999 |
| WO | WO99/31072 | 6/1999 |
| WO | WO99/54440 | 10/1999 |
| WO | WO99/67203 | 12/1999 |
| WO | WO00/34283 | 6/2000 |
| WO | WO01/92264 | 12/2001 |
| WO | WO02/079152 | 10/2002 |
| WO | WO03/067064 | 10/2003 |
| WO | WO03/093297 | 11/2003 |
| WO | WO03/096989 | 11/2003 |
| WO | WO2004/020415 | 3/2004 |
| WO | WO2004/055010 | 7/2004 |
| WO | WO2004/062601 | 7/2004 |
| WO | WO2004/065367 | 8/2004 |
| WO | WO2004/072086 | 8/2004 |
| WO | WO2005/009941 | 2/2005 |
| WO | WO2005/023761 | 3/2005 |
| WO | WO2005/025558 | 3/2005 |
| WO | WO2005/037843 | 4/2005 |
| WO | WO2005/058808 | 6/2005 |
| WO | WO2005/058864 | 6/2005 |
| WO | WO2005/058883 | 6/2005 |
| WO | WO2005/103003 | 11/2005 |
| WO | WO2006/071608 | 7/2006 |
| WO | WO2006/087206 | 8/2006 |
| WO | WO2007/000248 | 1/2007 |
| WO | WO2007/005896 | 1/2007 |
| WO | WO2007/015824 | 2/2007 |
| WO | WO2007/025144 | 3/2007 |
| WO | WO2007/025709 | 3/2007 |
| WO | WO2007/021839 | 7/2007 |
| WO | WO2007/106016 | 9/2007 |
| WO | WO2007/134799 | 11/2007 |
| WO | WO2008/033466 | 3/2008 |
| WO | WO2008/116156 | 9/2008 |
| WO | WO2008/127734 | 10/2008 |
| WO | WO2008/001132 | 12/2008 |
| WO | WO2009/023179 | 2/2009 |
| WO | WO2009/039134 | 3/2009 |
| WO | WO2009/052078 | 4/2009 |
| WO | WO2009/097278 | 8/2009 |
| WO | WO2009/109991 | 9/2009 |
| WO | WO2009/117515 | 9/2009 |
| WO | WO2009/145856 | 12/2009 |
| WO | WO2009/153197 | 12/2009 |
| WO | WO2009/011845 | 1/2010 |
| WO | WO2010/014921 | 2/2010 |
| WO | WO2010/030592 | 3/2010 |
| WO | WO2010/043721 | 4/2010 |
| WO | WO2010/084160 | 7/2010 |
| WO | WO2010/085749 | 7/2010 |
| WO | WO2010/099527 | 9/2010 |
| WO | WO2010/139784 | 12/2010 |
| WO | WO2010/143582 | 12/2010 |
| WO | WO2011/022489 | 2/2011 |
| WO | WO2011/031934 | 3/2011 |
| WO | WO2011/035941 | 3/2011 |
| WO | WO2011/042217 | 4/2011 |
| WO | WO2011/057262 | 5/2011 |
| WO | WO2011/106105 | 9/2011 |
| WO | WO2011/106106 | 9/2011 |
| WO | WO2011/113005 | 9/2011 |

(56) References Cited

FOREIGN PATENT DOCUMENTS

| | | |
|---|---|---|
| WO | WO2011/131576 | 10/2011 |
| WO | WO2011/131697 | 10/2011 |
| WO | WO2011/132083 | 10/2011 |
| WO | WO2012/001531 | 1/2012 |
| WO | WO2012/013728 | 2/2012 |
| WO | WO2012/034116 | 3/2012 |
| WO | WO2012/042042 | 4/2012 |
| WO | WO2012/045883 | 4/2012 |
| WO | WO2012/072713 | 6/2012 |
| WO | WO2012/107498 | 8/2012 |
| WO | WO2012/107499 | 8/2012 |
| WO | WO2012/135113 | 10/2012 |
| WO | WO2012/156531 | 11/2012 |
| WO | WO2012/156537 | 11/2012 |
| WO | WO2013/057320 | 4/2013 |
| WO | WO2013/057322 | 4/2013 |

OTHER PUBLICATIONS

Arya et al, "Synthesis of 5H-dibenzo[a,d]cycloheptene derivatives with diverse biological activities", Indian J Chemistry B, 1978, 16B,220-225.

Bar-Am et al, "Regulation of Bcl-2 family proteins, neurotrophic factors, and APP processing in the neurorescue activity of propargylamine", FASEB J, 2005, 19(13),1899-1901.

Barlesi et al, "Global histone modifications predict prognosis of resected non small-cell lung cancer",J Clin Oncol,2007,25, 4358-4364.

Benelkebir et al, "Enantioselective synthesis of tranylcypromine analogues as lysine demethylase (LSD1) inhibitors", Bioorg Med Chem, 2011,19(12),3709-3716.

Biljak et al,"Platelet count, mean platelet volume and smoking status in stable chronic obstructive pulmonary disease", Platelets, 2011,22(6), 466-70.

Binda et al, "Biochemical, structural, and biological evaluation of tranylcypromine derivatives as inhibitors of histone demethylases LSD1 and LSD2", J Am Chem Soc,2010,132(19),6827-6833.

Bisi et al, "Multidrug resistance reverting activity and antitumor profile of new phenothiazine derivatives", Bioorg Med Chem, 2008, 16(13), 6474-6482.

Boilard et al, "Platelets amplify inflammation in arthritis via collagen-dependent microparticle production", Science, 2010,327(5965), 580-683.

Bolesov et al, "Cyclopropanes and cyclobutanes LXIX", Zhurnal Organicheskoi Khimii (English Translation), 1974, 10(10), 2122-2128.

Bolesov et al, "Cyclopropanes and cyclobutanes LXVIII. N-mono and N,N-disubstituted 1-amino-2-phenylcyclopropanes", Zhurnal Organicheskoi Khimii (English Translation), 1974, 10(6), 1678-84.

Brand and Perrimon, "Targeted gene expression as a means of altering cell fates and generating dominant phenotypes", 1993, Development, 118, 401-415.

Brydon et al, "Platelets, coronary heart disease and stress", Brain, Behavior and Immunity,2006, 20(2), 113-119.

Burakova et al, "N- and O-alkylation of 3-indolylcyclopropylacetic acid derivatives", Russian Chemical Bulletin, 2002, 51(10) 1829-1840.

Burk et al, "Cognitive deficits in spinocerebellar ataxia 2", Brain, 1999,122(4), 769-777.

Cakmak et al, "Platelets: indicator of inflammation in COPD", Int J Med Med Sci, 2009, 1(5), 227-229.

Calogero et al, "Inhibition of cell growth by EGR-1 in human primary cultures from malignant glioma",Cancer Cell International,2004,4, 1.

Casero et al, "Recent advances in the development of polyamine analogues as antitumor agents", J Med Chem, 2009, 52(15),4551-4573.

Chen et al, "Association of insulin resistance and hematologic parameters: study of a middle-aged and elderly chinese population in Taiwan", J Chin Med Assoc,2006, 69(6), 248-253.

Chimenti et al "Synthesis, Stereochemical Identification, and Selective Inhibitory Activity against Human Monoamine Oxidase-B of 2-Methylcyclohexyildene-(4-arylthiazol-2-yl)hydrazones". (2008) J. Med. Chem. 51 (16) 4874-4880.

Choi et al "Histone demethylase LSD1 is required to induce skeletal muscle differentiation by regulating myogenic factors" (2010) Biochemical and Biophysical Research Communications 401(3), 327-332.

Choo et al, "Genetic organization and diversity of the hepatitis C virus", Proc Natl Acad Sci,1991, 88,2451-2455.

Culhane et al, A mechanism-based inactivator for histone demethylase LSD1, J Am Chem Soc, 2006, 128(14), 4536-4537.

Culhane et al, "Comparative analysis of small molecules and histone substrate analogues as LSD1 lysine demethylase inhibitors", J Am Chem Soc, 2010,132(9),3164-3176.

Danese et al, "Platelets in inflammatory bowel disease: clinical, pathogenic and therapeutic implications", Am J Gastroenterol, 2004,99(5), 938-45.

Di Stefano et al, Mutation of *Drosophila* Lsd1 disrupts H3-K4 methylation, resulting in tissue-specific defects during development, Curr Biol,2007, 17(9), 808-12.

East et al, "An orally bioavailabie positive allosteric modulator of the mGlu4 receptor with efficacy in an animal model of motor dysfunction", Bioorg Med Chem Lett, 2010, 20(16), 4901-5.

Ellis et al, "Expression of *Drosophila* glass protein and evidence for negative regulation of its activity in non-neuronal cells by another DNA-binding protein",Development,1993, 119, 855-865.

Elsheikh et al "Global histone modifications in breast cancer correlate with tumor phenotypes, prognostic factors and patient outcome", Canc Res, 2009,69, 3802-3809.

Erazo et al, "Varicella-zoster virus open reading frame 66 protein kinase is required for efficient viral growth in primary human corneal stromal fibroblast cells", J Virol, 2008,82, 7653-7665.

Faler et al, "The Kulinkovich reaction in the synthesis of constrained N,N-dialkyl neurotransmitter analogues", Organic Letters 2007,9(10),1987-1990.

Ferlay et al, "Estimates of the cancer incidence and mortality in Europe in 2006", Annals of Oncology 2007,18(3), 581-92.

Ferraro et al, "EGR1 predicts PTEN and survival in patients with non-small-cell lung cancer", J Clin Oncol, 2005, 23(9), 1921-26.

Fischer et al, "Recovery of learning and memory is associated with chromatin remodelling", Nature, 2007,447, 178-182.

Forneris et al "LSD1: oxidative chemistry for multifaceted functions in chromatin Regulation." Trends in Biochemical Sciences 2008,33(4), 181-189.

Gawaz et al, "Platelets in inflammation and atherogenesis", J Clin Invest, 2005,115(12), 3378-3384.

Gooden et al, "Facile synthesis of substituted trans-2-arylcyclopropylamine inhibitors of the human histone demethylase LSD1 and monoamine oxidases A and B", Bioorg Med Chem Lett 2008, 18(10), 3047-51.

Han et al "Modulation of breast cancer resistance protein (BCRP/ABCG2) by non-basic chalcone analogues" Eur. J. Pharma. 2008, 35(1-2) 30-41.

Han et al, "Antidepressants reveal differential effect against 1-methyl-4-phenylpyridinium toxicity in differentiated PC12 cells". Eur J Pharmacol, 2009, 604 (1-3),36-44.

Hayami et al, "Overexpression of LSD1 contributes to human carcinogenesis through chromatin regulation in various cancers", Int J Cancer, 2011, 128(3), 574-86.

Hruschka et al, "Fluorinated phenylcyclopropylamines. Part 5:Effect of electron-withdrawing or -donating aryl substituents on the inhibition of monoamine oxidases A and B by 2-aryl-2-fluoro-cyclopropylamines", Bioorg Med Chem,2008, 16(15), 7148-7166.

Huang et al, "Novel oligoamine analogues inhibit lysine-specific demethylase 1 (LSD1) and induce re-expression of epigeneticall silenced genes",Clin Cancer Res,2009, 15(23), 7217-28.

Huang et al, "p53 is regulated by the lysine demethylase LSD1",Nature,2007,449, 105-108.

Huang et al,"Inhibition of lysine-specific demethylase 1 by polyamine analogues results in reexpression of aberrantly silenced genes", PNAS,2007, 104(19), 8023-8028.

(56) References Cited

OTHER PUBLICATIONS

Jackson et al, "Polyglutamine-expanded human Huntingtin transgenes induce degeneration of *Drosophila* photoreceptor neurons", Neuron, 1998, 21, 633-642.
Kahl et al, "Androgen receptor coactivators lysine-specific histone demethylase 1 and four and a half LIM domain protein 2 predict risk of prostate cancer recurrence", Cancer Res, 2006, 66 (23), 11341-11347.
Kaiser et al, "2-substituted cyclopropylamines, I. Derivatives and analogs of 2-phenylcyclopropylamine", J Med Pharm Chem (ACS), 1962, 5, 1243-1265.
Kiefmann et al, "Red blood cells induce hypoxic lung inflammation", Blood, 2008,111(10), 5205-14.
Kim et al, "Flavin chemical models for monoamine oxidase inactivation by cyclopropylamines, α-silylamines, and hydrazines", J Am Chem Soc 1995, 117, 100-105.
Kinzel et al, "Identification of MK-5710 ((8aS)-8a-methyl-1,3-dioxo-2-[(1S,2R)-2-phenylcyclopropyl]-N-(1-phenyl-1H-pyrazol-5-yl)hexahydro-imidazo[1,5-a]pyrazine-7-(1H)-carboxamide, a potent smoothened antagonist for use in Hedgehog pathway dependent malignancies. Part 2", Bioorg Med Chem Lett 2011, 21(15), 4429-4435.
Kornerup et al, "The role of platelets in the pathophysiology of asthma" Platelets, 2007,18(5), 319-28.
Krieger et al, "Enhancement of hepatitis C virus RNA replication by cell culture-adaptive mutations", J Virol, 2001,75,4614-4624.
Lan et al "Mechanisms involved in the regulation of histone lysine demethylases", Current Opinion in Cell Biology, 2008,20, 316-325.
Lee et al, "Combinatorial lead optimization of [1,2]-diamines based on ethambutol as potential antituberculosis preclinical candidates", J Comb Chem, 2003, 5(2), 172-187.
Lee et al, "Histone H3 lysine 4 demethylation is a target of nonselective antidepressive medications", Chem Biol, 2006,13(6), 563-567.
Li et al, "Association between inflammatory mediators and angiographic morphologic features indicating thrombus formation in patients with acute myocardial infarction", Chin Med J, 2009,122(15), 1738-42.
Liang et al, "Inhibition of the histone demethylase LSD1 blocks alpha-herpesvirus lytic replication and reactivation from latency",Nat Med, 2009,15 (11), 1312-1317.
Lim et al, "Lysine-specific demethylase 1 (LSD1) is highly expressed in ER-negative breast cancers and a biomarker predicting aggressive biology", Carcinogenesis,2010, 31(3), 512-20.
Lucerna et al, "Sustained expression of early growth response protein-1 blocks angiogenesis and tumor growth",Cancer Research,2006, 66,6708-6713.
Lupu Roxana, "Up-to-date in the hematological malignancies treatment", Maedica, 2006,1(1), 63-65.
Maclay et al, "Increased platelet activation in patients with stable and acute exacerbation of COPD", Thorax, 2011,66(9), 769-74.
Mannaioni et al, "Platelets and inflammation: role of platelet-derived growth factor, adhesion molecules and histamine", Inflamm Res, 1997,46(1), 4-18.
McNicol et al, "Beyond hemostasis: the role of platelets in inflammation, malignancy and infection",Cardiovascular & Haematological Disorders-Drug Targets, 2008,8, 99-117.
Meanwell, "Synopsis of some recent tactical application of bioisosteres in drug design", J Med Chem, 2011, 54(8),2529-91.
Metzger et al, "LSD1 demethylates repressive histone marks to promote androgen-receptor-dependent transcription",Nature,2005, 437(7057),436-9.
Mimasu et al "Crystal structure of histone demethylase LSD1 and tranylcypromine at 2.25 Å" Biochemical and Biophysical Research Communications ,2008,366, 15-22.
Mimasu et al, "Structurally designed trans-2-phenylcyclopropylamine derivatives potently inhibit histone demethylase LSD1/KDM1", Biochemistry,2010,49(30), 6494-6503.
Moritani et al, "Activation of platelets in bronchial asthma", Chest, 1998,113, 452-458.
Nabil Aboul-Enein et al, "Synthesis of some 4-substituted amino-1-methylpiperidines structurally related to antihistaminics", Pharmaceutica Acta Helvetiae, 1973, 48(3): 151-156.
Neelamegan et al, "Brain penetrant LSD1 inhibitors can block memory consolidation", ACS Chem Neurosci, 2012, 3(2), 120-128.
Ogasawara et al, "Synthesis and biological activity of optically active NCL-1, a lysine-specific demethylase 1 selective inhibitor",Bioorg Med Chem, 2011, doi:10.1016/j.bmc.2010.12.024.
O'Sullivan et al, "The inflammatory role of platelets in cystic fibrosis", Am J Respir Crit Care Med, 2006,173, 483-90.
Pannala et al "Synthesis and structure-activity relationship of 4-(2-aryl-cyclopropylamino)-quinoline-3-carbonitriles as EGFR tyrosine kinase inhibitors", Bioorg & Med Chem Lett , 2007,17 (21) 5978-5082.
Pitchford et al, "Platelet P-selectin is required for pulmonary eosinophil and lymphocyte recruitment in a murine model of allergic inflammation", Blood, 2005,105, 2074-2081.
Pollock et al, Lysine-specific histone demethylase 1 inhibitors control breast cancer proliferation in ERalpha-dependent and -independent manners. ACS Chem Biol 2012,7,1221-1231.
Ravina et al, The relationship between CAG repeat length and clinical progression in Huntington's disease, Movement Disorders,2008,23(9), 1223-7.
Reddy et al, "Role of lysine-specific demethylase 1 in the proinflammatory phenotype of vascular smooth muscle cells of diabetic mice",Circ Res,2008,103, 615-23.
Riley et al, "Absolute configuration of (+)- and (−)-trans-2-phenylcyclopropylamine hydrochloride",J Med Chem, 1972,15(11), 1187-1188.
Rinder et al, "Correlation of thrombosis with increased platelet turnover in thrombocytosis", Blood, 1998,91(4), 1288-1294.
Schmidt et al,"trans-2-phenylcyclopropylamine is a mechanism-based inactivator of the histone demethylase LSD1", Biochemistry, 2007,46(14),4408-4416.
Schulte et al, "Lysine-specific demethylase 1 is strongly expressed in poorly differentiated neuroblastoma: implications for therapy", Cancer Res,2009,69(5),2065-71.
Scoumanne et al "Protein methylation: a new mechanism of p53 tumor suppressor regulation" Histol Histopathol 2008,23, 1143-1149.
Scoumanne et al, "The lysine-specific demethylase 1 is required for cell proliferation in both p53-dependent and -independent manners", J Biol Chem, 2007,282(21), 15471-5.
Seligson et al, "Global histone modification patterns predict risk of prostate cancer recurrence",Nature, 2005,435, 1262-1266.
Seligson et al,"Global levels of histone modifications predict prognosis in different cancers" ,Am J Path, 2009,174,1619-28.
Sharma et al, "(Bis)urea and (bis)thiourea inhibitors of lysine-specific demethylase 1 as epigenetic modulators", J Med Chem, 2010,53(14), 5197-5212.
Shi et al,"Histone demethylation mediated by the nuclear amine oxidase homolog LSD1", Cell, 2004,119,941-953.
Shi et al, "Histone lysine demethylases: emerging roles in development, physiology and disease", Nature Reviews Genetics 2007, 8:829-833.
Stephens et al, "The determination of the absolute configurations of chiral molecules using vibrational circular dichroism (VCD) spectroscopy",Chirality, 2008,20(5), 643-663.
Stoffel et al, "Leukocyte count and risk of thrombosis in patients undergoing haematopoietic stem cell transplantation or intensive chemotherapy",Thromb Haemost, 2010,103(6), 1228-32.
Stratmann et al, "Pathobiology and cell interactions of platelets in diabetes", Diabetes & Vascular Disease Research,2005, 2(1), 16-23.
Szewczuk et al, "Mechanistic analysis of a suicide inactivator of histone demethylase LSD1", Biochemistry, 2007,46, 6892-6902.
Tamagawa-Mineoka et al, "Elevated platelet activation in patients with atopic dermatitis and psoriasis: increased plasma levels of beta-thromboglobulin and platelet factor 4", Allergology International,2008, 57, 391-396.

(56) References Cited

OTHER PUBLICATIONS

Taylor et al,"Roscovitine, a cyclin-dependent kinase inhibitor, prevents replication of varicella-zoster virus", J Virol, 2004,78, 2853-2862.
Thaulow et al, "Blood platelet count and function are related to total and cardiovascular death in apparently healtht men", Circulation, 1991,84, 613-617.
Ueda et al, "Identification of cell-active lysine specific demethylase 1-selective inhibitors",J Am Chem Soc, 2009,131(48), 17536-17537.
Vagner et al, "Peptidomimetics, a synthetic tool of drug discovery", Current Opinion on Chemical Biology, 2008, 12:292-296.
Wagner et al, "Platelets in inflammation and thrombosis", Arteriosclerosis, Thrombosis and Vascular Biology, 2003, 23, 2131-2137.
Wang et al, "Novel histone demethylase LSD1 inhibitors selectively target cancer cells with pluripotent stem cell properties,", Cancer Research, 2011, 71(23): 7238-49.
Wang et al "LSD1 is a Subunit of the NuRD Complex and Targets the Metastasis Programs in Breast Cancer" Cell 2009, 138, 660-672.
Wang et al, "The lysine demethylase LSD1 (KDM1) is required for maintenance of global DNA methylation", Nature Genetcs, 2009, 41(1), 125-129.
Weinreb et al, "Novel neuroprotective mechanism of action of rasagiline is associated with its propargyl moiety: interaction of Bcl-2 family members with PKC pathway", Ann NY Acad Sci, 2005, 1053, 348-55.
Wermuth, "Molecular variations based on isosteric replacements", The Practice of Medicinal Chemistry (2nd edition), Academic Press, London, 2003, pp. 189-214.
Westland et al , "N-substituted derivatives of 2-aminoethanethiol and 2-hydraxinoethanethiol", JMedChem 1968, 11(4),824-829.
Whitlow et al,"Recruitment of the transcriptional coactivator HCF-1 to viral immediate-early promoters during initiation of reactivation from latency of herpes simplex virus type 1", J Virol, 2009,83(18)9591-5.
Willoughby et al, "Platelets and cardiovascular disease",Eur J Cardiovasc Nursing,2002,1,273-288.
XP002568777 Database chemcats, database accession No. 2088922753, order No. kbsb-0063197, Aurora screening library, Aug. 20, 2009.
Yang et al "Structural Basis for the Inhibition of the LSD1 Histone Demethylase by the Antidepressant trans-2-Phenylcyclopropylamine" Biochemistry 2007,46 (27), 8058-8065.
Yang et al "Structural basis of histone demethylation by LSD1 revealed by suicide inactivation" Nature Structural & Molecular Biology 2007, 14(6), 535-539.
Yoshida et al, "Fluorinated phenylcyclopropylamines. Part 3: inhibition of monoamine oxidase A and B",Bioorg Med Chem,2004,12(10),2645-2652.
Youdim et al, "Bifunctional drug derivatives of MAO-B inhibitor rasagiline and iron chelator VK-28 as a more effective approach to treatment of brain ageing and ageing neurodegenerative diseases", Mechanisms of Ageing and Development, 2005, 126: 317-326.
F. Zaragoza Dörwald "Side reactions in Organic Synthesis: a guide to successful synthesis design" Wiley-VCH Verlag GmbH & Co, KGaA, Wilenheim, Chapter 1, 2005.
Zirkle et al, "2-substituted cyclopropylamines. II. Effect of structure upon monoamine oxidase-inhibitory activity as measured in vivo by potentiation of tryptamine convulsions", J Med Pharm Chem (ACS), 1962, 5, 1265-84.
"Definition of Cancer"—MedicineNetcom Medical references for patients, http://www.medterms.com, 2005.
Johnson et al, CAPLUS, Document No. 157:576967, "Preparation of cyclopropylamines as LSD1 inhibitors in the treatment of cancer", 2012.
Delorme et al, HCAPLUS, Document No. 132:49802, "Preparation of 1-(N-substituted aminomethyl)-4-guanidinomethylcyclohexanes useful in pain management", 1999.
CAS Registry No. RN220351-33-7, entered STN Mar. 11, 1999.
CAS Registry No. RN844655-03-4, entered STN Mar. 9, 2005.
CAS Registry No. RN846596-02-9, entered STN Mar. 22, 2005.
CAS Registry No. RN848204-13-7, entered STN Apr. 11, 2005.
CAS Registry No. RN848732-87-6, entered STN Apr. 19, 2005.
CAS Registry No. RN848742-47-2, entered STN Apr. 19, 2005.
CAS Registry No. RN848753-47-9, entered STN Apr. 19, 2005.
CAS Registry No. RN903487-42-3, entered STN Aug. 23, 2006.
CAS Registry No. RN918305-55-2, entered STN Jan. 24, 2007.
CAS Registry No. RN959071-98-8, entered STN Dec. 20, 2007.
CAS Registry No. RN1026299-47-7, entered STN Jun. 8, 2008.
CAS Registry No. RN1157140-28-7, entered STN Jun. 14, 2009.
CAS Registry No. RN1218057-33-0, entered STN Apr. 11, 2010.
CAS Registry No. RN1247564-27-7, entered STN Oct. 27, 2010.
CAS Registry No. RN1247717-42-5, entered STN Oct. 27, 2010.
CAS Registry No. RN1247999-77-4, entered STN Oct. 28, 2010.
CAS Registry No. RN1248611-33-7, entered STN Oct. 29, 2010.
CAS Registry No. RN1245913-30-5, entered STN Nov. 1, 2010.
CAS Registry No. RN1248971-98-3, entered STN Nov. 1, 2010.
CAS Registry No. RN1250045-89-6, entered STN Nov. 1, 2010.
CAS Registry No. RN1250199-20-2, entered STN Nov. 1, 2010.
CAS Registry No. RN1250332-49-0, entered STN Nov. 1, 2010.
CAS Registry No. RN1251130-23-0, entered STN Nov. 3, 2010.
CAS Registry No. RN1270634-53-1, entered STN Mar. 27, 2011.
CAS Registry No. RN1273738-91-2, entered STN Apr. 3, 2011.
CAS Registry No. RN1274124-27-4, entered STN Apr. 3. 2011.
CAS Registry No. RN1274681-54-7, entered STN Apr. 4, 2011.
CAS Registry No. RN1280568-04-8, entered STN Apr. 15, 2011.
CAS Registry No. RN1280602-35-8, entered STN Apr. 15, 2011.
CAS Registry No. RN1281516-77-5, entered STN Apr. 17, 2011.
CAS Registry No. RN1281556-75-9, entered STN Apr. 17, 2011.
CAS Registry No. RN1281596-19-7, entered STN Apr. 17, 2011.
CAS Registry No. RN1281615-78-8, entered STN Apr. 17, 2011.
CAS Registry No. RN1281856-83-4, entered STN Apr. 18, 2011.
CAS Registry No. RN1281886-96-1, entered STN Apr. 18, 2011.
CAS Registry No. RN1282014-65-6, entered STN Apr. 18, 2011.
CAS Registry No. RN1282165-83-6, entered STN Apr. 19, 2011.
CAS Registry No. RN1282245-50-4, entered STN Apr. 19, 2011.
CAS Registry No. RN1282292-27-6, entered STN Apr. 19, 2011.
CAS Registry No. RN1282425-35-7, entered STN Apr. 19, 2011.
CAS Registry No. RN1282679-60-0, entered STN Apr. 20, 2011.
CAS Registry No. RN1282773-23-2, entered STN Apr. 20, 2011.
CAS Registry No. RN1282804-36-7, entered STN Apr. 20, 2011.
CAS Registry No. RN1282928-27-1, entered STN Apr. 20, 2011.
CAS Registry No. RN1283337-81-4, entered STN Apr. 21, 2011.
CAS Registry No. RN1283356-05-7, entered STN Apr. 21, 2011.
CAS Registry No. RN1283449-65-9, entered STN Apr. 21, 2011.
CAS Registry No. RN1283533-13-0, entered STN Apr. 21, 2011.
CAS Registry No. RN1283662-53-2, entered STN Apr. 21, 2011.
CAS Registry No. RN1283728-98-2, entered STN Apr. 21, 2011.
CAS Registry No. RN1283887-44-4, entered STN Apr. 22, 2011.
CAS Registry No. RN1284036-80-1, entered STN Apr. 22, 2011.
CAS Registry No. RN1284049-14-4, entered STN Apr. 22, 2011.
CAS Registry No. RN1284310-21-9, entered STN Apr. 22, 2011.
CAS Registry No. RN1285070-57-6, entered STN Apr. 24, 2011.
CAS Registry No. RN1285129-34-1, entered STN Apr. 24, 2011.
CAS Registry No. RN1285144-86-6, entered STN Apr. 24, 2011.
CAS Registry No. RN1285176-99-9, entered STN Apr. 24, 2011.
CAS Registry No. RN1285178-46-2, entered STN Apr. 24, 2011.
CAS Registry No. RN1285235-05-3, entered STN Apr. 24, 2011.
CAS Registry No. RN1285348-65-3, entered STN Apr. 25, 2011.
CAS Registry No. RN1285612-69-2, entered STN Apr. 25, 2011.
CAS Registry No. RN1290805-79-6, entered STN May 6, 2011.
CAS Registry No. RN129-906-73-8, entered STN May 6, 2011.
CAS Registry No. RN1290912-35-4, entered STN May 6, 2011.
CAS Registry No. RN1290912-36-5, entered STN May 6, 2011.
CAS Registry No. RN1290949-23-3, entered STN May 6, 2011.
CAS Registry No. RN1290949-24-4, entered STN May 6, 2011.
CAS Registry No. RN1290949-25-5, entered STN May 6, 2011.
CAS Registry No. RN1290971-74-2, entered STN May 6, 2011.
CAS Registry No. RN1290972-32-5, entered STN May 6, 2011.
CAS Registry No. RN1291186-57-6, entered STN May 8, 2011.
CAS Registry No. RN1291186-59-8, entered STN May 8, 2011.
CAS Registry No. RN1291186-62-3, entered STN May 8, 2011.
CAS Registry No. RN1291186-64-5, entered STN May 8, 2011.

(56) References Cited

OTHER PUBLICATIONS

CAS Registry No. RN1291230-78-8, entered STN May 8, 2011.
CAS Registry No. RN1291273-81-8, entered STN May 8, 2011.
CAS Registry No. RN1291273-82-9, entered STN May 8, 2011.
CAS Registry No. RN1291273-84-1, entered STN May 8, 2011.
CAS Registry No. RN1291273-86-3, entered STN May 8, 2011.
CAS Registry No. RN1291273-87-4, entered STN May 8, 2011.
CAS Registry No. RN1292446-11-7, entered STN May 10, 2011.
CAS Registry No. RN1304214-87-6, entered STN Jun. 2, 2011.
CAS Registry No. RN1304214-96-7, entered STN Jun. 2, 2011.
CAS Registry No. RN1304214-97-8, entered STN Jun. 2, 2011.
CAS Registry No. RN1304215-06-2, entered STN Jun. 2, 2011.
CAS Registry No. RN1304827-17-5, entered STN Jun. 3, 2011.
CAS Registry No. RN1304845-37-1, entered STN Jun. 3, 2011.
CAS Registry No. RN1304845-55-3, entered STN Jun. 3, 2011.
CAS Registry No. RN1304845-63-3, entered STN Jun. 3, 2011.
CAS Registry No. RN1304845-67-7, entered STN Jun. 3, 2011.
CAS Registry No. RN1304845-70-2, entered STN Jun. 3, 2011.
CAS Registry No. RN1304845-72-4, entered STN Jun. 3, 2011.
CAS Registry No. RN1304845-83-7, entered STN Jun. 3, 2011.
CAS Registry No. RN1305397-75-4, entered STN Jun. 5, 2011.
CAS Registry No. RN1305397-86-7, entered STN Jun. 5, 2011.
CAS Registry No. RN1305396-16-6, entered STN Jun. 5, 2011.
CAS Registry No. RN1306275-88-6, entered STN Jun. 5, 2011.
CAS Registry No. RN1306275-95-5, entered STN Jun. 5, 2011.
CAS Registry No. RN1306276-35-6, entered STN Jun. 5, 2011.
CAS Registry No. RN1306322-57-5, entered STN Jun. 6, 2011.
CAS Registry No. RN1306373-68-1, entered STN Jun. 6, 2011.
CAS Registry No. RN1306589-39-8, entered STN Jun. 6, 2011.
CAS Registry No. RN1307573-60-9, entered STN Jun. 8, 2011.
CAS Registry No. RN1307574-08-8, entered STN Jun. 8, 2011.
Co-pending U.S. Appl. No. 13/580,553, filed Aug. 22, 2012.
Co-pending U.S. Appl. No. 13/983,844, filed Aug. 6, 2013.
Co-pending U.S. Appl. No. 14/118,323, filed Nov. 18, 2013.
Co-pending U.S. Appl. No. 14/118,330, filed Nov. 18, 2013.
Co-pending U.S. Appl. No. 14/096,557, filed Dec. 4, 2013.
Co-pending U.S. Appl. No. 14/184,745, filed Feb. 20, 2014.
Co-pending U.S. Appl. No. 14/352,711, filed Apr. 18, 2014.
Co-pending U.S. Appl. No. 14/352,719, filed Apr. 18, 2014.
Co-pending U.S. Appl. No. 14/627,333, filed Feb. 20, 2015.
Co-pending U.S. Appl. No. 14/675,990, filed Apr. 1, 2015.
Co-pending U.S. Appl. No. 14/711,156, filed May 13, 2015.
Co-pending U.S. Appl. No. 14/843,095, filed Sep. 2, 2015.
Co-pending U.S. Appl. No. 14/848,649, filed Sep. 9, 2015.
International Search Report and Written Opinion of the International Searching Authority for PCT/EP2011/062947, dated Oct. 6, 2011.

US 9,676,701 B2

CYCLOPROPYLAMINE DERIVATIVES USEFUL AS LSD1 INHIBITORS

TECHNICAL FIELD

The invention relates to cyclopropylamine compounds, in particular the compounds of Formula (I), (II), (III), (IV) or (V), and their use in therapy, including, e.g., in the treatment or prevention of cancer, a neurological disease or condition, or viral infection.

BACKGROUND

Aberrant gene expression in affected tissue as compared to normal tissue is a common characteristic of many human diseases. This is true for cancer and many neurological diseases which are characterized by changes in gene expression patterns. Gene expression patterns are controlled at multiple levels in the cell. Control of gene expression can occur through modifications of DNA: DNA promoter methylation is associated with suppression of gene expression. Several inhibitors of DNA methylation are approved for clinical use including the blockbuster Vidaza™. Another class of modifications involve histones which form the protein scaffold that DNA is normally associated with (coiled around) in eukaryotic cells. Histones play a crucial role in organizing DNA and the regulated coiling and uncoiling of DNA around the histones is critical in controlling gene expression—coiled DNA is typically not accessible for gene transcription. A number of histone modification have been discovered including histone acetylation, histone lysine methylation, histone arginine methylation, histone ubiquinylation, and histone sumoylation, many of which modify accessibility to the associated DNA by the cells transcriptional machinery. These histone marks serve to recruit various protein complexes involved in transcription and repression. An increasing number of studies are painting an intricate picture of how various combinations of histone marks control gene expression in cell-type specific manner and a new term has been coined to capture this concept: the histone code.

The prototypical histone mark is histone acetylation. Histone acetyl transferase and histone deacetylases are the catalytic machines involved in modulation of this histone mark although typically these enzymes are parts of multi-protein complexes containing other proteins involved in reading and modifying histone marks. The components of these protein complexes are typically cell type and typically comprise transcriptional regulators, repressors, co-repressors, receptors associated with gene expression modulation (e.g., estrogen or androgen receptor). Histone deacetylase inhibitors alter the histone acetylation profile of chromatin. Accordingly, histone deacetylase inhibitors like SAHA, TSA, and many others have been shown to alter gene expression in various in vitro and in vivo animal models. Clinically, histone deacetylase inhibitor have demonstrated activity in the cancer setting and are being investigated for oncology indications as well as for neurological conditions and other diseases.

Another modification that is involved in regulating gene expression is histone methylation including lysine and arginine methylation. The methylation status of histone lysines has recently been shown to be important in dynamically regulating gene expression.

A group of enzymes known as histone lysine methyl transferases and histone lysine demethylases are involved in histone lysine modifications. One particular human histone lysine demethylase enzyme called Lysine Specific Demethylase-1 (LSD1) was recently discovered (Shi et al. (2004) *Cell* 119:941) to be involved in this crucial histone modification. LSD1 has a fair degree of structural similarity, and amino acid identity/homology to polyamine oxidases and monoamine oxidases, all of which (i.e., MAO-A, MAO-B and LSD1) are flavin dependent amine oxidases which catalyze the oxidation of nitrogen-hydrogen bonds and/or nitrogen carbon bonds.

Several groups have reported LSD1 inhibitors in the literature. Sharma et al. recently reported a new series of urea and thiourea analogs based on an earlier series of polyamines which were shown to inhibit LSD1 and modulate histone methylation and gene expression in cells (*J. Med. Chem.* 2010 PMID: 20568780). Sharma et al. note that "To date, only a few existing compounds have been shown to inhibit LSD1." Some efforts were made to make analogs of the histone peptide that is methylated by the enzyme, other efforts have focused on more small molecule like molecules based on known MAO inhibitors. Gooden et al. reported trans-2-arylcyclopropylamine analogues that inhibit LSD1 with Ki values in the range of 188-566 micromolar (Gooden et al. ((2008) *Bioorg. Med. Chem. Let.* 18:3047-3051)). Most of these compounds were more potent against MAO-A as compared to MAO-B. Ueda et al. ((2009) *J. Am. Chem. Soc.* 131(48):17536-17537) reported cyclopropylamine analogs selective for LSD1 over MAO-A and MAO-B that were designed based on reported X-ray crystal structures of these enzymes with a phenylcyclopropylamine-FAD adduct and a FAD-N-propargyl lysine peptide. The reported IC50 value for phenylcyclopropylamine was about 32 micromolar for LSD1 whereas compounds 1 and 2 had values of 2.5 and 1.9 micromolar respectively.

Binda et al. examined a series of phenylcyclopropylamine derivatives in relation to their inhibitory activity against LSD1 and LSD2 as well as examining stereochemical issues in relation to the cyclopropyl ring (*J. Am. Chem. Soc.* 2010 May 19; 132(19):6827-33). Binda et al. reported that their para substituted phenylcyclopropylamine derivatives are non-selective which as a group are appear to be better MAO-A inhibitors than MAO-B inhibitors. Furthermore, their inhibitory activities against MAO-A and LSD1 were roughly the same.

Mimasu et al. disclose a series of phenylcyclopropylamine derivatives having benzoyl substitutions at the ortho-position ((2010) *Biochemistry* PMID: 20568732. Ortho-substituted compounds from this series without a benzoyl group in the ortho-position e.g., phenyl, alkoxy, or having a combination of ortho- and para-substitution appeared to be less potent inhibitors of LSD1 than those compounds having benzoyl substituents in the ortho-position. The most active compounds from this series had a benzoyl group at the ortho-position and one or two meta-fluoro substitutions: biphenyls like S1310 and compounds having large groups in the para-position were less effective LSD1 inhibitors.

The phenylcyclopropylamines have been the subject of many studies designed to elucidate a SAR for MAO inhibition. Kaiser et al. ((1962) *J. Med. Chem.* 5:1243-1265); Zirkle et al. ((1962) *J. Med. Chem.* 1265-1284; U.S. Pat. Nos. 3,365,458; 3,471,522; 3,532,749) have disclosed the synthesis and activity of a number of phenylcyclopropylamine related compounds. Other phenylcyclopropylamine type compounds are disclosed in Bolesov et al. ((1974) *Zhurnal Organicheskoi Khimii* 10:8 1661-1669) and Russian Patent No. 230169 (19681030).

Studies have been conducted with phenylcyclopropylamine related compounds to determine selectivity for MAO-A versus MAO-B since MAO-A inhibitors can cause dangerous side-effects (see e.g., Yoshida et al. (2004) *Bioorg. Med. Chem.* 12(10):2645-2652; Hruschka et al. (2008) *Biorg Med Chem.* (16):7148-7166; Folks et al. (1983) *J. Clin. Psychopharmacol.* (3)249; and Youdim et al. (1983) *Mod. Probl. Pharmacopsychiatry* (19):63).

DISCLOSURE

In view of the lack of adequate treatments for conditions such as cancer and neurodegeneration, there is a desperate need for disease modifying drugs and drugs that work by inhibiting novel targets. There is a need for the development of better LSD1 selective inhibitors particularly those which selectively inhibit LSD1 and LSD1 in combination with MAO-B.

The present invention relates to the identification of compounds and their use in treating or preventing diseases. The present invention provides a compound of Formula (I) or a pharmaceutically acceptable salt thereof, pharmaceutical compositions comprising a compound of Formula (I) or a pharmaceutically acceptable salt thereof, and a pharmaceutically acceptable carrier, and their uses for treating diseases. One use of the compound of Formula (I) is for treating cancer. Another use for the compound of Formula (I) is to inhibit LSD1. The present invention thus relates to a compound of Formula (I) or an enantiomer, a diastereomer, or a mixture thereof, or a pharmaceutically acceptable salt or solvate thereof for use in treating or preventing cancer.

The invention provides a compound of Formula (I) or an enantiomer, a diastereomer, or a mixture thereof, or a pharmaceutically acceptable salt or solvate thereof and, furthermore, relates to its use as a medicament, in particular its use in treating or preventing human disease:

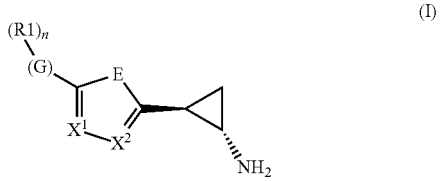

(I)

wherein:
E is —N(R3)-, —O—, or —S—, or is —X$^3$=X$^4$—;
X$^1$ and X$^2$ are independently C(R2) or N;
X$^3$ and X$^4$ when present are independently C(R2) or N;
(G) is a cyclyl group (as shown in formula (I), the cyclyl group (G) has n substituents (R1));
each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;
each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents, wherein said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate;
R3 is a —H or an (C$_1$-C$_6$)alkyl group;
each L1 is independently alkylene or heteroalkylene; and
n is 0, 1, 2, 3, 4 or 5.

In a related aspect, the invention provides a pharmaceutical composition comprising a compound of Formula (I) or an enantiomer, a diastereomer, or a mixture thereof, or a pharmaceutically acceptable salt or solvate thereof as defined above and a pharmaceutically acceptable carrier. Preferred embodiments of the compound of Formula (I), e.g., for use in the composition of the invention are defined and described herein below in more detail.

In another aspect, the invention provides a method of treating or preventing a disease or condition comprising administering, to a patient (preferably a human) in need of treatment or prevention, a therapeutically effective amount of a pharmaceutical composition comprising a compound of Formula (I) as described above or as in the embodiments thereof as described below, or a pharmaceutically acceptable salt thereof and a pharmaceutically acceptable carrier. This aspect can be reformulated as a compound of Formula (I) as defined above in the first aspect of the invention for use as a medicine. In a related aspect, the invention provides a pharmaceutical composition for use in treating or preventing a disease or condition wherein said composition comprises a therapeutically effective amount of a compound of Formula (I) sufficient for treating or preventing said disease or condition. In a more specific embodiment, the invention provides a compound of Formula (I) for use in the treatment of a disease associated with LSD1.

In yet another aspect, the invention provides a method of inhibiting LSD1 activity comprising administering, to a patient in need of treatment, a therapeutically effective amount of a composition comprising a compound of Formula (I) or a pharmaceutically acceptable salt thereof, and a pharmaceutically acceptable carrier sufficient to inhibit LSD1 activity. Preferably the patient is a human. This aspect can be reformulated as a compound of Formula (I) as herein defined for use as a LSD1 inhibitor. In a related aspect, a method for treating an individual is provided, said method comprising identifying an individual in need of treatment and administering to said individual a therapeutically effective amount of a compound of Formula (I). In a preferred aspect, the therapeutically effective amount of a compound of Formula (I) is an amount sufficient to inhibit LSD1. Preferred embodiments of the compounds of Formula (I) for use in the composition and method of this aspect of the invention are as described in more detail herein.

In again another aspect, the invention provides a method of treating or preventing cancer comprising administering, to a patient in need of treatment or prevention, a therapeutically effective amount of a composition comprising a compound of Formula (I) as defined above or as the embodiments described in more detail herein, and a pharmaceutically acceptable carrier. This aspect can be reformulated as a compound of Formula (I) as defined above in the first aspect of the invention for use in the treatment or prevention of cancer. In a related aspect, the invention provides a pharmaceutical composition for use in treating or preventing cancer wherein said composition comprises a therapeutically effective amount of a compound of Formula (I) sufficient for treating or preventing cancer.

In another related aspect, the invention provides a compound of Formula (I) or a pharmaceutical composition for the treatment or prevention of a cancer wherein said cancer is chosen from breast cancer, lung cancer, prostate cancer, colorectal cancer, brain cancer, skin cancer, blood cancer (e.g., leukemia) and lymphoma, wherein said composition comprises a therapeutically effective amount of a compound of Formula (I) sufficient for treating or preventing said cancer. In a preferred aspect, the therapeutically effective amount of a compound of Formula (I) is an amount sufficient to inhibit LSD1. In another preferred aspect, the therapeutically effective amount is an amount sufficient to modulate histone methylation levels. In another preferred aspect, the therapeutically effective amount is an amount sufficient to modulate histone-3 lysine-4 methylation levels.

In again another aspect, the invention provides a method of treating or preventing a neurological disease or condition comprising administering, to a patient in need of treatment or prevention, a therapeutically effective amount of a composition comprising a compound of Formula (I) as defined above or in the embodiments described in more detail herein, and a pharmaceutically acceptable carrier. This aspect can be reformulated as a compound of Formula (I) as defined above for use in the treatment or prevention of a neurological condition or disease. In a related aspect, the invention provides a pharmaceutical composition for use in treating or preventing a neurological condition or disease wherein said composition comprises a therapeutically effective amount of a compound of Formula (I) sufficient for treating or preventing said neurological disease or condition. In another related aspect, the invention provides a compound of Formula (I) or a pharmaceutical composition for the treatment or prevention of a neurological disease or condition wherein said neurological disease or condition is chosen from depression, Alzheimer's disease, Huntington disease, Parkinson's disease, and Dementia with Lewy Bodies, wherein said composition comprises a therapeutically effective amount of a compound of Formula (I) sufficient for treating or preventing said disease or condition. In a preferred aspect, the therapeutically effective amount of a compound of Formula (I) is an amount sufficient to inhibit LSD1. In another preferred aspect, the therapeutically effective amount is an amount sufficient to modulate histone methylation levels. In another preferred aspect, the therapeutically effective amount is an amount sufficient to modulate histone-3 lysine-4 methylation levels.

In still another aspect, the invention provides a method for identifying a compound which is a selective inhibitor of LSD1, the method comprising selecting or providing a compound of Formula (I) as defined herein, and determining the ability of the compound to inhibit LSD1 and MAO-A and/or MAO-B, wherein a compound that inhibits LSD1 to a greater extent than MAO-A and/or MAO-B is identified as a LSD1 selective inhibitor. The compound of this aspect that is an LSD1 inhibitor can be used to treat disease, particularly human disease.

In still another aspect, the invention provides a method for identifying a compound which is a dual inhibitor of LSD1 and MAO-B, the method comprising selecting or providing a compound of Formula (I) as defined herein, and determining the ability of the compound to inhibit LSD1, MAO-A, and MAO-B, wherein a compound that inhibits LSD1 and MAO-B to a greater extent than MAO-A is identified as a LSD1 MAO-B dual inhibitor. The compound of this aspect that is an LSD1 MAO-B inhibitor can be used to treat disease, particularly human disease.

Thus, in one embodiment of the invention, the pharmaceutical composition comprising a LSD1 selective inhibitor of Formula (I), or a pharmaceutically acceptable salt thereof is useful for treating and/or preventing a disease in an individual. In one aspect, a therapeutically effective amount of the composition is administered to an individual in an amount sufficient to prevent or treat a disease. In a more specific, the disease is cancer. In an even more specific aspect, the disease is a cancer chosen from prostate, brain, colorectal, lung, breast, skin, and blood cancer. In one specific aspect, the cancer is prostate cancer. In one specific aspect, the cancer is lung cancer. In one specific aspect, the cancer is brain cancer. In one specific aspect, the cancer is blood cancer (e.g., leukemia). In one specific aspect, the cancer is breast cancer. In one specific aspect, the cancer is colorectal cancer. In one specific aspect, the cancer is lymphoma. In another preferred aspect, the therapeutically effective amount is an amount sufficient to inhibit LSD1. In another preferred aspect, the therapeutically effective amount is an amount sufficient to modulate histone methylation levels. In another preferred aspect, the therapeutically effective amount is an amount sufficient to modulate histone-3 lysine-4 methylation levels.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

The present invention relates to the identification of compounds and their use in treating and preventing diseases. The present invention provides compounds of Formula (I), pharmaceutical compositions comprising a compound of Formula (I) or a pharmaceutically acceptable salt thereof and a pharmaceutically acceptable carrier, and their use for treating diseases. One use of the compounds of Formula (I) is for treating cancer. The compounds of Formula (I) can be used as LSD1 selective inhibitors that inhibit LSD1 to a greater extent than MAO-A and MAO-B or as LSD1/MAO-B dual inhibitors that they inhibit LSD1 and MAO-B to a greater extent than MAO-A. In particular it was found that heterocyclylpropylamine, phenylcyclopropylamine, and pyridinylcyclopropylamine analogues of Formula (I) yield unexpectedly potent LSD1 inhibitors. The compounds of Formula (I) as described herein are generally better inhibitors of LSD1 by a factor of about 20 or more as compared to tranylcypromine, with improved selectivity against MAO-A. Thus, these compounds are LSD1 selective in that they inhibit LSD1 to an extent greater than MAO-A and MAO-B or are LSD1/MAO-B duals inhibitors in that they inhibit LSD1 and MAO-B to a greater extent than MAO-A.

The invention provides a compound of Formula (I) or an enantiomer, a diastereomer, or a mixture thereof, or a pharmaceutically acceptable salt or solvate thereof and, furthermore, relates to its use in treating or preventing a disease or disorder:

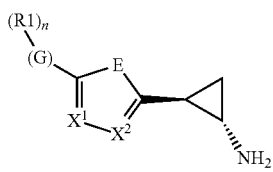

(I)

wherein:
E is —N(R3)-, —O—, or —S—, or is —X³=X⁴—;
X¹ and X² are independently C(R2) or N;
X³ and X⁴, when present, are independently C(R2) or N;
(G) is a cyclyl group (as shown in formula (I), the cyclyl group (G) has n substituents (R1));
each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;
each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents, wherein said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate;
R3 is —H or a (C₁-C₆)alkyl group;
each L1 is independently alkylene or heteroalkylene; and
n is 0, 1, 2, 3, 4 or 5.

Preferably, the compounds of the invention are used to treat a disease in a mammal and more preferably a human. More preferably, the human disease is chosen from cancer, a neurological condition or disease, or a viral infection.

Preferably, the optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

Preferably, (G) is an aryl or heterocyclyl group.
Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy.
More preferably, each (R1) is independently chosen from lower alkyl, lower aryl, amino, amido, nitro, halo, lower haloalkyl, cyano, heterocycle, sulfonyl, sulfonamide, hydroxyl, or alkoxy.
Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents (as defined and described herein).

Preferably, R3 is —H or (C₁-C₄)alkyl.
More preferably, (G) is a phenyl, thienyl, benzothienyl, or indolyl group.
More preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino (C₁-C₆)alkyl, halo, lower alkoxy, and amido.
More preferably, R3 is —H, methyl or ethyl.
Even more preferably, each (R1) is independently chosen from —CF₃, —F, —Cl, —CN, —CH₃, —OH, or —C(=O)NH₂.
Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —CH₂NH₂, —CH₂CH₂NH₂, or —OCH₃.
Even more preferably, (G) is a phenyl group.
Even more preferably R3 is —H.
Preferably, 0, 1, or 2 (R2) groups are not —H.
Preferably, n is 0, 1, 2, 3, or 4. More preferably, n is 0, 1, 2, or 3.

In one embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:
E is —X³=X⁴—.
X¹, X², X³ and X⁴ are independently C(R2) or N.
(G) is a cyclyl group. Preferably, (G) is an aryl or heterocyclyl group.
More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group Even more preferably, (G) is a phenyl, thienyl, benzothienyl, or indolyl group. Even more preferably, (G) is a phenyl group.
Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —CF₃, —F, —Cl, —CN, —CH₃, —OH, —OCH₃, —C(=O)NH₂, —NH—CO—CH₃, —NH—SO₂—CH₃, —NH—SO₂—CH₂—CH₃, —NH—SO₂—CH(CH₃)—CH₃, —NH—SO₂—(C₆H₅), —NH—SO₂—(C₆H₄)—CN (e.g., —NH—SO₂-(o-cyanophenyl), —NH—SO₂-(m-cyanophenyl), —NH—SO₂-(o-cyanophenyl)), —NHSO₂CF₃, or —S(=O)₂ NHCH₃. Even more preferably, each (R1) is independently chosen from —CF₃, —F, —Cl, —CN, —CH₃, —OH, —OCH₃, —C(=O)NH₂, —NH—CO—CH₃, —NH—SO₂—CH₃, —NH—SO₂—CH₂—CH₃, —NH—SO₂—CH (CH$_3$)—CH$_3$, or —NH—SO$_2$—(C$_6$H$_5$). Even more preferably, each (R1) is independently chosen from —CF$_3$, —F, —Cl, —CN, —CH$_3$, —OH, —OCH$_3$, or —C(=O)NH$_2$. Even more preferably, each (R1) is independently chosen from —CF$_3$, —F, —Cl, —CN, —CH$_3$, —OH, or —C(=O) NH$_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino(C$_1$-C$_6$)alkyl, halo, lower alkoxy, and amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —CH$_2$NH$_2$, —CH$_2$CH$_2$NH$_2$, or —OCH$_3$. Even more preferably, each (R2) is —H. Each L1 is independently alkylene or heteroalkylene.

n is 0, 1, 2, 3, 4 or 5. Preferably, n is 0, 1, 2, 3, or 4. More preferably, n is 0, 1, 2, or 3.

The present application describes compositions comprising one specific enantiomer of a compound according to the invention, such as a compound of Formula (I), (II), (III), (IV) or (V), which is "substantially free" of the other enantiomer (e.g., a composition comprising "the (1S,2R) enantiomer in respect to the substituents on the cyclopropyl ring, substantially free of the (1R,2S) enantiomer"). Whenever percentages of the individual enantiomers are indicated in this connection, the indicated percentages are mole percentages (mole-%). For example, the expression "the compound is more than 90% (1S,2R) enantiomer and less than 10% (1R,2S) enantiomer" thus refers to more than 90 mol-% of the (1S,2R) enantiomer and less than 10 mole-% of the (1R,2S) enantiomer being present.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S, 2R) enantiomer and less than 10% (1R,2S) enantiomer. More preferably, the compound is more than 95% (1S, 2R) enantiomer and less than 5% (1R, 2S) enantiomer. Even more preferably, the compound is more than 99% (1S, 2R) enantiomer and less than 1% (1R, 2S) enantiomer. As used herein, such percentages refer to mole-%.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S,2R) enantiomer. More preferably, the compound is more than 95% (1R,2S) enantiomer and less than 5% (1S, 2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —$X^3$=$X^4$—.

$X^1$, $X^2$, $X^3$ and $X^4$ are independently C(R2) or N.

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$) r. Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino($C_1$-$C_6$)alkyl, halo, lower alkoxy, and amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —$CH_2NH_2$, —$CH_2CH_2NH_2$, or —$OCH_3$. Even more preferably, each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S, 2R) enantiomer and less than 10% (1R,2S) enantiomer. More preferably, the compound is more than 95% (1S, 2R) enantiomer and less than 5% (1R, 2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R, 2S) enantiomer and less than 5% (1S, 2R) enantiomer. Even more preferably, the compound is more than 99% (1R, 2S) enantiomer and less than 1% (1S, 2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

In one specific embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —N(R3)-, —O—, or —S—, or is —$X^3$=$X^4$—;

$X^1$ and $X^2$ are independently C(R2) or N;

$X^3$ and $X^4$, when present, are independently C(R2) or N;

(G) is a cyclyl group (as shown in formula (I), the cyclyl group (G) has n substituents (R1)); each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein at least one group (R1) is sulfonamide;

each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents, wherein said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate;

R3 is —H or a $(C_1-C_6)$alkyl group;

each L1 is independently alkylene or heteroalkylene; and n is 0, 1, 2, 3, 4 or 5.

In this specific embodiment, the term "sulfonamide" refers to a group RS($=$O)$_2$N(R')— or a group —S($=$O)$_2$NRR', wherein R and R' are each independently selected from hydrogen, alkyl, haloalkyl (e.g., —CF$_3$), optionally substituted cycloalkyl, heteroalkyl, optionally substituted aryl, optionally substituted heteroaryl or optionally substituted heterocycloalkyl. Said cycloalkyl, said aryl, said heteroaryl and said heterocycloalkyl may each be substituted with 1, 2, 3 or 4 groups (particularly with one group) independently selected from lower alkyl, lower alkenyl, lower alkynyl, lower alkanoyl, lower heteroalkyl, lower heterocycloalkyl, lower haloalkyl, lower cycloalkyl, phenyl, aryl, aryloxy, lower alkoxy, lower haloalkoxy, lower acyloxy, carbonyl, carboxyl, lower alkylcarbonyl, lower carboxyester, lower carboxamido, cyano, halogen, hydroxyl, amino, lower alkylamino, arylamino, aminoalkyl, amido, nitro, thiol, lower alkylthio, lower haloalkylthio, lower perhaloalkylthio, arylthio, carbamate, or urea, and preferably selected independently from —CN, —CF$_3$, or halogen. Accordingly, exemplary non-limiting "sulfonamide" are NHSO$_2$CH$_3$, —NHSO$_2$CH$_2$CH$_3$, —NHSO$_2$(phenyl), —NHSO$_2$(isopropyl), —NHSO$_2$(-phenyl-CN), —NHSO$_2$CF$_3$, or —S($=$O)$_2$NHCH$_3$.

In the above specific embodiment, (G) is preferably an aryl or heterocyclyl group.

In the above specific embodiment, each (R1) is preferably independently chosen from alkyl, aryl, amino, amido, nitro, halo, haloalkyl, haloalkoxy, cyano, heterocycle, sulfonyl, sulfonamide, hydroxyl, or alkoxy.

In the above specific embodiment, each (R1) is more preferably independently chosen from lower alkyl, lower aryl, amino, amido, nitro, halo, lower haloalkyl, cyano, heterocycle, sulfonyl, sulfonamide, hydroxyl, or alkoxy, wherein at least one group (R1) is sulfonamide. Most preferably, at least one group (R1) is a sulfonamide group selected from —NH—SO$_2$—CH$_3$, —NH—SO$_2$—CH$_2$—CH$_3$, —NH—SO$_2$—CH(CH$_3$)—CH$_3$, —NH—SO$_2$—(C$_6$H$_5$), —NH—SO$_2$—(C$_6$H$_4$)—CN, —NHSO$_2$CF$_3$, or —S($=$O)$_2$NHCH$_3$.

In the above specific embodiment, each (R2) is preferably independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents (as defined and described herein).

In the above specific embodiment, R3 is preferably —H or $(C_1-C_4)$alkyl.

In the above specific embodiment, (G) is more preferably a phenyl, thienyl, benzothienyl, or indolyl group.

In the above specific embodiment, each (R2) is more preferably independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino$(C_1-C_6)$alkyl, halo, lower alkoxy, and amido. In the above specific embodiment, R3 is more preferably —H, methyl or ethyl.

In the above specific embodiment, each (R2) is even more preferably independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —CH$_2$NH$_2$, —CH$_2$CH$_2$NH$_2$, or —OCH$_3$.

In the above specific embodiment, (G) is even more preferably a phenyl group.

In the above specific embodiment, R3 is even more preferably —H.

In the above specific embodiment, preferably 0, 1, or 2 (R2) groups are not —H.

In the above specific embodiment, n is preferably 0, 1, 2, 3, or 4. More preferably, n is 0, 1, 2, or 3.

In a further specific embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —X$^3$—X$^4$—: and

X$^1$, X$^2$, X$^3$ and X$^4$ are independently C(R2) or N.

In the above specific embodiment, (G) is a cyclyl group. Preferably, (0) is an aryl or heterocyclyl group.

In the above specific embodiment, more preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group Even more preferably, (G) is a phenyl, thienyl, benzothienyl, or indolyl group. Even more preferably, (G) is a phenyl group.

In the above specific embodiment, each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein at least one group (R1) is sulfonamide. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy, wherein at least one group (R1) is sulfonamide. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy, wherein at least one group (R1) is sulfonamide. Even more preferably, each (R1) is independently chosen from —CF$_3$, —F, —Cl, —CN, —CH$_3$, —OH, —OCH$_3$, —C($=$O)NH$_2$, —NH—CO—CH$_3$, —NH—SO$_2$—CH$_3$, —NH—SO$_2$—CH$_2$—CH$_3$, —NH—SO$_2$—CH(CH$_3$)—CH$_3$, —NH—SO$_2$—(C$_6$H$_5$), —NH—SO$_2$—(C$_6$H$_4$)—CN (e.g., —NH—SO$_2$-(p-cyanophenyl), —NH—SO$_2$-(m-cyanophenyl), —NH—SO$_2$-(o-cyanophenyl)), —NHSO$_2$CF$_3$, or —S($=$O)$_2$ NHCH$_3$, wherein at least one group (R1) is —NH—SO$_2$—CH$_3$, —NH—SO$_2$—CH$_2$—CH$_3$, —NH—SO$_2$—CH(CH$_3$)—CH$_3$, —NH—SO$_2$—(C$_6$H), —NH—

SO$_2$—(C$_6$H$_4$)—CN, —NHSO$_2$CF$_3$, or —S(═O)$_2$NHCH$_3$. For all of the preferred definitions of (R1) provided above, it is most preferred that at least one group (R1) is selected from —NH—SO$_2$—CH$_3$, —NH—SO$_2$—CH$_2$—CH$_3$, —NH—SO$_2$—CH(CH$_3$)—CH$_3$, —NH—SO$_2$—(C$_6$H$_5$), —NH—SO$_2$—(C$_6$H$_4$)—CN, —NHSO$_2$CF$_3$, or —S(═O)$_2$NHCH$_3$.

In the above specific embodiment, the term "sulfonamide" refers to a group RS(═O)$_2$N(R')— or a group —S(═O)$_2$NRR', wherein R and R' are each independently selected from hydrogen, alkyl, haloalkyl (e.g., —CF$_3$), optionally substituted cycloalkyl, heteroalkyl, optionally substituted aryl, optionally substituted heteroaryl or optionally substituted heterocycloalkyl. Said cycloalkyl, said aryl, said heteroaryl and said heterocycloalkyl may each be substituted with 1, 2, 3 or 4 groups (particularly with one group) independently selected from lower alkyl, lower alkenyl, lower alkynyl, lower alkanoyl, lower heteroalkyl, lower heterocycloalkyl, lower haloalkyl, lower cycloalkyl, phenyl, aryl, aryloxy, lower alkoxy, lower haloalkoxy, lower acyloxy, carbonyl, carboxyl, lower alkylcarbonyl, lower carboxyester, lower carboxamido, cyano, halogen, hydroxyl, amino, lower alkylamino, arylamino, aminoalkyl, amido, nitro, thiol, lower alkylthio, lower haloalkylthio, lower perhaloalkylthio, arylthio, carbamate, or urea, and preferably selected independently from —CN, —CF$_3$, or halogen. Accordingly, exemplary non-limiting "sulfonamide" are NHSO$_2$CH$_3$, —NHSO$_2$CH$_2$CH$_3$, —NHSO$_2$(phenyl), —NHSO$_2$(isopropyl), —NHSO$_2$(-phenyl-CN), —NHSO$_2$CF$_3$, or —S(═O)$_2$NHCH$_3$.

In the above specific embodiment, each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino (C$_1$-C$_6$)alkyl, halo, lower alkoxy, and amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —CH$_2$NH$_2$, —CH$_2$CH$_2$NH$_2$, or —OCH$_3$. Even more preferably, each (R2) is —H. Each L1 is independently alkylene or heteroalkylene.

In the above specific embodiment, n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S,2R) enantiomer and less than 5% (1R,2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R, 2S) enantiomer and less than 5% (1S, 2R) enantiomer. Even more preferably, the compound is more than 99% (1R,2S) enantiomer and less than 1% (1S, 2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

Stereoisomers are typically resolved using chiral HPLC column techniques (e.g., Daicel CHIRALPAK® and CHIRALCEL® columns, Chirex® (utilizing the Pirkle-brush concept), Sumichiral OA® (available from Sumika Chemical Analysis Service, Ltd.), Regis Whelk-0 1® (available from Merck KGaA of Darmstadt, Del.), Lux® chiral columns available from Phenomenex, Inc. of Torrance, Calif., US) according to manufacturer's instructions or by outside specialist laboratory (e.g., Syncom BV of Groningen, NL or Chiral Technologies Europe of Illkirch, FR). A gas chromatography-mass spectrometry ("G-MS") method may also sometimes be used. Although such techniques typically work to separate a racemate into its respective stereoisomers, sometimes the procedures do not so work, and, for example, the more complicated separate enantioselective synthesis of each of the separate stereoisomers is performed (e.g., by utilizing chiral crystallization techniques) for both pharmacological and toxological testing.

As the ordinary skilled artisan is aware, the absolute configuration of the compounds of the invention can be determined according to standard techniques in the field of chiral compounds. In particular, the isomers of racemic compounds can be isolated by a variety of techniques as described herein and subjected to techniques such as xray crystallography, chiral shift reagent, circular dichrosim, chemical derivatization, optical rotation, and/or enantiospecific synthetic techniques to determine the absolute configuration (see e.g., Stephens et al. Chirality. 2008 May 15; 20(5):643-63); Shah et al. Curr Opin Drug Discov Devel. 2001 November; 4(6):764-75 and others.)

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —$X^3$=$X^4$—.

$X^1$, $X^2$, $X^3$ and $X^4$ are independently C(R2) or N.

(G) is a cyclyl group. Preferably, (G) is an aryl or heterocyclyl group. More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R, 2S) enantiomer. More preferably, the compound is more than 95% (1S, 2R) enantiomer and less than 5% (1R, 2S) enantiomer. Even more preferably, the compound is more than 99% (1S, 2R) enantiomer and less than 1% (1R, 2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R, 2S) enantiomer and less than 10% (1S,2R) enantiomer. More preferably, the compound is more than 95% (1R, 2S) enantiomer and less than 5% (1S, 2R) enantiomer. Even more preferably, the compound is more than 99% (1R, 2S) enantiomer and less than 1% (1S, 2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —$X^3$=$X^4$—.

$X^1$, $X^2$, $X^3$ and $X^4$ are independently C(R2) or N.

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S, 2R) enantiomer and less than 5% (1R, 2S) enantiomer. Even more preferably, the compound is more than 99% (1S,2R) enantiomer and less than 1% (1R, 2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R, 2S) enantiomer and less than 5% (1S, 2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —$X^3$=$X^4$—.

$X^1$, $X^2$, $X^3$ and $X^4$ are independently C(R2).

(G) is a cyclyl group. Preferably, (G) is an aryl or heterocyclyl group. More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—CH$_3$, —NH—SO$_2$—CH$_3$, —NH—SO$_2$—CH$_2$—CH$_3$, —NH—SO$_2$—CH(CH$_3$)—CH$_3$, or —NH—SO$_2$—(C$_6$H$_5$). Even more preferably, each (R1) is independently chosen from —CF$_3$, —F, —Cl, —CN, —CH$_3$, —OH, —OCH$_3$, or —C(=O)NH$_2$. Even more preferably, each (R1) is independently chosen from —CF$_3$, —F, —Cl, —CN, —CH$_3$, —OH, or —C(=O)NH$_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino(C$_1$-C$_6$)alkyl, halo, lower alkoxy, or amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —CH$_2$NH$_2$, —CH$_2$CH$_2$NH$_2$, or —OCH$_3$. Even more preferably, each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R, 2S) enantiomer. More preferably, the compound is more than 95% (1S, 2R) enantiomer and less than 5% (1R,2S) enantiomer. Even more preferably, the compound is more than 99% (1S, 2R) enantiomer and less than 1% (1R, 2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R,2S) enantiomer and less than 5% (1S, 2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%/0, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (T) have the following meanings:

E is —X$^3$=X$^4$—.

X$^1$, X$^2$, X$^3$ and X$^4$ are independently C(R2).

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2CH_2$—$CH_3$, —NH—$SO_2$—CH($CH_3$)—$CH_3$, or —NH—$SO_2$—($C_6$H). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino($C_1$-$C_6$)alkyl, halo, lower alkoxy, or amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —$CH_2NH_2$, —$CH_2CH_2NH_2$, or —$OCH_3$. Even more preferably, each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S,2R) enantiomer and less than 5% (1R, 2S) enantiomer. Even more preferably, the compound is more than 99% (1S, 2R) enantiomer and less than 1% (1R, 2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R,2S) enantiomer and less than 5% (1S, 2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —$X^3$=$X^4$—.

$X^1$, $X^2$, $X^3$ and $X^4$ are independently C(R2).

(G) is a cyclyl group. Preferably, (G) is an aryl or heterocyclyl group. More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —CF$_3$, —F, —Cl, —CN, —CH$_3$, —OH, —OCH$_3$, —C(=O)NH$_2$, —NH—CO—CH$_3$, —NH—SO$_2$—CH$_3$, —NH—SO$_2$—CH$_2$—CH$_3$, —NH—SO$_2$—CH(CH$_3$)—CH$_3$, or —NH—SO$_2$—(C$_6$H$_5$). Even more preferably, each (R1) is independently chosen from —CF$_3$, —F, —Cl, —CN, —CH$_3$, —OH, —OCH$_3$, or —C(=O)NH$_2$. Even more preferably, each (R1) is independently chosen from —CF$_3$, —F, —Cl, —CN, —CH$_3$, —OH, or —C(=O)NH$_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R, 2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S,2R) enantiomer. More preferably, the compound is more than 95% (1R, 2S) enantiomer and less than 5% (1S, 2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —X$^3$=X$^4$—.

X$^1$, X$^2$, X$^3$ and X$^4$ are independently C(R2).

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —CF$_3$, —F, —Cl, —CN, —CH$_3$, —OH, —OCH$_3$, —C(=O)NH$_2$, —NH—CO—CH$_3$, —NH—SO$_2$—CH$_3$, —NH—SO$_2$—CH$_2$—CH$_3$, —NH—SO$_2$—CH(CH$_3$)—CH$_3$, or —NH—SO$_2$—(C$_6$H$_5$). Even more preferably, each (R1) is independently chosen from —CF$_3$, —F, —Cl, —CN, —CH$_3$, —OH, —OCH$_3$, or —C(O)NH$_2$. Even more preferably, each (R1) is independently chosen from —CF$_3$, —F, —Cl, —CN, —CH$_3$, —OH, or —C(=O)NH$_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S, 2R) enantiomer and less than 10% (1R,2S) enantiomer.

More preferably, the compound is more than 95% (1S, 2R) enantiomer and less than 5% (1R,2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R, 2S) enantiomer and less than 10% (1S, 2R) enantiomer. More preferably, the compound is more than 95% (1R,2S) enantiomer and less than 5% (1S,2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99% a. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —$X^3$=$X^4$—.

$X^1$ is N, $X^2$, $X^3$ and $X^4$ are independently C(R2).

(G) is a cyclyl group. Preferably, (G) is an aryl or heterocyclyl group. More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino($C_1$-$C_6$)alkyl, halo, lower alkoxy, oramido. Even more preferably, each (R2) is independently chosen from —II, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —CH$_2$NH$_2$, —CH$_2$CH$_2$NH$_2$, or —OCH$_3$. Even more preferably, each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S, 2R) enantiomer and less than 10% (1R, 2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R, 2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R,2S) enantiomer and less than 5% (1S, 2R) enantiomer. Even more preferably, the compound is more than 99% (1R,2S) enantiomer and less than 1% (1S, 2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —X$^3$═X$^4$—.

X$^1$ is N, X$^2$, X$^3$ and X$^4$ are independently C(R2).

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —CF$_3$, —F, —Cl, —CN, —CH$_3$, —OH, —OCH$_3$, —C(═O)NH$_2$, —NH—CO—CH$_3$, —NH—SO$_2$—CH$_3$, —NH—SO$_2$—CH$_2$—CH$_3$, —NH—SO$_2$—CH(CH$_3$)—CH$_3$, or —NH—SO$_2$—(C$_6$H$_5$). Even more preferably, each (R1) is independently chosen from —CF$_3$, —F, —Cl, —CN, —CH$_3$, —OH, —OCH$_3$, or —C(═O)NH$_2$. Even more preferably, each (R1) is independently chosen from —CF$_3$, —F, —Cl, —CN, —CH$_3$, —OH, or —C(═O)NH$_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino(C$_1$-C$_6$)alkyl, halo, lower alkoxy, or amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —CH$_2$NH$_2$, —CH$_2$CH$_2$NH$_2$, or —OCH$_3$. Even more preferably, each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (T) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S, 2R) enantiomer and less than 5% (1R, 2S) enantiomer. Even more preferably, the compound is more than 99% (1S, 2R) enantiomer and less than 1% (1R, 2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R,2S) enantiomer and less than 5% (1S, 2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer disease, Huntington disease, Parkinson disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —X$^3$=X$^4$—.

X$^1$ is N, X$^2$, X$^3$ and X$^4$ are independently C(R2).

(G) is a cyclyl group. Preferably, (G) is an aryl or heterocyclyl group. More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —CF$_3$, —F, —Cl, —CN, —CH$_3$, —OH, —OCH$_3$, —C(=O)NH$_2$, —NH—CO—CH$_3$, —NH—SO$_2$—CH$_3$, —NH—SO$_2$—CH$_2$—CH$_3$, —NH—SO$_2$—CH(CH$_3$)—CH$_3$, or —NH—SO$_2$—(C$_6$H$_5$). Even more preferably, each (R1) is independently chosen from —CF$_3$, —F, —Cl, —CN, —CH$_3$, —OH, —OCH$_3$, or —C(=O)NH$_2$. Even more preferably, each (R1) is independently chosen from —CF$_3$, —F, —Cl, —CN, —CH$_3$, —OH, or —C(=O)NH$_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (T) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S, 2R) enantiomer and less than 10% (1R, 2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90%

(1R,2S) enantiomer and less than 10% (1S, 2R) enantiomer. More preferably, the compound is more than 95% (1R,2S) enantiomer and less than 5% (1S,2R) enantiomer. Even more preferably, the compound is more than 99% (1R, 2S) enantiomer and less than 1% (1S, 2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —X$^3$=X$^4$—.

X$^1$ is N, X$^2$, X$^3$ and X$^4$ are independently C(R2).

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —CF$_3$, —F, —Cl, —CN, —CH$_3$, —OH, —OCH$_3$, —C(=O)NH$_2$, —NH—CO—CH$_3$, —NH—SO$_2$—CH$_3$, —NH—SO$_2$—CH$_2$—CH$_3$, —NH—SO$_2$—CH(CH$_3$)—CH$_3$, or —NH—SO$_2$—(C$_6$H %). Even more preferably, each (R1) is independently chosen from —CF$_3$, —F, —Cl, —CN, —CH$_3$, —OH, —OCH$_3$, or —C(=O)NH$_2$. Even more preferably, each (R1) is independently chosen from —CF$_3$, —F, —Cl, —CN, —CH$_3$, —OH, or —C(=O)NH$_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S,2R) enantiomer. More preferably, the compound is more than 95% (1R,2S) enantiomer and less than 5% (1S,2R) enantiomer. Even more preferably, the compound is more than 99% (1R,2S) enantiomer and less than 1% (1S, 2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer disease, Huntington disease, Parkinson disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —$X^3$=$X^4$—.

$X^2$ is N, $X^1$, $X^3$ and $X^4$ are independently C(R2).

(G) is a cyclyl group. Preferably, (G) is an aryl or heterocyclyl group. More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$. —F, —Cl, —CN, —$CH_3$, —OH, or —C(=O)$NH_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino($C_1$-$C_6$)alkyl, halo, lower alkoxy, oramido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —$CH_2NH_2$, —$CH_2CH_2NH_2$, or —$OCH_3$. Even more preferably, each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S, 2R) enantiomer and less than 5% (1R,2S) enantiomer. Even more preferably, the compound is more than 99% (1S, 2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S,2R) enantiomer. More preferably, the compound is more than 95% (1R,2S) enantiomer and less than 5% (1S,2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —$X^3$=$X^4$—.

$X^2$ is N, $X^1$, $X^3$ and $X^4$ are independently C(R2).

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino($C_1$-$C_6$)alkyl, halo, lower alkoxy, or amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —$CH_2NH_2$, —$CH_2CH_2NH_2$, or —$OCH_3$. Even more preferably, each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S, 2R) enantiomer and less than 10% (1R,2S) enantiomer. More preferably, the compound is more than 95% (1S, 2R) enantiomer and less than 5% (1R, 2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R, 2S) enantiomer and less than 10% (1S, 2R) enantiomer. More preferably, the compound is more than 95% (1R,2S) enantiomer and less than 5% (1S, 2R) enantiomer. Even more preferably, the compound is more than 99% (1R, 2S) enantiomer and less than 1% (1S, 2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —$X^3$=$X^4$—.

$X^2$ is N, $X^1$, $X^3$ and $X^4$ are independently C(R2).

(G) is a cyclyl group. Preferably, (G) is an aryl or heterocyclyl group. More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1.2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S, 2R) enantiomer and less than 5% (1R,2S) enantiomer. Even more preferably, the compound is more than 99% (1S, 2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S,2R) enantiomer. More preferably, the compound is more than 95% (1R,2S) enantiomer and less than 5% (1S, 2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —$X^3$=$X^4$—.

$X^2$ is N, $X^1$, $X^3$ and $X^4$ are independently C(R2).

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($CH_1$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R, 2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S,2R) enantiomer. More preferably, the compound is more than 95% (1R,2S) enantiomer and less than 5% (1S, 2R) enantiomer. Even more preferably, the compound is more than 99% (1R, 2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —S—.

$X^1$ and $X^2$ are independently C(R2) or N.

(G) is a cyclyl group. Preferably, (G) is an aryl or heterocyclyl group. More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino($C_1$-$C_6$)alkyl, halo, lower alkoxy, and amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —$CH_2NH_2$, —$CH_2CH_2NH_2$, or —$OCH_3$. Even more preferably, each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S, 2R) enantiomer and less than 10% (1R,2S) enantiomer. More preferably, the compound is more than 95% (1S, 2R) enantiomer and less than 5% (1R, 2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 99% (1R,2S) enantiomer and less than 10% (1S, 2R) enantiomer. More preferably, the compound is more than 95% (1R, 2S) enantiomer and less than 5% (1S, 2R) enantiomer. Even more preferably, the compound is more than 99% (1R, 2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —S—.

$X^1$ and $X^2$ are independently C(R2) or N.

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino($C_1$-$C_6$)alkyl, halo, lower alkoxy, or amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —$CH_2NH_2$, —$CH_2CH_2NH_2$, or —$OCH_3$. Even more preferably, each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S, 2R) enantiomer and less than 10% (1R, 2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R,2S) enantiomer and less than 5% (1S,2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —S—.

$X^1$ and $X^2$ are independently C(R2) or N.

(G) is a cyclyl group. Preferably, (G) is an aryl or heterocyclyl group. More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 99% (1S,2R) enantiomer and less than 10% (1R,2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R, 2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R,2S) enantiomer and less than 5% (1S, 2R) enantiomer. Even more preferably, the compound is more than 99% (1R, 2S) enantiomer and less than 1% (1S, 2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —S—.

$X^1$ and $X^2$ are independently C(R2) or N.

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S, 2R) enantiomer and less than 10% (1R,2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R, 2S) enantiomer and less than 5% (1S, 2R) enantiomer. Even more preferably, the compound is more than 99% (1R, 2S) enantiomer and less than 1% (1S, 2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinsons disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —S—.

$X^1$ and $X^2$ are independently C(R2).

(G) is a cyclyl group. Preferably, (G) is an aryl or heterocyclyl group. More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino($C_1$-$C_6$)alkyl, halo, lower alkoxy, and amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —$CH_2NH_2$, —$CH_2CH_2NH_2$, or —$OCH_3$. Even more preferably, each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R, 2S) enantiomer.

More preferably, the compound is more than 95% (1S, 2R) enantiomer and less than 5% (1R,2S) enantiomer. Even more preferably, the compound is more than 99% (1S, 2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S,2R) enantiomer. More preferably, the compound is more than 95% (1R,2S) enantiomer and less than 5% (1S,2R) enantiomer. Even more preferably, the compound is more than 99% (1R,2S) enantiomer and less than 1% (1S, 2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 99%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —S—.

$X^1$ and $X^2$ are independently C(R2).

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —CF$_3$, —F, —Cl, —CN, —CH$_3$, —OH, —OCH$_3$, —C(=O)NH$_2$, —NH—CO—CH$_3$, —NH—SO$_2$—CH$_3$, —NH—SO$_2$—CH$_2$—CH$_3$, —NH—SO$_2$—CH(CH$_3$)—CH$_3$, or —NH—SO$_2$—(C$_6$H$_5$). Even more preferably, each (R1) is independently chosen from —CF$_3$, —F, —Cl, —CN, —CH$_3$, —OH, —OCH$_3$, or —C(=O)NH$_2$. Even more preferably, each (R1) is independently chosen from —CF$_3$, —F, —Cl, —CN, —CH$_3$, —OH, or —C(=O)NH$_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino(C$_1$-C$_6$)alkyl, halo, lower alkoxy, or amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —CH$_2$NH$_2$, —CH$_2$CH$_2$NH$_2$, or —OCH$_3$. Even more preferably, each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S, 2R) enantiomer and less than 5% (1R,2S) enantiomer. Even more preferably, the compound is more than 99% (1S, 2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R,2S) enantiomer and less than 5% (1S, 2R) enantiomer. Even more preferably, the compound is more than 99% (1R, 2S) enantiomer and less than 1% (1S, 2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —S—.

$X^1$ and $X^2$ are independently C(R2).

(G) is a cyclyl group. Preferably, (G) is an aryl or heterocyclyl group. More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S, 2R) enantiomer and less than 10% (1R,2S) enantiomer. More preferably, the compound is more than 95% (1S,2R) enantiomer and less than 5% (1R,2S) enantiomer. Even more preferably, the compound is more than 99% (1S,2R) enantiomer and less than 1% (1R, 2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R, 2S) enantiomer and less than 10% (1S, 2R) enantiomer. More preferably, the compound is more than 95% (1R,2S) enantiomer and less than 5% (1S,2R) enantiomer. Even more preferably, the compound is more than 99% (1R,2S) enantiomer and less than 1% (1S, 2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —S—.

$X^1$ and $X^2$ are independently C(R2).

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(═O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(═O)$NH_2$. Even more preferably, each (R1) is independently chosen from —$CF_3$, —F, —Cl, —CN, —$CH_3$, —OH, or —C(═O)$NH_2$.

Each (R2) is —H.

Each L is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R,2S) enantiomer and less than 5% (1S,2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —S—.

$X^1$ is N, and X is C(R2).

(G) is a cyclyl group. Preferably, (G) is an aryl or heterocyclyl group. More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —CF$_3$, —F, —Cl, —CN, —CH$_3$, —OH, —OCH$_3$, —C(=O)NH$_2$, —NH—CO—CH$_3$, —NH—SO$_2$—CH$_3$, —NH—SO$_2$—CH$_2$—CH$_3$, —NH—SO$_2$—CH(CH$_3$)—CH$_3$, or —NH—SO$_2$—(C$_6$H$_5$). Even more preferably, each (R1) is independently chosen from —CF$_3$, —F, —Cl, —CN, —CH$_3$, —OH, —OCH$_3$, or —C(=O)NH$_2$. Even more preferably, each (R1) is independently chosen from —CF$_3$, —F, —Cl, —CN, —CH$_3$, —OH, or —C(=O)NH$_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino(C$_1$-C$_6$)alkyl, halo, lower alkoxy, or amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —CH$_2$NH$_2$, —CH$_2$CH$_2$NH$_2$, or —OCH$_3$. Even more preferably, each (R2) is —H.

Each L is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R, 2S) enantiomer. More preferably, the compound is more than 95% (1S, 2R) enantiomer and less than 5% (1R,2S) enantiomer. Even more preferably, the compound is more than 99% (1S, 2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R,2S) enantiomer and less than 5% (1S, 2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meaning:

E is —S—.

$X^1$ is N, and $X^2$ is C(R2).

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —CF$_3$, —F, —Cl, —CN, —CH$_3$, —OH, —OCH$_3$, —C(=O)NH$_2$, —NH—CO—CH$_3$, —NH—SO$_2$—CH$_3$, —NH—SO$_2$—CH$_2$—CH$_3$, —NH—SO$_2$—CH(CH$_3$)—CH$_3$, or —NH—SO$_2$—(C$_6$H$_5$). Even more preferably, each (R1) is independently chosen from —CF$_3$, —F, —Cl, —CN, —CH$_3$, —OH, —OCH$_3$, or —C(=O)NH$_2$. Even more preferably, each (R1) is independently chosen from —CF$_3$, —F, —Cl, —CN, —CH$_3$, —OH, or —C(=O)NH$_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino(C$_1$-C$_6$)alkyl, halo, lower alkoxy, or amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —CH$_2$NH$_2$, —CH$_2$CH$_2$NH$_2$, or —OCH$_3$. Even more preferably, each (R2) is H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S,2R) enantiomer. More preferably, the compound is more than 95% (1R,2S) enantiomer and less than 5% (1S, 2R) enantiomer. Even more preferably, the compound is more than 99% (1R,2S) enantiomer and less than 1% (1S, 2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —S—.

$X^1$ is N, and $X^2$ is C(R2).

(G) is a cyclyl group. Preferably, (G) is an aryl or heterocyclyl group. More preferably, (0) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —CF$_3$, —F, —Cl, —CN, —CH$_3$, —OH, —OCH$_3$, —C(=O)NH$_2$, —NH—CO—CH$_3$, —NH—SO$_2$—CH$_3$, —NH—SO$_2$—CH$_2$—CH$_3$, —NH—SO$_2$—CH(CH$_3$)—CH$_3$, or —NH—SO$_2$—(C$_6$H$_5$). Even more preferably, each (R1) is independently chosen from —CF$_3$, —F, —Cl, —CN, —CH$_3$, —OH, —OCH$_3$, or —C(=O)NH$_2$. Even more preferably, each (R1) is independently chosen from —CF$_3$, —F, —Cl, —CN, —CH$_3$, —OH, or —C(=O)NH$_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S,2R) enantiomer and less than 5% (1R,2S) enantiomer. Even more preferably, the compound is more than 99% (1S,2R) enantiomer and less than 1% (1R, 2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R,2S) enantiomer and less than 5% (1S,2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —S—.

$X^1$ is N, and $X^2$ is C(R2).

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —$C(=O)NH_2$, —NH—CO—$CH_3$, —NH—$SO_2$—$CH_3$, —NH—$SO_2$—$CH_2$—$CH_3$, —NH—$SO_2$—$CH(CH_3)$—$CH_3$, or —NH—$SO_2$—$(CH_5)$. Even more preferably, each (R1) is independently chosen from —$CF_3$, —F, —Cl, —CN, —$CH_3$, —OH, —$OCH_3$, or —$C(=O)NH_2$. Even more preferably, each (R1) is independently chosen from —$CF_3$, —F, —Cl, —CN, —$CH_3$, —OH, or —$C(=O)NH_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S, 2R) enantiomer and less than 5% (1R, 2S) enantiomer. Even more preferably, the compound is more than 99% (1S, 2R) enantiomer and less than 1% (1R, 2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R,2S) enantiomer and less than 5% (1S, 2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer disease, Huntington disease, Parkinson disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —S—.

$X^1$ is C(R2), and $X^2$ is N.

(G) is a cyclyl group. Preferably, (G) is an aryl or heterocyclyl group. More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —$C(=O)NH_2$, —NH—CO—$CH_3$, —NH—$SO_2$—$CH_3$, —NH—$SO_2$—$CH_2$—$CH_3$, —NH—$SO_2$—$CH(CH_3)$—$CH_3$, or —NH—$SO_2$—$(C_6H_5)$. Even more preferably, each (R1) is independently chosen from —$CF_3$, —F, —Cl, —CN, —$CH_3$, —OH, —$OCH_3$, or —$C(=O)NH_2$. Even more preferably, each (R1) is independently chosen from —$CF_3$, —F, —Cl, —CN, —$CH_3$, —OH, or —$C(=O)NH_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino($C_1$-$C_6$)alkyl, halo, lower alkoxy, and amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —$CH_2NH_2$, —$CH_2CH_2NH_2$, or —$OCH_3$. Even more preferably, each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R, 2S) enantiomer and less than 5% (1S, 2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meaning:

E is —S—.

$X^1$ is C(R2), and $X^2$ is N.

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino($C_1$-$C_6$)alkyl, halo, lower alkoxy, or amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —$CH_2NH_2$, —$CH_2CH_2NH_2$, or —$OCH_3$. Even more preferably, each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S, 2R) enantiomer and less than 5% (1R, 2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R,2S) enantiomer and less than 5% (1S, 2R) enantiomer. Even more preferably, the compound is more than 99% (1R, 2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —S—.

$X^1$ is C(R2), and $X^2$ is N.

(G) is a cyclyl group. Preferably, (G) is an aryl or heterocyclyl group. More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S, 2R) enantiomer and less than 10% (1R, 2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S,2R) enantiomer. More preferably, the compound is more than 95% (1R2S) enantiomer and less than 5% (1S, 2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —S—.

$X^1$ is C(R2), and $X^2$ is N.

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —CF$_3$, —F, —Cl, —CN, —CH$_3$, —OH, —OCH$_3$, —C(=O)NH$_2$, —NH—CO—CH$_3$, —NH—SO$_2$—CH$_3$, —NH—SO$_2$—CH$_2$—CH$_3$, —NH—SO$_2$—CH(CH$_3$)—CH$_3$, or —NH—SO$_2$—(C$_6$H$_5$). Even more preferably, each (R1) is independently chosen from —CF$_3$, —F, —Cl, —CN, —CH$_3$, —OH, —OCH$_3$, or —C(=O)NH$_2$. Even more preferably, each (R1) is independently chosen from —CF$_3$, —F, —Cl, —CN, —CH$_3$, —OH, or —C(=O)NH$_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R, 2S) enantiomer. More preferably, the compound is more than 95% (1S, 2R) enantiomer and less than 5% (1R, 2S) enantiomer. Even more preferably, the compound is more than 99% (1S,2R) enantiomer and less than 1% (1R, 2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R, 2S) enantiomer and less than 10% (1S, 2R) enantiomer. More preferably, the compound is more than 95% (1R,2S) enantiomer and less than 5% (1S, 2R) enantiomer. Even more preferably, the compound is more than 99% (1R,2S) enantiomer and less than 1% (1S, 2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meaning:

E is —$X^3$=$X^4$—.

$X^1$ and $X^3$ are N, $X^2$ and $X^4$ are independently C(R2). Accordingly, the ring comprising $X^1$ to $X^4$ is a pyrimidine ring.

(G) is a cyclyl group. Preferably, (G) is an aryl or heterocyclyl group. More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino($C_1$-$C_6$)alkyl, halo, lower alkoxy, or amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —$CH_2NH_2$, —$CH_2CH_2NH_2$, or —$OCH_3$. Even more preferably, each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R, 2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R,2S) enantiomer.

In one aspect, the invention provides a composition as defined herein comprising a compound of Formula (T) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R, 2S) enantiomer and less than 10% (1S, 2R) enantiomer.

More preferably, the compound is more than 95% (1R, 2S) enantiomer and less than 5% (1S,2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meaning:

E is —X³=X⁴—.

X¹ and X³ are N, X² and X⁴ are independently C(R2). Accordingly, the ring comprising X¹ to X⁴ is a pyrimidine ring.

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —CF₃, —F, —Cl, —CN, —CH₃, —OH, —OCH₃, —C(=O)NH₂, —NH—CO—CH₃, —NH—SO₂—CH₃, —NH—SO₂—CH₂—CH₃, —NH—SO₂—CH(CH₃)—CH₃, or —NH—SO₂—(C₆H₅). Even more preferably, each (R1) is independently chosen from —CF₃, —F, —Cl, —CN, —CH₃, —OH, —OCH₃, or —C(=O)NH₂. Even more preferably, each (R1) is independently chosen from —CF₃, —F, —Cl, —CN, —CH₃, —OH, or —C(=O)NH₂.

Each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents. Preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents. More preferably, each (R2) is independently chosen from —H, alkyl, hydroxyl, haloalkyl, alkoxy, halo, amido, aryl, arylalkyl, heterocyclylalkyl, arylalkoxy, or heterocyclylalkoxy, wherein each (R2) has 1, 2, or 3 optional substituents. In the definitions of (R2), said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate. Preferably, said optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents chosen from lower alkyl, lower haloalkyl, lower haloalkoxy, amino(C₁-C₆)alkyl, halo, lower alkoxy, or amido. Even more preferably, each (R2) is independently chosen from —H, hydroxyl, haloalkyl, alkoxy, halo, amido, arylalkyl, heterocyclylalkyl, arylalkoxy, or heterocyclylalkoxy, wherein each (R2) has 1, 2, or 3 optional substituents independently chosen from chloro, fluoro, —CH₂NH₂, —CH₂CH₂NH₂, or —OCH₃. Even more preferably, each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S, 2R) enantiomer and less than 5% (1R,2S) enantiomer. Even more preferably, the compound is more than 99% (1S, 2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S,2R) enantiomer. More preferably, the compound is more than 95% (1R,2S) enantiomer and less than 5% (1S,2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meaning:

E is —$X^3$=$X^4$—.

$X^1$ and $X^3$ are N, $X^2$ and $X^4$ are independently C(R2). Accordingly, the ring comprising $X^1$ to $X^4$ is a pyrimidine ring.

(G) is a cyclyl group. Preferably, (G) is an aryl or heterocyclyl group. More preferably, (G) is a phenyl, thienyl, benzothienyl (e.g., benzo[b]thiophenyl, such as benzo[b]thiophen-2-yl or benzo[b]thiophen-3-yl), indolyl, indolinyl, indolinonyl (e.g., indolin-2-onyl), pyridinyl, pyridinonyl (e.g., pyridin-2(1H)-onyl), benzofuranyl, benzofuranonyl (e.g., benzofuran-2(3H)-onyl), indazolyl (e.g., 1H-indazol-6-yl), or carbazolyl (e.g., 9H-carbazol-2-yl) group. Even more preferably, (G) is a phenyl, thienyl, benzothienyl, or indolyl group. Even more preferably, (G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from —$CF_3$, —F, —Cl, —CN, —$CH_3$, —OH, or —C(=O)$NH_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90/a (1S,2R) enantiomer and less than 10% (1R, 2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R,2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R, 2S) enantiomer and less than 5% (1S,2R) enantiomer. Even more preferably, the compound is more than 99% (1R,2S) enantiomer and less than 1% (1S,2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

In a further embodiment, the invention provides a compound of Formula (I) or an enantiomer, a diastereomer, or a mixture thereof, or a pharmaceutically acceptable salt or solvate thereof, wherein the groups comprised in Formula (I) have the following meanings:

E is —$X^3$=$X^4$—.

$X^1$ and $X^3$ are N, $X^2$ and $X^4$ are independently C(R2). Accordingly, the ring comprising $X^1$ to $X^4$ is a pyrimidine ring.

(G) is a phenyl group.

Each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each (R1) is independently chosen from alkyl, aryl, amino, amido, nitro, halo, haloalkyl, haloalkoxy, cyano, heterocycle, sulfonyl, sulfonamide, hydroxyl, or alkoxy. More preferably, each (R1) is independently chosen from lower alkyl, lower aryl, amino, amido, nitro, halo, lower haloalkyl, cyano, heterocycle, sulfonyl, sulfonamide, hydroxyl, or alkoxy. Even more preferably, each (R1) is independently chosen from —$CF_3$, —F, —Cl, —CN, —$CH_3$, —OH, —$OCH_3$, —C(=O)$NH_2$, —NH—CO—$CH_3$, —NH—$SO_2$—$CH_3$, —NH—$SO_2$—$CH_2$—$CH_3$, —NH—$SO_2$—CH($CH_3$)—$CH_3$, or —NH—$SO_2$—($C_6H_5$). Even more preferably, each (R1) is independently chosen from —$CF_3$, —F, —Cl, —CN, —$CH_3$, —OH, —$OCH_3$, or —C(=O)$NH_2$. Even more preferably, each (R1) is independently chosen from $CF_3$, —F, —Cl, —CN, —$CH_3$, —OH, or —C(=O)$NH_2$.

Each (R2) is —H.

Each L1 is independently alkylene or heteroalkylene.

n is 0, 1, 2, 3, 4 or 5. Preferably, n is 0, 1, 2, 3, or 4. More preferably, n is 0, 1, 2, or 3.

In one aspect, the invention provides a composition as defined herein comprising a compound of Formula (I) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S, 2R) enantiomer and less than 5% (1R,2S) enantiomer. Even more preferably, the compound is more than 99% (1S, 2R) enantiomer and less than 1% (1R, 2S) enantiomer.

In one aspect, the invention provides a composition as defined herein comprising a compound of Formula (I) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R,2S) enantiomer and less than 5% (1S, 2R) enantiomer. Even more preferably, the compound is more than 99% (1R,2S) enantiomer and less than 1% (1S, 2R) enantiomer.

In one aspect, the invention provides a compound as defined in the above embodiment or a solvate or a pharmaceutically acceptable salt thereof, wherein the cyclopropyl ring carbon atom which is bound to the terminal amino group of the compound is in (S)-configuration and the cyclopropyl-ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

The invention further relates to the compound of Formula (I) or an enantiomer, a diastereomer, or a mixture thereof, or a pharmaceutically acceptable salt or solvate thereof, as defined in the above embodiment, for use in the treatment or prevention of a disease or condition, in particular cancer (e.g., breast cancer, lung cancer, prostate cancer, colorectal cancer, brain cancer, skin cancer, blood cancer, leukemia, or lymphoma), a neurological disease or condition (e.g., depression, Alzheimer's disease, Huntington disease, Parkinson's disease, or Dementia with Lewy Bodies), or a viral infection (e.g., a viral infection is caused by and/or associated with HIV, or a herpesvirus infection, such as a herpesvirus infection caused by and/or associated with a herpesvirus chosen from HSV-1, HSV-2, or Epstein-Barr virus) in a subject (preferably a mammal, more preferably a human).

Furthermore, in one aspect, the invention provides a compound of Formula (II) or an enantiomer, a diastereomer, or a mixture thereof, or a pharmaceutically acceptable salt or solvate thereof:

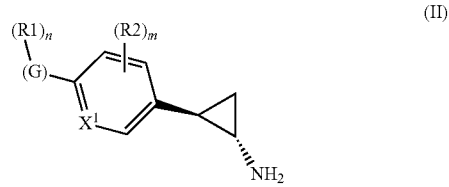

(II)

wherein:

X¹ is CH or N;

(G) is a cyclyl group;

each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;

each (R2) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 optional substituents, wherein said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate;

each L1 is alkylene or heteroalkylene;

m is 0, 1, 2 or 3; and n is 0, 1, 2, 3, 4 or 5, provided that n and m are chosen independently such that n+m is greater than zero (i.e., at least one of n and m is not 0) when X¹ is —CH— and (G) is an aryl;

with the proviso that the compound of Formula (II) is not: (1S,2R)-2-([1,1'-biphenyl]-4-yl)cyclopropanamine, (1S,2R)-2-(4'-chloro-[1,1'-biphenyl]-4-yl)cyclopropanamine, (1S,2R)-2-(3-chloro-4'-(trifluoromethyl)-[1,1'-biphenyl]-4-yl)cyclopropanamine, (1S,2R)-2-(6-(2,4-difluorophenyl)pyridin-3-yl)cyclopropanamine, tert-butyl 4'-((1R,2S)-2-aminocyclopropyl)-[1,1'-biphenyl]-4-carboxylate, 2-(3,4',5-trichloro-[1,1'-biphenyl]-4-yl)cyclopropanamine, 2-(3,3',4',5-tetrachloro-[1,1'-biphenyl]-4-yl)cyclopropanamine, 2-(3,3',4'-trichloro-[1,1'-biphenyl]-4-yl)cyclopropanamine, or 2-(3,5-dichloro-4'-methyl-[1,1'-biphenyl]-4-yl)cyclopropanamine.

In one embodiment of this aspect, the invention provides a composition as defined herein comprising a compound of Formula (II) as described herein or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R, 2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R,2S) enantiomer.

In one embodiment of this aspect, the invention provides a composition as defined herein comprising a compound of Formula (II) as described herein or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R, 2S) enantiomer and less than 5% (1S,2R) enantiomer. Even more preferably, the compound is more than 99% (1R,2S) enantiomer and less than 1% (1S,2R) enantiomer.

In one embodiment of this aspect, the invention provides a compound of Formula (II) as defined herein or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one embodiment of this aspect, the invention provides a compound of Formula (II) as defined herein or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

Preferably, the optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

In one specific embodiment of this aspect, the invention provides a compound of Formula (II) wherein X¹ is a nitrogen atom. In another specific embodiment of this aspect X¹ is CH.

In one embodiment of this aspect, the invention provides a compound of Formula (II) wherein, the (G) group is a cyclyl, and each (R1) is independently chosen from alkyl, aryl, amino, amido, nitro, halo, haloalkyl, cyano, heterocyclyl, sulfonyl, sulfonamide, hydroxyl, or alkoxy. In one specific embodiment of this aspect, said cyclyl (G) is an aryl or heterocyclyl.

In one particular embodiment of this aspect said cyclyl (G) is an aryl. In a preferred embodiment, said aryl is a phenyl.

In another particular embodiment of this aspect said cyclyl (G) is a heterocyclyl. In a more specific embodiment, said heterocyclyl is a heteroaryl or a heterocycloalkyl. In an even more specific embodiment, said heterocyclyl is a heteroaryl chosen from thiophenyl, benzo[b]thiophenyl, indolyl, benzofuran-2(3H)-onyl, 9H-carbazolyl, pyridin-2(1H)-onyl, indolin-2-onyl or indazolyl. Preferably, said heterocyclyl is a heteroaryl chosen from thiophenyl, benzo[b]thiophenyl or indolyl.

In one embodiment of this aspect, the invention provides, a compound of Formula (II) wherein X¹ is CH, the (G) group is a cyclyl, n is 0, 1, 2, 3, 4, or 5, and each (R1) is independently chosen from alkyl, aryl, amino, amido, nitro, halo, haloalkyl, cyano, heterocyclyl, sulfonyl, sulfonamide, hydroxyl, or alkoxy. In one specific embodiment said cyclyl is a phenyl, n=1 and m=0. Preferably the phenyl group (G) is bonded to one substituent (R1) which is —CF₃ in the meta-position in reference to the phenylcyclopropylamine core. In another preferred embodiment (R1) is a phenyl in the para-position in reference to the phenylcyclopropylamine core. In another preferred embodiment (R1) is a —OH in the meta- or para-position in reference to the phenylcyclopropylamine core. Preferable (R1) is an —OH in meta-position in reference to the phenylcyclopropylamine core.

In another preferred embodiment of the compounds described the paragraph above, (R1) is independently chosen from —NHSO$_2$CH$_3$, —NHSO$_2$(CH$_2$—CH$_3$) or —NHSO$_2$(C$_6$H$_5$) in the meta-position in reference to the phenylcyclopropylamine core. In yet another specific embodiment of the compounds described above (R1) is independently chosen from —CF$_3$, —Cl, —F, —OCH$_3$, —CH$_3$, —OH, —C(=O)NH$_{2,[a1]}$—NHC(=O)CH$_3$, —NHSO$_2$CH$_3$, —NHSO$_2$(CH$_2$—CH$_3$), —NHSO$_2$(C$_6$H$_5$) or —CN.

In one embodiment the invention provides a compound of Formula (II) wherein $X^1$ is CH, the (G) group is cyclyl, wherein said cyclyl has 0, 1, 2, 3, 4, or 5 substituents (R1) independently chosen from alkyl, aryl, amino, amido, nitro, halo, haloalkyl, cyano, heterocycle, sulfonyl, sulfonamide, hydroxyl or alkoxy. In one specific embodiment said cyclyl is a phenyl, n=2 and m=0. In a more specific embodiment, said phenyl group has two (n=2) substituents (R1) independently chosen from —CF$_3$, —OH, —CN, —OCH$_3$, —CH$_3$, chloro, —NHSO$_2$CH$_3$, —NHSO$_2$(CH$_2$—CH$_3$) or —NHSO$_2$(C$_6$H$_5$) and the second (R1) is —CF$_3$, —OH, —CN, —OCH$_3$, —CH$_3$, fluoro, chloro, —NHSO$_2$CH$_3$, —NHSO$_2$(CH$_2$—CH$_3$) or —NHSO$_2$(C$_6$H$_5$). In another specific embodiment one substituent (R1) is —OCH$_3$ and the second substituent (R1) is independently chosen from —CN or —NHSO$_2$CH$_3$. In another specific embodiment one substituent (R1) is —OH and the second substituent (R1) is independently chosen from —CN or —NHSO$_2$CH$_3$.

In one embodiment of this aspect, the invention provides a compound of Formula (II) wherein $X^1$ is a nitrogen atom, the (G) group is cyclyl, n=0 and m=0. In a more specific embodiment, (G) is heterocyclyl and n is 0. In yet a more specific embodiment, said (G) is a heteroaryl or heterocycloalkyl and n is 0. In yet an even more specific embodiment (G) is a heteroaryl and n is 0. In a specific preferred embodiment said cyclyl is thiophenyl, benzo[b]thiophenyl, or indolyl, and n is 0.

In a specific preferred embodiment of the compound as described in the paragraph above, said cyclyl is thiophenyl, benzo[b]thiophenyl, indolyl, benzofuran-2(3H)-onyl, 9H-carbazolyl, pyridin-2(1H)-onyl, indolin-2-onyl or indazolyl, and n is 0.

In one specific embodiment of this aspect, the invention provides a compound of Formula (II) wherein $X^1$ is a nitrogen atom and the (G) group is a phenyl with one (n=1) substituent (R1) chosen from —CF$_3$, chloro, —OCH$_3$, —CH$_3$, —OH, —C(=O)NH$_2$ or —CN. Preferably said substituent (R1) is in the meta- or para-position, and more preferably the substituent (R1) is in the meta-position in respect to the pyridylcyclopropylamine core.

In one specific embodiment of this aspect, the invention provides a compound of Formula (II) wherein $X^1$ is a nitrogen atom and the (G) group is a phenyl with one (n=1) substituent (R1) chosen from —CF$_3$, chloro, —OCH$_3$, —CH$_3$, —OH, —C(=O)NH$_2$, —NHC(=O)CH$_3$, —NHSO$_2$CH$_3$, —NHSO$_2$(CH$_2$—CH$_3$), —NHSO$_2$(C$_6$H$_5$) or —CN. Preferably said substituent (R1) is in the meta- or para-position, and more preferably the substituent (R1) is in the meta-position in respect to the pyridylcyclopropylamine core.

In one embodiment of this aspect, the invention provides a compound of Formula (II) wherein $X^1$ is a nitrogen atom and the (G) group is a cyclyl, wherein said cyclyl is bonded to 0, 1, 2, 3, 4, or 5 substituents (R1) independently chosen from alkyl, aryl, amino, amido, nitro, halo, haloalkyl, cyano, heterocyclyl, sulfonyl, sulfonamide, hydroxyl and alkoxy. In one specific embodiment said cyclyl is independently chosen from thiophenyl, benzo[b]thiophenyl or indolyl. In an even more specific embodiment, the cyclyl group is thiophenyl bonded to one (n=1) substituent (R1) which is —CN, —CH$_3$, chloro, or fluoro.

In one embodiment of this aspect, the invention provides a compound of Formula (II) wherein $X^1$ is a nitrogen atom and the (G) group is a cyclyl, wherein said cyclyl is bonded to 0, 1, 2, 3, 4, or 5 substituents (R1) independently chosen from alkyl, aryl, amino, amido, nitro, halo, haloalkyl, cyano, heterocyclyl, sulfonyl, sulfonamide, hydroxyl or alkoxy. In one specific embodiment said cyclyl is independently chosen from thiophenyl, benzo[b]thiophenyl, indolyl, benzofuran-2(3H)-onyl, 9H-carbazolyl, pyridin-2(1H)-onyl, indolin-2-onyl or indazolyl. In an even more specific embodiment, the cyclyl group is thiophenyl bonded to one (n=1) substituent (R1) which is —CN, —CH$_3$, chloro, or fluoro.

In one embodiment of this aspect, the invention provides a compound of Formula (H) wherein the (G) group is phenyl, wherein said phenyl has 0, 1, 2, 3, 4, or 5 substituents (R1) independently chosen from alkyl, aryl, amino, amido, nitro, halo, haloalkyl, cyano, heterocycle, sulfonyl, sulfonamide, hydroxyl or alkoxy. In a more specific embodiment, $X^1$ is a nitrogen atom and the phenyl group has two (n=2) substituents (R1), wherein one (R1) is independently chosen from —CF$_3$, —OH, —CN, —OCH$_3$, —CH$_3$ or chloro and the second (R1) is —CF$_3$, —OH, —CN, —OCH$_3$, —CH$_3$, fluoro or chloro. In a more specific embodiment said (R1) substituents are in meta- and ortho-positions with respect to the cyclopropylamine core. In a more specific embodiment the two substituents (R1) are in para- and ortho-position with respect to the cyclopropylamine core. In an even more specific embodiment, the two substituents (R1) are both in the meta-positions.

In one embodiment of this aspect, the invention provides a compound of Formula (II) wherein the (G) group is phenyl, wherein said phenyl has 0, 1, 2, 3, 4, or 5 substituents (R1) independently chosen from alkyl, aryl, amino, amido, nitro, halo, haloalkyl, cyano, heterocycle, sulfonyl, sulfonamide, hydroxyl or alkoxy. In a more specific embodiment, $X^1$ is a nitrogen atom and the phenyl group has two (n=2) substituents (R1), wherein one (R1) is independently chosen from —CF$_3$, —OH, —CN, —OCH$_3$, —CH$_3$, chloro, —NHSO$_2$CH$_3$, —NHSO$_2$(CH$_2$—CH$_3$) or —NHSO$_2$(C$_6$H$_5$) and the second (R1) is —CF$_3$, —OH, —CN, —OCH$_3$, —CH$_3$, fluoro, chloro, —NHSO$_2$CH$_3$, —NHSO$_2$(CH$_2$—CH$_3$) or —NHSO$_2$(C$_6$H$_5$). In one specific embodiment the two substituents (R1) are chloro. In another specific embodiment one substituent (R1) is —OCH$_3$ and the second substituent (R1) is independently chosen from —CH$_3$, —F, —Cl, —CF$_3$ or —CN. In another specific embodiment one substituent (R1) is —OH and the second substituent (R1) is independently chosen from —F, —Cl, —CH$_3$, —CN, —NHSO$_2$CH$_3$ or —NHSO$_2$(CH$_2$—CH$_3$). In another yet specific embodiment one substituent (R1) is —CF$_3$ the second substituent (R1) is independently chosen from —F, —OH, —CF$_3$ or —Cl. In a more specific embodiment said (R1) substituents are in meta- and ortho-positions with respect to the cyclopropylamine core. In a more specific embodiment the two substituents (R1) are in para- and ortho-position with respect to the cyclopropylamine core. In an even more specific embodiment, the two substituents (R1) are both in the meta-positions.

In one embodiment of this aspect, the invention provides a compound of Formula (II) wherein the (G) group is a cyclyl, wherein said cyclyl has three (n=3) substituents (R1) independently chosen from alkyl, aryl, amino, amido, nitro, halo, haloalkyl, cyano, heterocycle, sulfonyl, sulfonamide, hydroxyl or alkoxy. In a more specific embodiment the cyclyl is a phenyl group with three (n=3) substituents (R1), independently chosen from —CF₃, —OH, —CN, —OCH₃, —CH₃, fluoro, or chloro.

In one embodiment of this aspect, the invention provides a compound of Formula (II), wherein the (G) group is a cyclyl, wherein said cyclyl has four (n=4) substituents (R1) independently chosen from alkyl, aryl, amino, amido, nitro, halo, haloalkyl, cyano, alkoxy, heterocyclyl, sulfonyl, sulfonamide, hydroxyl and alkoxy. In one specific embodiment the cyclyl is a phenyl group with three (n=4) substituents (R1), independently chosen from —CF₃, —OH, —CN, —OCH₃, —CH₃, fluoro, or chloro.

In one embodiment of this aspect, the invention provides a compound of Formula (II) wherein, X¹ is a nitrogen atom and the (G) group is phenyl, wherein said phenyl has 0, 1, 2, 3 or substituents (R1) independently chosen from alkyl, aryl, amino, amido, nitro, halo, haloalkyl, cyano, heterocyclyl, sulfonyl, sulfonamide, hydroxyl or alkoxy. In a more specific embodiment the phenyl group has two (n=2) substituents (R1), wherein one (R1) is chosen from —CF₃, —OH, —CN, —OCH₃, —CH₃ or chloro and the second (R1) is chosen from —CF₃, —OH, —CN, —OCH₃, —CH₃, fluoro or chloro. In a more specific embodiment said substituents (R1) are in the meta- and ortho-position. In another specific embodiment, the two substituents (R1) are in the para- and ortho-position. In another specific embodiment, the two substituents (R1) are both in the meta-positions.

In one specific embodiment of this aspect, the invention provides a compound of Formula (II) wherein the (G) group is a cyclyl with one (n=1) substituent (R1) chosen from alkyl, aryl, amino, amido, nitro, halo, haloalkyl, cyano, heterocyclyl, sulfonyl, sulfonamide, hydroxyl or alkoxy; and one (m=1) substituent (R2) independently chosen from alkyl, optionally substituted cyclyl, amino, amido, nitro, halo, haloalkyl, cyano, sulfonyl, sulfonamide, hydroxyl or alkoxy. In one preferred embodiment X¹ is a N atom and said cyclyl group is phenyl. In one specific embodiment (R1) is —OH and (R2) is —CH₃. In another specific embodiment (R1) is —CF₃ and (R2) is —CH₃.

In one specific embodiment of this aspect, the invention provides a compound of Formula (II) wherein the (G) group is a cyclyl with one (n=1) substituent (R1) chosen from alkyl, aryl, amino, amido, nitro, halo, haloalkyl, cyano, heterocyclyl, sulfonyl, sulfonamide, hydroxyl or alkoxy; and one (m=1) substituent (R2) independently chosen from alkyl, optionally substituted cyclyl, amino, amido, nitro, halo, haloalkyl, cyano, sulfonyl, sulfonamide, hydroxyl or alkoxy. In one specific embodiment X¹ is a nitrogen atom, X², X³ and X⁴ are CH and said cyclyl group (G) is phenyl. In a more specific embodiment (R1) is independently chosen from —OH, or —CF₃ and (R2) is independently chosen from —CH₃, —Cl or an optionally substituted cyclyl. In a even more specific embodiment (R2) is an optionally substituted phenyl wherein (R2) has 1 optional substituent chosen from —Cl, —OH, or —C(═O)NH₂.

In one particular embodiment of the first aspect, the invention provides a compound of Formula (II) for use in treating or preventing cancer:

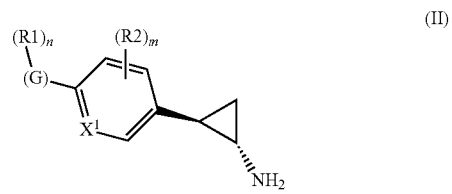

wherein
X¹ is CH or N;
(G) is a cyclyl;
each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;
each (R2) is independently chosen from alkyl, optionally substituted cyclyl, optionally substituted -L1-cyclyl, amino, amido, nitro, halo, haloalkyl, cyano, sulfonyl, sulfonamide, hydroxyl and alkoxy, wherein the optionally substituted cyclyl group of said (R2) group has 1, 2, or 3 optional substituents independently chosen from hydroxyl, haloalkyl, alkoxy, halo, aminoalkyl, and amido;
each L is independently alkylene or heteroalkylene;
m is 0, 1, 2 or 3;
n is 0, 1, 2, 3, 4 or 5; and
n and m are chosen independently, such that n+m is greater than zero (i.e., at least one of n and m is not 0) when X¹ is CH and (G) is an aryl.

In one aspect, the invention provides a composition as defined herein comprising a compound of Formula (II) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S, 2R) enantiomer and less than 10% (1R,2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R,2S) enantiomer.

In one aspect, the invention provides a composition as defined herein comprising a compound of Formula (II) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R,2S) enantiomer and less than 5% (1S,2R) enantiomer. Even more preferably, the compound is more than 99% (1R,2S) enantiomer and less than 1% (1S,2R) enantiomer.

In one aspect, the invention provides a compound of Formula (II) as defined in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound of Formula (II) as defined in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

In one embodiment of this aspect, the cancer is prostate cancer. In another specific embodiment of this aspect the cancer is breast cancer. In another yet specific embodiment of this aspect the cancer is lung cancer. In another yet specific embodiment of this aspect the cancer is colorectal cancer. In another yet specific embodiment of this aspect the cancer is brain cancer. In another yet specific embodiment of this aspect the cancer is skin cancer. In another yet specific embodiment of this aspect the cancer is blood cancer (e.g., leukemia) or a lymphoma.

In another specific embodiment of this aspect, the invention provides a compound of Formula (II) for use in treating or preventing cancer where, $X^1$ is a nitrogen atom, the (G) group is a cyclyl wherein n=0 and m=0. In a more specific embodiment, said cyclyl is thiophenyl, benzo[b]thiophenyl, phenyl or indolyl.

In another specific embodiment of this aspect, the invention provides a compound of Formula (II) for use in treating or preventing cancer where, $X^1$ is a nitrogen atom, the (G) group is a cyclyl wherein n=0 and m=0. In a more specific embodiment, said cyclyl is thiophenyl, benzo[b]thiophenyl, phenyl, indolyl, benzofuran-2(3H)-onyl, 9H-carbazolyl, pyridin-2(1H)-onyl, indolin-2-onyl or indazolyl.

In one specific embodiment of this aspect, the invention provides a compound of Formula (II) for use in treating or preventing cancer where n=1 and m=0. In one specific embodiment, n=2 and m=0. In another specific embodiment, n=1 and m=1. In a yet another specific embodiment, n=3 and m=0. In again another specific embodiment, n=2 and m=1. In yet another specific embodiment, n=3 and m=0. In again another specific embodiment, n=4 and m=0.

In one embodiment of this aspect, the invention provides a compound of Formula (II) for use in treating or preventing cancer wherein, the (G) group is cyclyl wherein said cyclyl has 0, 1, 2, or 3 substituents (R1) independently chosen from alkyl, aryl, amino, amido, nitro, halo, haloalkyl, cyano, alkoxy, heteroaryl, sulfonyl, sulfonamide, hydroxyl, or alkoxy. In a more specific embodiment, (G) is a heterocyclyl group. In another specific embodiment, (G) is a heteroaryl or heterocycloalkyl group. In one specific embodiment, (G) is a heteoraryl group. In one specific embodiment said cyclyl is independently chosen from thiophenyl, benzo[b]thiophenyl, phenyl or indolyl. In a more specific embodiment the cyclyl group has one (n=1) substituent (R1) which is chosen from —CF$_3$, phenyl, —OH, —CN, —OCH$_3$, —CH$_3$, chloro, or fluoro.

In one embodiment of this aspect, the invention provides a compound of Formula (III) for use in treating or preventing cancer wherein, the (G) group is cyclyl wherein said cyclyl has 0, 1, 2, or 3 substituents (R1) independently chosen from alkyl, aryl, amino, amido, nitro, halo, haloalkyl, cyano, alkoxy, heteroaryl, sulfonyl, sulfonamide, hydroxyl, or alkoxy. In a more specific embodiment, (G) is a heterocyclyl group. In another specific embodiment, (G) is a heteroaryl or heterocycloalkyl group. In one specific embodiment, (G) is a heteroaryl group. In one specific embodiment said cyclyl is independently chosen from thiophenyl, benzo[b]thiophenyl, phenyl, or indolyl. In a more specific embodiment the cyclyl group has one (n=1) substituent (R1) which is chosen from —CF$_3$, phenyl, —OH, —CN, —OCH$_3$, —CH$_{3,[a2]}$— NHC(=O)CH$_3$, —NHSO$_2$CH$_3$, —NHSO$_2$(CH$_2$—CH$_3$), —NHSO$_2$(C$_6$H$_5$) chloro, or fluoro.

In one specific embodiment of this aspect, the invention provides a compound of Formula (II) for use in treating or preventing cancer where the (G) group is a cyclyl with 0, 1, 2, 3, 4, or 5 substituents (R1) independently chosen from alkyl, aryl, amino, amido, nitro, halo, haloalkyl, cyano, alkoxy, heteroaryl, sulfonyl, sulfonamide, hydroxyl or alkoxy; and (R2) is independently chosen from alkyl, optionally substituted cyclyl, optionally substituted -L1-cyclyl, amino, amido, nitro, halo, haloalkyl, cyano, alkoxy, sulfonyl, sulfonamide, hydroxyl or alkoxy. In one preferred embodiment of this aspect, n=1 and m=1. In another preferred embodiment $X^1$ is a N atom. In one specific embodiment (R2) is an optionally substituted cyclyl or -L1-cyclyl, which has 1, 2, or 3 optional substituents independently chosen from hydroxyl, haloalkyl, alkoxy, halo, aminoalkyl, and C-amido.

In one embodiment of this aspect, the invention provides a compound of Formula (II) for use in treating or preventing cancer where the (G) group is a cyclyl, wherein said cyclyl has 0, 1, 2, 3, 4, or 5 substituents (R1) independently chosen from alkyl, aryl, amino, amido, nitro, halo, haloalkyl, cyano, alkoxy, heteroaryl, sulfonyl, sulfonamide, hydroxyl or alkoxy. In a more specific embodiment m=0 and the cyclyl group (G) has two (n=2) substituents (R1) which are independently chosen from —CF$_3$, —OH, —CN, —OCH$_3$, —CH$_3$, fluoro, or chloro.

In one embodiment of this aspect, the invention provides a compound of Formula (III) for use in treating or preventing cancer where the (G) group is a cyclyl, wherein said cyclyl has 0, 1, 2, 3, 4, or 5 substituents (R1) independently chosen from alkyl, aryl, amino, amido, nitro, halo, haloalkyl, cyano, alkoxy, heteroaryl, sulfonyl, sulfonamide, hydroxyl or alkoxy. In a more specific embodiment m=0 and the cyclyl group (G) has two (n=2) substituents (R1) which are independently chosen from —CF$_3$, —OH, —CN, —OCH$_3$, —CH$_3$, fluoro, chloro, —NHSO$_2$CH$_3$ or —NHSO$_2$(CH$_2$—CH$_3$).

In one specific embodiment of third aspect, the invention provides a compound of Formula (II) for use in treating or preventing cancer where m=0 and the (G) group is a cyclyl, wherein said cyclyl has 0, 1, 2, 3, 4, or 5 substituents (R1) independently chosen from alkyl, aryl, amino, amido, nitro, halo, haloalkyl, cyano, alkoxy, heteroaryl, sulfonyl, sulfonamide, hydroxyl, or alkoxy. In a more specific embodiment said cyclyl group (G) has three (n=3) substituents (R1) which are independently chosen from —CF$_3$, —OH, —CN, —OCH$_3$, —CH$_3$, fluoro, or chloro.

In another specific embodiment of this aspect, the invention provides a compound of Formula (II) for use in treating or preventing cancer where m=0, n=4 and the four substituents (R1) are independently chosen from alkyl, aryl, amino, amido, nitro, halo, haloalkyl, cyano, alkoxy, heteroaryl, sulfonyl, sulfonamide, hydroxyl, or alkoxy. In a more specific embodiment said cyclyl group (G) has four (n=4) substituents (R1) which are independently chosen from —CF$_3$, —OH, —CN, —OCH$_3$, —CH$_3$, fluoro, or chloro.

In one specific embodiment of the first aspect, the compound of Formula (I) is a compound of Formula (III) or an enantiomer, a diastereomer, or a mixture thereof, or a solvate or a pharmaceutically acceptable salt thereof. The general structure of compounds of Formula (III) is:

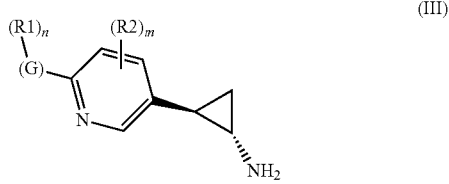

wherein:
- (G) is a cyclyl group;
- each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;
- each (R2) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 0, 1, 2, or 3 optional substituents, wherein said optional substituents are, preferably, independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate;
- each L1 is independently alkylene or heteroalkylene;
- m is 0, 1, 2 or 3; and
- n is 0, 1, 2, 3, 4 or 5;

with the proviso that the compound of Formula (III) is not: (1S,2R)-2-(6-(2,4-difluorophenyl)pyridin-3-yl)cyclopropanamine.

In one aspect, the invention provides a composition as defined herein comprising a compound of Formula (III) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S, 2R) enantiomer and less than 10% (1R, 2S) enantiomer. More preferably, the compound is more than 95% (1S, 2R) enantiomer and less than 5% (1R, 2S) enantiomer. Even more preferably, the compound is more than 99% (1S,2R) enantiomer and less than 1% (1R, 2S) enantiomer.

In one aspect, the invention provides a composition as defined herein comprising a compound of Formula (III) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R, 2S) enantiomer and less than 5% (1S, 2R) enantiomer. Even more preferably, the compound is more than 99% (1R,2S) enantiomer and less than 1% (1S, 2R) enantiomer.

In one aspect, the invention provides a compound of Formula (III) as described in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound of Formula (III) as described in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

Preferably, the compound of Formula (III) is used to treat a disease in a mammal and more preferably a human. More preferably, the human disease is chosen from cancer, a neurological condition or disease, or a viral infection.

Preferably, the optional substituents of Formula (III) are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

Preferably, the compound of Formula (III) is where (G) is an aryl or heterocyclyl group.

Preferably, the compound of Formula (III) is where each (R1) is independently chosen from alkyl, aryl, amino, amido, nitro, halo, haloalkyl, haloalkoxy, cyano, heterocycle, sulfonyl, sulfonamide, hydroxyl or alkoxy.

Preferably, the compound of Formula (III) is where each (R2) is independently chosen from hydroxyl, haloalkyl, alkoxy, halo, amido, arylalkyl, heterocyclylalkyl, arylalkoxy, and heterocyclylalkoxy and wherein each (R2) has 1, 2, or 3 optional substituents.

More preferably, the compound of Formula (III) is where (G) is a phenyl, thienyl, benzothienyl, indolyl, benzofuran-2(3H)-onyl, 9H-carbazolyl, pyridin-2(1H)-onyl, indolin-2-onyl or indazolyl group.

Even more preferably, the compound of Formula (III) is where (G) is a phenyl, thienyl, benzothienyl, or indolyl group.

More preferably, the compound of Formula (III) is where each (R1) is independently chosen from lower alkyl, lower aryl, amino, amido, nitro, halo, lower haloalkyl, cyano, heterocycle, sulfonyl, sulfonamide, hydroxyl, or alkoxy.

More preferably, the compound of Formula (III) is where each (R2) is independently chosen from hydroxyl, haloalkyl, alkoxy, halo, amido, arylalkyl, heterocyclylalkyl, arylalkoxy, or heterocyclylalkoxy, and further wherein each (R2) has 1, 2, or 3 optional substituents independently chosen from lower alkyl, lower haloalkyl, lower haloalkoxy, amino ($C_1$-$C_6$)alkyl, halo, hydroxyl, lower alkoxy, or amido.

Even more preferably, the compound of Formula (III) is where each (R2) is independently chosen from hydroxyl, haloalkyl, alkoxy, halo, amido, arylalkyl, heterocyclylalkyl, arylalkoxy, or heterocyclylalkoxy, and further wherein each (R2) has 1, 2, or 3 optional substituents independently chosen from lower alkyl, lower haloalkyl, lower haloalkoxy, amino($C_1$-$C_6$)alkyl, halo, lower alkoxy, and amido.

Even more preferably, the compound of Formula (III) is where each (R1) is independently chosen from —$CF_3$, —F, —Cl, —CN, —$CH_3$, —OH, —$OCH_3$, —NHC(=O)$CH_3$, —NHSO$_2$$CH_3$, —NHSO$_2$($CH_2$—$CH_3$)—NHSO$_2$($C_6H_5$), or —C(=O)$NH_2$.

Even more preferably, the compound of Formula (III) is where each (R1) is independently chosen from —$CF_3$, —F, —Cl, —CN, —$CH_3$, —OH, and —C(=O)$NH_2$.

Even more preferably, the compound of Formula (III) is where each (R2) is independently chosen from hydroxyl, haloalkyl, alkoxy, halo, amido, arylalkyl, heterocyclylalkyl, arylalkoxy, and heterocyclylalkoxy, wherein each (R2) has 1, 2, or 3 optional substituents independently chosen from chloro, fluoro, —$CH_2NH_2$, —$CH_2CH_2NH_2$, —OH, —C(=O)$NH_2$ or —$OCH_3$.

Even more preferably, the compound of Formula (III) is where each (R2) is independently chosen from hydroxyl, haloalkyl, alkoxy, halo, amido, arylalkyl, heterocyclylalkyl, arylalkoxy, and heterocyclylalkoxy, wherein each (R2) has 1, 2, or 3 optional substituents independently chosen from chloro, fluoro, —$CH_2NH_2$, —$CH_2CH_2NH_2$, or —$OCH_3$.

Even more preferably, the compound of Formula (III) is where (G) is a phenyl, thienyl, benzothienyl, or indolyl group.

Preferably, the compound of Formula (III) is where m is 0, 1, or 2.

Preferably, the compound of Formula (III) is where n is 0, 1, 2, 3, or 4.

In one preferred aspect, each (R2) is independently chosen from alkyl, optionally substituted cyclyl, optionally substituted -L1-cyclyl, amino, amido, nitro, halo, haloalkyl, cyano, sulfonyl, sulfonamide, hydroxyl and alkoxy.

In one specific embodiment of the first aspect, the invention provides a compound of Formula (III) wherein (G) is a cyclyl group, n=0, and m=0, wherein said cyclyl group is chosen from phenyl, thiophenyl, benzo[b]thiophenyl, indolyl, benzofuran-2(3H)-onyl, 9H-carbazolyl, pyridin-2(1H)-onyl, indolin-2-onyl or indazolyl.

In one specific embodiment of the first aspect, the invention provides a compound of Formula (III) wherein (G) is a cyclyl group, n=0, and m=0, wherein said cyclyl group is chosen from phenyl, thiophenyl, benzo[b]thiophenyl, phenyl or indolyl.

In one embodiment of this aspect, the invention provides a compound of Formula (III) wherein the (G) group is a cyclyl, wherein said cyclyl has 0, 1, 2, 3, 4, or 5 substituents (R1) independently chosen from alkyl, aryl, amino, amido, nitro, halo, haloalkyl, cyano, heterocyclyl, sulfonyl, sulfonamide, hydroxyl or alkoxy. In one specific embodiment said cyclyl is a phenyl substituted with one (n=1) substituent (R1) independently chosen from —$CF_3$, —OH, —CN, —$OCH_3$, —$CH_3$, —C(=O)$NH_2$,-[a2]—NHC(=O)$CH_3$, —NHSO$_2$$CH_3$, —NHSO$_2$$CH_3$, —NHSO$_2$($CH_2$—$CH_3$), —NHSO$_2$($C_6H_5$) fluoro or chloro. In a more specific embodiment said substituent (R1) is in meta-position with respect to the cyclopropylamine core. In another specific embodiment the substituent (R1) is in para-position with respect to the cyclopropylamine core. In yet another specific embodiment the substituent (R1) is in ortho-position with respect to the cyclopropylamine core.

In one embodiment of this aspect, the invention provides a compound of Formula (III) wherein, the (G) group is a cyclyl, wherein said cyclyl has 0, 1, 2, 3, 4, or 5 substituents (R1) independently chosen from alkyl, aryl, amino, amido, nitro, halo, haloalkyl, cyano, heterocycle, sulfonyl, sulfonamide, hydroxyl or alkoxy. In one specific embodiment said cyclyl is a thiophenyl with one (n=1) substituent (R1) chosen from —$CF_3$, —OH, —CN, —$OCH_3$, —$CH_3$, —C(=O)$NH_2$, fluoro, or chloro. In a more specific embodiment said substituent (R1) is a chloro. In another specific embodiment the substituent (R1) is a —$CH_3$. In another specific embodiment the substituent (R1) is a —CN.

In one embodiment of this aspect, the invention provides a compound of Formula (III) wherein the (G) group is a cyclyl, wherein said cyclyl has 0, 1, 2, 3, 4, or 5 substituents (R1) independently chosen from alkyl, aryl, amino, amido, nitro, halo, haloalkyl, cyano, heterocyclyl, sulfonyl, sulfonamide, hydroxyl or alkoxy. In one specific embodiment said cyclyl is a phenyl substituted with one (n=1) substituent (R1) independently chosen from —$CF_3$, —OH, —CN, —$OCH_3$, —$CH_3$, —C(=O)$NH_2$, fluoro or chloro. In a more specific embodiment said substituent (R1) is in meta-position with respect to the cyclopropylamine core. In another specific embodiment the substituent (R1) is in para-position with respect to the cyclopropylamine core. In yet another specific embodiment the substituent (R1) is in ortho-position with respect to the cyclopropylamine core.

In one embodiment of this aspect, the invention provides a compound of Formula (III) wherein, the (G) group is a cyclyl, wherein said cyclyl has 0, 1, 2, 3, 4, or 5 substituents (R1) independently chosen from alkyl, aryl, amino, amido, nitro, halo, haloalkyl, cyano, heterocycle, sulfonyl, sulfonamide, hydroxyl or alkoxy. In one specific embodiment said cyclyl is a thiophenyl with one (n=1) substituent (R1) chosen from —$CF_3$, —OH, —CN, —$OCH_3$, —$CH_3$, —C(=O)$NH_2$, fluoro, or chloro. In a more specific embodiment said substituent (R1) is a chloro. In another specific embodiment the substituent (R1) is a —$CH_3$.

In one embodiment of this aspect, the invention provides a compound of Formula (III) wherein, the (G) group is a cyclyl, wherein said cyclyl has two (n=2) substituents (R1) independently chosen from alkyl, aryl, amino, amido, nitro, halo, haloalkyl, cyano, heterocycle, sulfonyl, sulfonamide, hydroxyl or alkoxy. In one specific embodiment said cyclyl is a phenyl. In one specific embodiment said phenyl has two (n=2) substituents (R1), wherein one (R1) is independently chosen from —$CF_3$, —OH, —CN, —$OCH_3$, —$CH_3$, chloro, —NHSO$_2$$CH_3$, —NHSO$_2$($CH_2$—$CH_3$) or —NHSO$_2$($C_6H_5$) and the second (R1) is independently chosen from —$CF_3$, —OH, —CN, —$OCH_3$, —$CH_3$, chloro, fluoro, —NHSO$_2$$CH_3$, —NHSO$_2$($CH_2$—$CH_3$) or —NHSO$_2$($C_6H_5$). In one specific embodiment the two substituents (R1) are chloro. In another specific embodiment one substituent (R1) is —$OCH_3$ and the second substituent (R1) is independently chosen from —$CH_3$, —F, —Cl, —$CF_3$ or —CN. In another specific embodiment one substituent (R1) is —OH and the second substituent (R1) is independently chosen from —F, —Cl, —$CH_3$, —CN, —NHSO$_2$$CH_3$ or —NHSO$_2$($CH_2$—$CH_3$). In another yet specific embodiment one substituent (R1) is —$CF_3$ the second substituent (R1) is independently chosen from —F, —OH, —$CF_3$ or —Cl. In a more specific embodiment said substituents (R1) are in the meta- and ortho-position with respect to the cyclopropylamine core. In another specific embodiment the two substituents (R1) are in the para- and ortho-position with respect to the cyclopropylamine core. In another specific embodiment the two substituents (R1) are both in the meta-positions with respect to the cyclopropylamine core.

In one embodiment of this aspect, the invention provides a compound of Formula (III) wherein, the (G) group is a cyclyl, wherein said cyclyl has two (n=2) substituents (R1) independently chosen from alkyl, aryl, amino, amido, nitro, halo, haloalkyl, cyano, heterocycle, sulfonyl, sulfonamide, hydroxyl or alkoxy. In one specific embodiment said cyclyl is a phenyl. In one specific embodiment said phenyl has two (n=2) substituents (R1), wherein one (R1) is independently chosen from —CF$_3$, —OH, —CN, —OCH$_3$, —CH$_3$, or chloro and the second (R1) is independently chosen from —CF$_3$, —OH, —CN, —OCH$_3$, —CH$_3$, chloro, or fluoro. In one specific embodiment the two (R1) are chloro. In another specific embodiment the two (R1) are —OCH$_3$ and —CH$_3$. In another specific embodiment the two (R1) are —OH and F. In another yet specific embodiment the two (R1) are chloro and —OH. In a more specific embodiment said substituents (R1) are in the meta- and ortho-position with respect to the cyclopropylamine core. In another specific embodiment the two substituents (R1) are in the para- and ortho-position with respect to the cyclopropylamine core. In another specific embodiment the two substituents (R1) are both in the meta-positions with respect to the cyclopropylamine core.

In one embodiment of this aspect, the invention provides a compound of Formula (III) with three (n=3) substituents (R1) independently chosen from alkyl, aryl, amino, amido, nitro, halo, haloalkyl, cyano, alkoxy, heterocyclyl, sulfonyl, sulfonamide, hydroxyl or alkoxy. In one specific embodiment n=3 and each (R1) is independently chosen from —CF$_3$, —OH, —CN, —OCH$_3$, —CH$_3$, fluoro, or chloro. In one preferred embodiment the invention provides a compound of Formula (III) where the three (n=3) substituents (R1) are two fluoros and one —OH. In another specific embodiment the three substituents (R1) are —Cl, —F and —OH. In another specific embodiment the three substituents (R1) are —Cl, —F and —OCH$_3$.

In one embodiment of this aspect, the invention provides a compound of Formula (III) with three (n=3) substituents (R1) independently chosen from alkyl, aryl, amino, amido, nitro, halo, haloalkyl, cyano, heterocyclyl, sulfonyl, sulfonamide, hydroxyl or alkoxy. In one specific embodiment n=3 and each (R1) is independently chosen from —CF$_3$, —OH, —CN, —OCH$_3$, —CH$_1$, fluoro, or chloro. In one preferred embodiment the invention provides a compound of Formula (II) where the three (n=3) substituents (R1) are two fluoros and one —OH.

In one embodiment of this aspect, the invention provides a compound of Formula (III) with four (n=4) substituents (R1) independently chosen from alkyl, aryl, amino, amido, nitro, halo, haloalkyl, cyano, heterocyclyl, sulfonyl, sulfonamide, hydroxyl and alkoxy. In one specific embodiment n=4 and each (R1) is independently chosen from —CF$_3$, —OH, —CN, —OCH$_3$, —CH$_3$, fluoro, or chloro. In one preferred embodiment the invention provides a compound of Formula (III) with four (n=4) substituents (R1) which are three fluoros and one —OH.

In one embodiment of this aspect, the invention provides a compound of Formula (III) wherein, the (G) group is a phenyl, n=1 and m=1. In one specific embodiment the phenyl (G) has one (n=1) substituent (R1) chosen from alkyl, aryl, amino, amido, nitro, halo, haloalkyl, cyano, alkoxy, heteroaryl, sulfonyl, sulfonamide, hydroxyl or alkoxy, and (R2) is chosen from alkyl, optionally substituted cyclyl, optionally substituted -L1-cyclyl, amino, amido, nitro, halo, haloalkyl, cyano, alkoxy, sulfonyl, sulfonamide, hydroxyl or alkoxy. In a more specific embodiment (R1) is —OH and (R2) is —CH$_3$. In another yet specific embodiment (R1) is —Cl and (R2) is —CH$_3$.

In one embodiment of this aspect, the invention provides a compound of Formula (III) wherein, the (G) group is a phenyl, n=1 and m=1. In one specific embodiment the phenyl (G) has one (n=1) substituent (R1) chosen from alkyl, aryl, amino, amido, nitro, halo, haloalkyl, cyano, alkoxy, heteroaryl, sulfonyl, sulfonamide, hydroxyl or alkoxy, and (R2) is chosen from alkyl, optionally substituted cyclyl, optionally substituted -L1-cyclyl, amino, amido, nitro, halo, haloalkyl, cyano, alkoxy, sulfonyl, sulfonamide, hydroxyl and alkoxy. In a more specific embodiment (R1) is —OH and (R2) is —CH$_3$.

In another specific embodiment (R1) is —CF$_3$ and (R2) is independently chosen from —CH$_3$, —Cl or an optionally substituted cyclyl. In a even more specific embodiment (R2) is an optionally substituted phenyl wherein (R2) has 1 optional substituent chosen from —Cl, —OH, or —C(=O)NH$_2$.

Furthermore, in one aspect, the compound of Formula (I) is a compound of Formula (IV) or an enantiomer, a diastereomer, or a mixture thereof, or a pharmaceutically acceptable salt or solvate thereof. The general structure of compounds of Formula (IV) is:

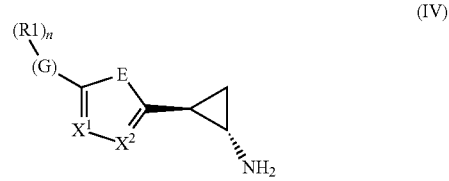

wherein:
E is —N(R3)-, —O—, or —S—, or is —X$^3$=X$^4$—;
X$^1$, X$^2$, X$^3$ and X$^4$ are independently C(R2) or N, provided that at least one of X$^1$, X$^2$, X$^3$ or X$^4$ is N when E is —X$^3$=X$^4$—;
(G) is a cyclyl group;
each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;
each (R2) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 optional substituents, wherein said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate;
R3 is —H or a (C$_1$-C$_6$)alkyl group;
each L1 is alkylene or heteroalkylene; and
n is 0, 1, 2, 3, 4 or 5;

with the proviso that the compound of Formula (IV) is not: (1S,2R)-2-(6-(2,4-difluorophenyl)pyridin-3-yl)cyclopropanamine.

In one aspect, the invention provides a composition as defined herein comprising a compound of Formula (IV) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S, 2R) enantiomer and less than 5% (1R, 2S) enantiomer. Even more preferably, the compound is more than 99% (1S,2R) enantiomer and less than 1% (1R, 2S) enantiomer.

In one aspect, the invention provides a composition as defined herein comprising a compound of Formula (TV) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R, 2S) enantiomer and less than 5% (1S,2R) enantiomer. Even more preferably, the compound is more than 99% (1R,2S) enantiomer and less than 1% (1S, 2R) enantiomer.

In one aspect, the invention provides a compound of Formula (IV) as described in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound of Formula (IV) as described in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

Preferably, the compound of the invention of Formula (IV) is used to treat a disease in a mammal and more preferably a human. More preferably, the human disease is chosen from cancer, a neurological condition or disease, or a viral infection.

Preferably, the optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

In one specific embodiment of this aspect, the invention provides a compound of Formula (IV) wherein, E is —S— or is —$X^3$=$X^4$—. Preferably, E is —$X^3$—$X^4$—.

In one specific embodiment of this aspect, the invention provides a compound of Formula (IV) wherein $X^1$ is a nitrogen atom and $X^2$, $X^3$ and $X^4$ are CH. In another specific embodiment of this aspect $X^2$ is a nitrogen atom and $X^1$, $X^3$ and $X^4$ are CH. In yet another specific embodiment, $X^1$ and $X^3$ are nitrogen atoms and $X^2$ and $X^4$ are CH.

In one specific embodiment of this aspect, the invention provides a compound of Formula (IV) wherein, E is —S— and $X^1$ and $X^2$ are CH. In another specific embodiment of this aspect E is —S—, $X^1$ is a nitrogen atom and $X^2$ is CH. In another specific embodiment E is —S—, $X^1$ is CH and $X^2$ is a nitrogen atom.

In one embodiment of this aspect, the invention provides a compound of Formula (IV) wherein the (G) group is a cyclyl and each (R1) is independently chosen from alkyl, aryl, amino, amido, nitro, halo, haloalkyl, cyano, heterocyclyl, sulfonyl, sulfonamide, hydroxyl, or alkoxy. In one specific embodiment of this aspect, said cyclyl (G) is an aryl or heterocyclyl.

In one particular embodiment of this aspect said cyclyl (G) is an aryl. In a preferred embodiment, said aryl is a phenyl.

In another particular embodiment of this aspect said cyclyl (G) is a heterocyclyl. In a more specific embodiment, said heterocyclyl is a heteroaryl or a heterocycloalkyl. Preferably, said heterocyclyl is a heteroaryl chosen from thiophenyl, benzo[b]thiophenyl, indolyl, benzofuran-2(3H)-onyl, 9H-carbazolyl, pyridin-2(1H)-onyl, indolin-2-onyl or indazolyl.

In one embodiment of this aspect, the invention provides a compound of Formula (IV) wherein $X^1$ is a nitrogen atom, $X^2$, $X^3$ and $X^4$ are CH, the (G) group is a cyclyl, and n=4. In a more specific embodiment, (G) is heterocyclyl and n is 0. In yet a more specific embodiment, said (G) is a heteroaryl or heterocyloalkyl and n is 0. In yet an even more specific embodiment (G) is a heteroaryl and n is 0. In a specific preferred embodiment said cyclyl is thiophenyl, benzo[b]thiophenyl, indolyl, benzofuran-2(3H)-onyl, 91H-carbazolyl, pyridin-2(1H)-onyl, indolin-2-onyl or indazolyl, and n is 0.

In one embodiment of this aspect, the invention provides a compound of Formula (IV) wherein the (0) group is a phenyl, wherein said phenyl has 0, 1, 2, 3, 4, or 5 substituents (R1) independently chosen from alkyl, aryl, amino, amido, nitro, halo, haloalkyl, cyano, heterocycle, sulfonyl, sulfonamide, hydroxyl or alkoxy. In a more specific embodiment, $X^1$ is a nitrogen atom $X^2$, $X^3$ and $X^4$ are CH and the phenyl group has one (n=1) substituents (R1), wherein (R1) is chosen from —$CF_3$, —Cl, —F, —$OCH_3$, —$CH_3$, —OH, —C(=O)$NH_{2,-[a2]}$—NHC(=O)$CH_3$, —$NHSO_2CH_3$, —$NHSO_2(CH_2$—$CH_3)$, —$NHSO_2(C_6H_5)$ or —CN.

In one embodiment of this aspect, the invention provides a compound of Formula (IV) wherein $X^1$ is a nitrogen atom, $X^2$, $X^3$ and $X^4$ are CH and the (G) group is a cyclyl, wherein said cyclyl is bonded to 0, 1, 2, 3, 4, or 5 substituents (R1) independently chosen from alkyl, aryl, amino, amido, nitro, halo, haloalkyl, cyano, heterocyclyl, sulfonyl, sulfonamide, hydroxyl or alkoxy. In one specific embodiment said cyclyl is independently chosen from thiophenyl, benzo[b]thiophenyl, indolyl, benzofuran-2(3H)-onyl, 9H-carbazolyl, pyridin-2(1H)-onyl, indolin-2-onyl or indazolyl. In an even more specific embodiment said cyclyl group is a thiophenyl with one (n=1) substituent (R1) independently chosen from —$CF_3$, —OH, —CN, —$OCH_3$, —$CH_3$, —C(=O)$NH_2$, chloro or fluoro. In a more specific embodiment said substituent (R1) is a chloro. In another specific embodiment the substituent (R1) is a —CH₃. In another specific embodiment the substituent (R1) is a —CN.

In one embodiment of this aspect, the invention provides a compound of Formula (IV) wherein the (G) group is phenyl, wherein said phenyl has 0, 1, 2, 3, 4, or 5 substituents (R1) independently chosen from alkyl, aryl, amino, amido, nitro, halo, haloalkyl, cyano, heterocycle, sulfonyl, sulfonamide, hydroxyl or alkoxy. In a more specific embodiment, $X^1$ is a nitrogen atom, $X^2$, $X^3$ and $X^4$ are CH and the phenyl group has two (n=2) substituents (R1), wherein one (R1) is independently chosen from —CF₃, —OH, —CN, —OCH₃, —CH₃, chloro, —NHSO₂CH₃, —NHSO₂(CH₂—CH₃) or —NHSO₂(C₆H₅) and the second (R1) is —CF₃, —OH, —CN, —OCH₃, —CH₃, fluoro, chloro, —NHSO₂CH₃, —NHSO₂(CH₂—CH₃) or —NHSO₂(C₆H₅). In one specific embodiment the two substituents (R1) are chloro. In another specific embodiment one substituent (R1) is —OCH₃ and the second substituent (R1) is independently chosen from —CH₃, —F, —Cl, —CF₃ or —CN. In another specific embodiment one substituent (R1) is —OH and the second substituent (R1) is independently chosen from —F, —Cl, —CH₃, —CN, —NHSO₂CH₃ or —NHSO₂(CH₂—CH₃). In another yet specific embodiment one substituent (R1) is —CF₃ the second substituent (R1) is independently chosen from —F, —OH, —CF₃ or —Cl.

In one embodiment of this aspect, the invention provides a compound of Formula (IV) wherein the (G) group is a cyclyl, wherein said cyclyl has three (n=3) substituents (R1) independently chosen from alkyl, aryl, amino, amido, nitro, halo, haloalkyl, cyano, heterocycle, sulfonyl, sulfonamide, hydroxyl or alkoxy. In one specific embodiment $X^1$ is a nitrogen atom, $X^2$, $X^3$ and $X^4$ are CH and the cyclyl (G) is a phenyl group with three (n=3) substituents (R1), independently chosen from —CF₃, —OH, —CN, —OCH₃, —CH₃, fluoro, or chloro.

In one embodiment of this aspect, the invention provides a compound of Formula (IV), wherein the (G) group is a cyclyl, wherein said cyclyl has four (n=4) substituents (R1) independently chosen from alkyl, aryl, amino, amido, nitro, halo, haloalkyl, cyano, alkoxy, heterocyclyl, sulfonyl, sulfonamide, hydroxyl or alkoxy. In one specific embodiment $X^1$ is a nitrogen atom, $X^2$, $X^3$ and $X^4$ are CH, and said cyclyl (G) is a phenyl group with four (n=4) substituents (R1) independently chosen from —CF₃, —OH, —CN, —OCH₃, —CH₃, fluoro, or chloro. In one preferred embodiment the invention provides a compound of Formula (IV) with four (n=4) substituents (R1) which are three fluoros and one —OH.

In one specific embodiment of this aspect, the invention provides a compound of Formula (IV) wherein the (G) group is a cyclyl with one (n=1) substituent (R1) chosen from alkyl, aryl, amino, amido, nitro, halo, haloalkyl, cyano, heterocyclyl, sulfonyl, sulfonamide, hydroxyl or alkoxy; and one substituent (R2) independently chosen from alkyl, optionally substituted cyclyl, amino, amido, nitro, halo, haloalkyl, cyano, sulfonyl, sulfonamide, hydroxyl or alkoxy. In one preferred embodiment $X^1$ is a nitrogen atom, $X^2$, $X^3$ and $X^4$ are CH, and said cyclyl group (G) is phenyl. In one specific embodiment (R1) is —OH and (R2) is —CH₃. In another specific embodiment (R1) is —CF₃ and (R2) is independently chosen from —CH₃, —Cl or an optionally substituted cyclyl. In a even more specific embodiment (R2) is an optionally substituted phenyl wherein (R2) has 1 optional substituent chosen from —Cl, —OH, or —C(=O)NH₂.

In one embodiment of this aspect, the invention provides a compound of Formula (IV) wherein $X^2$ is a nitrogen atom, $X^1$, $X^3$ and $X^4$ are CH, and the (G) group is a cyclyl, wherein said cyclyl has 0, 1, 2, 3, 4, or 5 substituents (R1) independently chosen from alkyl, aryl, amino, amido, nitro, halo, haloalkyl, cyano, heterocyclyl, sulfonyl, sulfonamide, hydroxyl or alkoxy. In one specific embodiment, said cyclyl group (G) is a phenyl substituted with one (n=1) substituent (R1) independently chosen from —OH[a2] or —OCH₃.

In one embodiment of this aspect, the invention provides a compound of Formula (IV) wherein $X^1$ and $X^3$ are a nitrogen atoms, $X^2$ and $X^4$ are CH, and the (G) group is a cyclyl, wherein said cyclyl has 0, 1, 2, 3, 4, or 5 substituents (R1) independently chosen from alkyl, aryl, amino, amido, nitro, halo, haloalkyl, cyano, heterocyclyl, sulfonyl, sulfonamide, hydroxyl or alkoxy. In one specific embodiment, said cyclyl group (G) is a phenyl substituted with one (n=1) substituent (R1) which is —OH.

In one embodiment of this aspect, the invention provides a compound of Formula (IV) wherein E is a sulfur atom, $X^1$ and $X^2$ are CH, and the (G) group is a cyclyl, wherein said cyclyl has 0, 1, 2, 3, 4, or 5 substituents (R1) independently chosen from alkyl, aryl, amino, amido, nitro, halo, haloalkyl, cyano, heterocyclyl, sulfonyl, sulfonamide, hydroxyl or alkoxy. In one specific embodiment, said cyclyl group (G) is a phenyl substituted with one (n=1) substituent (R1) which is a —OH.

In one embodiment of this aspect, the invention provides a compound of Formula (IV) wherein E is a sulfur atom, $X^1$ is nitrogen atom, $X^2$ is CH, and the (G) group is a cyclyl, wherein said cyclyl has 0, 1, 2, 3, 4, or 5 substituents (R1) independently chosen from alkyl, aryl, amino, amido, nitro, halo, haloalkyl, cyano, heterocyclyl, sulfonyl, sulfonamide, hydroxyl or alkoxy. In one specific embodiment, said cyclyl group (G) is a phenyl substituted with one (n=1) substituent (R1) which is a —OH.

In one embodiment of this aspect, the invention provides a compound of Formula (IV) wherein E is a sulfur atom, $X^1$ is CH, $X^2$ is a nitrogen atom and the (G) group is a cyclyl, wherein said cyclyl has 0, 1, 2, 3, 4, or 5 substituents (R1) independently chosen from alkyl, aryl, amino, amido, nitro, halo, haloalkyl, cyano, heterocyclyl, sulfonyl, sulfonamide, hydroxyl or alkoxy. In one specific embodiment, said cyclyl group (G) is a phenyl substituted with one (n=1) substituent (R1) which is —OH.

In one specific embodiment of the invention, the compound of Formula (I) is a compound of Formula (V) or an enantiomer, a diastereomer, or a mixture thereof, or a pharmaceutically acceptable salt or solvate thereof. A compound of Formula (V) is as follows:

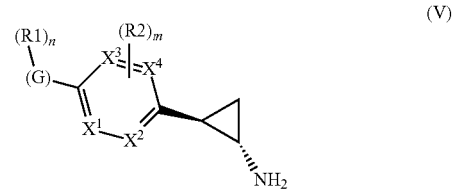

wherein:
$X^1$, $X^2$, $X^3$ and $X^4$ are independently CH or N, provided that at least one of $X^1$, $X^2$, $X^3$ or $X^4$ is a N;
(G) is a cyclyl group;
each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;

each (R2) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 optional substituents, wherein said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate;

each L1 is alkylene or heteroalkylene;

m is 0, 1, 2 or 3; and n is 0, 1, 2, 3, 4 or 5;

with the proviso that the compound of Formula (V) is not: (1S,2R)-2-(6-(2,4-difluorophenyl)pyridin-3-yl)cyclopropanamine.

In one aspect, the invention provides a composition as defined herein comprising a compound of Formula (V) as described in the above embodiment or a solvate or pharmaceutically acceptable salt thereof, wherein said compound is the (1S,2R) enantiomer (in respect to the substituents on the cyclopropyl ring) substantially free of the (1R,2S) enantiomer. Preferably, the compound is more than 90% (1S,2R) enantiomer and less than 10% (1R,2S) enantiomer. More preferably, the compound is more than 95% (1S, 2R) enantiomer and less than 5% (1R,2S) enantiomer. Even more preferably, the compound is more than 99% (1S,2R) enantiomer and less than 1% (1R,2S) enantiomer.

In one aspect, the invention provides a composition as defined herein comprising a compound of Formula (V) as described in the above embodiment or a solvate or pharmaceutically acceptable salt thereof, wherein said compound is the (1R,2S) enantiomer (in respect to the substituents on the cyclopropyl ring) substantially free of the (1S,2R) enantiomer. Preferably, the compound is more than 90% (1R,2S) enantiomer and less than 10% (1S, 2R) enantiomer. More preferably, the compound is more than 95% (1R,2S) enantiomer and less than 5% (1S, 2R) enantiomer. Even more preferably, the compound is more than 99% (1R,2S) enantiomer and less than 1% (1S,2R) enantiomer.

In one aspect, the invention provides a compound of Formula (V) as described in the above embodiment or a solvate or a pharmaceutically acceptable salt thereof, wherein the cyclopropyl ring carbon atom which is bound to the terminal amino group of the compound is in (S)-configuration and the cyclopropyl ring carbon atom which is bound to the cyclic group adjacent to the cyclopropyl ring of the compound is in (R)-configuration. Preferably, said compound is provided in an enantiomeric excess of at least 90%, more preferably at least 95%, even more preferably at least 99%. The enantiomeric excess can, for example, be determined as described in Example 63.

In one aspect, the invention provides a compound of Formula (V) as described in the above embodiment or a solvate or a pharmaceutically acceptable salt thereof, wherein the cyclopropyl ring carbon atom which is bound to the terminal amino group of the compound is in (R)-configuration and the cyclopropyl ring carbon atom which is bound to the cyclic group adjacent to the cyclopropyl ring of the compound is in (S)-configuration. Preferably, said compound is provided in an enantiomeric excess of at least 90%, more preferably at least 95%, even more preferably at least 99%. The enantiomeric excess can, for example, be determined as described in Example 63.

Preferably, the compounds of the invention are used to treat a disease in a mammal and more preferably a human. More preferably, the human disease is chosen from cancer, a neurological condition or disease, or a viral infection.

Preferably, the optional substituents are independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

In one specific embodiment of this aspect, the invention provides a compound of Formula (V) wherein $X^1$ is a nitrogen atom and $X^2$, $X^3$ and $X^4$ are CH. In another specific embodiment of this aspect $X^2$ is a nitrogen atom and $X^1$, $X^3$ and $X^4$ are CH. In another specific embodiment, $X^1$, and $X^3$ are nitrogen atoms and $X^2$ and $X^4$ are CH.

In one embodiment of this aspect, the invention provides a compound of Formula (V) wherein, the (G) group is a cyclyl, and each (R1) is independently chosen from alkyl, aryl, amino, amido, nitro, halo, haloalkyl, cyano, heterocyclyl, sulfonyl, sulfonamide, hydroxyl, or alkoxy. In one specific embodiment of this aspect, said cyclyl (G) is an aryl or heterocyclyl.

In one particular embodiment of this aspect said cyclyl (G) is an aryl. In a preferred embodiment, said aryl is a phenyl.

In another particular embodiment of this aspect said cyclyl (G) is a heterocyclyl. In a more specific embodiment, said heterocyclyl is a heteroaryl or a heterocycloalkyl. Preferably, said heterocyclyl is a heteroaryl chosen from thiophenyl, benzo[b]thiophenyl, indolyl, benzofuran-2(3H)-onyl, 9H-carbazolyl, pyridin-2(1H)-onyl, indolin-2-onyl or indazolyl.

In one embodiment of this aspect, the invention provides a compound of Formula (V) wherein $X^1$ is a nitrogen atom, $X^2$, $X^3$ and $X^4$ are CH, the (G) group is cyclyl, n=0 and m=0. In a more specific embodiment, (G) is heterocyclyl and n is 0. In yet a more specific embodiment, said (G) is a heteroaryl or heterocyloalkyl and n is 0. In yet an even more specific embodiment (G) is a heteroaryl and n is 0. In a specific preferred embodiment said cyclyl is thiophenyl, benzo[b]thiophenyl, indolyl, benzofuran-2(3H)-onyl, 9H-carbazolyl, pyridin-2(1H)-onyl, indolin-2-onyl or indazolyl, and n is 0.

In one embodiment of this aspect, the invention provides a compound of Formula (V) wherein the (G) group is phenyl, wherein said phenyl has 0, 1, 2, 3, 4, or 5 substituents (R1) independently chosen from alkyl, aryl, amino, amido, nitro, halo, haloalkyl, cyano, heterocycle, sulfonyl, sulfonamide, hydroxyl or alkoxy. In a more specific embodiment, $X^1$ is a nitrogen atom, $X^2$, $X^3$ and $X^4$ are CH, and the phenyl group has one (n=1) substituents (R1), wherein (R1) is independently chosen from —$CF_3$, —Cl, —F, —$OCH_1$, —$CH_3$, —OH, —C(=O)$NH_2$, —[a2]—NHC(=O)$CH_3$, —$NHSO_2CH_3$, —$NHSO_2(CH_2—CH_3)$, —$NHSO_2(C_6H_5)$ or —CN.

In one embodiment of this aspect, the invention provides a compound of Formula (V) wherein $X^1$ is a nitrogen atom, $X^2$, $X^3$ and $X^4$ are CH and the (G) group is a cyclyl, wherein said cyclyl has 0, 1, 2, 3, 4, or 5 substituents (R1) independently chosen from alkyl, aryl, amino, amido, nitro, halo, haloalkyl, cyano, heterocyclyl, sulfonyl, sulfonamide, hydroxyl or alkoxy. In one specific embodiment said cyclyl is independently chosen from thiophenyl, benzo[b]thiophenyl, indolyl, benzofuran-2(3H)-onyl, 9H-carbazolyl, pyridin-2(1H)-onyl, indolin-2-onyl or indazolyl. In an even more specific embodiment said cyclyl group is a thiophenyl with one (n=1) substituent (R1) independently chosen from —$CF_3$, —OH, —CN, —$OCH_3$, —$CH_3$, —C(=O)$NH_2$, chloro or fluoro. In a more specific embodiment said substituent (R1) is chloro. In another specific embodiment the substituent (R1) is —$CH_3$. In another specific embodiment the substituent (R1) is —CN.

In one embodiment of this aspect, the invention provides a compound of Formula (V) wherein the (G) group is phenyl, wherein said phenyl has 0, 1, 2, 3, 4, or 5 substituents (R1) independently chosen from alkyl, aryl, amino, amido, nitro, halo, haloalkyl, cyano, heterocycle, sulfonyl, sulfonamide, hydroxyl, or alkoxy. In a more specific embodiment, $X^1$ is a nitrogen atom, $X^2$, $X^3$ and $X^4$ are CH, and the phenyl group has two (n=2) substituents (R1), wherein one (R1) is independently chosen from —$CF_3$, —OH, —CN, —$OCH_3$, —$CH_3$, chloro, —$NHSO_2CH_3$, —$NHSO_2(CH_2$—$CH_3)$ or —$NHSO_2(C_6H_5)$ and the second (R1) is —$CF_3$, —OH, —CN, —$OCH_3$, —$CH_3$, fluoro, chloro, —$NHSO_2CH_3$, —$NHSO_2(CH_2$—$CH_3)$ or —$NHSO_2(C_6H_5)$. In one specific embodiment the two substituents (R1) are chloro. In another specific embodiment one substituent (R1) is —$OCH_3$ and the second substituent (R1) is independently chosen from —$CH_3$, —F, —Cl, —$CF_3$ or —CN. In another specific embodiment one substituent (R1) is —OH and the second substituent (R1) is independently chosen from —F, —Cl, —$CH_3$, —CN, —$NHSO_2CH_3$ or —$NHSO_2(CH_2$—$CH_3)$. In another yet specific embodiment one substituent (R1) is —$CF_3$ the second substituent (R1) is independently chosen from —F, —OH, —$CF_3$ or —Cl.

In one embodiment of this aspect, the invention provides a compound of Formula (V) wherein the (G) group is a cyclyl, wherein said cyclyl has three (n=3) substituents (R1) independently chosen from alkyl, aryl, amino, amido, nitro, halo, haloalkyl, cyano, heterocycle, sulfonyl, sulfonamide, hydroxyl or alkoxy. In one specific embodiment $X^1$ is a nitrogen atom $X^2$, $X^3$ and $X^4$ are CH, and said cyclyl (G) is a phenyl group with three (n=3) substituents (R1) independently chosen from —$CF_3$, —OH, —CN, —$OCH_3$, —$CH_3$, fluoro, or chloro.

In one embodiment of this aspect, the invention provides a compound of Formula (V), wherein the (G) group is a cyclyl, wherein said cyclyl has four (n=4) substituents (R1) independently chosen from alkyl, aryl, amino, amido, nitro, halo, haloalkyl, cyano, alkoxy, heterocyclyl, sulfonyl, sulfonamide, hydroxyl or alkoxy. In one specific embodiment $X^1$ is a nitrogen atom, $X^2$, $X^3$ and $X^4$ are CH, and said cyclyl (G) is a phenyl group with four (n=4) substituents (R1) independently chosen from —$CF_3$, —OH, —CN, —$OCH_3$, —$CH_3$, fluoro, or chloro. In one preferred embodiment the invention provides a compound of Formula (V) with four (n=4) substituents (R1) which are three fluoros and one —OH.

In one specific embodiment of this aspect, the invention provides a compound of Formula (V) wherein the (G) group is a cyclyl with one (n=1) substituent (R1) chosen from alkyl, aryl, amino, amido, nitro, halo, haloalkyl, cyano, heterocyclyl, sulfonyl, sulfonamide, hydroxyl or alkoxy; and one (m=1) substituent (R2) independently chosen from alkyl, optionally substituted cyclyl, amino, amido, nitro, halo, haloalkyl, cyano, sulfonyl, sulfonamide, hydroxyl or alkoxy. In one preferred embodiment $X^1$ is a nitrogen atom, $X^2$, $X^3$ and $X^4$ are CH, and said cyclyl group (G) is phenyl.

In one specific embodiment (R1) is —OH and (R2) is —$CH_3$. In another specific embodiment (R1) is —$CF_3$ and (R2) is independently chosen from —$CH_3$, —Cl or an optionally substituted cyclyl. In a even more specific embodiment (R2) is an optionally substituted phenyl wherein (R2) has 1 optional substituent chosen from —Cl, —OH, or —C(=O)$NH_2$.

In one embodiment of this aspect, the invention provides a compound of Formula (V) wherein $X^2$ is a nitrogen atom, $X^1$, $X^3$ and $X^4$ are CH, and the (0) group is a cyclyl, wherein said cyclyl has 0, 1, 2, 3, 4, or 5 substituents (R1) independently chosen from alkyl, aryl, amino, amido, nitro, halo, haloalkyl, cyano, heterocyclyl, sulfonyl, sulfonamide, hydroxyl or alkoxy. In one specific embodiment, said cyclyl group (G) is a phenyl substituted with one (n=1) substituent (R1) independently chosen from —$OH_{[a2]}$ or —$OCH_3$.

In one embodiment of this aspect, the invention provides a compound of Formula (V) wherein $X^1$ and $X^3$ are a nitrogen atoms, $X^2$ and $X^4$ are CH, and the (G) group is a cyclyl, wherein said cyclyl has 0, 1, 2, 3, 4, or 5 substituents (R1) independently chosen from alkyl, aryl, amino, amido, nitro, halo, haloalkyl, cyano, heterocyclyl, sulfonyl, sulfonamide, hydroxyl or alkoxy. In one specific embodiment, said cyclyl group (G) is a phenyl substituted with one (n=11) substituent (R1) which is —OH.

In one aspect, the invention provides a stereoisomer or a mixture thereof, of a compound of Formula (I), (II), (ITT), (IV) or (V).

In another aspect, the invention relates to a derivative or analog of a compound of Formula (I), (II), (III), (IV) or (V).

In yet another aspect, the invention relates to a solvate or polymorph of a compound of Formula (I), (II), (III), (IV) or (V).

In yet another aspect, the invention relates to a prodrug of a compound of Formula (I), (II), (III), (IV) or (V).

In yet another aspect, the invention relates to a metabolite of a compound of Formula (I), (II), (III), (IV) or (V).

In another aspect, the invention provides a method of treating or preventing a disease or condition comprising administering, to a patient (preferable human) in need of treatment, a therapeutically effective amount of a pharmaceutical composition comprising a compound of Formula (I), (II), (III), (IV) or (V) as defined above, or a pharmaceutically acceptable salt thereof and a pharmaceutically acceptable carrier. This aspect can be reformulated as a compound of Formula (I), (II), (III), (IV) or (V) for use as a medicine. In a related aspect, the invention provides a pharmaceutical composition for use in treating or preventing a disease or condition wherein said composition comprises a therapeutically effective amount of a compound of Formula (I), (II), (III), (IV) or (V) sufficient for treating or preventing said disease or condition. In a more specific embodiment the invention provides a compound of Formula (I), (II), (III), (IV) or (V) for use in the treatment of a disease associated with LSD1. In another preferred aspect, the therapeutically effective amount of a compound of Formula (I), (II), (III), (IV) or (V) is an amount sufficient to modulate the level of histone 3 lysine 4 methylation.

In yet another aspect, the invention provides a pharmaceutical composition comprising a compound of Formula (I), (II), (III), (IV) or (V) and a pharmaceutically acceptable carrier. In a more specific aspect, the pharmaceutical composition comprises a therapeutically effective amount of a compound of Formula (I), (II), (III), (IV) or (V). In an even more specific aspect, the therapeutically effective amount of a compound of Formula (I), (II), (III), (IV) or (V) is an amount effective to inhibit LSD1. In another preferred aspect, the therapeutically effective amount of a compound of Formula (I), (II), (III), (IV) or (V) is an amount sufficient to modulate the level of histone 3 lysine 4 methylation.

In again another aspect, the invention provides a method of inhibiting LSD1 activity comprising administering, to a patient in need of treatment, a therapeutically effective amount of a composition comprising a compound of Formula (I), (II), (III), (IV) or (V) or a pharmaceutically acceptable salt thereof, and a pharmaceutically acceptable carrier sufficient to inhibit LSD1 activity. This aspect can be reformulated as a compound of Formula (I), (II), (III), (IV) or (V) as herein defined for use as a LSD1 inhibitor. This aspect can also be reformulated as a compound of Formula (I), (II), (III), (IV) or (V) for the manufacture of a medicament for the treatment of a disease associated to LSD1. In a related aspect, a method for treating an individual is provided, said method comprising identifying an individual in need of treatment and administering to said individual a therapeutically effective amount of a compound of Formula (I), (II), (III), (IV) or (V). In a preferred aspect, the therapeutically effective amount of a compound of Formula (I), (II), (III), (IV) or (V) is an amount sufficient to inhibit LSD1. In another preferred aspect, the therapeutically effective amount of a compound of Formula (I), (II), (III), (IV) or (V) is an amount sufficient to modulate the level of histone 4 lysine 3 methylation.

Preferred embodiments of the compounds of Formula (I), (II), (III), (IV) or (V) for use in the composition and method of this four aspect of the invention are as defined herein above in the first aspect of the invention.

In still another aspect, the invention provides a method of treating or preventing cancer comprising administering, to a patient in need of treatment, a therapeutically effective amount of a composition comprising a compound of Formula (T), (II), (III), (IV) or (V) as defined above in the first aspect of the invention, and a pharmaceutically acceptable carrier. This aspect can be reformulated as a compound of Formula (I), (II), (III), (IV) or (V) as defined above in the first aspect of the invention for use in the treatment or prevention of cancer. In a related aspect, the invention provides a pharmaceutical composition for use in treating or preventing cancer wherein said composition comprises a therapeutically effective amount of a compound of Formula (I), (II), (III), (IV) or (V) sufficient for treating or preventing cancer. In another related aspect, the invention provides a compound of Formula (I), (II), (III), (IV) or (V) or a pharmaceutical composition for the treatment or prevention of a cancer wherein said cancer is chosen from testicular cancer, breast cancer, lung cancer, prostate cancer, colorectal cancer, brain cancer, skin cancer, blood cancer (e.g., leukemia) and lymphoma, wherein said composition comprises a therapeutically effective amount of a compound of Formula (I), (II), (III), (IV) or (V) sufficient for treating or preventing the said cancer. In a preferred aspect, the therapeutically effective amount of a compound of Formula (I), (II), (III), (IV) or (V) is an amount sufficient to inhibit LSD1. In another preferred aspect, the therapeutically effective amount of a compound of Formula (I), (II), (III), (IV) or (V) is an amount sufficient to modulate the level of histone-3 lysine-4 methylation.

In a still yet aspect, the invention provides a method for identifying a compound which is a selective inhibitor of LSD1, the method comprising selecting or providing a compound of Formula (I), (II), (III), (IV) or (V), and determining the ability of the said compound to inhibit LSD1 and MAO-A and/or MAO-B, wherein a compound that inhibits LSD1 to a greater extent than MAO-A and/or MAO-B is identified as a LSD1 selective inhibitor. Thus, the invention provides a pharmaceutical composition comprising a pharmaceutically acceptable carrier and a compound of Formula (I), (II), (III), (IV) or (V) which is a selective inhibitor of LSD1. LSD1 selective inhibitors have Ki values for LSD1 which are lower than the Ki value for MAO-A and/or MAO-B. Preferably, the Ki values for LSD1 are two-fold lower than for MAO-A and/or MAO-B. In one aspect of this embodiment, the LSD1 Ki value is at least 5-fold lower than the Ki value for MAO-A and/or MAO-B. In one aspect of this embodiment, the LSD1 Ki value is at least 10-fold lower than the Ki value for MAO-A and/or MAO-B. In one embodiment of this sixth aspect of the invention, the pharmaceutical composition comprising a LSD1 selective inhibitor of Formula (I), (II), (II), (IV) or (V), or a pharmaceutically acceptable salt or solvate thereof is useful for treating and/or preventing a disease in an individual. In one specific embodiment, a therapeutically effective amount of the composition is administered to an individual in an amount sufficient to prevent or treat a disease. In a more specific, the disease is cancer. In an even more specific aspect, the disease is a cancer chosen from prostate, testicular, brain, colorectal, lung, breast, skin, and blood cancer.

Recent studies have implicated LSD1 in viral infection and reactivation. In particular it was shown that pharmacological inhibitors of LSD1 like parnate and siRNA knock down of LSD1 caused reduced viral infectivity and reduced reactivation after latency (Liang et al. (2009) *Nat. Med.* 15:1312-1317). Therefore it is believed that the compounds of the invention can be used for treating or preventing viral infection. Furthermore, it is believed that the compounds of the invention can treat or prevent viral reactivation after latency.

Thus, in another aspect, the invention provides a method for treating or preventing a viral infection, the method comprising administering to an individual (preferably a human) a compound of Formula (I), (II), (III), (IV) or (V) as defined above in any of the aspects and embodiments of the invention or a pharmaceutically acceptable salt or solvate thereof. Accordingly, the invention also provides a compound of Formula (I), (II), (III), (IV) or (V) as defined above in any of the aspects and embodiments of the invention or a pharmaceutically acceptable salt or solvate thereof for use in treating or preventing a viral infection. In one specific embodiment, the viral infection is a herpesvirus infection. In a more specific embodiment, the herpesvirus infection is caused by and/or associated with a herpesvirus chosen from HSV-1, HSV-2, and Epstein-Barr virus. In another embodiment of this seventh aspect, the viral infection is caused by and/or associated with HIV. In even more specific embodiment, the invention provides a method for treating or preventing viral reactivation after latency, the method comprising administering to an individual (preferably a human) a compound of Formula (I), (II), (III), (IV) or (V) as defined above in any of the aspects and embodiments of the invention or a pharmaceutically acceptable salt or solvate thereof. Accordingly, the invention also provides a compound of Formula (I), (II), (III), (IV) or (V) as defined above in any of the aspects and embodiments of the invention or a pharmaceutically acceptable salt or solvate thereof for use in treating or preventing viral reactivation after latency. In a specific embodiment, the virus that is reactivating is a herpesvirus. In a more specific embodiment, the herpesvirus that is reactivating is chosen from HSV-1, HSV-2, and Epstein-Barr virus. In an even more specific embodiment, the virus that is reactivating is HSV.

In one embodiment of the invention provides a compound Formula (I), (II), or (III) or a solvate or pharmaceutically acceptable salt thereof, wherein the compound is:
(trans)-2-(3'-(trifluoromethyl)biphenyl-4-yl)cyclopropanamine;
(trans)-2-(terphenyl-4-yl)cyclopropanamine;
4'-((trans)-2-aminocyclopropyl)biphenyl-4-ol;
4'-((trans)-2-aminocyclopropyl)biphenyl-3-ol;
(trans)-2-(6-(3-(trifluoromethyl)phenyl)pyridin-3-yl)cyclopropanamine;
(Trans)-2-(6-(3,5-dichlorophenyl)pyridin-3-yl)cyclopropanamine;
(trans)-2-(6-(4-chlorophenyl)pyridin-3-yl)cyclopropanamine;
(trans)-2-(6-(3-chlorophenyl)pyridin-3-yl)cyclopropanamine;
(trans)-2-(6-(4-(trifluoromethyl)phenyl)pyridin-3-yl)cyclopropanamine;
(trans)-2-(6-(4-methoxyphenyl)pyridin-3-yl)cyclopropanamine;
(trans)-2-(6-(3-methoxyphenyl)pyridin-3-yl)cyclopropanamine;
4-(5-((trans)-2-aminocyclopropyl)pyridin-2-yl)benzonitrile;
3-(5-((trans)-2-aminocyclopropyl)pyridin-2-yl)benzonitrile;
(Trans)-2-(6-p-tolylpyridin-3-yl)cyclopropanamine;
(Trans)-2-(6-m-tolylpyridin-3-yl)cyclopropanamine;
4-(5-((trans)-2-amninocyclopropyl)pyridin-2-yl)phenol;
3-(5-((trans)-2-aminocyclopropyl)pyridin-2-yl)phenol;
4-(5-((trans)-2-aminocyclopropyl)pyridin-2-yl)benzamide;
3-(5-((trans)-2-aminocyclopropyl)pyridin-2-yl)benzamide;
2-(5-((trans)-2-aminocyclopropyl)pyridin-2-yl)phenol;
3-(5-((trans)-2-aminocyclopropyl)pyridin-2-yl)phenol;
(Trans)-2-(6-(3-methoxy-4-methylphenyl)pyridin-3-yl)cyclopropanamine;
5-(5-((trans)-2-aminocyclopropyl)pyridin-2-yl)-2-fluorophenol;
3-(5-((trans)-2-aminocyclopropyl)pyridin-2-yl)-5-fluorophenol;
3-(5-((trans)-2-aminocyclopropyl)pyridin-2-yl)-4-fluorophenol;
3-(5-((trans)-2-aminocyclopropyl)pyridin-2-yl)-2-fluorophenol;
3-(5-((trans)-2-aminocyclopropyl)pyridin-2-yl)-2,4-difluorophenol;
3-(5-((trans)-2-aminocyclopropyl)pyridin-2-yl)-2,4,6-trifluorophenol;
3-(5-((trans)-2-amninocyclopropyl)pyridin-2-yl)-5-chorophenol;
(Trans)-2-(6-(2-fluoro-3-(trifluoromethyl)phenyl)pyridin-3-yl)cyclopropanamine;
(Trans)-2-(6-(5-chlorothiophen-2-yl)pyridin-3-yl)cyclopropanamine;
(Trans)-2-(6-(5-methylthiophen-2-yl)pyridin-3-yl)cyclopropanamine;
(Trans)-2-(6-(1H-indol-6-yl)pyridin-3-yl)cyclopropanamine;
(Trans)-2-(6-(benzo[b]thiophen-5-yl)pyridin-3-yl)cyclopropanamine; or
3-(5-((trans)-2-aminocyclopropyl)-3-methylpyridin-2-yl)phenol.

In one embodiment of the invention provides a compound Formula (I), (II), (III), (IV) or (V) or a solvate or pharmaceutically acceptable salt thereof, wherein the compound is:
(trans)-2-(6-(3-chlorophenyl)-5-methylpyridin-3-yl)cyclopropanamine;
(trans)-2-(5-methyl-6-(3-(trifluoromethyl)phenyl)pyridin-3-yl)cyclopropanamine;
(trans)-2-(6-(4-fluoro-3-methoxyphenyl)pyridin-3-yl)cyclopropanamine;
(trans)-2-(6-(3-fluoro-5-methoxyphenyl)pyridin-3-yl)cyclopropanamine;
(trans)-2-(6-(2-fluoro-5-methoxyphenyl)pyridin-3-yl)cyclopropanamine;
(trans)-2-(6-(2-fluoro-3-methoxyphenyl)pyridin-3-yl)cyclopropanamine;
(trans)-2-(6-(3-chloro-5-methoxyphenyl)pyridin-3-yl)cyclopropanamine;
(trans)-2-(6-(2-chloro-5-methoxyphenyl)pyridin-3-yl)cyclopropanamine;
(trans)-2-(6-(3-methoxy-5-(trifluoromethyl)phenyl)pyridin-3-yl)cyclopropanamine;
3-(5-((trans)-2-aminocyclopropyl)pyridin-2-yl)-5-methoxybenzonitrile;
5-(5-((trans)-2-aminocyclopropyl)pyridin-2-yl)-2-methylphenol;
3-(5-((trans)-2-aminocyclopropyl)pyridin-2-yl)-4-chlorophenol;
3-(5-((trans)-2-aminocyclopropyl)pyridin-2-yl)-5-(trifluoromethyl)phenol;
(trans)-2-(6-(2-fluoro-5-(trifluoromethyl)phenyl)pyridin-3-yl)cyclopropanamine;
(trans)-2-(6-(2-chloro-5-(trifluoromethyl)phenyl)pyridin-3-yl)cyclopropanamine;
(trans)-2-(6-(3,5-bis(trifluoromethyl)phenyl)pyridin-3-yl)cyclopropanamine;
N-(3-(5-((trans)-2-aminocyclopropyl)pyridin-2-yl)phenyl)acetamide;
N-(3-(5-((trans)-2-aminocyclopropyl)pyridin-2-yl)phenyl)methanesulfonamide;
(trans)-2-(6-(benzo[b]thiophen-2-yl)pyridin-3-yl)cyclopropanamine;
(trans)-2-(6-(benzo[b]thiophen-3-yl)pyridin-3-yl)cyclopropanamine;
5-(5-((trans)-2-aminocyclopropyl)pyridin-2-yl)thiophene-2-carbonitrile;
(trans)-2-(6-(4-methylthiophen-3-yl)pyridin-3-yl)cyclopropanamine;
(trans)-2-(2-chloro-6-(3-(trifluoromethyl)phenyl)pyridin-3-yl)cyclopropanamine;
(trans)-2-(2-(4-chlorophenyl)-6-(3-(trifluoromethyl)phenyl)pyridin-3-yl)cyclopropanamine;
4-(3-((trans)-2-amninocyclopropyl)-6-(3-(trifluoromethyl)phenyl)pyridin-2-yl)phenol;
4-(3-((trans)-2-aminocyclopropyl)-6-(3-(trifluoromethyl)phenyl)pyridin-2-yl)benzamide;
(trans)-2-(2-methyl-6-(3-(trifluoromethyl)phenyl)pyridin-3-yl)cyclopropanamine;
3-(5-((trans)-2-aminocyclopropyl)pyridin-2-yl)-5-hydroxybenzonitrile;
(trans)-2-(6-(3,4-difluoro-5-methoxyphenyl)pyridin-3-yl)cyclopropanamine;
5-(5-((trans)-2-aminocyclopropyl)pyridin-2-yl)-2,3-difluorophenol;
(trans)-2-(6-(3-chloro-4-fluoro-5-methoxyphenyl)pyridin-3-yl)cyclopropanamine;
5-(5-((trans)-2-aminocyclopropyl)pyridin-2-yl)-3-chloro-2-fluorophenol;
(trans)-2-(6-(1H-indazol-6-yl)pyridin-3-yl)cyclopropanamine;
(trans)-2-(6-(9H-carbazol-2-yl)pyridin-3-yl)cyclopropanamine;
6-(5-((trans)-2-aminocyclopropyl)pyridin-2-yl)indolin-2-one;

6-(5-((trans)-2-aminocyclopropyl)pyridin-2-yl)benzofuran-2(3H)-one;
4-(5-((trans)-2-aminocyclopropyl)pyridin-2-yl)pyridin-2(1H)-one;
N-(3-(5-((trans)-2-aminocyclopropyl)pyridin-2-yl)phenyl)benzenesulfonamide;
N-(3-(5-((trans)-2-aminocyclopropyl)pyridin-2-yl)phenyl)propane-2-sulfonamide;
4'-((trans)-2-aminocyclopropyl)-4-fluorobiphenyl-3-ol;
4'-((trans)-2-aminocyclopropyl)-5-chlorobiphenyl-3-ol;
4'-((trans)-2-aminocyclopropyl)-5-chloro-4-fluorobiphenyl-3-ol;
N-(4'-((trans)-2-aminocyclopropyl)biphenyl-3-yl)benzenesulfonamide;
N-(4'-((trans)-2-aminocyclopropyl)biphenyl-3-yl)propane-2-sulfonamide;
N-(4'-((trans)-2-aminocyclopropyl)biphenyl-3-yl)methanesulfonamide;
N-(2-(5-((trans)-2-aminocyclopropyl)pyridin-2-yl)phenyl)methanesulfonamide;
3-(5-((trans)-2-aminocyclopropyl)pyridin-2-yl)-4-methoxybenzonitrile;
N-(4'-((trans)-2-aminocyclopropyl)biphenyl-2-yl)methanesulfonamide;
4'-((trans)-2-aminocyclopropyl)-6-methoxybiphenyl-3-carbonitrile;
N-(4'-((trans)-2-aminocyclopropyl)-6-methoxybiphenyl-3-yl)methanesulfonamide;
4'-((trans)-2-aminocyclopropyl)-6-hydroxybiphenyl-3-carbonitrile;
N-(4'-((trans)-2-aminocyclopropyl)-6-hydroxybiphenyl-3-yl)methanesulfonamide;
3-(5-((trans)-2-aminocyclopropyl)pyridin-2-yl-4-hydroxybenzonitrile;
N-(3-(5-((trans)-2-aminocyclopropyl)pyridin-2-yl)-4-hydroxyphenyl)methanesulfonamide;
N-(3-(5-((trans)-2-aminocyclopropyl)pyridin-2-yl)-5-(trifluoromethyl)phenyl)ethanesulfonamide;
N-(3-(5-((trans)-2-aminocyclopropyl)pyridin-2-yl)-5-(trifluoromethyl)phenyl)methanesulfonamide;
3-(6-((trans)-2-aminocyclopropyl)pyridin-3-yl)phenol;
(Trans)-2-(5-(3-methoxyphenyl)pyridin-2-yl)cyclopropanamine;
4-(6-((trans)-2-aminocyclopropyl)pyridin-3-yl)phenol;
2-(6-((trans)-2-aminocyclopropyl)pyridin-3-yl)phenol;
2-(5-((trans)-2-aminocyclopropyl)thiophen-2-yl)phenol;
3-(5-((trans)-2-aminocyclopropyl)thiophen-2-yl)phenol;
4-(5-((trans)-2-aminocyclopropyl)thiophen-2-yl)phenol;
2-(5-((trans)-2-aminocyclopropyl)thiazol-2-yl)phenol;
3-(5-((trans)-2-aminocyclopropyl)thiazol-2-yl)phenol;
4-(5-((trans)-2-aminocyclopropyl)thiazol-2-yl)phenol;
2-(2-((trans)-2-aminocyclopropyl)thiazol-5-yl)phenol;
3-(2-((trans)-2-aminocyclopropyl)thiazol-5-yl)phenol;
2-(2-((trans)-2-aminocyclopropyl)thiazol-5-yl)phenol;
3-(2-((trans)-2-aminocyclopropyl)thiazol-5-yl)phenol;
3-(5-((trans)-2-aminocyclopropyl)pyrimidin-2-yl)phenol; or
4-(5-((trans)-2-aminocyclopropyl)pyrimidin-2-yl)phenol.

In one embodiment of the invention provides a compound Formula (I), (II), (III), (NV) or (V) or a solvate or pharmaceutically acceptable salt thereof, wherein the compound is:
(trans)-2-(3'-(trifluoromethyl)biphenyl-4-yl)cyclopropanamine;
(trans)-2-(terphenyl-4-yl)cyclopropanamine;
4'-((trans)-2-aminocyclopropyl)biphenyl-4-ol;
4'-((trans)-2-aminocyclopropyl)biphenyl-3-ol;
(trans)-2-(6-(3-(trifluoromethyl)phenyl)pyridin-3-yl)cyclopropanamine;
(Trans)-2-(6-(3,5-dichlorophenyl)pyridin-3-yl)cyclopropanamine;
(trans)-2-(6-(4-chlorophenyl)pyridin-3-yl)cyclopropanamine;
(trans)-2-(6-(3-chlorophenyl)pyridin-3-yl)cyclopropanamine;
(trans)-2-(6-(4-(trifluoromethyl)phenyl)pyridin-3-yl)cyclopropanamine;
(trans)-2-(6-(4-methoxyphenyl)pyridin-3-yl)cyclopropanamine;
(trans)-2-(6-(3-methoxyphenyl)pyridin-3-yl)cyclopropanamine;
4-(5-((trans)-2-aminocyclopropyl)pyridin-2-yl)benzonitrile;
3-(5-((trans)-2-aminocyclopropyl)pyridin-2-yl)benzonitrile;
(Trans)-2-(6-p-tolylpyridin-3-yl)cyclopropanamine;
(Trans)-2-(6-m-tolylpyridin-3-yl)cyclopropanamine;
4-(5-((trans)-2-aminocyclopropyl)pyridin-2-yl)phenol;
3-(5-((trans)-2-aminocyclopropyl)pyridin-2-yl)phenol;
4-(5-((trans)-2-aminocyclopropyl)pyridin-2-yl)benzamide;
3-(5-((trans)-2-aminocyclopropyl)pyridin-2-yl)benzamide;
2-(5-((trans)-2-aminocyclopropyl)pyridin-2-yl)phenol;
3-(5-((trans)-2-aminocyclopropyl)pyridin-2-yl)phenol;
(Trans)-2-(6-(3-methoxy-4-methylphenyl)pyridin-3-yl)cyclopropanamine;
5-(5-((trans)-2-amninocyclopropyl)pyridin-2-yl)-2-fluorophenol;
3-(5-((trans)-2-aminocyclopropyl)pyridin-2-yl)-5-fluorophenol;
3-(5-((trans)-2-aminocyclopropyl)pyridin-2-yl)-4-fluorophenol;
3-(5-((trans)-2-aminocyclopropyl)pyridin-2-yl)-2-fluorophenol;
3-(5-((trans)-2-aminocyclopropyl)pyridin-2-yl)-2,4-di fluorophenol;
3-(5-((trans)-2-aminocyclopropyl)pyridin-2-yl)-2,4,6-trifluorophenol;
3-(5-((trans)-2-aminocyclopropyl)pyridin-2-yl)-5-chorophenol;
(Trans)-2-(6-(2-fluoro-3-trifluoromethyl)phenyl)pyridin-3-yl)cyclopropanamine;
(Trans)-2-(6-(5-chlorothiophen-2-yl)pyridin-3-yl)cyclopropanamine;
(Trans)-2-(6-(5-methylthiophen-2-yl)pyridin-3-yl)cyclopropanamine;
(Trans)-2-(6-(1H-indol-6-yl)pyridin-3-yl)cyclopropanamine;
(Trans)-2-(6-(benzo[b]thiophen-5-yl)pyridin-3-yl)cyclopropanamine;
3-(5-((trans)-2-aminocyclopropyl)-3-methylpyridin-2-yl)phenol;
(trans)-2-(6-(3-chlorophenyl)-5-methylpyridin-3-yl)cyclopropanamine;
(trans)-2-(5-methyl-6-(3-(trifluoromethyl)phenyl)pyridin-3-yl)cyclopropanamine;
(trans)-2-(6-(4-fluoro-3-methoxyphenyl)pyridin-3-yl)cyclopropanamine;
(trans)-2-(6-(3-fluoro-5-methoxyphenyl)pyridin-3-yl)cyclopropanamine;
(trans)-2-(6-(2-fluoro-5-methoxyphenyl)pyridin-3-yl)cyclopropanamine;
(trans)-2-(6-(2-fluoro-3-methoxyphenyl)pyridin-3-yl)cyclopropanamine;
(trans)-2-(6-(3-chloro-5-methoxyphenyl)pyridin-3-yl)cyclopropanamine;
(trans)-2-(6-(2-chloro-5-methoxyphenyl)pyridin-3-yl)cyclopropanamine;

(trans)-2-(6-(3-methoxy-5-(trifluoromethyl)phenyl)pyridin-3-yl)cyclopropanamine;
3-(5-((trans)-2-aminocyclopropyl)pyridin-2-yl)-5-methoxybenzonitrile;
5-(5-((trans)-2-aminocyclopropyl)pyridin-2-yl)-2-methylphenol;
3-(5-((trans)-2-aminocyclopropyl)pyridin-2-yl)-4-chorophenol;
3-(5-((trans)-2-aminocyclopropyl)pyridin-2-yl)-5-(trifluoromethyl)phenol;
(trans)-2-(6-(2-fluoro-5-(trifluoromethyl)phenyl)pyridin-3-yl)cyclopropanamine;
(trans)-2-(6-(2-chloro-5-(trifluoromethyl)phenyl)pyridin-3-yl)cyclopropanamine;
(trans)-2-(6-(3,5-bis(trifluoromethyl)phenyl)pyridin-3-yl)cyclopropanamine;
N-(3-(5-((trans)-2-aminocyclopropyl)pyridin-2-yl)phenyl)acetamide;
N-(3-(5-((trans)-2-aminocyclopropyl)pyridin-2-yl)phenyl)methanesulfonamide;
(trans)-2-(6-(benzo[b]thiophen-2-yl)pyridin-3-yl)cyclopropanamine;
(trans)-2-(6-(benzo[b]thiophen-3-yl)pyridin-3-yl)cyclopropanamine;
5-(5-((trans)-2-aminocyclopropyl)pyridin-2-yl)thiophene-2-carbonitrile;
(trans)-2-(6-(4-methylthiophen-3-yl)pyridin-3-yl)cyclopropanamine;
(Trans)-2-(6-(3,4-difluoro-5-methoxyphenyl)pyridin-3-yl)cyclopropanamine;
5-(5-((trans)-2-aminocyclopropyl)pyridin-2-yl)-2,3-difluorophenol;
(Trans)-2-(6-(1H-indazol-6-yl)pyridin-3-yl)cyclopropanamine;
(Trans)-2-(6-(9H-carbazol-2-yl)pyridin-3-yl)cyclopropanamine;
6-(5-((trans)-2-aminocyclopropyl)pyridin-2-yl)indolin-2-one;
N-(3-(5-((trans)-2-aminocyclopropyl)pyridin-2-yl)phenyl)benzenesulfonamide;
N-(3-(5-((trans)-2-aminocyclopropyl)pyridin-2-yl)phenyl)propane-2-sulfonamide;
4'-((trans)-2-aminocyclopropyl)-4-fluorobiphenyl-3-ol;
4'-((trans)-2-aminocyclopropyl)-5-chlorobiphenyl-3-ol;
N-(4'-((trans)-2-aminocyclopropyl)biphenyl-3-yl)benzenesulfonamide;
N-(4'-((trans)-2-aminocyclopropyl)biphenyl-3-yl)propane-2-sulfonamide;
N-(4'-((trans)-2-aminocyclopropyl)biphenyl-3-yl)methanesulfonamide;
N-(2-(5-((trans)-2-aminocyclopropyl)pyridin-2-yl)phenyl)methanesulfonamide;
3-(5-((trans)-2-aminocyclopropyl)pyridin-2-yl)-4-methoxybenzonitrile;
N-(4'-((trans)-2-aminocyclopropyl)biphenyl-2-yl)methanesulfonamide;
4'-((trans)-2-aminocyclopropyl)-6-methoxybiphenyl-3-carbonitrile;
N-(4'-((trans)-2-amninocyclopropyl)-6-methoxybiphenyl-3-yl)methanesulfonamide;
(Trans)-2-(2-chloro-6-(3-(trifluoromethyl)phenyl)pyridin-3-yl)cyclopropanamine;
(Trans)-2-(2-(4-chlorophenyl)-6-(3-(trifluoromethyl)phenyl)pyridin-3-yl)cyclopropanamine;
4-(3-((trans)-2-aminocyclopropyl)-6-(3-(trifluoromethyl)phenyl)pyridin-2-yl)phenol;
4-(3-((trans)-2-aminocyclopropyl)-6-(3-(trifluoromethyl)phenyl)pyridin-2-yl)benzamide;
(Trans)-2-(2-methyl-6-(3-(trifluoromethyl)phenyl)pyridin-3-yl)cyclopropanamine;
3-(5-((trans)-2-aminocyclopropyl)pyridin-2-yl)-5-hydroxybenzonitrile;
(Trans)-2-(6-(3-chloro-4-fluoro-5-methoxyphenyl)pyridin-3-yl)cyclopropanamine;
5-(5-((trans)-2-aminocyclopropyl)pyridin-2-yl)-3-chloro-2-fluorophenol;
6-(5-((trans)-2-aminocyclopropyl)pyridin-2-yl)benzo furan-2(3H)-one;
4-(5-((trans)-2-aminocyclopropyl)pyridin-2-yl)pyridin-2(1H)-one;
4'-((trans)-2-aminocyclopropyl)-5-chloro-4-fluorobiphenyl-3-ol;
4'-((trans)-2-aminocyclopropyl)-6-hydroxybiphenyl-3-carbonitrile;
N-(4'-((trans)-2-aminocyclopropyl)-6-hydroxybiphenyl-3-yl)methanesulfonamide;
3-(5-((trans)-2-aminocyclopropyl)pyridin-2-yl)-4-hydroxybenzonitrile;
N-(3-(5-((trans)-2-aminocyclopropyl)pyridin-2-yl)-4-hydroxyphenyl)methanesulfonamide;
N-(3-(5-((trans)-2-aminocyclopropyl)pyridin-2-yl)-5-(trifluoromethyl)phenyl)ethanesulfonamide;
N-(3-(5-((trans)-2-aminocyclopropyl)pyridin-2-yl)-5-(trifluoromethyl)phenyl)methanesulfonamide;
3-(6-((trans)-2-aminocyclopropyl)pyridin-3-yl)phenol;
(Trans)-2-(5-(3-methoxyphenyl)pyridin-2-yl)cyclopropanamine;
4-(6-((trans)-2-aminocyclopropyl)pyridin-3-yl)phenol;
2-(6-((trans)-2-aminocyclopropyl)pyridin-3-yl)phenol;
2-(5-((trans)-2-aminocyclopropyl)thiophen-2-yl)phenol;
3-(5-((trans)-2-aminocyclopropyl)thiophen-2-yl)phenol;
4-(5-((trans)-2-aminocyclopropyl)thiophen-2-yl)phenol;
2-(5-((trans)-2-aminocyclopropyl)thiazol-2-yl)phenol;
3-(5-((trans)-2-aminocyclopropyl)thiazol-2-yl)phenol;
4-(5-((trans)-2-aminocyclopropyl)thiazol-2-yl)phenol;
2-(2-((trans)-2-aminocyclopropyl)thiazol-5-yl)phenol;
3-(2-((trans)-2-aminocyclopropyl)thiazol-5-yl)phenol;
2-(2-((trans)-2-aminocyclopropyl)thiazol-5-yl)phenol;
3-(2-((trans)-2-aminocyclopropyl)thiazol-5-yl)phenol;
3-(5-((trans)-2-aminocyclopropyl)pyrimidin-2-yl)phenol; or
4-(5-((trans)-2-aminocyclopropyl)pyrimidin-2-yl)phenol.

In one embodiment, the invention provides a compound Formula (I), (II), (III), (IV) or (V) or a pharmaceutically acceptable salt or solvate thereof, wherein the compound is:
N-(3-(5-((trans)-2-aminocyclopropyl)pyridin-2-yl)-4-methoxyphenyl)methanesulfonamide;
N-(4'-((trans)-2-aminocyclopropyl)-5-chloro-[1,1'-biphenyl]-3-yl)methanesulfonamide;
N-(3-(5-((trans)-2-aminocyclopropyl)pyridin-2-yl)-5-chlorophenyl)methanesulfonamide;
N-(4'-((trans)-2-aminocyclopropyl)-4-fluoro-[1,1'-biphenyl]-3-yl)methanesulfonamide;
N-(5-(5-((trans)-2-aminocyclopropyl)pyridin-2-yl)-2-fluorophenyl)methanesulfonamide;
N-(3-(5-((trans)-2-aminocyclopropyl)pyridin-2-yl)phenyl)ethanesulfonamide;
N-(3-(5-((trans)-2-aminocyclopropyl)pyridin-2-yl)phenyl)-4-cyanobenzenesulfonamide;
N-(3-(5-((trans)-2-aminocyclopropyl)pyridin-2-yl)phenyl)-3-cyanobenzenesulfonamide;
N-(3-(5-((trans)-2-aminocyclopropyl)pyridin-2-yl)phenyl)-2-cyanobenzenesulfonamide;

N-(3-(5-((trans)-2-aminocyclopropyl)pyridin-2-yl)-5-(trifluoromethyl)phenyl)-4-cyanobenzenesulfonamide;
N-(4'-((trans)-2-aminocyclopropyl)-[1,1'-biphenyl]-3-yl)-1,1,1-trifluoromethanesulfonamide;
4'-((trans)-2-aminocyclopropyl)-6-hydroxy-[1,1'-biphenyl]-3-carbonitrile;
4'-((trans)-2-aminocyclopropyl)-[1,1'-biphenyl]-2-ol;
4'-((trans)-2-aminocyclopropyl)-3'-methoxy-[1,1'-biphenyl]-3-ol; or
N-(3-(5-((trans)-2-aminocyclopropyl)thiazol-2-yl)phenyl)-2-cyanobenzenesulfonamide.

In one specific aspect, the invention relates to a composition comprising a compound of Formula (I), (II), (III), (IV) or (V) as described and defined herein, in particular a heterocyclylpropylamine, phenylcyclopropylamine, or pyridinylcyclopropylamine as described herein, or a solvate or pharmaceutically acceptable salt thereof, wherein said compound is the (1S,2R) enantiomer (in respect to the substituents on the cyclopropyl ring) substantially free of the (1R,2S) enantiomer. As used herein "substantially free" means there is an excess of one enantiomer as compared to the other. Preferably "substantially free of (1R,2S) enantiomer" refers to more than 60% (1S, 2R) enantiomer and less than 40% (1R, 2S) enantiomer. Even more preferably, more than 75% (1S, 2R) enantiomer and less than 25% (1R,2S) enantiomer. Even more preferably, more than 90% (1S, 2R) enantiomer and less than 10% (1R,2S) enantiomer. Even more preferably, more than 95% (1S, 2R) enantiomer and less than 5% (1R,2S) enantiomer. Even more preferably, more than 99% (1S, 2R) enantiomer and less than 1% (1R, 2S) enantiomer. In calculating the total percent of the composition only the amounts of the 2 enantiomers (i.e., the (1S,2R) enantiomer and the (1R,2S) enantiomer) are used and sum to give 100%.

As used herein, the term "enantiomeric excess" or "ee" or "percent enantiomeric excess" refers to the difference between the mole fraction of one specific enantiomer (i.e., the specified enantiomer) and the mole fraction of the other enantiomer in relation to the sum of the mole fractions of both enantiomers, expressed as a percent value, and thus describes the extent of the excess of one specific enantiomer in relation to the other enantiomer. If, for example, a specific enantiomer is provided in the absence of the other enantiomer, the enantiomeric excess will be 100%, while a racemate comprising equal molar amounts of the two enantiomers will have an enantiomeric excess of 0%. Accordingly, the "enantiomeric excess" or "ee" or "percent enantiomeric excess" is defined by the following formula:

$$\frac{(\text{mole fraction of the specified enantiomer}) - (\text{mole fraction of the other enantiomer})}{(\text{mole fraction of the specified enantiomer}) + (\text{mole fraction of the other enantiomer})} \cdot 100$$

Thus, the invention relates to a composition comprising a compound of Formula (I), (II), (III), (IV) or (V) as described and defined herein, in particular a heterocyclylpropylamine, phenylcyclopropylamine, or pyridinylcyclopropylamine as described herein, or a solvate or pharmaceutically acceptable salt thereof, wherein said composition comprises the (1S,2R) enantiomer (in respect to the substituents on the cyclopropyl ring) of said compound substantially free of the (1R,2S) enantiomer, wherein said compound is chosen from:
(1S,2R)-2-(3'-(trifluoromethyl)biphenyl-4-yl)cyclopropanamine;
(1S,2R)-2-(terphenyl-4-yl)cyclopropanamine;
4'-((1S,2R)-2-aminocyclopropyl)biphenyl-4-ol;
4'-((1S,2R)-2-aminocyclopropyl)biphenyl-3-ol;
(1S,2R)-2-(6-(3-(trifluoromethyl)phenyl)pyridin-3-yl)cyclopropanamine;
(1S,2R)-2-(6-(3,5-dichlorophenyl)pyridin-3-yl)cyclopropanamine;
(1S,2R)-2-(6-(4-chlorophenyl)pyridin-3-yl)cyclopropanamine;
(1S,2R)-2-(6-(3-chlorophenyl)pyridin-3-yl)cyclopropanamine;
(1S,2R)-2-(6-(4-(trifluoromethyl)phenyl)pyridin-3-yl)cyclopropanamine;
(1S,2R)-2-(6-(4-methoxyphenyl)pyridin-3-yl)cyclopropanamine;
(1S,2R)-2-(6-(3-methoxyphenyl)pyridin-3-yl)cyclopropanamine;
4-(5-((1S,2R)-2-aminocyclopropyl)pyridin-2-yl)benzonitrile;
3-(5-((1S,2R)-2-aminocyclopropyl)pyridin-2-yl)benzonitrile;
(1S,2R)-2-(6-p-tolylpyridin-3-yl)cyclopropanamine;
(1S,2R)-2-(6-m-tolylpyridin-3-yl)cyclopropanamine;
4-(5-((1S,2R)-2-aminocyclopropyl)pyridin-2-yl)phenol;
3-(5-((1S,2R)-2-aminocyclopropyl)pyridin-2-yl)phenol;
4-(5-((1S,2R)-2-aminocyclopropyl)pyridin-2-yl)benzamide;
3-(5-((1S,2R)-2-aminocyclopropyl)pyridin-2-yl)benzamide;
2-(5-((1S,2R)-2-aminocyclopropyl)pyridin-2-yl)phenol;
3-(5-((1S,2R)-2-aminocyclopropyl)pyridin-2-yl)phenol;
(1S,2R)-2-(6-(3-methoxy-4-methylphenyl)pyridin-3-yl)cyclopropanamine;
5-(5-((1S,2R)-2-aminocyclopropyl)pyridin-2-yl)-2-fluorophenol;
3-(5-((1S,2R)-2-amninocyclopropyl)pyridin-2-yl)-5-fluorophenol;
3-(5-((1S,2R)-2-aminocyclopropyl)pyridine-2-yl)-4-fluorophenol;
3-(5-((1S,2R)-2-aminocyclopropyl)pyridin-2-yl)-2-fluorophenol;
3-(5-((1S,2R)-2-aminocyclopropyl)pyridin-2-yl)-2,4-difluorophenol;
3-(5-((1S,2R)-2-aminocyclopropyl)pyridin-2-yl)-2,4,6-trifluorophenol;
3-(5-((1S,2R)-2-aminocyclopropyl)pyridin-2-yl)-5-chlorophenol;
(1S,2R)-2-(6-(2-fluoro-3-(trifluoromethyl)phenyl)pyridin-3-yl)cyclopropanamine;
(1S,2R)-2-(6-(5-chlorothiophen-2-yl)pyridin-3-yl)cyclopropanamine;
(1S,2R)-2-(6-(5-methylthiophen-2-yl)pyridin-3-yl)cyclopropanamine;
(1S,2R)-2-(6-(1H-indol-6-yl)pyridin-3-yl)cyclopropanamine;
(1S,2R)-2-(6-(benzo[b]thiophen-5-yl)pyridin-3-yl)cyclopropanamine;
3-(5-((1S,2R)-2-aminocyclopropyl)-3-methylpyridin-2-yl)phenol;
(1S,2R)-2-(6-(3-chlorophenyl)-5-methylpyridin-3-yl)cyclopropanamine;
(1S,2R)-2-(5-methyl-6-(3-(trifluoromethyl)phenyl)pyridin-3-yl)cyclopropanamine;
(1S,2R)-2-(6-(4-fluoro-3-methoxyphenyl)pyridin-3-yl)cyclopropanamine;
(1S,2R)-2-(6-(3-fluoro-5-methoxyphenyl)pyridin-3-yl)cyclopropanamine;

(1S,2R)-2-(6-(2-fluoro-5-methoxyphenyl)pyridin-3-yl)cyclopropanamine;
(1S,2R)-2-(6-(2-fluoro-3-methoxyphenyl)pyridin-3-yl)cyclopropanamine;
(1S,2R)-2-(6-(3-chloro-5-methoxyphenyl)pyridin-3-yl)cyclopropanamine;
(1S,2R)-2-(6-(2-chloro-5-methoxyphenyl)pyridin-3-yl)cyclopropanamine;
(1S,2R)-2-(6-(3-methoxy-5-(trifluoromethyl)phenyl)pyridin-3-yl)cyclopropanamine;
3-(5-((1S,2R)-2-aminocyclopropyl)pyridin-2-yl)-5-methoxybenzonitrile;
5-(5-((1S,2R)-2-aminocyclopropyl)pyridin-2-yl)-2-methylphenol;
3-(5-((1S,2R)-2-aminocyclopropyl)pyridin-2-yl)-4-chlorophenol;
3-(5-((1S,2R)-2-aminocyclopropyl)pyridin-2-yl)-5-(trifluoromethyl)phenol;
(1S,2R)-2-(6-(2-fluoro-5-(trifluoromethyl)phenyl)pyridin-3-yl)cyclopropanamine;
(1S,2R)-2-(6-(2-chloro-5-(trifluoromethyl)phenyl)pyridin-3-yl)cyclopropanamine;
(1S,2R)-2-(6-(3,5-bis(trifluoromethyl)phenyl)pyridin-3-yl)cyclopropanamine;
N-(3-(5-((1S,2R)-2-aminocyclopropyl)pyridin-2-yl)phenyl)acetamide;
N-(3-(5-((1S,2R)-2-aminocyclopropyl)pyridin-2-yl)phenyl)methanesulfonamide;
(1S,2R)-2-(6-(benzo[b]thiophen-2-yl)pyridin-3-yl)cyclopropanamine;
(1S,2R)-2-(6-(benzo[b]thiophen-3-yl)pyridin-3-yl)cyclopropanamine;
5-(5-((1S,2R)-2-aminocyclopropyl)pyridin-2-yl)thiophene-2-carbonitrile;
(1S,2R)-2-(6-(4-methylthiophen-3-yl)pyridin-3-yl)cyclopropanamine;
(1S,2R)-2-(6-(3,4-difluoro-5-methoxyphenyl)pyridin-3-yl)cyclopropanamine;
5-(5-((1S,2R)-2-aminocyclopropyl)pyridin-2-yl)-2,3-difluorophenol;
(1S,2R)-2-(6-(1H-indazol-6-yl)pyridin-3-yl)cyclopropanamine;
(1S,2R)-2-(6-(9H-carbazol-2-yl)pyridin-3-yl)cyclopropanamine;
6-(5-((1S,2R)-2-amninocyclopropyl)pyridine-2-yl)indolin-2-one;
N-(3-(5-((1S,2R)-2-aminocyclopropyl)pyridin-2-yl)phenyl)benzenesulfonamide;
N-(3-(5-((1S,2R)-2-aminocyclopropyl)pyridin-2-yl)phenyl)propane-2-sulfonamide;
4'-((1S,2R)-2-aminocyclopropyl)-4-fluorobiphenyl-3-ol;
4'-((1S,2R)-2-aminocyclopropyl)-5-chlorobiphenyl-3-ol;
N-(4'-((1S,2R)-2-aminocyclopropyl)biphenyl-3-yl)benzenesulfonamide;
N-(4'-((1S,2R)-2-aminocyclopropyl)biphenyl-3-yl)propane-2-sulfonamide;
N-(4'-((1S,2R)-2-aminocyclopropyl)biphenyl-3-yl)methanesulfonamide;
N-(2-(5-((1S,2R)-2-aminocyclopropyl)pyridin-2-yl)phenyl)methanesulfonamide;
3-(5-((1S,2R)-2-aminocyclopropyl)pyridin-2-yl)-4-methoxybenzonitrile;
N-(4'-((1S,2R)-2-aminocyclopropyl)biphenyl-2-yl)methanesulfonamide;
4'-((1S,2R)-2-aminocyclopropyl)-6-methoxybiphenyl-3-carbonitrile;
N-(4'-((1S,2R)-2-aminocyclopropyl)-6-methoxybiphenyl-3-yl)methanesulfonamide;
(1S,2R)-2-(2-chloro-6-(3-(trifluoromethyl)phenyl)pyridin-3-yl)cyclopropanamine;
(1S,2R)-2-(2-(4-chlorophenyl)-6-(3-(trifluoromethyl)phenyl)pyridin-3-yl)cyclopropanamine;
4-(3-((1S,2R)-2-aminocyclopropyl)-6-(3-(trifluoromethyl)phenyl)pyridin-2-yl)phenol;
4-(3-((1S,2R)-2-aminocyclopropyl)-6-(3-(trifluoromethyl)phenyl)pyridin-2-yl)benzamide;
(1S,2R)-2-(2-methyl-6-(3-(trifluoromethyl)phenyl)pyridin-3-yl)cyclopropanamine;
3-(5-((1S,2R)-2-aminocyclopropyl)pyridin-2-yl)-5-hydroxybenzonitrile;
(1S,2R)-2-(6-(3-chloro-4-fluoro-5-methoxyphenyl)pyridin-3-yl)cyclopropanamine;
5-(5-((1S,2R)-2-aminocyclopropyl)pyridin-2-yl)-3-chloro-2-fluorophenol;
6-(5-((1S,2R)-2-aminocyclopropyl)pyridin-2-yl)benzofuran-2(3H)-one;
4-(5-((1S,2R)-2-aminocyclopropyl)pyridin-2-yl)pyridin-2(1H)-one;
4'-((1S,2R)-2-aminocyclopropyl)-5-chloro-4-fluorobiphenyl-3-ol;
4'-((1S,2R)-2-aminocyclopropyl)-6-hydroxybiphenyl-3-carbonitrile;
N-(4'-((1S,2R)-2-aminocyclopropyl)-6-hydroxybiphenyl-3-yl)methanesulfonamide;
3-(5-((1S,2R)-2-aminocyclopropyl)pyridin-2-yl)-4-hydroxybenzonitrile;
N-(3-(5-((1S,2R)-2-aminocyclopropyl)pyridin-2-yl)-4-hydroxyphenyl)methanesulfonamide;
N-(3-(5-((1S,2R)-2-aminocyclopropyl)pyridin-2-yl)-5-(trifluoromethyl)phenyl)ethanesulfonamide;
N-(3-(5-((1S,2R)-2-aminocyclopropyl)pyridin-2-yl)-5-(trifluoromethyl)phenyl)methanesulfonamide;
3-(6-((1S,2R)-2-aminocyclopropyl)pyridin-3-yl)phenol;
(1S,2R)-2-(5-(3-methoxyphenyl)pyridin-2-yl)cyclopropanamine;
4-(6-((1S,2R)-2-aminocyclopropyl)pyridin-3-yl)phenol;
2-(6-((1S,2R)-2-aminocyclopropyl)pyridin-3-yl)phenol;
2-(5-((1S,2R)-2-aminocyclopropyl)thiophen-2-yl)phenol;
3-(5-((1S,2R)-2-aminocyclopropyl)thiophen-2-yl)phenol;
4-(5-((1S,2R)-2-aminocyclopropyl)thiophen-2-yl)phenol;
2-(5-((1S,2R)-2-aminocyclopropyl)thiazol-2-yl)phenol;
3-(5-((1S,2R)-2-aminocyclopropyl)thiazol-2-yl)phenol;
4-(5-((1S,2R)-2-aminocyclopropyl)thiazol-2-yl)phenol;
2-(2-((1S,2R)-2-aminocyclopropyl)thiazol-5-yl)phenol;
3-(2-((1S,2R)-2-aminocyclopropyl)thiazol-5-yl)phenol;
2-(2-((1S,2R)-2-aminocyclopropyl)thiazol-5-yl)phenol;
3-(2-((1S,2R)-2-aminocyclopropyl)thiazol-5-yl)phenol;
3-(5-((1S,2R)-2-aminocyclopropyl)pyrimidin-2-yl)phenol;
4-(5-((1S,2R)-2-aminocyclopropyl)pyrimidin-2-yl)phenol;
N-(3-(5-((1S,2R)-2-aminocyclopropyl)pyridin-2-yl)-4-methoxyphenyl)methanesulfonamide;
N-(4'-((1S,2R)-2-amninocyclopropyl)-5-chloro-[1,1'-biphenyl]-3-yl)methanesulfonamide;
N-(3-(5-((1S,2R)-2-aminocyclopropyl)pyridin-2-yl)-5-chlorophenyl)methanesulfonamide;
N-(4'-((1S,2R)-2-aminocyclopropyl)-4-fluoro-[1,1'-biphenyl]-3-yl)methanesulfonamide;
N-(5-(5-((1S,2R)-2-aminocyclopropyl)pyridin-2-yl)-2-fluorophenyl)methanesulfonamide;
N-(3-(5-((1S,2R)-2-aminocyclopropyl)pyridin-2-yl)phenyl)ethanesulfonamide;
N-(3-(5-((1S,2R)-2-aminocyclopropyl)pyridin-2-yl)phenyl)-4-cyanobenzenesulfonamide;

N-(3-(5-((1S,2R)-2-aminocyclopropyl)pyridin-2-yl)phenyl)-3-cyanobenzenesulfonamide;
N-(3-(5-((1S,2R)-2-aminocyclopropyl)pyridin-2-yl)phenyl)-2-cyanobenzenesulfonamide;
N-(3-(5-((1S,2R)-2-aminocyclopropyl)pyridin-2-yl)-5-(trifluoromethyl)phenyl)-4-cyanobenzenesulfonamide;
N-(4'-((1S,2R)-2-aminocyclopropyl)-[1,1'-biphenyl]-3-yl)-1,1,1-trifluoromethanesulfonamide;
4'-((1S,2R)-2-aminocyclopropyl)-6-hydroxy-[1,1'-biphenyl]-3-carbonitrile;
4'-((1S,2R)-2-aminocyclopropyl)-[1,1'-biphenyl]-2-ol;
4'-((1S,2R)-2-aminocyclopropyl)-3'-methoxy-[1,1'-biphenyl]-3-ol; or
N-(3-(5-((1S,2R)-2-amninocyclopropyl)thiazol-2-yl)phenyl)-2-cyanobenzenesulfonamide.

In one embodiment the invention provides a compound of Formula (T), (II), (III), (IV) or (V) as defined herein or a solvate or pharmaceutically acceptable salt thereof, wherein said compound is the (1S,2R) enantiomer (in respect to the substituents on the cyclopropyl ring) substantially free of the (1R,2S) enantiomer.

In one embodiment the invention provides a compound of Formula (I), (II), (III), (IV) or (V) as defined herein or a solvate or pharmaceutically acceptable salt thereof, wherein said compound is the (1S,2R) enantiomer (in respect to the substituents on the cyclopropyl ring) substantially free of the (1R,2S) enantiomer for use in treating human disease. In one aspect, according to this embodiment, the human disease is chosen from cancer, a neurological discase or condition, or a viral infection. In one specific aspect, the cancer is prostate cancer. In another specific embodiment of this aspect the cancer is breast cancer. In another yet specific embodiment of this aspect the cancer is lung cancer. In another yet specific embodiment of this aspect the cancer is colorectal cancer. In another yet specific embodiment of this aspect the cancer is brain cancer. In another yet specific embodiment of this aspect the cancer is skin cancer. In another yet specific embodiment of this aspect the cancer is blood cancer (e.g., leukemia) or a lymphoma. In one aspect, the neurological disease or condition is depression, Huntington disease, Parkinson's disease, or Alzheimer's disease. In one aspect, the viral infection is HSV1 or HSV2.

In one specific aspect, the invention relates to a composition comprising a compound of Formula (I), (II), (III), (IV) or (V) as described and defined herein, in particular a heterocyclylpropylamine, phenylcyclopropylamine, or pyridinylcyclopropylamine as described herein, or a solvate or pharmaceutically acceptable salt thereof, wherein said compound is the (1R, 2S) enantiomer (in respect to the substituents on the cyclopropyl ring) substantially free of the (1S, 2R) enantiomer. As used herein "substantially free" means there is an excess of one enantiomer as compared to the other. Preferably "substantially free of the (1S,2R) enantiomer" refers to more than 60% (1R,2S) enantiomer and less than 40% (1S, 2R) enantiomer. Even more preferably, more than 75% (1R,2S) enantiomer and less than 25% (1S, 2R) enantiomer. Even more preferably, more than 90% (1R,2S) enantiomer and less than 10% (1S,2R) enantiomer. Even more preferably, more than 95% (1R, 2S) enantiomer and less than 5% (1S, 2R) enantiomer. Even more preferably, more than 99% (1R,2S) enantiomer and less than 1% (1S,2R) enantiomer. In calculating the total percent of the composition only the amounts of the 2 enantiomers (i.e., the (1R,2S) enantiomer and the (1S,2R) enantiomer) are used and sum to give 100%.

Thus, the invention relates to a composition comprising a compound of Formula (I), (II), (III), (IV) or (V) as described and defined herein, in particular a heterocyclylpropylamine, phenylcyclopropylamine, or pyridinylcyclopropylamine as described herein, or a solvate or pharmaceutically acceptable salt thereof, wherein said composition comprises the (1R,2S) enantiomer (in respect to the substituents on the cyclopropyl ring) of said compound substantially free of the (1S,2R) enantiomer wherein said compound is chosen from:

(1R,2S)-2-(3'-(trifluoromethyl)biphenyl-4-yl)cyclopropanamine;
(1R,2S)-2-(terphenyl-4-yl)cyclopropanamine;
4'-((1R,2S)-2-aminocyclopropyl)biphenyl-4-ol;
4'-((1R,2S)-2-aminocyclopropyl)biphenyl-3-ol;
(1R,2S)-2-(6-(3-(trifluoromethyl)phenyl)pyridin-3-yl)cyclopropanamine,
(1R,2S)-2-(6-(3,5-dichlorophenyl)pyridin-3-yl)cyclopropanamine;
(1R,2S)-2-(6-(4-chlorophenyl)pyridin-3-yl)cyclopropanamine;
(1R,2S)-2-(6-(3-chlorophenyl)pyridin-3-yl)cyclopropanamine;
(1R,2S)-2-(6-(4-(trifluoromethyl)phenyl)pyridin-3-yl)cyclopropanamine;
(1R,2S)-2-(6-(4-methoxyphenyl)pyridin-3-yl)cyclopropanamine;
(1R,2S)-2-(6-(3-methoxyphenyl)pyridin-3-yl)cyclopropanamine;
4-(5-((1R,2S)-2-aminocyclopropyl)pyridin-2-yl)benzonitrile;
3-(5-((1R,2S)-2-aminocyclopropyl)pyridin-2-yl)benzonitrile;
(1R,2S)-2-(6-p-tolylpyridin-3-yl)cyclopropanamine;
(1R,2S)-2-(6-m-tolylpyridin-3-yl)cyclopropanamine;
4-(5-((1R,2S)-2-aminocyclopropyl)pyridin-2-yl)phenol;
3-(5-((1R,2S)-2-aminocyclopropyl)pyridin-2-yl)phenol;
4-(5-((1R,2S)-2-aminocyclopropyl)pyridin-2-yl)benzamide;
3-(5-((1R,2S)-2-aminocyclopropyl)pyridin-2-yl)benzamide;
2-(5-((1R,2S)-2-aminocyclopropyl)pyridin-2-yl)phenol;
3-(5-((1R,2S)-2-aminocyclopropyl)pyridin-2-yl)phenol;
(1R,2S)-2-(6-(3-methoxy-4-methylphenyl)pyridin-3-yl)cyclopropanamine;
5-(5-((1R,2S)-2-aminocyclopropyl)pyridin-2-yl)-2-fluorophenol;
3-(5-((1R,2S)-2-amninocyclopropyl)pyridin-2-yl)-5-fluorophenol;
3-(5-((1R,2S)-2-amninocyclopropyl)pyridin-2-yl)-4-fluorophenol;
3-(5-((1R,2S)-2-aminocyclopropyl)pyridin-2-yl)-2-fluorophenol;
3-(5-((1R,2S)-2-aminocyclopropyl)pyridin-2-yl)-2,4-difluorophenol;
3-(5-((1R,2S)-2-aminocyclopropyl)pyridin-2-yl)-2,4,6-trifluorophenol;
3-(5-((1R,2S)-2-aminocyclopropyl)pyridin-2-yl)-5-chlorophenol;
(1R,2S)-2-(6-(2-fluoro-3-(trifluoromethyl)phenyl)pyridin-3-yl)cyclopropanamine;
(1R,2S)-2-(6-(5-chlorothiophen-2-yl)pyridin-3-yl)cyclopropanamine;
(1R,2S)-2-(6-(5-methylthiophen-2-yl)pyridin-3-yl)cyclopropanamine;
(1R,2S)-2-(6-(1H-indol-6-yl)pyridin-3-yl)cyclopropanamine;
(1R,2S)-2-(6-(benzo[b]thiophen-5-yl)pyridin-3-yl)cyclopropanamine;

3-(5-((1R,2S)-2-aminocyclopropyl)-3-methylpyridin-2-yl) phenol;
(1R,2S)-2-(6-(3-chlorophenyl)-5-methylpyridin-3-yl)cyclopropanamine;
(1R,2S)-2-(5-methyl-6-(3-(trifluoromethyl)phenyl)pyridin-3-yl)cyclopropanamine;
(1R,2S)-2-(6-(4-fluoro-3-methoxyphenyl)pyridin-3-yl)cyclopropanamine;
(1R,2S)-2-(6-(3-fluoro-5-methoxyphenyl)pyridin-3-yl)cyclopropanamine;
(1R,2S)-2-(6-(2-fluoro-5-methoxyphenyl)pyridin-3-yl)cyclopropanamine;
(1R,2S)-2-(6-(2-fluoro-3-methoxyphenyl)pyridin-3-yl)cyclopropanamine;
(1R,2S)-2-(6-(3-chloro-5-methoxyphenyl)pyridin-3-yl)cyclopropanamine;
(1R,2S)-2-(6-(2-chloro-5-methoxyphenyl)pyridin-3-yl)cyclopropanamine;
(1R,2S)-2-(6-(3-methoxy-5-(trifluoromethyl)phenyl)pyridin-3-yl)cyclopropanamine;
3-(5-((1R,2S)-2-aminocyclopropyl)pyridin-2-yl)-5-methoxybenzonitrile;
5-(5-((1R,2S)-2-aminocyclopropyl)pyridin-2-yl)-2-methylphenol;
3-(5-((1R,2S)-2-amninocyclopropyl)pyridin-2-yl)-4-chlorophenol;
3-(5-((1R,2S)-2-aminocyclopropyl)pyridin-2-yl)-5-(trifluoromethyl)phenol;
(1R,2S)-2-(6-(2-fluoro-5-(trifluoromethyl)phenyl)pyridin-3-yl)cyclopropanamine;
(1R,2S)-2-(6-(2-chloro-5-(trifluoromethyl)phenyl)pyridin-3-yl)cyclopropanamine;
(1R,2S)-2-(6-(3,5-bis(trifluoromethyl)phenyl)pyridin-3-yl) cyclopropanamine;
N-(3-(5-((1R,2S)-2-aminocyclopropyl)pyridin-2-yl)phenyl) acetamide;
N-(3-(5-((1R,2S)-2-aminocyclopropyl)pyridin-2-yl)phenyl) methanesulfonamide;
(1R,2S)-2-(6-(benzo[b]thiophen-2-yl)pyridin-3-yl)cyclopropanamine;
(1R,2S)-2-(6-(benzo[b]thiophen-3-yl)pyridin-3-yl)cyclopropanamine;
5-(5-((1R,2S)-2-aminocyclopropyl)pyridin-2-yl)thiophene-2-carbonitrile;
(1R,2S)-2-(6-(4-methylthiophen-3-yl)pyridin-3-yl)cyclopropanamine;
(1R,2S)-2-(6-(3,4-difluoro-5-methoxyphenyl)pyridin-3-yl) cyclopropanamine;
5-(5-((1R,2S)-2-aminocyclopropyl)pyridin-2-yl)-2,3-difluorophenol;
(1R,2S)-2-(6-(1H-indazol-6-yl)pyridin-3-yl)cyclopropanamine;
(1R,2S)-2-(6-(9H-carbazol-2-yl)pyridin-3-yl)cyclopropanamine;
6-(5-((1R,2S)-2-aminocyclopropyl)pyridin-2-yl)indolin-2-one;
N-(3-(5-((1R,2S)-2-aminocyclopropyl)pyridin-2-yl)phenyl) benzenesulfonamide;
N-(3-(5-((1R,2S)-2-aminocyclopropyl)pyridin-2-yl)phenyl) propane-2-sulfonamide;
4'-((1R,2S)-2-aminocyclopropyl)-4-fluorobiphenyl-3-ol;
4'-((1R,2S)-2-aminocyclopropyl)-5-chlorobiphenyl-3-ol;
N-(4'-((1R,2S)-2-aminocyclopropyl)biphenyl-3-yl)benzenesulfonamide;
N-(4'-((1R,2S)-2-aminocyclopropyl)biphenyl-3-yl)propane-2-sulfonamide;
N-(4'-((1R,2S)-2-aminocyclopropyl)biphenyl-3-yl)methanesulfonamide;
N-(2-(5-((1R,2S)-2-aminocyclopropyl)pyridin-2-yl)phenyl) methanesulfonamide;
3-(5-((1R,2S)-2-aminocyclopropyl)pyridin-2-yl)-4-methoxybenzonitrile;
N-(4'-((1R,2S)-2-aminocyclopropyl)biphenyl-2-yl)methanesulfonamide;
4'-((1R,2S)-2-aminocyclopropyl)-6-methoxybiphenyl-3-carbonitrile;
N-(4'-((1R,2S)-2-aminocyclopropyl)-6-methoxybiphenyl-3-yl)methanesulfonamide;
(1R,2S)-2-(2-chloro-6-(3-(trifluoromethyl)phenyl)pyridin-3-yl)cyclopropanamine;
(1R,2S)-2-(2-(4-chlorophenyl)-6-(3-(trifluoromethyl)phenyl)pyridin-3-yl)cyclopropanamine;
4-(3-(1R,2S)-2-aminocyclopropyl)-6-(3-(trifluoromethyl) phenyl)pyridin-2-yl)phenol;
4-(3-(1R,2S)-2-aminocyclopropyl)-6-(3-(trifluoromethyl) phenyl)pyridin-2-yl)benzamide;
(1R,2S)-2-(2-methyl-6-(3-(trifluoromethyl)phenyl)pyridin-3-yl)cyclopropanamine;
3-(5-((1R,2S)-2-aminocyclopropyl)pyridin-2-yl)-5-hydroxybenzonitrile;
(1R,2S)-2-(6-(3-chloro-4-fluoro-5-methoxyphenyl)pyridin-3-yl)cyclopropanamine;
5-(5-((1R,2S)-2-aminocyclopropyl)pyridin-2-yl)-3-chloro-2-fluorophenol;
6-(5-((1R,2S)-2-aminocyclopropyl)pyridin-2-yl)benzofuran-2(3H)-one;
4-(5-((1R,2S)-2-aminocyclopropyl)pyridin-2-yl)pyridin-2 (1H)-one;
4'-((1R,2S)-2-aminocyclopropyl)-5-chloro-4-fluorobiphenyl-3-ol;
4'-((1R,2S)-2-aminocyclopropyl)-6-hydroxybiphenyl-3-carbonitrile;
N-(4'-((1R,2S)-2-aminocyclopropyl)-6-hydroxybiphenyl-3-yl)methanesulfonamide;
3-(5-((1R,2S)-2-amninocyclopropyl)pyridin-2-yl)-4-hydroxybenzonitrile;
N-(3-(5-((1R,2S)-2-aminocyclopropyl)pyridin-2-yl)-4-hydroxyphenyl)methanesulfonamide;
N-(3-(5-((1R,2S)-2-aminocyclopropyl)pyridin-2-yl)-5-(trifluoromethyl)phenyl)ethanesulfonamide;
N-(3-(5-((1R,2S)-2-aminocyclopropyl)pyridin-2-yl)-5-(trifluoromethyl)phenyl)methanesulfonamide;
3-(6-((1R,2S)-2-aminocyclopropyl)pyridin-3-yl)phenol;
(1R,2S)-2-(5-(3-methoxyphenyl)pyridin-2-yl)cyclopropanamine;
4-(6-((1R,2S)-2-aminocyclopropyl)pyridin-3-yl)phenol;
2-(6-((1R,2S)-2-aminocyclopropyl)pyridin-3-yl)phenol;
2-(5-((1R,2S)-2-aminocyclopropyl)thiophen-2-yl)phenol;
3-(5-((1R,2S)-2-aminocyclopropyl)thiophen-2-yl)phenol;
4-(5-((1R,2S)-2-aminocyclopropyl)thiophen-2-yl)phenol;
2-(5-((1R,2S)-2-aminocyclopropyl)thiazol-2-yl)phenol;
3-(5-((1R,2S)-2-aminocyclopropyl)thiazol-2-yl)phenol;
4-(5-((1R,2S)-2-aminocyclopropyl)thiazol-2-yl)phenol;
2-(2-((1R,2S)-2-aminocyclopropyl)thiazol-5-yl)phenol;
3-(2-((1R,2S)-2-amninocyclopropyl)thiazol-5-yl)phenol;
2-(2-((1R,2S)-2-aminocyclopropyl)thiazol-5-yl)phenol;
3-(2-((1R,2S)-2-aminocyclopropyl)thiazol-5-yl)phenol;
3-(5-((1R,2S)-2-aminocyclopropyl)pyrimidin-2-yl)phenol;
4-(5-((1R,2S)-2-aminocyclopropyl)pyrimidin-2-yl)phenol;
N-(3-(5-((1R,2S)-2-aminocyclopropyl)pyridin-2-yl)-4-methoxyphenyl)methanesulfonamide;
N-(4'-((1R,2S)-2-aminocyclopropyl)-5-chloro-[1,1'-biphenyl]-3-yl)methanesulfonamide;

N-(3-(5-((1R,2S)-2-aminocyclopropyl)pyridin-2-yl)-5-chlorophenyl)methanesulfonamide;
N-(4'-((1R,2S)-2-aminocyclopropyl)-4-fluoro-[1,1'-biphenyl]-3-yl)methanesulfonamide;
N-(5-(5-((1R,2S)-2-aminocyclopropyl)pyridin-2-yl)-2-fluorophenyl)methanesulfonamide;
N-(3-(5-((1R,2S)-2-aminocyclopropyl)pyridin-2-yl)phenyl)ethanesulfonamide;
N-(3-(5-((1R,2S)-2-aminocyclopropyl)pyridin-2-yl)phenyl)-4-cyanobenzenesulfonamide;
N-(3-(5-((1R,2S)-2-aminocyclopropyl)pyridin-2-yl)phenyl)-3-cyanobenzenesulfonamide;
N-(3-(5-((1R,2S)-2-aminocyclopropyl)pyridin-2-yl)phenyl)-2-cyanobenzenesulfonamide;
N-(3-(5-((1R,2S)-2-aminocyclopropyl)pyridin-2-yl)-5-(trifluoromethyl)phenyl)-4-cyanobenzenesulfonamide;
N-(4'-((1R,2S)-2-aminocyclopropyl)-[1,1'-biphenyl]-3-yl)-1,1,1-trifluoromethanesulfonamide;
4'-((1R,2S)-2-aminocyclopropyl)-6-hydroxy-[1,1'-biphenyl]-3-carbonitrile;
4'-((1R,2S)-2-aminocyclopropyl)-[1,1'-biphenyl]-2-ol;
4'-((1R,2S)-2-aminocyclopropyl)-3'-methoxy-[1,1'-biphenyl]-3-ol; or
N-(3-(5-((1R,2S)-2-aminocyclopropyl)thiazol-2-yl)phenyl)-2-cyanobenzenesulfonamide.

In one embodiment, the invention provides a compound of Formula (I), (II), (III), (IV) or (V) as defined herein or a solvate or pharmaceutically acceptable salt thereof, wherein said compound is the (1R,2S) enantiomer (in respect to the substituents on the cyclopropyl ring) substantially free of the (1S,2R) enantiomer.

In one embodiment the invention provides a compound of Formula (I), (II), (III), (IV) or (V) as defined herein or a solvate or pharmaceutically acceptable salt thereof, wherein said compound is the (1R,2S) enantiomer (in respect to the substituents on the cyclopropyl ring) substantially free of the (1S,2R) enantiomer for use in treating human disease. In one aspect, according to this embodiment, the human disease is chosen from cancer, a neurological disease or condition, or a viral infection. In one specific aspect, the cancer is prostate cancer. In another specific embodiment of this aspect the cancer is breast cancer. In another yet specific embodiment of this aspect the cancer is lung cancer. In another yet specific embodiment of this aspect the cancer is colorectal cancer. In another yet specific embodiment of this aspect the cancer is brain cancer. In another yet specific embodiment of this aspect the cancer is skin cancer. In another yet specific embodiment of this aspect the cancer is blood cancer (e.g., leukemia) or a lymphoma. In one aspect, the neurological disease or condition is depression, Huntington disease, Parkinson disease, or Alzheimer disease. In one aspect, the viral infection is HSV1 or HSV2.

DETAILED DESCRIPTION OF THE INVENTION

Definitions

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

As used herein, the term "acyl," refers to a carbonyl attached to an alkenyl, alkyl, aryl, cycloalkyl, heteroaryl, heterocyclyl, or any other moiety where the atom attached to the carbonyl is carbon. An "acetyl" group refers to a $-C(=O)CH_3$ group. An "alkylcarbonyl" or "alkanoyl" group refers to an alkyl group attached to the parent molecular moiety through a carbonyl group. Examples of such groups include, but are not limited to, methylcarbonyl or ethylcarbonyl. Examples of acyl groups include, but are not limited to, formyl, alkanoyl or aroyl.

As used herein, the term "acyloxy," refers to an acyl group attached to the parent moiety through an oxygen atom.

As used herein, the term "alkenyl," refers to a straight-chain or branched-chain hydrocarbon group having one or more double bonds and containing from 2 to 20 carbon atoms. A (C2-C6)alkenyl has from 2 to 6 carbon atoms.

As used herein, the term "alkenylene," refers to a carbon-carbon double bond system attached at two or more positions such as ethenylene e.g., $-CH=CH-$. Examples of suitable alkenyl groups include, but are not limited to, ethenyl, propenyl, 2-methylpropenyl, or 1,4-butadienyl.

As used herein, the term "alkoxy," refers to an alkyl ether group, wherein the term alkyl is as defined below. Examples of suitable alkyl ether groups include, but are not limited to, methoxy, ethoxy, n-propoxy, isopropoxy, n-butoxy, iso-butoxy, sec-butoxy, tert-butoxy, or n-pentoxy.

As used herein, the term "alkyl," refers to a straight-chain or branched-chain alkyl group containing from 1 to 20 carbon atoms. A (C1-C10)alkyl has from 1 to 10 carbon atoms and a (C1-C6)alkyl has from 1 to 6 carbon atoms and a (C1-C4)alkyl has from 1 to 4 carbon atoms. Examples of alkyl groups include, but are not limited to, methyl, ethyl, n-propyl, isopropyl, n-butyl, isobutyl, sec-butyl, tert-butyl, pentyl, isopentyl, neo-pentyl, iso-amyl, hexyl, heptyl, octyl, or noyl.

As used herein, the term "alkylene," refers to a saturated aliphatic group having from 1 to 20 carbons and is derived from a straight or branched chain saturated hydrocarbon attached at two or more positions. Alkylene groups include, but are not limited to, methylene ($-CH_2-$), ethylene $-CH_2CH_2-$, propylene ($-CH_2CH_2CH_2-$) or isopropylene ($-CH(CH_3)CH_2-$).

As used herein, the term "alkylamino," refers to an alkyl group attached to the parent molecular moiety through an amino group. Suitable alkylamino groups may be mono- or dialkylated, forming groups including, but not limited to N-methylamino, N-ethylamino, N,N-dimethylamino, N,N-ethylmethylamino, N,N-diethylamino, N-propylamino, or N,N-methylpropylamino.

As used herein, the term "alkylidene," refers to an alkenyl group in which one carbon atom of the carbon-carbon double bond belongs to the moiety to which the alkenyl group is attached.

As used herein, the term "alkylthio," refers to an alkyl thioether (R—S—) group wherein the term R is an alkyl is as defined above wherein the group is attached to the parent molecule through the sulfur group. Examples of suitable alkyl thioether groups include, but are not limited to, methylthio, ethylthio, n-propylthio, isopropylthio, n-butylthio, iso-butylthio, sec-butylthio, or tert-butylthio.

As used herein, the term "alkynyl," as used herein, refers to a straight-chain or branched-chain hydrocarbon group having one or more triple bonds and containing from 2 to 20 carbon atoms. A (C2-C6)alkynyl has from 2 to 6 carbon atoms. A (C2-C4)alkynyl has from 2 to 4 carbon atoms. Examples of alkynyl groups include, but are not limited to, ethynyl, propynyl, hydroxypropynyl, butyn-1-yl, butyn-2-yl, pentyn-1-yl, 3-methylbutyn-1-yl, or hexyn-2-yl.

As used herein, the term "alkynylene," refers to a carbon-carbon triple bond attached at two positions such as ethynylene (—C≡C—).

As used herein, the terms "amido" and "carbamoyl," refer to an amino group as described below attached to the parent molecular moiety through a carbonyl group (e.g., —C(=O)NRR'), or vice versa (—N(R)C(=O)NR'). "Amido" and "carbamoyl" encompass "C-amido", "N-amido" and "acylamino" as defined herein. R and R' are as defined herein.

As used herein, the term "C-amido," refers to a —C(=O)NRR' group with R and R' as defined herein.

As used herein, the term "N-amido," refers to a R'C(=O)NR— group, with R and R' as defined herein.

As used herein, the term "acylamino," refers to an acyl group attached to the parent moiety through an amino group. An example of an "acylamino" group includes, but is not limited to, acetylamino (CH$_3$C(=O)NH—).

As used herein, the term "amino," refers to —NRR', wherein R and R' are independently selected from the group consisting of hydrogen, alkyl, heteroalkyl, aryl, carbocyclyl, and heterocyclyl. Additionally, R and R' may be combined to form a heterocyclyl.

As used herein, the term "aryl," refers a carbocyclic aromatic system containing one ring, or two or three rings fused together where in the ring atoms are all carbon. The term "aryl" groups includes, but is not limited to groups such as phenyl, naphthyl, or anthracenyl.

As used herein, the term "arylalkenyl" or "aralkenyl," refers to an aryl group attached to the parent molecular moiety through an alkenyl group.

As used herein, the term "arylalkoxy" or "aralkoxy," refers to an aryl group attached to the parent molecular moiety through an alkoxy group. Examples of arylalkoxy groups include, but are not limited to, benzyloxy or phenethoxy.

As used herein, the term "arylalkyl" or "aralkyl," refers to an aryl group attached to the parent molecular moiety through an alkyl group.

As used herein, the term "arylalkynyl" or "aralkynyl," refers to an aryl group attached to the parent molecular moiety through an alkynyl group.

As used herein, the term "arylalkanoyl" or "aralkanoyl" or "aroyl," refers to an acyl group derived from an aryl-substituted alkanecarboxylic acid including, but not limited to, benzoyl, napthoyl, phenylacetyl, 3-phenylpropionyl (hydrocinnamoyl), 4-phenylbutyryl, (2-naphthyl)acetyl, or 4-chlorohydrocinnamoyl.

As used herein, the term "aryloxy," refers to an aryl group attached to the parent molecular moiety through an oxy (—O—).

As used herein, the terms "benzo" and "benz," refer to the divalent group C$_6$H$_4$=derived from benzene. Examples include, but are not limited to, benzothiophene or benzimidazole.

As used herein, the term "carbamate," refers to an O-carbamyl or N-carbamyl group as defined herein.

As used herein, the term "O-carbamyl" refers to a —OC(=O)NRR', group- with R and R' as defined herein.

As used herein, the term "N-carbamyl" refers to a ROC(=O)NR'— group, with R and R' as defined herein.

As used herein, the term "carbonyl," when alone includes formyl —C(=O)H and in combination is a —C(=O)— group.

As used herein, the term "carboxyl" or "carboxy" refers to —C(=O)OH or the corresponding "carboxylate" anion, such as is in a carboxylic acid salt. An "O-carboxy" group refers to a RC(=O)O— group, where R is as defined herein. A "C-carboxy" group refers to a —C(=O)OR groups where R is as defined herein.

As used herein, the term "cyano" refers to —CN.

As used herein, the term "carbocyclyl" refers to a saturated or partially saturated monocyclic or a fused bicyclic or tricyclic group wherein the ring atoms of the cyclic system are all carbon and wherein each cyclic moiety contains from 3 to 12 carbon atom ring members. "Carbocyclyl" encompasses benzo fused to a carbocyclyl ring system. One group of carbocyclyls have from 5 to 7 carbon atoms. Examples of carbocyclyl groups include, but are not limited to, cyclopropyl, cyclobutyl, cyclopentyl, cyclohexyl, and cycloheptyl, tetrahydronapthyl, indanyl, octahydronaphthyl, 2,3-dihydro-1H-indenyl, or adamantyl.

As used herein, the term "cycloalkyl" refers to a saturated monocyclic, bicyclic or tricyclic group wherein the ring atoms of the cyclic system are all carbon and wherein each cyclic moiety contains from 3 to 12 carbon atom ring members. One group of cycloalkyls has from 5 to 7 carbon atoms. Examples of cycloalkyl groups include, but are not limited to, cyclopropyl, cyclobutyl, cyclopentyl, cyclohexyl, cycloheptyl, or adamantyl.

As used herein, the term "cycloalkenyl" refers to a partially saturated monocyclic, bicyclic or tricyclic group wherein the ring atoms of the cyclic system are all carbon and wherein each cyclic moiety contains from 3 to 12 carbon atom ring members. One group of carboalkenyls have from 5 to 7 carbon atoms. Examples of cycloalkenyl groups include, but are not limited to, cyclobutenyl, cyclopentenyl, or cyclohexenyl.

As used herein, the term "cyclyl" refers to an aryl, heterocyclyl, or carbocyclyl group as defined herein.

As used herein, the term "ester" refers to a carboxy group bridging two moieties linked at carbon atoms.

As used herein, the term "ether" refers to an oxy group bridging two moieties linked at carbon atoms.

As used herein, the term "halo" or "halogen" refers to fluorine, chlorine, bromine, or iodine.

As used herein, the term "haloalkoxy" refers to a haloalkyl group attached to the parent molecular moiety through an oxygen atom. Examples of haloalkoxy groups include, but are not limited to, trifluoromethoxy, 2-fluoroethoxy, or 3-chloropropoxy.

As used herein, the term "haloalkyl" refers to an alkyl group having the meaning as defined above wherein one or more hydrogens are replaced with a halogen. Specifically embraced are monohaloalkyl, dihaloalkyl or polyhaloalkyl groups. A monohaloalkyl group, for one example, may have an iodo, bromo, chloro or fluoro atom within the group. Dihalo or polyhaloalkyl groups may have two or more of the same halo atoms or a combination of different halo groups. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl or dichloropropyl.

As used herein, "haloalkylene" refers to a haloalkyl group attached at two or more positions. Examples include, but are not limited to, fluoromethylene (—CFH—), difluoromethylene (—CF$_2$—), or chloromethylene (—CHCl—).

As used herein, the term "heteroalkyl" refers to a straight or branched alkyl chain, wherein one, two, or three carbons forming the alkyl chain are each replaced by a heteroatom independently selected from the group consisting of O, N, and S, and wherein the nitrogen and/or sulfur heteroatom(s) (if present) may optionally be oxidized and the nitrogen heteroatom(s) (if present) may optionally be quaternized. The heteroatom(s) O, N and S may, for example, be placed at an interior position of the heteroalkyl group, i.e., the heteroalkyl may be bound to the remainder of the molecule via a carbon atom. Up to two heteroatoms may be consecutive, such as, for example, —CH$_2$—NH—OCH$_3$.

As used herein, the term "heteroalkylene" refers to a heteroalkyl group attached at two positions. Examples include, but are not limited to, —CH$_2$OCH$_2$—, —CH$_2$SCH$_2$—, and —CH$_2$NHCH$_2$—, —CH$_2$S—, or —CH$_2$NHCH(CH$_3$)CH$_2$—.

As used herein, the term "heteroaryl," refers to a 3 to 7 membered unsaturated monocyclic ring, or a fused monocyclic, bicyclic, or tricyclic ring system in which the rings are aromatic and which at least one ring contains at least one atom selected from the group consisting of O, S, and N. One group of heteroaryls has from 5 to 7 carbon atoms. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "heterocyclyl" or "hetercycle," each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur wherein the nitron or sulfur atoms may be oxidized (e.g., —N═O, —S(═O)—, or —S(═O)$_2$—). Additionally, 1, 2, or 3 of the carbon atoms of the heterocyclyl may be optionally oxidized (e.g., to give an oxo group or ═O). One group of heterocyclyls has from 1 to 4 heteroatoms as ring members. Another group of heterocyclyls has from 1 to 2 heteroatoms as ring members. One group of heterocyclyls has from 3 to 8 ring members in each ring. Yet another group of heterocyclyls has from 3 to 7 ring members in each ring. Again another group of heterocyclyls has from 5 to 6 ring members in each ring. "Heterocyclyl" is intended to encompass a heterocyclyl group fused to a carbocyclyl or benzo ring systems. Examples of heterocyclyl groups include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, or imidazolidinyl. Examples of heteroaryls that are heterocyclyls include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "heterocycloalkyl," refers to a heterocyclyl group that is not fully saturated e.g., one or more of the rings systems of a heterocycloalkyl is not aromatic. Examples of heterocycloalkyls include piperazinyl, morpholinyl, piperidinyl, or pyrrolidinyl.

As used herein, the term "hydroxyl," as used herein, refers to —OH.

As used herein, the term "hydroxyalkyl," as used herein, refers to a hydroxyl group attached to the parent molecular moiety through an alkyl group.

As used herein, the phrase "in the main chain," refers to the longest contiguous or adjacent chain of carbon atoms starting at the point of attachment of a group to the compounds of any one of the formulas disclosed herein.

As used herein, the term "isocyanato," refers to a —N═C═O group.

As used herein, the term "isothiocyanato," refers to a —N═C═S group.

As used herein, the term phrase "linear chain of atoms" refers to the longest straight chain of atoms independently selected from carbon, nitrogen, oxygen and sulfur.

As used herein, the term "lower," where not otherwise specifically defined, means containing from 1 to and including 6 carbon atoms.

As used herein, the term "lower aryl," means phenyl or naphthyl.

As used herein, the term "lower heteroaryl," means either 1) monocyclic heteroaryl comprising five or six ring members, of which between one and four said members may be heteroatoms selected from O, S, or N.

As used herein, the term "lower cycloalkyl," refers to a monocyclic cycloalkyl having between three and six ring members. Examples of lower cycloalkyl include, but are not limited to, cyclopropyl, cyclobutyl, cyclopentyl, and cyclohexyl.

As used herein, the term "lower heterocyclyl," refers to a monocyclic heterocyclyls having between three and six ring members, of which between one and four may be heteroatoms selected from the group consisting of O, S, and N wherein the N and S group may be optionally oxidized (e.g., —N(═O)—, —S(═O)—, and —S(═O)$_2$—)). Examples of lower heterocyclyls include, but are not limited to, pyrrolidinyl, imidazolidinyl, pyrazolidinyl, piperidinyl, piperazinyl, and morpholinyl. Lower heterocyclyls may be saturated or partially unsaturated which is a lower heterocycloalkyl.

As used herein, the term "lower amino," refers to —NRR', wherein R and R' are independently selected from the group consisting of hydrogen, lower alkyl, and lower heteroalkyl. Additionally, the R and R' of a lower amino group may combine to form a five- or six-membered heterocycloalkyl.

As used herein, the term "mercaptyl," refers to an RS— group, where R is as defined herein.

As used herein, the term "nitro," refers to —NO$_2$.

As used herein, the terms "oxy" or "oxa," refer to —O—.

As used herein, the term "oxo," refers to ═O.

As used herein, the terms "sulfonate" "sulfonic acid" and "sulfonic," refers to the —SO$_3$H group and its anion as the sulfonic acid is used in salt formation.

As used herein, the term "sulfanyl," to —S—.

As used herein, the term "sulfinyl," refers to —S(═O)(R)—, with R as defined herein.

As used herein, the term "sulfonyl," refers to —S(═O)$_2$R, with R as defined herein.

As used herein, the term "sulfonamide", refers to an N-sulfonamido or S-sulfonamido group as defined herein.

As used herein, the term "N-sulfonamido," refers to a $RS(=O)_2N(R')$— group with R and R' as defined herein. Exemplary, non-limiting N-sulfonamido groups are —$NHSO_2CH_3$, —$NHSO_2CH_2CH_3$, —$NHSO_2$(phenyl), —$NHSO_2$(isopropyl), —$NHSO_2$(-phenyl-CN), or —$NHSO_2CF_3$, particularly —$NHSO_2CH_3$, —$NHSO_2CH_2CH_3$, —$NHSO_2$(phenyl), or —$NHSO_2$(isopropyl).

As used herein, the term "S-sulfonamido," refers to a —$S(=O)_2NRR'$, group, with R and R' as defined herein. An exemplary, non-limiting S-sulfonamido group is —$S(=O)_2NHCH_3$.

As used herein, the terms "thia" and "thio," refer to a —S— group or another wherein the oxygen is replaced with sulfur. The oxidized derivatives of the thio group, namely sulfinyl and sulfonyl, are included in the definition of thia and thio.

As used herein, the term "thiol," refers to an —SH group.

As used herein, the term "thiocarbonyl," when alone includes thioformyl —$C(=S)R$ group with R as defined herein.

As used herein, the term "N-thiocarbamyl," refers to an $ROC(=S)N(R')$— group, with R and R' as defined herein.

As used herein, the term "O-thiocarbamyl," refers to a —$OC(=S)NRR'$ group with R and R' as defined herein.

As used herein, the term "thiocyanato," refers to a —S—C≡N group.

As used herein, the term "trihalomethanesulfonamido," refers to a $X_3CS(=O)_2N(R)$— group where X is an independently chosen halogen and R as defined herein.

As used herein, the term "trihalomethanesulfonyl," refers to a $X_3CS(=O)_2$— group where X is an independently chosen halogen.

As used herein, the term "trihalomethoxy," refers to a $X_3CO$— group where X is an independently chosen halogen.

As used herein, the term "trisubstituted silyl," refers to a silicone group substituted at its three free valences with groups as listed herein under the definition of for R and R'. Examples include, but are not limited to, trimethysilyl, tert-butyldimethylsilyl, or triphenylsilyl.

As used herein, the term "urea," refers to a —$N(R)C(=O)N(R)$ group wherein R and R' are as defined herein.

As used herein, the term "optionally substituted" means the proceeding or anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxyl, amino, lower alkylamino, arylamino, aminoalkyl, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, carbamate, and urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g. —$CF_2CF_3$), monosubstituted (e.g. —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with." In one specific definition, the optional substituents are chosen from hydroxyl, halo, alkyl, alkoxy, haloalkyl, haloalkoxy, —$N((C1-C3)alkyl)_2$, —$NH((C1-C3)alkyl)$, —$NHC(=O)((C1-C3)alkyl)$, —$C(=O)OH$, —$C(=O)O((C1-C3)alkyl)$, —$C(=O)(C1-C3)alkyl)$, —$C(=O)NH_2$, —$C(=O)NH(C1-C3)alkyl)$, —$C(=O)NH(cycloalkyl)$, —$C(=O)N(C1-C3)alkyl)_2$, —$S(=O)_2((C1-C3)alkyl)$, —$S(=O)_2NH_2$, —$S(=O)_2N((C1-C3)alkyl)_2$, —$S(=O)_2NH((C1-C3)alkyl)$, —$CHF_2$, —$OCF_3$, —$OCHF_2$, —$SCF_3$, —$CF_3$, —CN, —$NH_2$, —$NO_2$, or tetrazolyl.

The term R or the term R', appearing by itself and without a number designation, unless otherwise defined, refers to a moiety selected from the group consisting of hydrogen, alkyl, haloalkyl (e.g., —$CF_3$), cycloalkyl, heteroalkyl, aryl, heteroaryl and heterocycloalkyl. Said cycloalkyl, said aryl, said heteroaryl and/or said heterocycloalkyl may each be substituted with 1, 2, 3 or 4 groups (particularly with one group) independently selected from lower alkyl, lower alkenyl, lower alkynyl, lower alkanoyl, lower heteroalkyl, lower heterocycloalkyl, lower haloalkyl, lower cycloalkyl, phenyl, aryl, aryloxy, lower alkoxy, lower haloalkoxy, lower acyloxy, carbonyl, carboxyl, lower alkylcarbonyl, lower carboxyester, lower carboxamido, cyano, halogen, hydroxyl, amino, lower alkylamino, arylamino, aminoalkyl, amido, nitro, thiol, lower alkylthio, lower haloalkylthio, lower perhaloalkylthio, arylthio, carbamate, or urea, and preferably selected independently from —CN, —$CF_3$, or halogen. Accordingly, said aryl (e.g., phenyl) may, e.g., be substituted with 1, 2, 3 or 4 groups (preferably one group) independently selected from —CN, —$CF_3$, or halogen (for example, R and/or R' may be phenyl substituted with one group —CN). It is preferred that said cycloalkyl, said aryl, said heteroaryl and said heterocycloalkyl are each unsubstituted. Most preferably, the term R and the term R', appearing by itself and without a number designation, each refer to a moiety selected from the group consisting of hydrogen, alkyl, cycloalkyl, heteroalkyl, aryl, heteroaryl and heterocycloalkyl (wherein said cycloalkyl, said aryl, said heteroaryl and said heterocycloalkyl are each unsubstituted). Whether an R group has a number designation or not, every R group, including R, R' and $R^p$ where p=(1, 2, 3, . . . p), every substituent, and every term should be understood to be independent of every other in terms of selection from a group. Should any variable, substituent, or term (e.g., aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —$C(=O)N(R)$— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

As used herein, the terms "(1S,2R) enantiomer" and "(1R,2S) enantiomer" of a compound according to the invention, in particular of a compound of Formula (I), (II), (III), (IV) or (V), refer to the two possible enantiomers of the trans-isomer (in respect of the substituents on the cyclopropyl ring) of the respective compound. In this connection, the 1-position of the cyclopropyl ring refers to the carbon atom of the cyclopropyl ring which is bound to the terminal amino group of the compound and the 2-position of the cyclopropyl ring refers to the carbon atom which is bound to the adjacent cyclic group (i.e., the cyclic group comprising E, $X^1$ and $X^2$ in Formula (I)) of the compound, unless defined otherwise by the chemical name of any particular compound.

As used herein, the term "preventing an increase in a symptom," refers to both not allowing a symptom to increase or worsen, as well as reducing the rate of increase in the symptom. For example, a symptom can be measured as the amount of particular disease marker, i.e., a protein (e.g., cancer biomarker). In another example the symptom can be cognitive decline. Preventing an increase, according to the definition provided herein, means that the amount of symptom (e.g., protein or cognitive decline) does not increase or that the rate at which it increases is reduced.

As used herein, the term "treating a disease or disorder," refers to a slowing of or a reversal of the progress of the disease. Treating a disease or disorder includes treating a symptom and/or reducing the symptoms of the disease.

As used herein, the term "preventing a disease or disorder," refers to a slowing of the disease or of the onset of the disease or the symptoms thereof. Preventing a disease or disorder can include stopping the onset of the disease or symptoms thereof. As used herein, the term "unit dosage form" refers to a physically discrete unit, such as a capsule or tablet suitable as a unitary dosage for a human patient. Each unit contains a predetermined quantity of a compound of Formula (I), (II), (III), (TV) or (V) which was discovered or believed to produce the desired pharmacokinetic profile which yields the desired therapeutic effect. The dosage unit is composed of a compound of Formula (I), (II), (III), (IV) or (V) in association with at least one pharmaceutically acceptable carrier, salt, excipient, or combination thereof.

As used herein, the term "subject" or "patient" or "individual", such as the subject in need of treatment or prevention, may be a eukaryote, an animal, a vertebrate animal, a mammal, a rodent (e.g. a guinea pig, a hamster, a rat, a mouse), a murine (e.g. a mouse), a canine (e.g. a dog), a feline (e.g. a cat), an equine (e.g. a horse), a primate, a simian (e.g. a monkey or ape), a monkey (e.g. a marmoset, a baboon), an ape (e.g. gorilla, chimpanzee, orangutang, gibbon), or a human. The meaning of the terms "eukaryote", "animal", "mammal", etc. is well known in the art and can, for example, be deduced from Wehner und Gehring (1995; Thieme Verlag). In the context of this invention, it is particularly envisaged that animals are to be treated which are economically, agronomically or scientifically important. Scientifically important organisms include, but are not limited to, mice, rats, and rabbits. Lower organisms such as, e.g., fruit flies like *Drosophila melagonaster* and nematodes like *Caenorhabditis elegans* may also be used in scientific approaches. Non-limiting examples of agronomically important animals are sheep, cattle and pig, while, for example, cats and dogs may be considered as economically important animals. Preferably, the subject/patient/individual is a mammal; more preferably, the subject/patient/individual is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orangutang, a gibbon, a sheep, cattle, or a pig); even more preferably, the subject/patient/individual is a human.

As used herein, the term "dose" or "dosage," refers the amount of active ingredient that an individual takes or is administered at one time. For example, a 40 mg dose of a compound of Formula (I), (II), (III), (IV) or (V) refers to, in the case of a twice-daily dosage regimen, a situation where the individual takes 40 mg of a compound of Formula (I), (II), (III), (IV) or (V) twice a day, e.g., 40 mg in the morning and 40 mg in the evening. The 40 mg of a compound of Formula (I), (II), (III), (IV) or (V) dose can be divided into two or more dosage units, e.g., two 20 mg dosage units of a compound of Formula (I), (II), (III), (IV) or (V) in tablet form or two 20 mg dosage units of a compound of Formula (I), (II), (III), (IV) or (V) in capsule form.

As used herein, a "pharmaceutically acceptable prodrug" is a compound that may be converted under physiological conditions or by solvolysis to the specified compound or to a pharmaceutically acceptable salt of such compound.

As used herein, a "pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

As used herein, a "pharmaceutically acceptable salt" is intended to mean a salt that retains the biological effectiveness of the free acids and bases of the specified compound and that is not biologically or otherwise undesirable. A compound for use in the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrophosphates, dihydrophosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, propanesulfonates, naphthalene-1-sulfonates, naphthalene-2-sulfonates, or mandelates.

As used herein, a "pharmaceutically acceptable carrier" refers to a non-API (API refers to Active Pharmaceutical Ingredient) substances such as disintegrators, binders, fillers, and lubricants used in formulating pharmaceutical products. They are generally safe for administering to humans according to established governmental standards, including those promulgated by the United States Food and Drug Administration and the European Medical Agency.

As is understood by the skilled artisan, certain variables in the list of substituents are repetitive (different name for the same substituent), generic to other terms in the list, and/or partially overlap in content with other terms. In the compounds of the invention, the skilled artisan recognizes that substituents may be attached to the remainder of the molecule via a number of positions and the preferred positions are as illustrated in the Examples.

Additionally, the compound of Formula (I), (II), (III), (IV) or (V) can contain asymmetric carbon atoms and can therefore exist in racemic and optically active forms. Thus, optical isomers or enantiomers, racemates, tautomers, and diastereomers are also encompassed in the compounds of Formula (I), (II), (III), (IV) or (V). The methods of present invention include the use of all such isomers and mixtures thereof. Methods of separation of enantiomeric and diastereomeric mixtures are well known to one skilled in the art. The present invention encompasses any isolated racemic or optically active form of compounds described in Formula (I), (II), (III), (IV) or (V), or any mixture thereof. In one aspect, the compounds of the invention have a trans configuration around the cyclopropyl ring as in trans-phenylcyclopropylamine. In one aspect, the compounds of the invention have a cis configuration around the cyclopropyl ring as in cis-phenylcyclopropylamine. In a preferred aspect, the compounds of Formula (I), (II), (III), (IV) or (V) have the trans configuration.

Typically, compounds according to Formula (I), (II), (III), (IV) or (V) can be effective at an amount of from about 0.01 gig/kg to about 100 mg/kg per day based on total body weight. The active ingredient may be administered at once, or may be divided into a number of smaller doses to be administered at predetermined intervals of time. The suitable dosage unit for each administration can be, e.g., from about 1 μg to about 2000 mg, preferably from about 5 μg to about 1000 mg.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the case of absorption, distribution, and excretion of the active compound by the body, the age and sensitivity of the patient to be treated, and the like, as will be apparent to a skilled artisan. The amount of administration can be adjusted as the various factors change over time.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al. (1988) *Ann. Rev. Med.* 39:221-229 which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al. (1984) *J. Clin. Psych.* 45:242-247. Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly(glycolic-co-L1-lactic acid) may be useful. See, e.g., Phillips et al. (1984) *J. Pharmaceut. Sci.,* 73: 1718-1720.

The active compounds can also be conjugated, to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham (1994) *Am. J. Hosp. Pharm.* 15:210-218. PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art. Other pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., Methods in Cell Biology, Volume XIV, Academic Press, New York, N.Y. (1976).

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, antiviral agents, antibiotics, antifungal agents, antithrombotic agents, cardiovascular drugs, cholesterol lowering agents, anti-cancer drugs, hypertension drugs, and the like.

Examples of antineoplastic agents that can be used in combination with the compounds and methods of the present invention include, in general, and as appropriate, alkylating agents, anti-metabolites, epidophyllotoxins, antineoplastic enzymes, topoisomerase inhibitors, procarbazines, mitoxantrones, platinum coordination complexes, biological response modifiers and growth inhibitors, hormonal/anti-hormonal therapeutic agents and haematopoietic growth factors. Exemplary classes of antineoplastic include the anthracyclines, vinca drugs, mitomycins, bleomycins, cytotoxic nucleosides, epothilones, discodermolides, pteridines, diynenes and podophyllotoxins. Particularly useful members of those classes include, for example, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

General Synthetic Route Description

Compounds of Formula (I), (II), (III), (IV) or (V) can be synthesized by the general route described in the Scheme 1, 2 (including Schemes 2(a) and (b) and 3. As is known by the ordinary skilled artisan, other synthetic routes can be employed to arrive at the reactant, intermediates and final products of the invention with the following schemes being preferred routes to the indicated compounds.

SCHEME 1: ACN (acetonitrile), DMSO (Dimethyl sulfoxide), THF (Tetrahydrofurane).

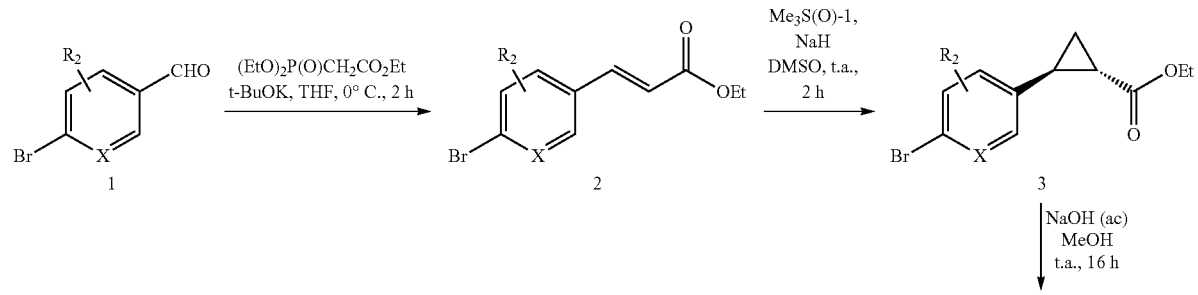

-continued

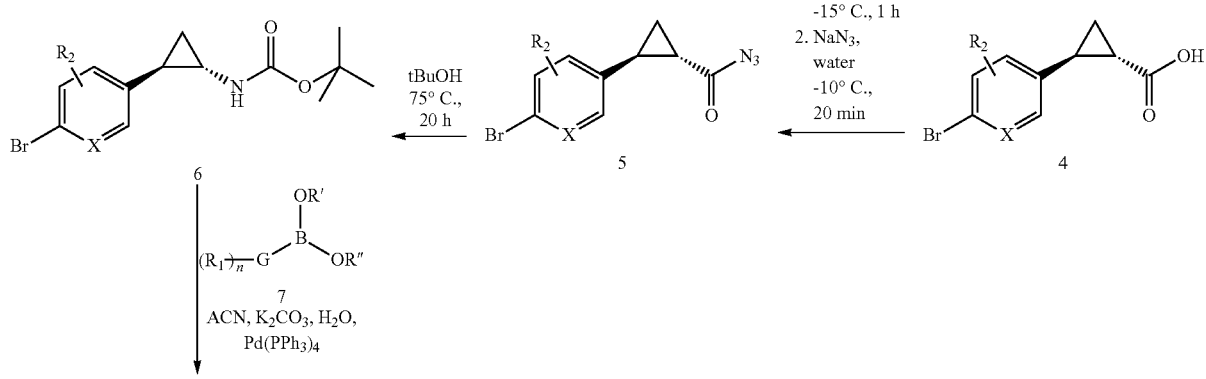

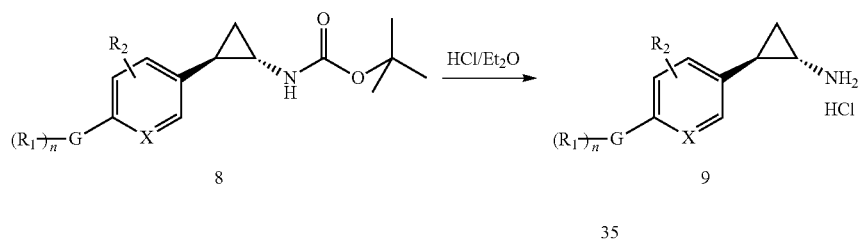

Commercially availables aldehydes of formula (I) have been subjected to a Horner-Wadsworth-Emmons reaction using triethyl phosphono acetate and potassium tert-butoxide in tetrahydrofuran at 0° C. to give the ethyl acrylate derivative of formula (2) which is subjected to cyclopropanation reaction using trimetilsulfoxonium iodide and sodium hydride in dimethyl sulfoxide as a solvent leading to (trans)-ethyl cyclopropanecarboxylate derivatives of formula (3) (being trans ((1S,2R), (1R,2S)) mixture although the individual diastereoisomers corresponding to (1S, 2R) and (1R, 2S) can be used). Hydrolysis to the corresponding (trans)-cyclopropanecarboxylic acid derivatives of formula (4) was performed using NaOH in MeOH. The reaction, first with ethyl chloroformate and triethylamine in acetone and later with sodium azide in water leads to the formation of (trans)-cyclopropanecarbonyl azide derivatives of formula (5). Reaction with tert-butanol results in the formation of tert-butyl (trans)-cyclopropylcarbamate derivatives of formula (6). Their reaction with commercially available boronic acid or boronate ester derivatives of formula (7) using acetonitrile and water as a solvent, potassium carbonate as a base and Tetrakis(triphenylphospine) Paladium (0) as a catalyst leads to the formation of tert-butyl (trans)-cyclopropylcarbamate derivatives of formula (8). Deprotection of the Boc-group using HCl 2M in diethyl ether using diethyl ether as a solvent leads to the formation of the corresponding hydrochloride salt of the (trans)-cyclopropanamine derivatives of formula (9), which are subject of the present invention as defined above.

SCHEME 2 (a): ACN (acetonitrile), DCM (dichloromethane), DMSO (dimethyl sulfoxide), THF (tetrahydrofurane), m-CPBA (meta-chloroperoxybenzoic acid).

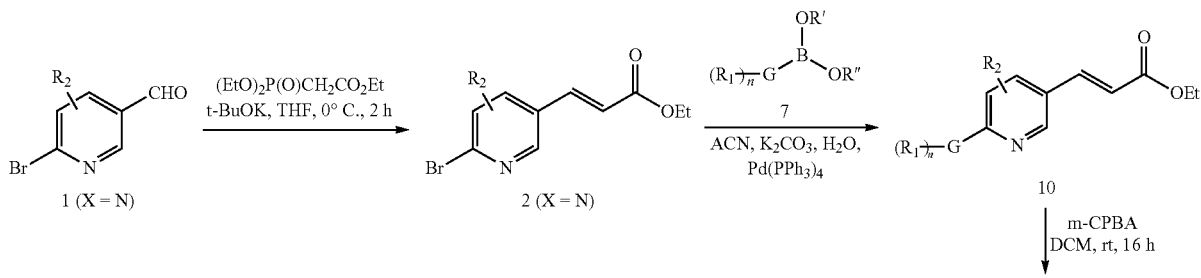

-continued

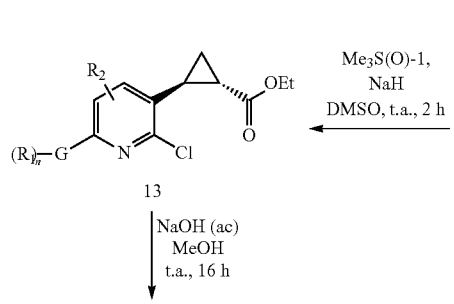

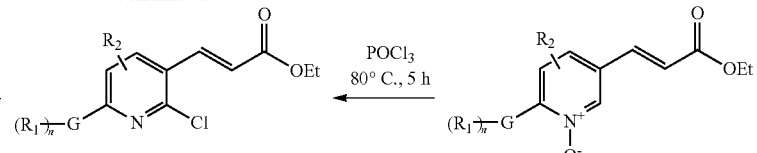

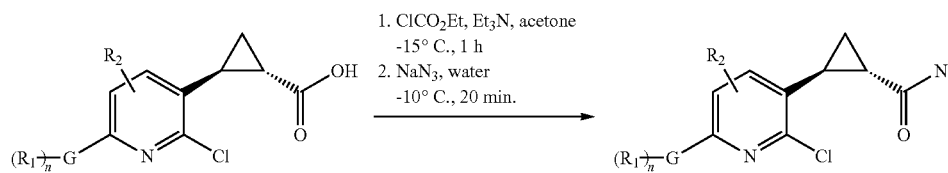

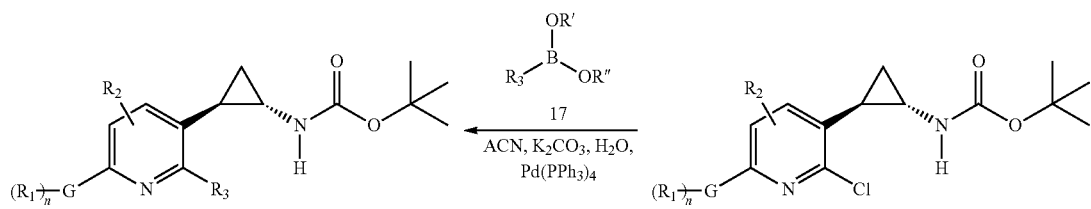

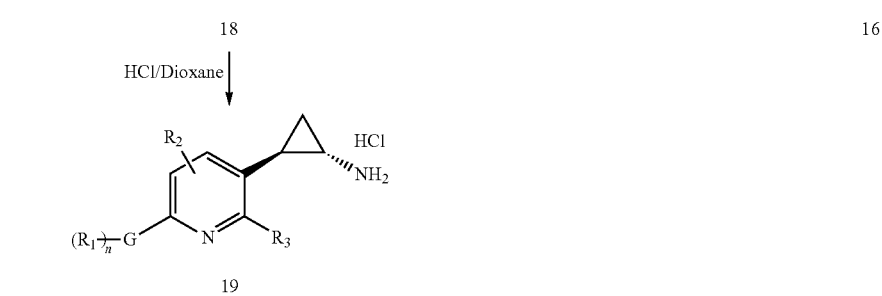

Commercially availables 6-bromonicotinaldehydes of formula (I) (X=N), have been subjected to a Horner-Wadsworth-Emmons reaction using triethyl phosphono acetate and potassium tert-butoxide in tetrahydrofurane at 0° C. to get the ethyl acrylate derivative of formula (2) (X=N). Their reaction with commercially available boronic acid or boronate ester derivatives of formula (7) using acetonitrile and water as a solvent, potassium carbonate as a base and Tetrakis(triphenylphospine) Paladium (0) as a catalyst leads to the formation of derivatives of formula (10). N-oxidation with meta-chloroperoxybenzoic acid in dichloromethane results in the formation of derivatives of formula (11). Reaction with phosphorus oxychloride provide compounds of formula (12) which are subjected to cyclopropanation reaction using trimetilsulfoxonium iodide and sodium hydride in dimethyl sulfoxide as a solvent leading to (trans)-ethyl cyclopropanecarboxylate derivatives of formula (13) (being trans ((1S, 2R), (1R, 2S)) mixture although the individual isomers corresponding to (1S,2R) and (1R,2S) can be used). Hydrolysis to the corresponding (trans)-cyclopropanecarboxylic acid derivatives of formula (14) was performed using NaOH in MeOH. The reaction, first with ethyl chloroformate and triethylamine in acetone and later with sodium azide in water leads to the formation of (trans)-cyclopropanecarbonyl azide derivatives of formula (15). Reaction with tert-butanol results in the formation of tert-butyl (trans)-cyclopropylcarbamate derivatives of formula (16). Later reaction with commercially available boronic acid or boronate ester derivatives of formula (17) using acetonitrile and water as a solvent, potassium carbonate as a base and Tetrakis(triphenylphospine) Paladium (0) as a catalyst leads to the formation of tert-butyl (trans)-cyclopropylcarbamate derivatives of formula (18). Deprotection of the Boc-group using HCl in dioxane leads to the formation of the corresponding hydrochloride salt of the (trans)-cyclopropanamine derivatives of formula (19), which are also subjects of the present invention.

SCHEME 2[a2] (b): ACN (acetonitrile), DCM (dichloromethane), DMSO (dimethyl sulfoxide), THF (tetrahydrofurane), m-CPBA (meta-chloroperoxybenzoic acid).

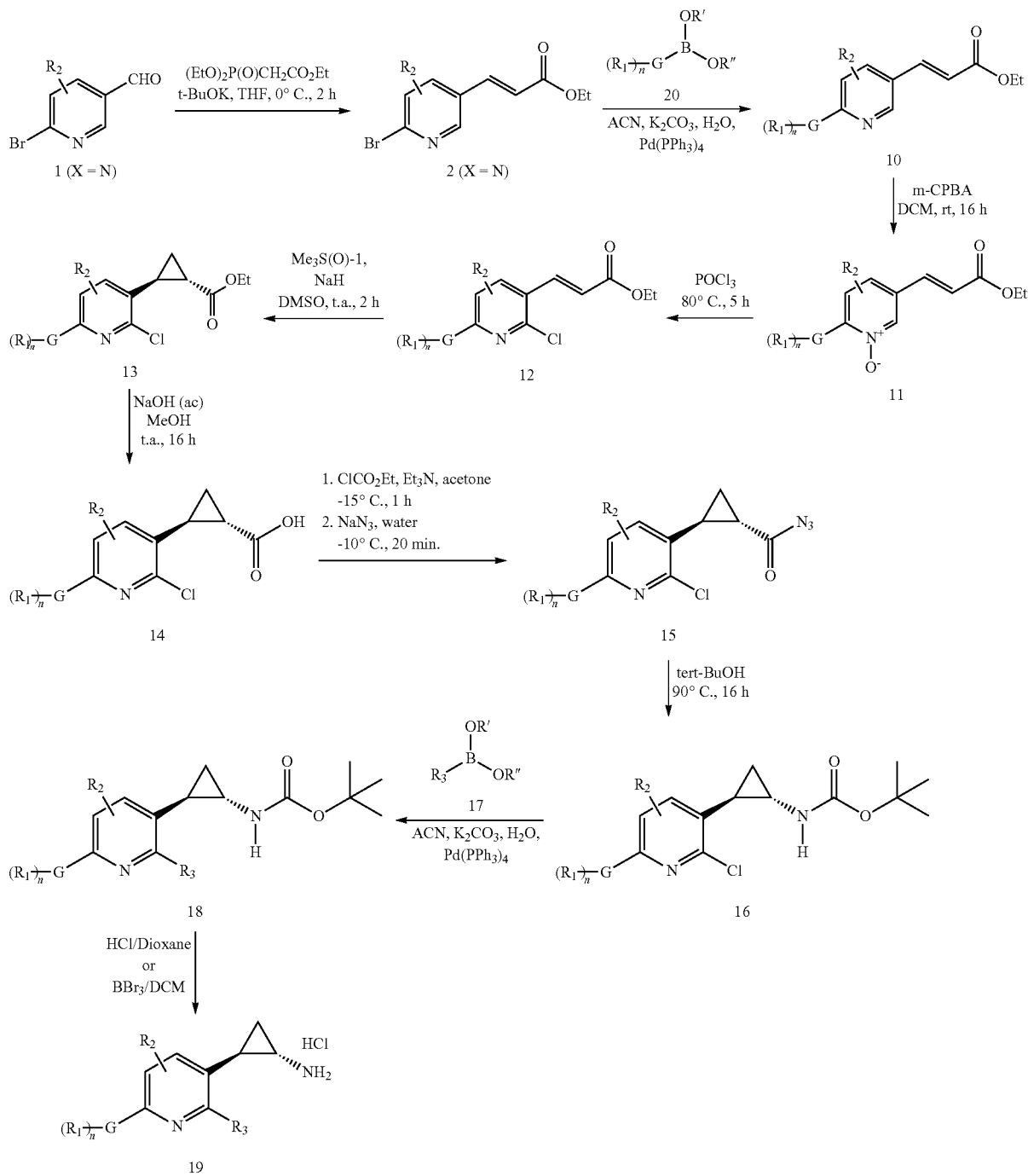

Commercially availables 6-bromonicotinaldehydes of formula (I) (X═N), have been subjected to a Horner-Wadsworth-Emmons reaction using triethyl phosphono acetate and potassium tert-butoxide in tetrahydrofuran at 0° C. to get the ethyl acrylate derivative of formula (2) (X═N). Their reaction with commercially available boronic acid or boronate ester derivatives of formula (20) using acetonitrile and water as a solvent, potassium carbonate as a base and Tetrakis(triphenylphospine) Paladium (0) as a catalyst leads to the formation of derivatives of formula (10). N-oxidation with meta-chloroperoxybenzoic acid in dichloromethane results in the formation of derivatives of formula (11). Reaction with phosphorus oxychloride provide compounds of formula (12) which are subjected to cyclopropanation reaction using trimethylsulfoxonium iodide and sodium hydride in dimethyl sulfoxide as a solvent leading to (trans)-ethyl cyclopropanecarboxylate derivatives of formula (13) (being trans ((1S,2R), (1R,2S)) mixture although the individual isomers corresponding to (1S, 2R) and (1R,2S) can be used). Hydrolysis to the corresponding (trans)-cyclopropanecarboxylic acid derivatives of formula (14) was performed using NaOH in MeOH. The reaction, first with ethyl chloroformate and triethylamine in acetone and later with sodium azide in water leads to the formation of (trans)-cyclopropanecarbonyl azide derivatives of formula (15). Reaction with tert-butanol results in the formation of tert-butyl (trans)-cyclopropylcarbamate derivatives of formula (16). Later reaction with commercially available boronic acid or boronate ester derivatives of formula (17) using acetonitrile and water as a solvent, potassium carbonate as a base and Tetrakis(triphenylphospine) Paladium (0) as a catalyst leads to the formation of tert-butyl (trans)-cyclopropylcarbamate derivatives of formula (18). Deprotection of the Boc-group using HCl in dioxane or BBr$_3$ in dichloromethane with later HCl 2M in diethyl ether leads to the formation of the corresponding hydrochloride salt of the (trans)-cyclopropanamine derivatives of formula (19), which are also subjects of the present invention.

SCHEME 3: ACN (acetonitrile), DCM (dichloromethane), DMSO (Dimethyl sulfoxide), THF (Tetrahydrofurane)

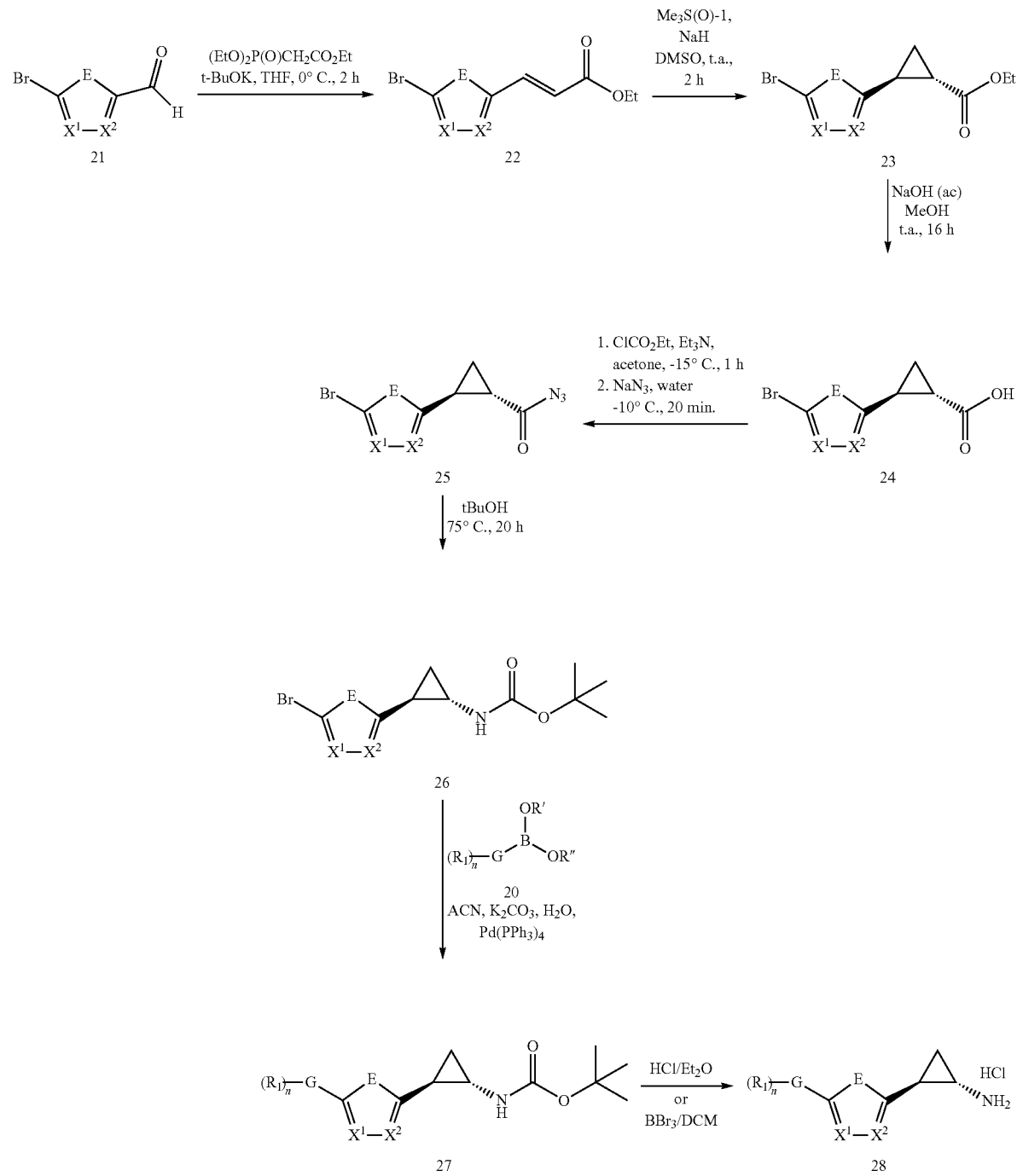

Commercially availables aldehydes of formula (21) have been subjected to a Horner-Wadsworth-Emmons reaction using triethyl phosphono acetate and potassium tert-butoxide in tetrahydrofurane at 0° C. to get the ethyl acrylate derivative of formula (22) which is subjected to cyclopropanation reaction using trimethylsulfoxonium iodide and sodium hydride in dimethyl sulfoxide as a solvent leading to (trans)-ethyl cyclopropanecarboxylate derivatives of formula (23) (being trans ((1S, 2R), (1R,2S)) mixture although the individual diastereoisomers corresponding to (1S,2R) and (1R,2S) can be used). Hydrolysis to the corresponding (trans)-cyclopropanecarboxylic acid derivatives of formula (24) was performed using NaOH in MeOH. The reaction, first with ethyl chloroformate and triethylamine in acetone and later with sodium azide in water leads to the formation of (trans)-cyclopropanecarbonyl azide derivatives of formula (25). Reaction with tert-butanol results in the formation of tert-butyl (trans)-cyclopropylcarbamate derivatives of formula (26). Their reaction with commercially available boronic acid or boronate ester derivatives of formula (20) using acetonitrile and water as a solvent, potassium carbonate as a base and Tetrakis(triphenylphospine) Paladium (0) as a catalyst leads to the formation of tert-butyl (trans)-cyclopropylcarbamate derivatives of formula (27). Deprotection of the Boc-group using HCl 2M in diethyl ether using diethyl ether as a solvent or $BBr_3$ in dichloromethane with later HCl 2M in diethyl ether leads to the formation of the corresponding hydrochloride salt of the (trans)-cyclopropanamine derivatives of formula (28), which are also subject of the present invention.

Thus, the invention further relates to methods synthesizing a compound of formula (I) according to the methods described herein.

Furthermore, the invention also relates to an intermediate of formula (1), formula (2), formula (3), formula (4), formula (5), formula (6), formula (7), formula (8), formula (9), formula (10), formula (11), formula (13), formula (14), formula (15), formula (16), formula (17), formula (18), formula (19), formula (20), formula (21), formula (22), formula (23), formula (24), formula (25), formula (26), formula (27), or formula (28) wherein the various R groups are as defined herein.

Furthermore, the invention also relates to a method of preparing an intermediate of formula (1), formula (2), formula (3), formula (4), formula (5), formula (6), formula (7), formula (8), formula (9), formula (10), formula (11), formula (13), formula (14), formula (15), formula (16), formula (17), formula (18), formula (19), formula (20), formula (21), formula (22), formula (23), formula (24), formula (25), formula (26), formula (27), or formula (28) wherein the various R-groups are as defined herein said method comprising contacting the starting materials and reagents under conditions sufficient to catalyze the reaction as illustrated in Scheme 1, 2, or 3.

EXAMPLES

The program used to generate the names corresponding to the structures in the Example compounds below was ChemBioDraw Ultra 11.0.1. This program named the molecules as the (1S,2R) configuration due to the configuration of the input structure and the "trans" term has been substituted in the place of the (1S,2R) term specified by the program. The structures depicted below for the Example compounds below are shown as having one particular stereochemical configuration around the cyclopropyl carbon atoms of the phenylcyclopropylamine core (1S,2R). All the compounds synthesized in the Examples are mixtures having both configurations (1R,2S) and (1S, 2R), that is to say they are "trans" in respect to the cyclopropyl ring of the cyclopropyl ring system. This is due to the fact the cyclopropyl derivatives used as starting material are "trans". It is contemplated that the cis configuration starting material or the individual diastereomers could be used as starting material, all of which are either commercially or synthetically available. Thus, the invention relates to compounds of Formula (I), (II), (III), (IV) or (V) and those of the examples that have specific stereochemical configurations around the cyclopropyl ring e.g., trans ((1R,2S) and (1S,2R)) and cis ((1R, 2R) and (1S, 2S)). A preferred stereochemical configuration around the cyclopropyl ring is trans.

The compounds of the examples can also be synthesized or provided in a salt form. The skilled artisan is aware and capable of making salt forms and/or converting salt forms of the compounds of the invention, e.g., compounds of Formula (I), (II), (III), (IV) or (V) and those of the Examples. In some cases the compounds of Formula (I), (II), (III), (IV) or (V) and the Examples can be more stable as salt forms as compared to free base.

In reference to the synthetic schemes described herein the following intermediates (and analogous intermediates or derivatives thereof) can be made using the following procedures.

Intermediate A: (E)-ethyl 3-(4-bromophenyl)acrylate

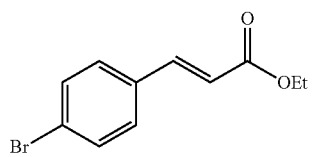 [SMILES: CCOC(=O)/C=C/c1ccc(Br)cc1]

A solution of triethyl phosphonoacetate (13.1 g, 0.0589 mol) was added slowly (dropwise) to a solution of Potassium-tert-butoxide (6.59 g, 0.0589 mol), in dry THF (150 mL) at −5° C., stirred for 30-45 mins at the same temperature, then a solution of 4-Bromo benzaldehyde (10 g, 0.054 mol), in dry THF (50 mL) was slowly added dropwise at −5° C. over a period of 15 mins, stirred the reaction mixture for 30 mins at the same temperature. After completion of reaction by TLC, the reaction mixture was poured into ice water (300 mL), extracted with EtOAc (2×200 mL). The combined organic extracts were washed with sat $NaHCO_3$ solution (200 mL), water (200 mL), brine (200 mL) and dried over anhydrous $Na_2SO_4$, filtered and evaporated to get crude (E)-ethyl 3-(4-bromophenyl) acrylate (10 g, 72%) as pale green liquid. This is carried to next step without further purification.

Intermediate B: (Trans)-ethyl 2-(4-bromophenyl)cyclopropanecarboxylate

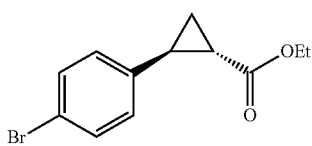 [SMILES: CCOC(=O)[C@H]1C[C@@H]1c1ccc(Br)cc1]

Trimethyl sulfoxonium iodide (5.19 g, 0.0236 mol) was added slowly in small portions over a period of 20 min. to a suspension of sodium hydride (0.44 g, 0.0236 mol) in dry DMSO (80 mL) at rt, stirred for 1 h, till the formation of clear solution. Then a solution of (E)-ethyl 3-(4-bromophenyl) acrylate (Intermediate A, 5 g, 0.01968), in dry DMSO (20 mL) was added slowly dropwise, stirred at rt for 30 mins. After completion of reaction, checked by TLC, the reaction mixture was poured into ice water (200 mL), extracted with EtOAc (2×150 mL). Combined organic extracts were washed with ice water (2×150 mL), brine (150 mL), dried over anhydrous $Na_2SO_4$, filtered and evaporated to get (trans)-ethyl 2-(4-bromophenyl)cyclopropanecarboxylate (4 g, 75.9%) as a green liquid. The crude is carried to next step without further purification.

Intermediate C: (Trans)-2-(4-bromophenyl)cyclopropanecarboxylic acid

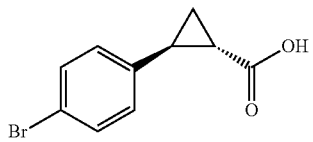 [SMILES: O=C(O)[C@H]1C[C@@H]1c1ccc(Br)cc1]

NaOH 4N (20 mL) was added to a solution of (trans)-ethyl 2-(4-bromophenyl)cyclopropanecarboxylate (Intermediate B, 4 g, 0.0149 mol), in Methanol (40 mL) and stirred at rt for 2 h. After completion of reaction, checked by TLC, the solvent was evaporated and the residue was diluted with water (50 mL), acidified with HCl 4 N solution, the solid formed was filtered and dried to get (trans)-2-(4-bromophenyl)cyclopropanecarboxylic acid (2.59 g, 72%), as a white solid.

Intermediate D: (Trans)-2-(4-bromophenyl)cyclopropanecarbonyl azide

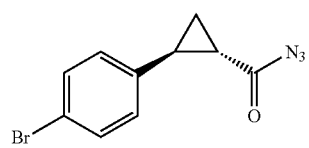

Ethyl chloroformate (1.9 mL) was added to a solution of (trans)-2-(4-bromophenyl)cyclopropanecarboxylic acid (Intermediate C, 4 g, 0.0165 mol) and $Et_3N$ (2.51 mL, 0.0199 mol) in acetone (60 mL) at −20° C., stirred at same temperature for 1 h, then a solution of $NaN_3$ (1.3 g, 0.0199 mol) in water (5 mL), was added and stirred for 30 mins at rt. After completion of reaction, checked by TLC, the solvent was evaporated and crude residue was dissolved in ethyl acetate (100 mL), washed with water (40 mL), dried over anhydrous $Na_2SO_4$, filtered and evaporated to get (trans)-2-(4-bromophenyl)cyclopropanecarbonyl azide (4 g). The crude residue is carried to next step without further purification.

Intermediate E: tert-butyl (trans)-2-(4-bromophenyl)cyclopropylcarbamate

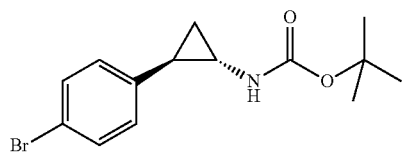 [SMILES: CC(C)(C)OC(=O)N[C@H]1C[C@@H]1c1ccc(Br)cc1]

A solution of (trans)-2-(4-bromophenyl)cyclopropanecarbonyl azide (Intermediate D, 4 g) in tert-Butanol (40 mL) was heated at 90° C. for 16 h. After completion of reaction, checked by TLC, the solvent was evaporated residue was poured into water (50 mL), extracted with EtOAc (2×50 mL). The combined organic extracts were washed with water (50 mL), brine (50 mL), dried over anhydrous $Na_2SO_4$, filtered and evaporated. The crude residue was purified by column chromatography ($SiO_2$) by eluting with EtOAc: Petroleum ether (2:98), to get tert-butyl (trans)-2-(4-bromophenyl)cyclopropylcarbamate (2.5 g, 48% overall 2 steps) as a white solid. $^1$H-NMR ($CDCl_3$, 250 MHz) δ: 1.07-1.19 (m, 2H), 1.44 (s, 9H); 2.05-1.94 (m, 1H); 2.72-2.62 (m, 1H); 4.85 (br, 1H,); 7.09-6.96 (m, 2H); 7.44-7.33 (m, 2H).

Intermediate F: (E)-ethyl 3-(6-bromopyridin-3-yl)acrylate

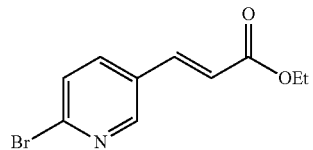

Triethyl phosphonoacetate (26.6 g, 118.8 mmol) was added slowly dropwise to a mixture of Potassium-tert-butoxide (14.5 g, 129.6 mmol) in dry THF (200 mL) at −5° C., stirred for 20 min and then a solution of 6-bromopyridine-3-carboxaldehyde (20 g, 108 mmol) in dry THF (100 mL) was added slowly dropwise at −5° C. and stirred for 30 min. After completion, the reaction mixture was poured into ice water (350 mL) and extracted with EtOAc (2×300 mL). The combined organic extracts were washed with saturated $NaHCO_3$ solution (250 mL), water (250 mL) and brine (250 mL) and dried over anhydrous $Na_2SO_4$, filtered and evaporated to get (E)-ethyl 3-(6-bromopyridin-3-yl) acrylate (20 g, 72.9%) as brown color liquid. This is carried to next step without further purification.

Intermediate G: (Trans)-ethyl-2-(6-bromopyridin-3-yl)cyclopropanecarboxylate

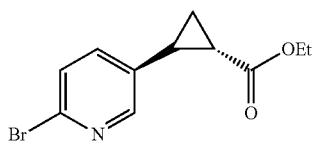

Trimethyl sulfoxonium iodide (20.8 g, 94.7 mmol) was added in small portions to a suspension of sodium hydride (4 g, 170.6 mmol) in dry DMSO (400 mL) at rt., stirred for 1 h until clear solution was obtained. A solution of (E)-ethyl 3-(6-bromopyridin-3-yl) acrylate (Intermediate F, 20 g, 78.7 mmol) in dry DMSO (20 mL) was added and stirred for 4 h. After completion, the reaction mixture was poured into ice water (700 mL), extracted with EtOAc (2×350 mL). The combined organic extracts were washed with water (250 mL), brine (250 mL) and dried over anhydrous Na$_2$SO$_4$, filtered and evaporated to give (trans)-ethyl-2-(6-bromopyridin-3-yl)cyclopropanecarboxylate (10 g, 47%) as brown liquid.

Intermediate H: (Trans)-2-(6-bromopyridin-3-yl) cyclopropanecarboxylic acid hydrochloride

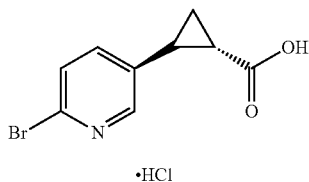

·HCl

NaOH 4N solution (60 mL) was added to a solution of (trans)-ethyl-2-(6-bromopyridin-3-yl)cyclopropanecarboxylate (Intermediate G, 10 g, 37.1 mmol) in methanol (100 mL) and the reaction mixture was stirred at RT for 4 h. After completion, the solvent was evaporated and the residue was diluted with ice water (250 mL) and acidified with 4 N HCl solution, the aqueous layer was extracted with EtOAc (2×350 mL). The combined organic extracts were washed with water (250 mL), brine (250 mL) and dried over anhydrous Na$_2$SO$_4$, filtered and evaporated to give (trans)-2-(6-bromopyridin-3-yl)cyclopropanecarboxylic acid hydrochloride (5 g, 55.8%) as a light brown color solid.

Intermediate I: (Trans)-2-(6-bromopyridin-3-yl) cyclopropanecarbonyl azide

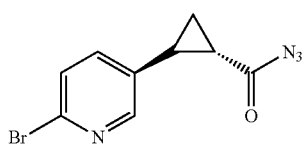

Ethyl chloroformate (5.8 mL, 62 mmol) was added to a solution of (trans)-2-(6-bromopyridin-3-yl)cyclopropanecarboxylic acid hydrochloride (Intermediate H, 5 g, 20.7 mmol) and Et$_3$N (14.2 mL, 103.7 mmol) in Acetone (100 mL) at −5° C., then reaction mixture was stirred at −5° C. for 1 h, then a solution of NaN$_3$ (2.7 g, 41.4 mmol) in water (10 mL) was added and stirred for 30 mins at RT. After completion the solvent was evaporated under vacuum. The crude residue was dissolved in ethyl acetate (200 mL), washed with water (80 mL), brine (80 mL), dried over anhydrous Na$_2$SO$_4$, filtered and evaporated to get (trans)-2-(6-bromopyridin-3-yl)cyclopropanecarbonyl azide (2.5 g, 45.5%) as a brown color gummy liquid.

Intermediate J: tert-butyl(trans)-2-(6-bromopyridin-3-yl)cyclopropylcarbamate

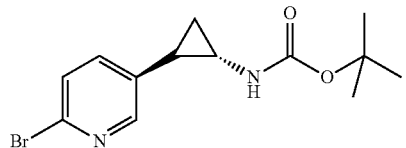

A solution of (trans)-2-(6-bromopyridin-3-yl)cyclopropanecarbonyl azide (Intermediate I, 2.5 g, 9.36 mmol) in tert-butanol (80 mL) was heated at 90° C. for 16 h. After completion, the solvent was evaporated under vacuum and the residue was taken in water (100 mL) and extracted with EtOAc (2×100 mL). The combined organic extracts were washed with water (100 mL), brine (100 mL) and dried over anhydrous Na$_2$SO$_4$, filtered and evaporated. The crude residue was purified by flash column chromatography (SiO$_2$) by eluting with EtOAc: Hexane (2:8) to get tert-butyl (trans)-2-(6-bromopyridin-3-yl)cyclopropylcarbamate (1.1 g, 37.5%) as a light yellow solid. $^1$H-NMR (CDCl$_3$) δ (ppm): 1.16 (q, 18), 1.23 (quin, 1H), 1.45 (s, 9H), 2.01 (m, 1H), 2.69 (m, 1H), 4.88 (br, 1H), 7.36 (s, 2H), 8.20 (s, 1H).

Example 1: (trans)-2-(3'-(trifluoromethyl)biphenyl-4-yl)cyclopropanamine hydrochloride

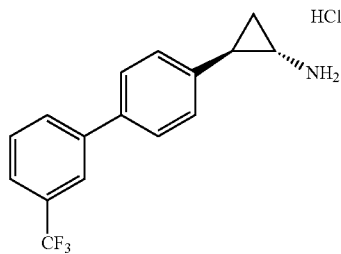 [SMILES: N[C@H]1C[C@@H]1c1ccc(-c2cccc(C(F)(F)F)c2)cc1 ; Cl]

Step 1:

To a solution of tert-butyl (trans)-2-(4-bromophenyl)cyclopropylcarbamate (Intermediate E$_{[a2]}$) (1 g, 3.2 mmol), potassium carbonate (1.31 g, 9.6 mmol), 3-(trifluoromethyl) phenylboronic acid (0.73 g, 3.8 mmol) in acetonitrile: water (4:1) were degassed for 30 mins, added tetrakis triphenylphosphine palladium (36 mg, 0.032 mmol), degassed again for 10 mins, heated the reaction mixture at reflux temperature for 5 h. After completion, the reaction mixture was poured in ice water (50 mL), extracted with, ethyl acetate (2×50 mL). Combined extracts were washed with water (70 mL), brine (70 mL), dried over anhydrous Na$_2$SO$_4$, filtered and evaporated. The crude residue was purified by column chromatography (SiO$_2$), by using EtOAc: Petroleum ether (2:8) to get tert-butyl (trans)-2-(3'-(trifluoromethyl)biphenyl-4-yl)cyclopropylcarbamate (0.8 g, 66%) as a white solid.

Step 2:

To a solution of tert-butyl (trans)-2-(3'-(trifluoromethyl) biphenyl-4-yl)cyclopropylcarbamate (200 mg, 0.53 mmol), in diethyl ether (5 mL) at 10° C. was added HCl in diethyl ether (3 mL), slowly dropwise over a period of 10 min, stirred the reaction mixture for 4 h. After completion, the solvent was evaporated, residue was triturated with hexane (5 mL) and diethyl ether (5 mL), and dried under reduced pressure to get (trans)-2-(3'-(trifluoromethyl)biphenyl-4-yl)cyclopropanamine hydrochloride (140 mg, 77.8%) as a white solid. $^1$H-NMR (DMSO-d6) δ (ppm): 1.27 (q, 1H), 1.46 (quin, 1H), 2.41 (m, 1H), 2.86 (m, 1H), 7.29 (d, 2H), 7.69 (m, 4H), 7.96 (m, 2H), 8.53 (s, 1H), 8.61 (br, 2H). MS (M+H): 278.3

The following compounds can be synthesized following the method described for example 1 using the corresponding commercial available boronic acid/boronate ester.

Example 2: (trans)-2-(terphenyl-4-yl)cyclopropanamine hydrochloride

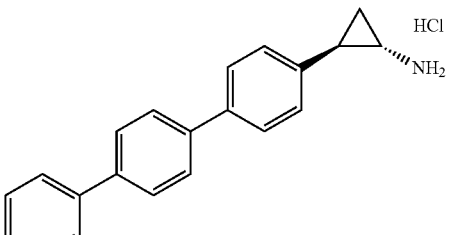

$^1$H-NMR (DMSO-d6) δ (ppm): 1.27 (q, 1H), 1.43 (quin, 1H), 2.40 (m, 1H), 2.87 (m, 1H), 7.27 (d, 2H), 7.38 (t, 1H), 7.49 (t, 2H), 7.67 (d, 2H), 7.72 (d, 2H), 7.76 (s, 4H), 8.51 (s, 2H). MS (M+H): 286.4.

Example 3: 4'-((trans)-2-aminocyclopropyl)biphenyl-4-ol hydrochloride

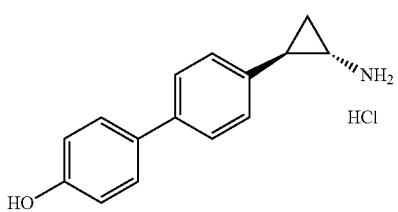 [SMILES: N[C@H]1C[C@@H]1c1ccc(-c2ccc(O)cc2)cc1 ; Cl]

$^1$H-NMR (DMSO-d6) δ (ppm): 1.22 (q, 1H), 1.4 (m, 1H), 2.35 (m, 1H), 2.85 (m, 1H), 6.8 (d, 2H), 7.2 (d, 2H), 7.45 (d, 2H), 7.5 (d, 2H), 8.4 (brs, 3H), 9.6 (s, 1H). MS (M+H): 226.1.

Example 4: 4'-((trans)-2-aminocyclopropyl)biphenyl-3-ol hydrochloride

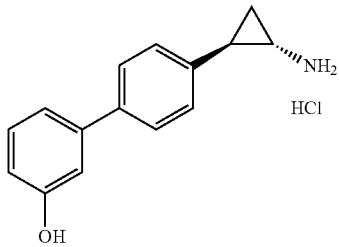 [SMILES: N[C@H]1C[C@@H]1c1ccc(-c2cccc(O)c2)cc1 ; Cl]

$^1$H-NMR (DMSO-d6) δ (ppm): 1.24 (q, 2H), 1.43 (quin, 1H), 2.39 (m, 1H), 2.83 (m, 1H), 6.75 (d, 1H), 7.02 (m, 2H), 7.23 (d, 3H), 7.51 (d, 2H), 8.56 (br, 3), 9.54 (s, 1H). MS (M+H): 226.1.

Example 5: (trans)-2-(6-(3-(trifluoromethyl)phenyl)pyridin-3-yl)cyclopropanamine dihydrochloride

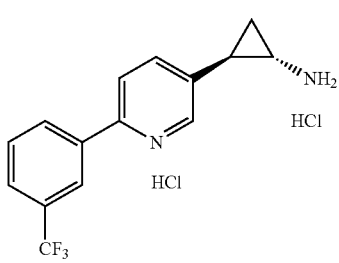 [SMILES: N[C@H]1C[C@@H]1c1ccc(-c2cccc(C(F)(F)F)c2)nc1 ; Cl ; Cl]

Step 1:
A solution of tert-butyl (trans)-2-(6-bromopyridin-3-yl)cyclopropylcarbamate (Intermediate J$_{[a2]}$) (100 mg, 0.32 mmol), potassium carbonate (132 mg, 0.96 mmol) and 3-trifluoromethylbenzeneboronic acid (72 mg, 0.38 mmol) in CH$_3$CN: H$_2$O (4:1) (10 mL) was degassed for 30 mins, added tetrakis triphenylphosphine palladium (37 mg, 0.032 mmol), degassed for 10 mins and heated the reaction mixture at reflux temperature for 2 h. After completion, the reaction mixture was poured in ice water (100 mL), extracted with ethyl acetate (5×40 mL). The combined extract were washed with water (70 mL), brine (70 mL), dried over anhydrous Na$_2$SO$_4$, filtered and evaporated. The crude residue was purified by column chromatography (SiO$_2$), by using EtOAc:Petroleum ether (1:9) to get tert-butyl (trans)-2-(6-(3-(trifluoromethyl)phenyl)pyridin-3-yl)cyclopropylcarbamate (70 mg, 58.3%) as a white solid.
$^1$H-NMR (CDCl$_3$) δ (ppm): 1.26 (m, 2H), 1.46 (s, 9H), 2.10 (m, 1H), 2.78 (m, 1H), 4.86 (br, 1H), 7.55 (m, 2H), 7.65 (t, 2H), 8.14 (d, 1H), 8.24 (s, 1H), 8.54 (s, 1H). MS (M+H): 379.1.

Step 2:
To a solution of tert-butyl (trans)-2-(6-(3-(trifluoromethyl)phenyl)pyridin-3-yl)cyclopropylcarbamate (70 mg, 0.185 mmol), in diethyl ether (10 mL) at 0° C. was added HCl in diethyl ether (5 mL) slowly dropwise over a period of 10 mins, stirred the reaction mixture for 2 h. After completion, the reaction mixture was filtered under inert atmosphere and washed with hexane (10 mL) and EtOAC (5 mL), and dried under reduced pressure to get (50 mg, 86.2%) of (trans)-2-(6-(3-(trifluoromethyl)phenyl)pyridin-3-yl)cyclopropanamine dihydrochloride as a pale yellow powder. $^1$H-NMR (D$_2$O) S (ppm): 1.52 (q, 1H), 1.63 (quin, H), 2.66 (m, 1H), 3.08 (m, 1H), 7.72 (t, 1H), 7.89 (d, 1H), 7.98 (d, 1H), 8.09 (s, 1H), 8.14 (d, 1H), 8.27 (d, 1H), 8.61 (s, 1H). MS (M+H): 279.1.

The following compounds can be synthesized following the method described for example 5 using the corresponding commercial available boronic acid/boronate ester.

Example 6: (Trans)-2-(6-(3,5-dichlorophenyl)pyridin-3-yl)cyclopropanamine hydrochloride

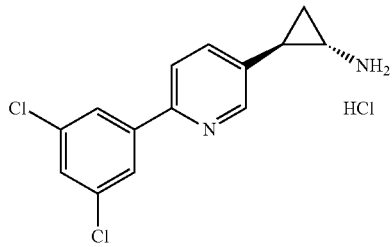 [SMILES: N[C@H]1C[C@@H]1c1ccc(-c2cc(Cl)cc(Cl)c2)nc1 ; Cl]

$^1$H-NMR (D2O) δ (ppm): 1.58 (q, 2H), 1.69 (quin, 1H), 2.69 (m, 1H), 3.13 (m, 1H), 7.67 (s, 1H), 7.76 (s, 2H), 8.07 (d, 1H), 8.22 (m, 1H), 8.64 (s, 1H). MS (M+H): 279.1.

Example 7: (trans)-2-(6-(4-chlorophenyl)pyridin-3-yl)cyclopropanamine hydrochloride

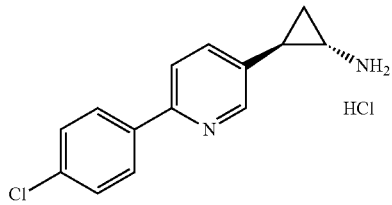 [SMILES: N[C@H]1C[C@@H]1c1ccc(-c2ccc(Cl)cc2)nc1 ; Cl]

$^1$H-NMR (CD3OD) δ (ppm): 1.70-1.75 (m, 2H), 2.75 (m, 1H), 3.2 (m, 1H), 7.69 (d, 2H), 7.93 (d, 2H), 8.3 (m, 1H), 8.45 (s, 1H), 8.8 (s, 1H). MS (M+H): 245.1.

Example 8: (trans)-2-(6-(3-chlorophenyl)pyridin-3-yl)cyclopropanamine hydrochloride

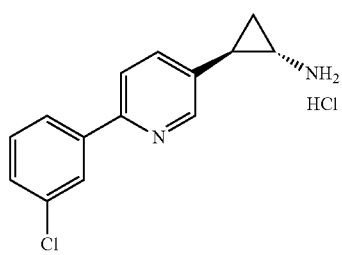 [SMILES: N[C@H]1C[C@@H]1c1ccc(-c2cccc(Cl)c2)nc1 ; Cl]

$^1$H-NMR (CD3OD) δ (ppm): 1.7 (m, 2H), 2.75 (br, 1H), 3.2 (br, 1H), 7.65 (m, 2H), 7.85 (d, 1H), 8.0 (s, 1H), 8.3 (d, 1H), 8.4 (br, 1H), 8.8 (s, 1H). MS (M+H): 245.1.

Example 9: (trans)-2-(6-(4-(trifluoromethyl)phenyl)pyridin-3-yl)cyclopropanamine hydrochloride

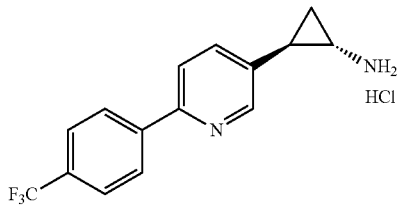 [SMILES: N[C@H]1C[C@@H]1c1ccc(-c2ccc(C(F)(F)F)cc2)nc1 ; Cl]

$^1$H-NMR (CD3OD) δ (ppm): 1.67-1.73 (m, 2H), 2.78 (br, 1H), 3.21 (br, 1H), 7.97 (d, 2H), 8.14 (d, 2H), 8.35 (m, 1H), 8.45 (m, 1H), 8.88 (s, 1H). MS (M+H): 279.2.

Example 10: (trans)-2-(6-(4-methoxyphenyl)pyridin-3-yl)cyclopropanamine hydrochloride

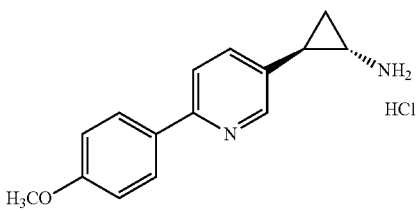 [SMILES: COc1ccc(-c2ccc([C@H]3C[C@@H]3N)cn2)cc1 ; Cl]

$^1$H-NMR (CD3OD) δ (ppm): 1.7-1.75 (m, 2H), 2.75 (m, 1H), 3.2 (m, 1H), 3.92 (s, 3H), 7.21 (d, 1H), 7.95 (d, 2H), 8.3 (d, 1H), 8.40 (d, 1H), 8.71 (s, 1H). MS (M+H): 241.2.

Example 11: (trans)-2-(6-(3-methoxyphenyl)pyridin-3-yl)cyclopropanamine hydrochloride

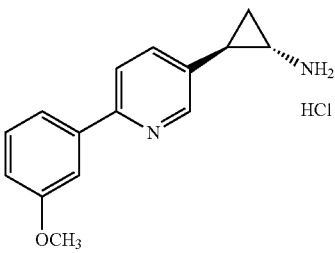 [SMILES: COc1cccc(-c2ccc([C@H]3C[C@@H]3N)cn2)c1 ; Cl]

$^1$H-NMR (CD3OD) δ (ppm): 1.73 (m, 2H), 2.75 (br, 1H), 3.22 (br, 1H), 3.9 (s, 3H), 7.26 (d, 1H), 7.48 (s, 2H), 7.60 (t, 1H), 8.32 (d, 1H), 8.45 (d, 1H), 8.8 (s, 1H). MS (M+H): 241.1.

Example 12: 4-(5-((trans)-2-aminocyclopropyl)pyridin-2-yl)benzonitrile dihydrochloride

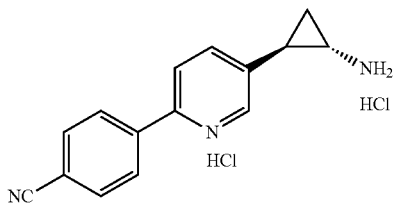 [SMILES: N#Cc1ccc(-c2ccc([C@H]3C[C@@H]3N)cn2)cc1 ; Cl ; Cl]

¹H-NMR (CD3OD) δ (ppm): 1.6-1.69 (br, 2H), 2.71 (br, 1H), 3.20 (br, 1H), 8.01 (d, 2H), 8.12 (d, 2H), 8.27 (m, 1H), 8.44 (br, 1H), 8.85 (m, 1H). MS (M+H): 236.2.

Example 13: 3-(5-((trans)-2-aminocyclopropyl)pyridin-2-yl)benzonitrile hydrochloride

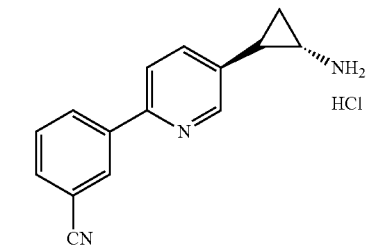

¹H-NMR (CD3OD) δ (ppm): 1.65 (m, 2H), 2.73 (br, 1H), 3.18 (br, 1H), 7.82 (m, 1H), 8.02 (m, 1H), 8.23-8.34 (m, 4H), 8.83 (br, 1H). MS (M+H): 236.1.

Example 14: (Trans)-2-(6-p-tolylpyridin-3-yl)cyclopropanamine hydrochloride

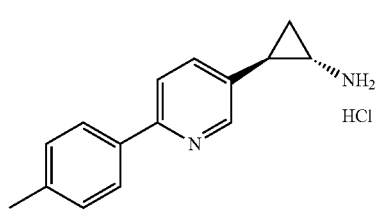 [SMILES: Cc1ccc(-c2ccc([C@H]3C[C@@H]3N)cn2)cc1 ; Cl]

¹H-NMR (CD3OD) δ (ppm): 1.64-1.71 (m, 2H), 2.47 (s, 3H), 2.74 (m, 1H), 3.2 (m, 1H), 7.5 (d, 2H), 7.84 (d, 2H), 8.3 (d, 1H), 8.43 (d, 1H), 8.75 (s, 1H). MS (M+H): 225.2.

Example 15: (Trans)-2-(6-m-tolylpyridin-3-yl)cyclopropanamine hydrochloride

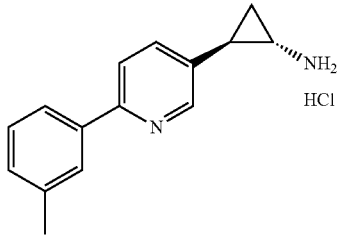 [SMILES: Cc1cccc(-c2ccc([C@H]3C[C@@H]3N)cn2)c1 ; Cl]

¹H-NMR (CD3OD) δ (ppm): 1.63-1.71 (m, 2H), 2.49 (s, 3H), 2.76 (br, 1H), 3.2 (m, 1H), 7.55 (m, 2H), 7.74 (d, 1H), 7.78 (s, 1H), 8.31 (d, 1H), 8.46 (br, 1H), 8.79 (s, 1H). MS (M+H): 225.2.

Example 16: 4-(5-((trans)-2-aminocyclopropyl)pyridin-2-yl)phenol hydrochloride

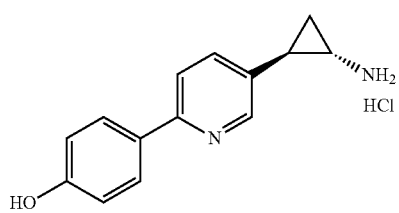 [SMILES: N[C@H]1C[C@@H]1c1ccc(-c2ccc(O)cc2)nc1 ; Cl]

¹H-NMR (CD3OD) δ (ppm): 1.65 (m, 2H), 2.71 (m, 1H), 3.16 (m, 1H), 7.04 (d, 1H), 7.85 (d, 2H), 8.24 (d, 1H), 8.37 (d, 1H), 8.66 (s, 1H). MS (M+H): 227.2.

The following compounds can be synthesized following the methodology described in Scheme 1.

Example 17: 3-(5-((trans)-2-aminocyclopropyl)pyridin-2-yl)phenol dihydrochloride

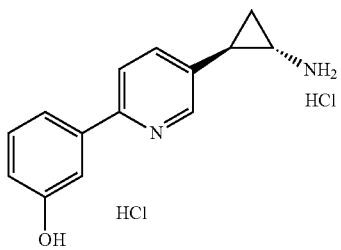 [SMILES: N[C@H]1C[C@@H]1c1ccc(-c2cccc(O)c2)nc1 ; Cl ; Cl]

¹H-NMR (400 MHz, DMSO-D6) δ: 8.6-8.8 (brd, 4H), 8-7.8 (brs, 2H), 7.43 (s, 2H), 7.3 (s, 1H), 6.9 (brs, 1H), 3.0 (brs, 1H), 2.57 (brs, 1H), 1.6 (brs 1H), 1.4 (brs, 1H). MS (M+H): 227.2.

Example 18: 4-(5-((trans)-2-aminocyclopropyl)pyridin-2-yl)benzamide hydrochloride

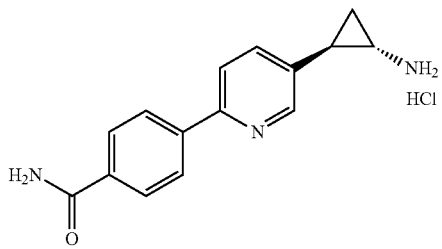 [SMILES: NC(=O)c1ccc(-c2ccc([C@H]3C[C@@H]3N)cn2)cc1 ; Cl]

¹H-NMR (400 MHz CD3OD): δ 8.8 (s, 1H), 8.46-8.33 (m, 2H), 8.14-8.01 (band, 2H), 3.2 (m, 1H), 2.75 (brs, 1H), 1.74-1.64 (m, 2H). MS (M+H): 254.2.

Example 19: 3-(5-((trans)-2-aminocyclopropyl)pyridin-2-yl)benzamide hydrochloride

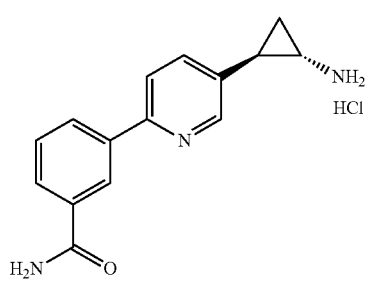 [SMILES: NC(=O)c1cccc(-c2ccc([C@H]3C[C@@H]3N)cn2)c1 ; Cl]

1H-NMR (400 MHz CD3OD): δ 8.83 (s, 1H), 8.45-8.33 (band, 3H), 8.15 (m, 2H), 7.77 (m, 1H), 3.21 (brs, 1H), 2.75 (m, 1H), 1.69 (m, 2H). MS (M+H): 254.2.

Example 20: 2-(5-((trans)-2-aminocyclopropyl)pyridin-2-yl)phenol hydrochloride

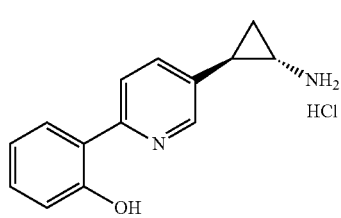

¹H-NMR (400 MHz, D2O) δ: 8.65 (s, 1H), 8.3 (m, 2H), 7.75 (d, 1H), 7.58 (t, 1H), 7.2 (m, 2H), 3.2 (brs, 1H), 2.88 (brs, 1H), 1.75 (m, 1H), 1.6 (q, 1H). MS (M+H): 227.2.

Example 21: 3-(5-((trans)-2-aminocyclopropyl)pyridin-2-yl)phenol[a2]

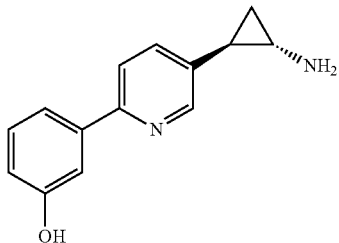 [SMILES: N[C@H]1C[C@@H]1c1ccc(-c2cccc(O)c2)nc1]

Example 22: (trans)-2-(6-(3-methoxy-4-methylphenyl)pyridin-3-yl)cyclopropanamine hydrochloride

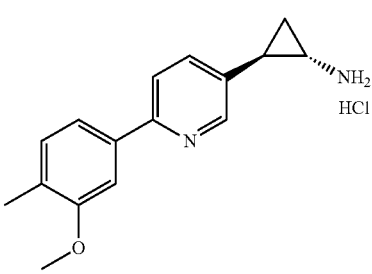 [SMILES: COc1cc(-c2ccc([C@H]3C[C@@H]3N)cn2)ccc1C ; Cl]

¹H-NMR (400 MHz, DMSO D6) δ: 8.8-8.6 (brd, 4H), 8.18 (brs, 1H), 8.0 (brs, 1H), 7.7 (brs, 1H), 7.55 (brs, 1H), 7.3 (brs, 1H), 3.9 (s, 3H), 3.0 (brs, 1H), 2.6 (brs, 1H), 2.2 (s, 3H), 1.6 (brs, 1H), 1.4 (brs, 1H). MS (M+H): 255.2.

Example 23: 5-(5-((trans)-2-aminocyclopropyl)pyridin-2-yl)-2-fluorophenol hydrochloride

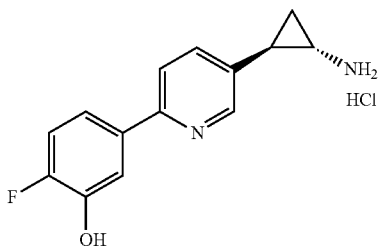 [SMILES: N[C@H]1C[C@@H]1c1ccc(-c2ccc(F)c(O)c2)nc1 ; Cl]

¹H-NMR (400 MHz, D2O) δ: 8.55 (s, 1H), 8.24 (d, 1H), 8.07 (d, 1H), 7.4-7.3 (m, 3H), 3.12-3.08 (m, 1H), 2.69-2.64 (m, 1H), 1.67-1.62 (m, 1H), 1.56-1.51 (m, 1H). MS (M+H): 244.9.

Example 24: 3-(5-((trans)-2-aminocyclopropyl)pyridin-2-yl)-5-fluorophenol hydrochloride

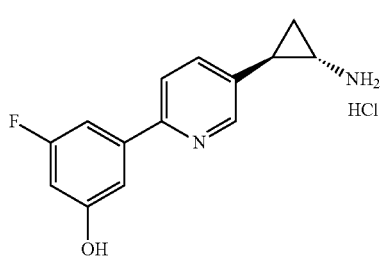 [SMILES: N[C@H]1C[C@@H]1c1ccc(-c2cc(O)cc(F)c2)nc1 ; Cl]

¹H-NMR (400 MHz, DMSO D6) δ: 8.6 (s, 1H), 8.25 (d, 1H), 8.1 (d, 1H), 7.1 (d, 2H), 6.85 (d, 1H), 3.1 (brs, 1H), 2.67 (brs, 1H), 1.68 (m, 1H), 1.55 (q, 1H). MS (M+H): 245.0.

Example 25: 3-(5-((trans)-2-aminocyclopropyl)pyridin-2-yl)-4-fluorophenol hydrochloride

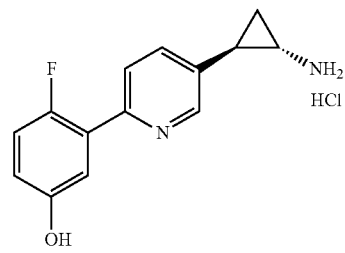 [SMILES: N[C@H]1C[C@@H]1c1ccc(-c2cc(O)ccc2F)nc1 ; Cl]

¹H-NMR (400 MHz, DMSO D6) δ: 8.49 (s, 1H), 8.17 (d, 1H), 7.94 (d, 1H), 7.07 (t, 1H), 6.95 (m, 2H), 2.98 (m, 1H), 2.58 (m, 1H), 1.56 (m, 1H), 1.44 (q, 1H). MS (M+H): 244.9.

Example 26: 3-(5-((trans)-2-aminocyclopropyl)pyridin-2-yl)-2-fluorophenol hydrochloride

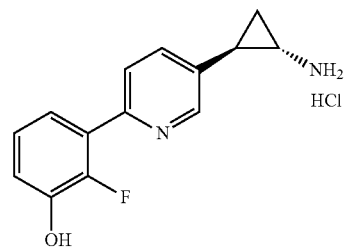 [SMILES: N[C@H]1C[C@@H]1c1ccc(-c2cccc(O)c2F)nc1 ; Cl]

¹H-NMR (400 MHz, D2O) δ: 8.63 (s, 1H), 8.24 (d, 1H), 8.05 (d, 1H), 7.23-7.14 (m, 3H), 3.1 (m, 1H), 2.7 (t, 1H), 1.63-1.66 (m, 1H), 1.54-1.57 (q, 1H). MS (M+H): 245.0.

Example 27: 3-(5-((trans)-2-aminocyclopropyl)pyridin-2-yl)-2,4-difluorophenol

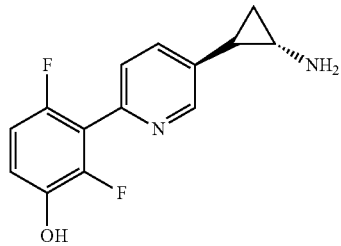

Example 28: 3-(5-((trans)-2-aminocyclopropyl)pyridin-2-yl)-2,4,6-trifluorophenol

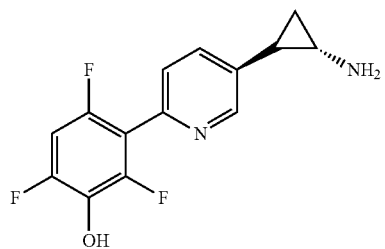

Example 29: 3-(5-((trans)-2-aminocyclopropyl)pyridin-2-yl)-5-chlorophenol hydrochloride

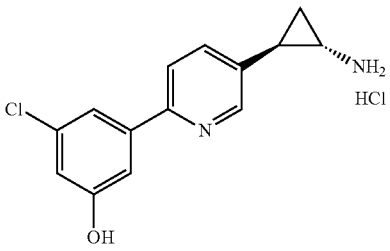 [SMILES: N[C@H]1C[C@@H]1c1ccc(-c2cc(O)cc(Cl)c2)nc1 ; Cl]

¹H-NMR (400 MHz, D2O) δ: 8.59 (s, 1H), 8.23 (d, 1H), 8.06 (d, 1H), 7.36 (d, 1H), 7.13 (d, 2H), 3.1 (brs, 1H), 2.68 (brs, 1H), 1.66 (m, 1H), 1.54 (q, 1H). MS (M+H): 260.9.

Example 30: (trans)-2-(6-(2-fluoro-3-(trifluoromethyl)phenyl)pyridin-3-yl)cyclopropanamine hydrochloride

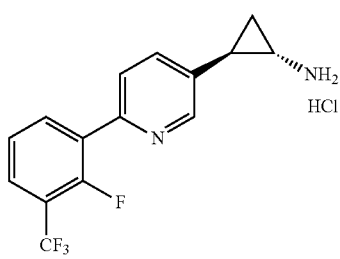 [SMILES: N[C@H]1C[C@@H]1c1ccc(-c2cccc(C(F)(F)F)c2F)nc1 ; Cl]

¹H-NMR (400 MHz, D2O) δ: 8.69 (s, 1H), 8.26 (d, 1H), 8.10 (d, 1H), 7.95 (q, 1H), 7.55 (t, 1H), 3.14 (brs, 1H), 2.71 (brs, 1H), 1.68 (m, 1H), 1.59 (q, 1H). MS (M+H): 296.9.

Example 31: (trans)-2-(6-(5-chlorothiophen-2-yl)pyridin-3-yl)cyclopropanamine hydrochloride

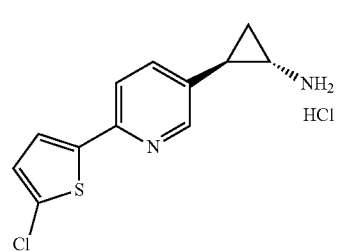 [SMILES: N[C@H]1C[C@@H]1c1ccc(-c2ccc(Cl)s2)nc1 ; Cl]

¹H-NMR (400 MHz, D2O) δ: 8.38 (s, 1H), 8.02 (d, 2H), 7.90 (d, 1H), 7.58 (s, 1H), 7.09 (s, 1H), 3.04 (brs, 1H), 2.58 (brs, 1H), 1.62 (m, 1H), 1.51 (q, 1H). MS (M+H): 251.1.

Example 32: (Trans)-2-(6-(5-methylthiophen-2-yl)pyridin-3-yl)cyclopropanamine

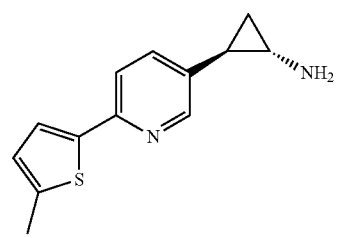 [SMILES: Cc1ccc(-c2ccc([C@H]3C[C@@H]3N)cn2)s1]

Example 33: (Trans)-2-(6-(1H-indol-6-yl)pyridin-3-yl)cyclopropanamine

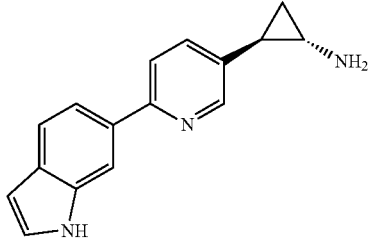 [SMILES: N[C@H]1C[C@@H]1c1ccc(-c2ccc3cc[nH]c3c2)nc1]

Example 34: (trans)-2-(6-(benzo[b]thiophen-5-yl)pyridin-3-yl)cyclopropanamine hydrochloride

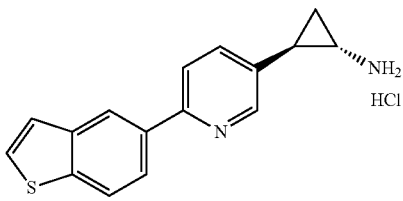 [SMILES: N[C@H]1C[C@@H]1c1ccc(-c2ccc3sccc3c2)nc1 ; Cl]

¹H-NMR (400 MHz, D2O) δ: 8.52 (S, 1H), 8.24 (brm, 3H), 8.12 (s, 1H), 7.72-7.70 (brm, 2H), 7.49 (d, 1H), 3.10 (brs, 1H), 2.66 (brs, 1H), 1.68 (brs, 1H), 1.57 (q, 1H). MS (M+H): 267.1.

Example 35: 3-(5-((trans)-2-aminocyclopropyl)-3-methylpyridin-2-yl)phenol hydrochloride

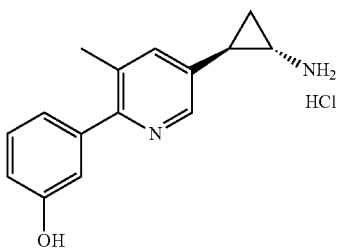 [SMILES: Cc1cc([C@H]2C[C@@H]2N)cnc1-c1cccc(O)c1 ; Cl]

¹H-NMR (400 MHz, CD3OD) δ: 8.6 (m, 1H), 8.30 (brs, 1H), 7.47-7.43 (m, 1H), 7.07-6.98 (m, 3H), 3.24-3.15 (m, 1H), 2.66 (brs, 1H), 2.47 (s, 3H), 1.63-1.66 (2H, m). MS (M+H): 241.2.

Example 36: (trans)-2-(6-(3-chlorophenyl)-5-methylpyridin-3-yl)cyclopropanamine

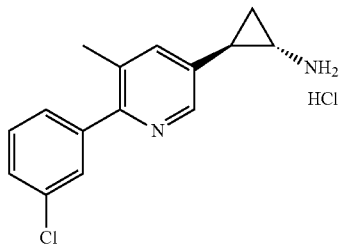 [SMILES: Cc1cc([C@H]2C[C@@H]2N)cnc1-c1cccc(Cl)c1 ; Cl]

¹H-NMR (400 MHz, CD₃OD) δ: 8.70 (s, 1H), 8.39 (s, 1H), 7.72-7.57 (band, 4H), 3.21 (m, 1H), 2.73 (brs, 1H), 2.47 (s, 3H), 1.68 (2H, band). MS (M+H): 259.1.

Example 37: (trans)-2-(5-methyl-6-(3-(trifluoromethyl)phenyl)pyridin-3-yl)cyclopropanamine hydrochloride

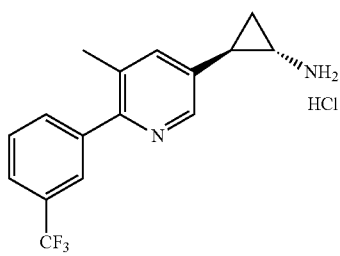 [SMILES: Cc1cc([C@H]2C[C@@H]2N)cnc1-c1cccc(C(F)(F)F)c1 ; Cl]

¹H-NMR (400 MHz, CD₃OD) δ: 8.73 (brs, 1H), 8.40 (m, 1H), 8.02-8.00 (m, 2H), 7.93-7.85 (m, 2H), 3.20-3.24 (m, 1H), 2.76-2.71 (brs, 1H), 2.46 (s, 3H), 1.72-1.66 (2H, m). MS (M+H): 293.2.

Example 38: (trans)-2-(6-(4-fluoro-3-methoxyphenyl)pyridin-3-yl)cyclopropanamine hydrochloride

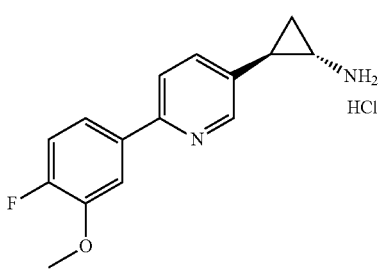 [SMILES: COc1cc(-c2ccc([C@H]3C[C@@H]3N)cn2)ccc1F ; Cl]

¹H-NMR (400 MHz, DMSO D6) δ: 8.8, (m, 4H), 8.1 (m, 1H), 7.9 (2H, m), 7.65 (brs, 1H), 7.4 (t, 1H), 4.0 (s, 3H), 3.0 (brs, 1H), 2.5 (brs, 1H), 1.6 (brs, 1H), 1.4 (q, 1H). MS (M+H): 259.2.

Example 39: (trans)-2-(6-(3-fluoro-5-methoxyphenyl)pyridin-3-yl)cyclopropanamine hydrochloride

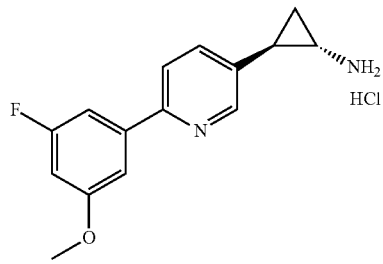 [SMILES: COc1cc(F)cc(-c2ccc([C@H]3C[C@@H]3N)cn2)c1 ; Cl]

¹H-NMR (400 MHz, DMSO D6) δ: 8.8-8.6 (brs, 4H), 8.0 (brs, 1H), 7.8-7.6 (brs, 1H), 7.5 (brs, 2H), 6.9 (brs, 1H), 3.8 (s, 3H), 3.0 (s, 1H), 1.5 (brs, 1H), 1.4 (brs, 1H). MS (M+H): 259.2.

Example 40: (trans)-2-(6-(2-fluoro-5-methoxyphenyl)pyridin-3-yl)cyclopropanamine hydrochloride

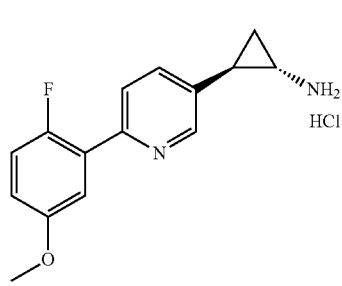 [SMILES: COc1ccc(F)c(-c2ccc([C@H]3C[C@@H]3N)cn2)c1 ; Cl]

¹H-NMR (400 MHz, DMSO D6) δ: 8.9 (d, 4H), 7.8 (s, 2H), 7.45 (s, 1H), 7.3 (t, 1H), 7.07 (brs, 1H), 3.8 (s, 3H), 3.0 (brs, 1H), 2.5 (s, 1H), 1.6 (m, 1H), 1.4 (q, 1H). MS (M+H): 259.2.

Example 41: (trans)-2-(6-(2-fluoro-3-methoxyphenyl)pyridin-3-yl)cyclopropanamine hydrochloride

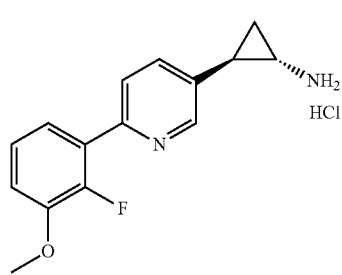 [SMILES: COc1cccc(-c2ccc([C@H]3C[C@@H]3N)cn2)c1F ; Cl]

¹H-NMR (400 MHz, D2O) δ: 8.8 (s, 1H), 8.4 (d, 1H), 8.2 (d, 1H), 7.45 (m, 2H), 7.3 (m, 1H), 4.0 (s, 3H), 3.2 (brs, 1H), 2.8 (brs, 1H), 1.8 (brs, 1H), 1.65 (q, 1H). MS (M+H): 259.2.

Example 42: (trans)-2-(6-(3-chloro-5-methoxyphenyl)pyridin-3-yl)cyclopropanamine hydrochloride

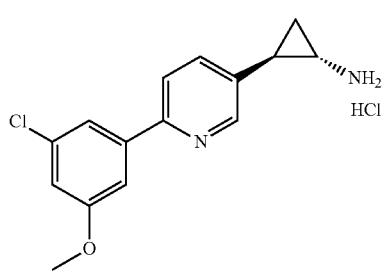

$^1$H-NMR (400 MHz, DMSO D6) δ: 8.8-8.6 (brd, 4H), 8.1 (m, 1H), 7.8 (m, 2H), 7.6 (s, 1H), 7.17 (s, 1H), 3.8 (s, 3H), 3.0 (brs, H), 2.5 (s, 1H), 1.58 (brs, 1H), 1.4 (q, 1H). MS (M+H): 275.2.

Example 43: (trans)-2-(6-(2-chloro-5-methoxyphenyl)pyridin-3-yl)cyclopropanamine hydrochloride

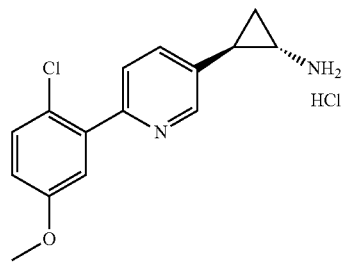 [SMILES: COc1ccc(Cl)c(-c2ccc([C@H]3C[C@@H]3N)cn2)c1 ; Cl]

$^1$H-NMR (400 MHz, DMSO D6) δ: 8.9-8.6 (brd, 4H), 8.0-7.8 (brd, 2H), 7.5 (m, 1H), 7.2-7.1 (brd, 2H), 3.9 (s, 3H), 3.0 (brs, 1H), 2.6 (brs, 1H), 1.6 (brs, 1H), 1.4 (brs, 1H). MS (M+H): 274.9.

Example 44: (trans)-2-(6-(3-methoxy-5-(trifluoromethyl)phenyl)pyridin-3-yl)cyclopropanamine hydrochloride

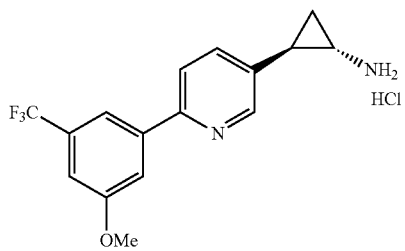 [SMILES: COc1cc(-c2ccc([C@H]3C[C@@H]3N)cn2)cc(C(F)(F)F)c1 ; Cl]

$^1$H-NMR (400 MHz, DMSO 136) δ: 8.7-8.4 (brd, 4H), 8.10 (d, 1H), 8.02 (s, 1H), 7.92 (s, 1H), 7.71 (d, 1H), 7.31 (s, 1H), 3.94 (s, 3H), 3.0 (brs, 1H), 2.42 (brs, 1H), 1.50 (brs, 1H), 1.38 (q, 1H). MS (M+H): 309.1.

Example 45: 3-(5-((trans)-2-aminocyclopropyl)pyridin-2-yl)-5-methoxybenzonitrile hydrochloride

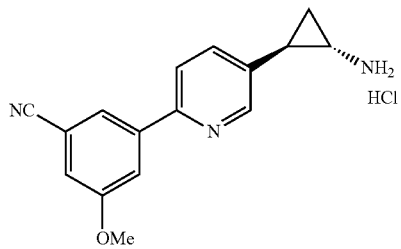 [SMILES: COc1cc(C#N)cc(-c2ccc([C@H]3C[C@@H]3N)cn2)c1 ; Cl]

$^1$H-NMR (400 MHz, D2O) δ: 8.65 (s, 1H), 8.27 (br, 1H), 8.10 (br, 1H), 7.73 (br, 1H), 7.61 (br, 1H), 7.53 (br, 1H), 3.90 (s, 3H) 3.12 (brs, 1H), 2.7 (brs, 1H), 1.69 (quin, 1H), 1.57 (q, 1H). MS (M+H): 266.2.

Example 46: 5-(5-((trans)-2-aminocyclopropyl)pyridin-2-yl)-2-methylphenol hydrochloride

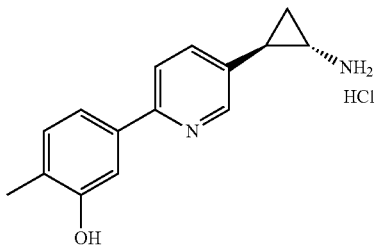 [SMILES: Cc1ccc(-c2ccc([C@H]3C[C@@H]3N)cn2)cc1O ; Cl]

$^1$H-NMR (400 MHz, DMSO D6) δ: 8.55 (s, 1H), 8.25 (d, 1H), 8.1 (d 1H), 7.37-7.23 (m, 3H), 3.09-3.11 (brs, 1H), 2.67 (brs, 1H), 2.23 (s, 3H), 1.66 (brs, 1H), 1.53 (q, 1H). MS (M+H): 241.0.

Example 47: 3-(5-((trans)-2-aminocyclopropyl)pyridin-2-yl)-4-chlorophenol hydrochloride

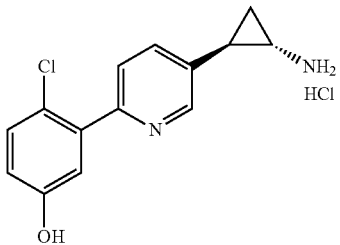 [SMILES: N[C@H]1C[C@@H]1c1ccc(-c2cc(O)ccc2Cl)nc1 ; Cl]

$^1$H-NMR (400 MHz, DMSO D6) δ: 8.69 (s, 1H), 8.31 (d, 1H), 8.03 (d, 1H), 7.45 (d, 1H), 7.04 (m 2H), 3.12 (brs, 1H), 2.72 (brs, 1H), 1.73 (brs, 1H), 1.58 (q, 1H). MS (M+H): 260.9.

Example 48: 3-(5-((trans)-2-amninocyclopropyl)pyridin-2-yl)-5-(trifluoromethyl)phenol hydrochloride

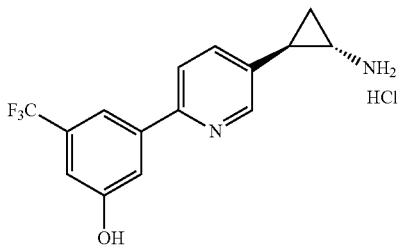 [SMILES: N[C@H]1C[C@@H]1c1ccc(-c2cc(O)cc(C(F)(F)F)c2)nc1 ; Cl]

$^1$H-NMR (400 MHz, D2O) δ: 8.62 (s, 1H), 8.24 (d, 1H), 8.12 (d, 1H), 7.67 (s, 1H), 7.48 (s, 1H), 7.38 (s, 1H), 3.12 (brs, 1H), 2.69 (brs, 1H), 1.67 (brs, 1H), 1.57 (q, 1H). MS (M+H): 295.1.

Example 49: (trans)-2-(6-(2-fluoro-5-(trifluoromethyl)phenyl)pyridin-3-yl)cyclopropanamine hydrochloride

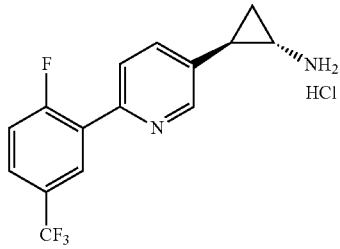 [SMILES: N[C@H]1C[C@@H]1c1ccc(-c2cc(C(F)(F)F)ccc2F)nc1 ; Cl]

$^1$H-NMR (400 MHz, D2O) δ: 8.73 (s, 1H), 8.34 (d, 1H), 8.15 (d, 1H), 8.09 (d, 1H), 7.9 (q, 1H), 7.5 (q, 1H), 3.18 (brs, 1H), 2.74 (brs, 1H), 1.71 (brs, 1H), 1.62 (q, 1H); MS (M+H): 296.9.

Example 50: (trans)-2-(6-(2-chloro-5-(trifluoromethyl)phenyl)pyridin-3-yl)cyclopropanamine hydrochloride

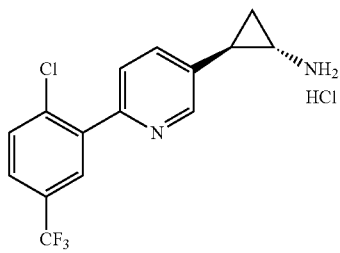 [SMILES: N[C@H]1C[C@@H]1c1ccc(-c2cc(C(F)(F)F)ccc2Cl)nc1 ; Cl]

$^1$H-NMR (400 MHz, D$_2$O) δ: 8.72 (s, 1H), 8.32 (d, 1H), 8.04 (d, 1H), 7.9 (d, 1H), 7.81 (d, 2H), 3.14 (brs, 1H), 2.73 (m, 1H), 1.69 (brs, 1H), 1.59 (q, 1H). MS (M+H): 312.9.

Example 51: (trans)-2-(6-(3,5-bis(trifluoromethyl)phenyl)pyridin-3-yl)cyclopropanamine hydrochloride

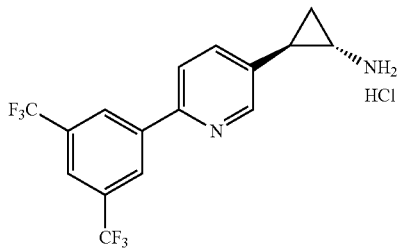 [SMILES: N[C@H]1C[C@@H]1c1ccc(-c2cc(C(F)(F)F)cc(C(F)(F)F)c2)nc1 ; Cl]

$^1$H-NMR (400 MHz, D$_2$O D6) δ: 8.68 (s, 1H), 8.41 (s, 2H), 8.29 (s, 1H), 8.18 (q, 2H), 3.14 (brs, 1H), 2.69 (brs, 1H), 1.69 (brs, 1H), 1.60 (q, 1H). MS (M+H): 346.8.

Example 52: N-(3-(5-((trans)-2-aminocyclopropyl)pyridin-2-yl)phenyl)acetamide hydrochloride

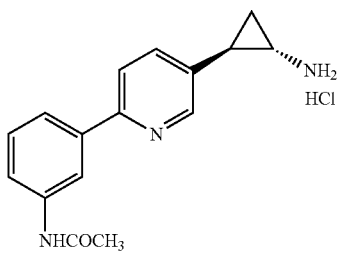

$^1$H-NMR (400 MHz, D2O) δ: 8.62 (s, 1H), 8.30 (d, 1H), 8.16 (d, 1H), 7.98 (s, 1H), 7.7-7.5 (m, 3H), 3.10 (brs, 4H), 2.69 (brs, 1H), 2.18 (s, 3H), 1.69 (m, 1H), 1.57 (q, 1H). MS (M+H): 268.2

Example 53: N-(3-(5-((trans)-2-aminocyclopropyl)pyridin-2-yl)phenyl)methanesulfonamide hydrochloride

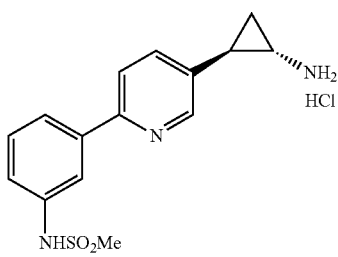

$^1$H-NMR (400 MHz, D2O) δ: 8.64 (s, 1H), 8.30 (d, 1H), 8.14 (d, 1H), 7.68-7.56 (m, 1H), 7.46 (d, 1H), 3.10 (brs, 4H), 2.68 (brs, 1H), 1.68 (m, 1H), 1.58 (q, 1H). MS (M+H): 304.1.

Example 54: (trans)-2-(6-(benzo[b]thiophen-2-yl)pyridin-3-yl)cyclopropanamine hydrochloride

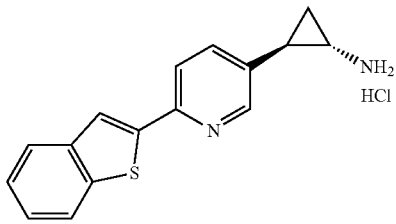 [SMILES: N[C@H]1C[C@@H]1c1ccc(-c2cc3ccccc3s2)nc1 ; Cl]

¹H-NMR (400 MHz, D2O) δ: 8.23 (d, 1H), 7.89-7.90 (brm, 5H), 7.42 (d, 2H), 2.97 (brs, 1H), 2.46 (brs, 1H), 1.58 (m, 1H), 1.44 (q, 1H). MS (M+H): 267.1.

Example 55: (trans)-2-(6-(benzo[b]thiophen-3-yl)pyridin-3-yl)cyclopropanamine hydrochloride

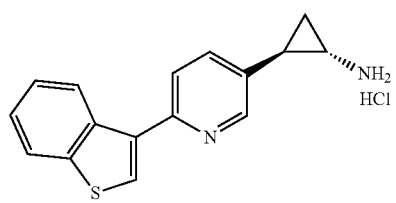 [SMILES: N[C@H]1C[C@@H]1c1ccc(-c2csc3ccccc23)nc1 ; Cl]

¹H-NMR (400 MHz, D2O) δ: 8.63 (S, 1H), 8.32 (d, 1H), 8.19 (s, 1H), 8.13 (d, 1H), 8.06 (d, 1H), 7.92 (d, 1H), 7.53 (d, 2H), 3.15 (m, 1H), 2.71 (m, 1H), 1.64 (m, 1H), 1.57 (q, 1H). MS (M+H): 267.1.

Example 56: 5-(5-((trans)-2-aminocyclopropyl)pyridin-2-yl)thiophene-2-carbonitrile hydrochloride

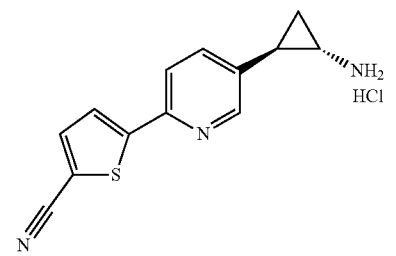 [SMILES: N#Cc1ccc(-c2ccc([C@H]3C[C@@H]3N)cn2)s1 ; Cl]

¹H-NMR (400 MHz, D2O) δ: 8.35 (S, 1H), 7.8 (brs, 1H), 7.79 (s, 1H), 7.69 (s, 1H), 7.57 (s, 1H), 3.0 (brs, 1H), 2.53 (brs, 1H), 1.56 (brs, 1H), 1.48 (q, 1H); Mass (M+H): 242.1.

Example 57: (trans)-2-(6-(4-methylthiophen-3-yl)pyridin-3-yl)cyclopropanamine hydrochloride

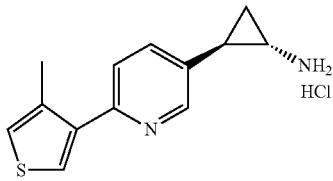 [SMILES: Cc1cscc1-c1ccc([C@H]2C[C@@H]2N)cn1 ; Cl]

¹H-NMR (400 MHz, D2O) δ: 8.6 (s, 1H), 8.35 (d, 1H), 8.0 (d, 1H), 7.85 (d, 1H), 7.35 (d, 1H), 3.15 (m, 1H), 2.7 (m, 1H), 2.3 (s, 3H), 1.65 (m, 1H), 1.55 (q, 1H). MS (M+H): 231.1.

Example 58: (Trans)-2-(6-(3,4-difluoro-5-methoxyphenyl)pyridin-3-yl)cyclopropanamine hydrochloride

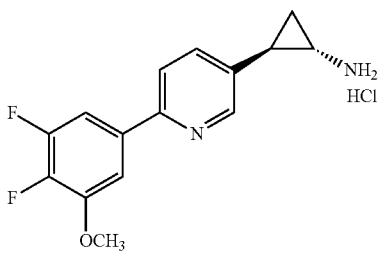 [SMILES: COc1cc(-c2ccc([C@H]3C[C@@H]3N)cn2)cc(F)c1F ; Cl]

¹H-NMR (400 MHz, DMSO-d6) δ: 8.60-8.66 (m, 4H), 8.07 (brs, 1H), 7.74 (brs, 3H), 3.99 (s, 3H), 2.97 (brs, 1H), 2.47 (brs, 1H), 1.52 (brs, 1H), 1.37 (q, 1H). MS (M+H): 277.1.

Example 59: 5-(5-((trans)-2-aminocyclopropyl)pyridin-2-yl)-2,3-difluorophenol hydrochloride

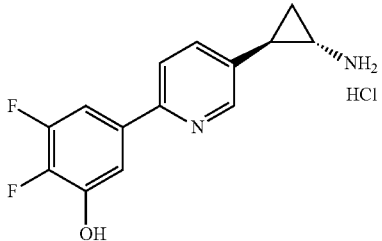 [SMILES: N[C@H]1C[C@@H]1c1ccc(-c2cc(O)c(F)c(F)c2)nc1 ; Cl]

¹H-NMR (400 MHz, D2O) δ: 8.60 (s, 1H), 8.23 (d, 4H), 8.05 (brs, 1H), 7.22 (m, 2H), 3.10 (m, 1H), 2.67 (m, 1H), 1.66 (quin, 1H), 1.55 (q, 1H), MS (M+H): 263.1.

Example 60: (Trans)-2-(6-(1H-indazol-6-yl)pyridin-3-yl)cyclopropanamine hydrochloride

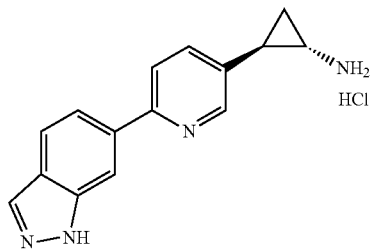 [SMILES: N[C@H]1C[C@@H]1c1ccc(-c2ccc3cn[nH]c3c2)nc1 ; Cl]

$^1$H-NMR (400 MHz, D2O) δ: 8.64 (brs, 1H), 8.35 (m, 1H), 8.25 (m, 2H), 8.07 (m, 2H), 7.56 (br, 1H), 3.15 (brs, 1H), 2.72 (brs, 1H), 1.70 (quin, 1H), 1.58 (q, 1H). MS (M+H): 251.1.

Example 61: (Trans)-2-(6-(9H-carbazol-2-yl)pyridin-3-yl)cyclopropanamine hydrochloride

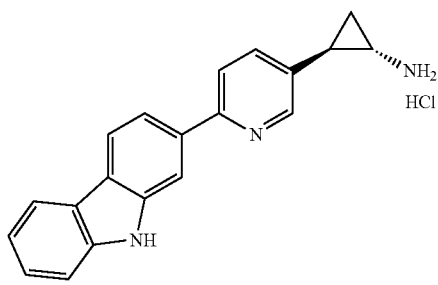 [SMILES: N[C@H]1C[C@@H]1c1ccc(-c2ccc3c(c2)[nH]c2ccccc23)nc1 ; Cl]

$^1$H-NMR (400 MHz, DMSO-d6) δ: 8.70 (s, 1H), 8.32 (d, 1H), 8.16-8.24 (m, 3H), 8.04 (d, 1H), 7.82 (d, 1H), 7.58 (d, 1H), 7.49 (t, 1H), 7.24 (t, 1H), 3.03 (brs, 1H), 2.57 (brs, 1H), 1.56 (brs, 1H), 1.44 (brs, 1H). MS (M+H): 300.1.

Example 62: 6-(5-((trans)-2-aminocyclopropyl)pyridin-2-yl)indolin-2-one hydrochloride

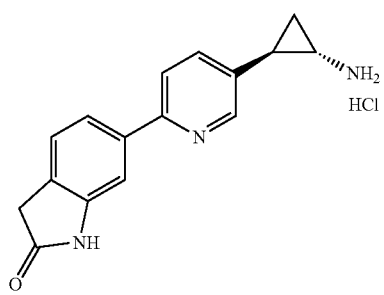 [SMILES: N[C@H]1C[C@@H]1c1ccc(-c2ccc3c(c2)NC(=O)C3)nc1 ; Cl]

$^1$H-NMR (400 MHz, DMSO-d6) δ: 8.62 (s, 1H), 7.96 (d, 1H), 7.80 (d, 1H), 7.62 (d, 1H), 7.51 (s, 1H), 7.33 (d, 1H), 2.98 (brs, 1H), 2.47 (brs, 1H), 1.51 (quin, 1H), 1.39 (q, 1H). MS (M+H): 266.1.

Example 63: Enantiomers of 4'-((trans)-2-aminocyclopropyl)biphenyl-3-ol hydrochloride

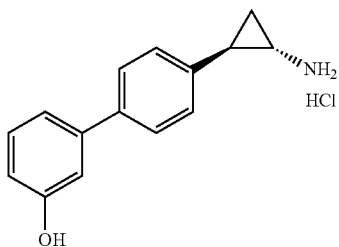

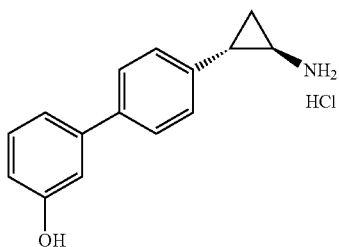

Each of these compounds corresponds to each of the possible trans-isomers [(1R,2S) and (1S,2R)] of the product described in Example 4. The synthetic procedure used for their synthesis was similar to the one described in Example 4. Chiral HPLC resolution of the diastereomeric mixture was performed at the N-Boc stage, followed by final carbamate deprotection of each of these two enantiomers.

The conditions used to perform this chiral separation are:

Separation by chiral preparative HPLC: Every injection is prepared from 40 mg of the racemic mixture dissolved in a mixture of EtOH, Hexane, THF and diethylamine. These injections were separated on a Chiral Pak-IC (250×30 mm ID) 5 µm at ambient temperature eluting with 0.2% DEA in 93/7 hexane/EtOH at 35 ml/min. The solutions from the chiral separation were concentrated in vacuum to afford the resolved enantiomers.

Analytical determination of enantiomeric excess (ee): ChiralCel OD-H 250×4.6 mm ID, 5 µm, 0.1% TFA in 75/25 hexane/EtOH at 1 mL/min at ambient temperature, with UV analysis at 260 nm. Enantiomers eluted at 4.93 and 7.90 min, each with >98% enantiomeric excess.

Analytical purity: Acquity UPLC BEH C18 100×2.1 mm ID, 1.71 m, 0.025% TFA in a gradient H2O:ACN (T/% B, 0/10, 4/80, 6/80, 6.1/10) at 0.3 mL/min at ambient temperature, with UV analysis at 259 nm. Elution at 2.40 min, each with >99.5% purity. Without being bound by theory, it is believed that mixtures, e.g., racemates corresponding to a compound of Formula (I), (II), (III), (IV) or (V) can be resolved in the individual enantiomers or an enantiomer substantially free of the other enantiomer. Thus, the skilled artisan, in view of the disclosure described herein can isolate or purify enantiomers from racemates or mixtures of enantiomers in view of the disclosure herein utilizing standard organic chemistry techniques for separating enantiomers.

Example 64: N-(3-(5-((trans)-2-aminocyclopropyl)pyridin-2-yl)phenyl)benzenesulfonamide hydrochloride

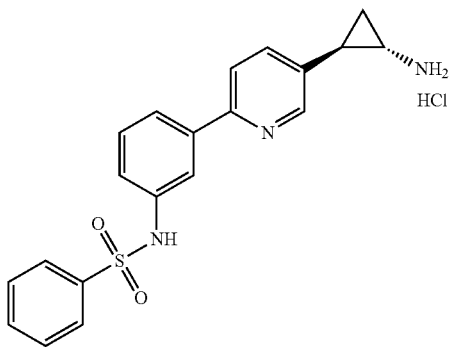 [SMILES: N[C@H]1C[C@@H]1c1ccc(-c2cccc(NS(=O)(=O)c3ccccc3)c2)nc1 ; Cl]

¹H-NMR (400 MHz, CD3OD) δ: 8.74 (s, 1H), 8.34 (m, 1H), 8.14 (m, 1H), 7.82 (d, 2H), 7.73 (br, 1H), 7.58 (t, 2H), 7.49 (t, 3H), 7.30 (t, 1H), 3.17 (m, 1H), 2.68 (m, 1H), 1.65 (m, 2H). MS (M+H): 366.0.

Example 65: N-(3-(5-((trans)-2-aminocyclopropyl)pyridin-2-yl)phenyl)propane-2-sulfonamide hydrochloride

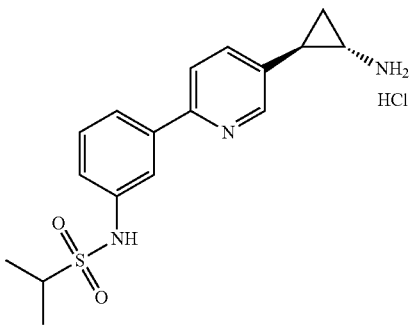 [SMILES: CC(C)S(=O)(=O)Nc1cccc(-c2ccc([C@H]3C[C@@H]3N)cn2)c1 ; Cl]

¹H-NMR (400 MHz, CD3OD) δ: 8.77 (s, 1H), 8.31 (d, 1H), 8.19 (d, 1H), 7.83 (s, 1H), 7.55-7.65 (m, 2H), 7.48 (d, 1H), 3.38 (m, 1H), 3.17 (m, 1H), 2.70 (m, 1H), 1.65 (m, 2H), 1.36 (d, 6H). MS (M+H): 332.3.

Example 66: 4'-((trans)-2-aminocyclopropyl)-4-fluorobiphenyl-3-ol hydrochloride

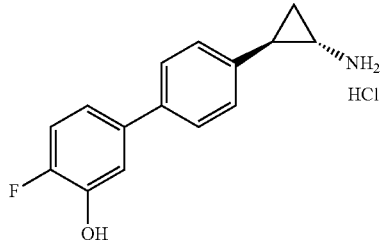 [SMILES: N[C@H]1C[C@@H]1c1ccc(-c2ccc(F)c(O)c2)cc1 ; Cl]

¹H-NMR (400 MHz, D2O) δ: 7.56 (m, 2H), 7.2-7.32 (m, 4H), 7.1-7.2 (m, 1H), 2.90 (m, 1H), 2.45 (m, 1H), 1.45 (quin, 1H), 1.37 (q, 1H). MS (M+H): 242.1.

Example 67: 4'-((trans)-2-aminocyclopropyl)-5-chlorobiphenyl-3-ol hydrochloride

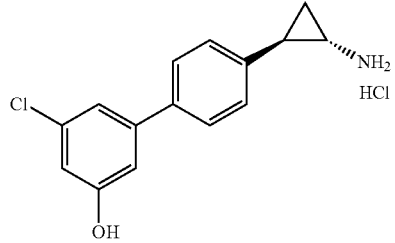

¹H-NMR (400 MHz, D2O) δ: 7.2-7.4 (m, 2H), 6.86-7.15 (m, 3H), 6.65-6.85 (m, 2H), 2.72 (brs, 1H), 2.28 (brs, 1H), 1.29 (brs, 1H), 1.18 (brs, 1H). MS (M+H): 258.1.

Example 68: N-(4'-((trans)-2-aminocyclopropyl)biphenyl-3-yl)benzenesulfonamide hydrochloride

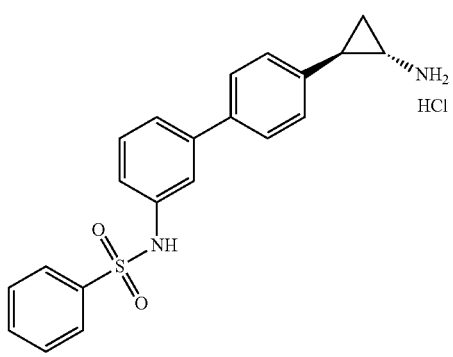 [SMILES: N[C@H]1C[C@@H]1c1ccc(-c2cccc(NS(=O)(=O)c3ccccc3)c2)cc1 ; Cl]

¹H-NMR (400 MHz, DMSO-d6) δ: 10.45 (s, 1H), 8.42 (brs, 3H), 7.80 (d, 2H), 7.61 (m, 1H), 7.57 (q, 2H), 7.43 (d, 2H), 7.32 (m, 3H), 7.24 (d, 2H), 7.06 (m, 1H), 2.85 (m, 1H), 2.35 (m, 1H), 1.42 (quin, 1H), 1.26 (q, 1H). MS (M+H): 363.3.

Example 69: N-(4'-((trans)-2-aminocyclopropyl)biphenyl-3-yl)propane-2-sulfonamide hydrochloride

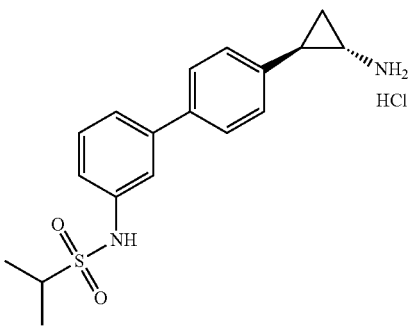 [SMILES: CC(C)S(=O)(=O)Nc1cccc(-c2ccc([C@H]3C[C@@H]3N)cc2)c1 ; Cl]

¹H-NMR (400 MHz, DMSO-d6) δ: 7.55 (d, 2H), 7.47 (s, 1H), 7.43 (t, 1H), 7.36 (d, 1H), 7.26 (d, 2H), 7.22 (d, 1H), 3.31 (m, 1H), 2.84 (m, 1H), 2.33 (m, 1H), 1.40 (m, 1H), 1.25 (d, 7H). MS (M+H): 329.0

Example 70: N-(4'-((trans)-2-aminocyclopropyl)biphenyl-3-yl)methanesulfonamide hydrochloride

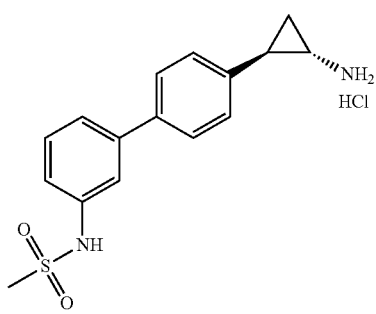 [SMILES: CS(=O)(=O)Nc1cccc(-c2ccc([C@H]3C[C@@H]3N)cc2)c1 ; Cl]

¹H-NMR (400 MHz, D2O) δ: 7.55 (d, 2H), 7.47 (d, 3H), 7.23 (d, 3H), 3.07 (s, 3H), 2.90 (m, 1H), 2.45 (m, 1H), 1.46 (quin, 1H), 1.37 (q, 1H). MS (M+H): 301.2.

Example 71: N-(2-(5-((trans)-2-aminocyclopropyl)pyridin-2-yl)phenyl)methanesulfonamide hydrochloride

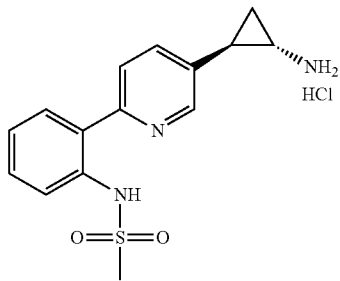 [SMILES: CS(=O)(=O)Nc1ccccc1-c1ccc([C@H]2C[C@@H]2N)cn1 ; Cl]

¹H-NMR (400 MHz, DMSO-d6) δ: 8.63 (s, 1H), 8.01 (d, 1H), 7.86 (t, 1H), 7.54 (m, 2H), 7.33 (t, 1H), 2.99 (m, 1H), 2.94 (s, 3H), 2.47 (m, 1H), 1.40-1.55 (m, 2H). MS (M+H): 304.0.

Example 72: 3-(5-((trans)-2-aminocyclopropyl)pyridin-2-yl)-4-methoxybenzonitrile hydrochloride

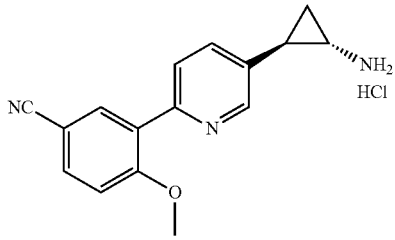 [SMILES: COc1ccc(C#N)cc1-c1ccc([C@H]2C[C@@H]2N)cn1 ; Cl]

¹H-NMR (400 MHz, CD3OD) δ: 8.83 (s, 1H), 8.40 (d, 1H), 8.20 (d, 1H), 8.15 (s, 1H), 8.05 (dd, 1H), 7.46 (d, 1H), 4.01 (s, 3H), 3.21 (m, 1H), 2.74 (m, 1H), 1.60-1.75 (m, 2H). MS (M+H): 266.3.

Example 73: N-(4'-((trans)-2-aminocyclopropyl)biphenyl-2-yl)methanesulfonamide hydrochloride

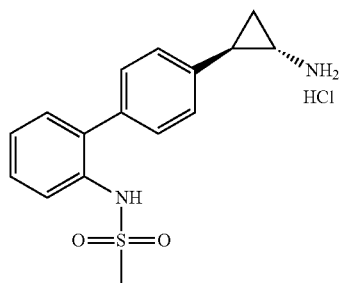 [SMILES: CS(=O)(=O)Nc1ccccc1-c1ccc([C@H]2C[C@@H]2N)cc1 ; Cl]

¹H-NMR (400 MHz, DMSO-d6) δ: 7.37-7.42 (m, 5H), 7.34 (d, 1H), 7.24 (d, 2H), 2.85 (m, 1H), 2.75 (s, 3H), 2.37 (m, 1H), 1.42 (quin, 1H), 1.31 (q, 1H). MS (M−H): 301.2.

Example 74: 4'-((trans)-2-aminocyclopropyl)-6-methoxybiphenyl-3-carbonitrile hydrochloride

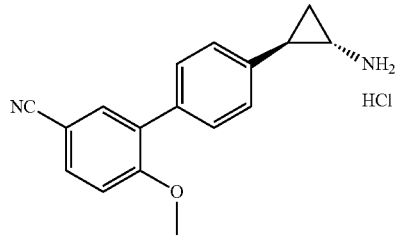 [SMILES: COc1ccc(C#N)cc1-c1ccc([C@H]2C[C@@H]2N)cc1 ; Cl]

¹H-NMR (400 MHz, DMSO-d6) δ: 8.82 (d, 1H), 7.69 (s, 1H), 7.44 (d, 2H), 7.30 (d, 1H), 7.24 (d, 2H), 3.84 (s, 3H), 2.84 (m, 1H), 2.36 (m, 1H), 1.40 (quin, 1H), 1.31 (q, 1H). MS (M+H): 265.3

Example 75: N-(4'-((trans)-2-aminocyclopropyl)-6-methoxybiphenyl-3-yl)methanesulfonamide hydrochloride

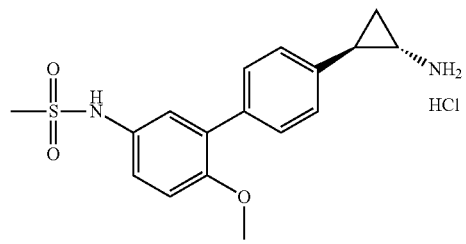 [SMILES: COc1ccc(NS(C)(=O)=O)cc1-c1ccc([C@H]2C[C@@H]2N)cc1 ; Cl]

¹H-NMR (400 MHz, DMSO-d6) δ: 9.47 (s, 1H), 8.38 (brs, 3H), 7.37 (d, 2H), 7.20 (t, 3H), 7.05-7.18 (m, 2H), 3.73 (s, 3H), 2.92 (s, 3H), 2.84 (m, 1H), 2.34 (m, 1H), 1.39 (quin, 1H), 1.25 (q, 1H). MS (M−H): 331.3 The following compounds can be synthesized following the methodology described in Scheme 2

Example 76: (trans)-2-(2-chloro-6-(3-(trifluoromethyl)phenyl)pyridin-3-yl)cyclopropanamine hydrochloride

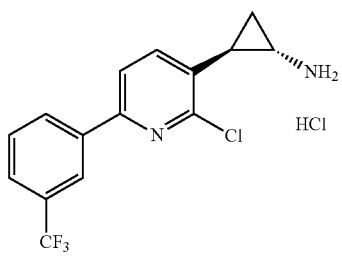 [SMILES: N[C@H]1C[C@@H]1c1ccc(-c2cccc(C(F)(F)F)c2)nc1Cl ; Cl]

Step 1:

A solution of (E)-ethyl 3-(6-bromopyridin-3-yl)acrylate (Int-F) (20 g, 78.125 mmol), 3-trifloro methyl boronic acid (17.7 g, 93.75 mmol) and $K_2CO_3$ (32 g, 234 mmol) in ACN:$H_2O$ (4:1), was degassed for 20 minutes. Pd ($PPh_3$)$_4$ (900 mg, 0.078 mmol) was added and heated at reflux for 4 h. After completion, the reaction mixture was poured into water (200 mL) and extracted with EtOAc (2×200 mL). The combined extracts were washed with water (100 mL), brine (100 mL), dried over anhydrous $Na_2SO_4$, filtered and evaporated. The crude residue was purified by column chromatography ($SiO_2$) by using EtOAc: Pet ether (2:8) to afford (E)-ethyl 3-(6-(3-(trifluoromethyl)phenyl)pyridin-3-yl)acrylate (13 g, 52%) as yellow solid.

Step 2:

m-CPBA (13.9 g, 80.97 mmol) was added portion wise to a solution of trans-ethyl 3-(6-(3-(trifluoromethyl)phenyl)pyridin-3-yl)acrylate (13 g, 40.47 mmol) in DCM (150 mL) at 0° C. over a period of 30 min. and stirred at RT for 16 h. After completion, the reaction mixture was poured into ice water (100 mL), extracted with DCM (2×100 mL). Combined organic extracts were treated with sodium metabisulphite, washed with water (100 mL), brine (100 mL), dried over anhydrous $Na_2SO_4$, filtered and evaporated. The crude residue was purified by column chromatography ($SiO_2$) by using MeOH: chloroform (1:99) to afford (9 g, 66%) (E)-5-(3-ethoxy-3-oxoprop-1-enyl)-2-(3-(trifluoromethyl)phenyl)pyridine 1-oxide as yellow solid.

Step 3:

A solution of (E)-5-(3-ethoxy-3-oxoprop-1-enyl)-2-(3-(trifluoromethyl)phenyl)pyridine 1-oxide (9 g, 26.7 mmol) in $POCl_3$ (45 mL) was stirred at 80° C. for 5 h. After completion, reaction mixture was poured into ice water (150 mL), extracted with EtOAc (2×100 mL), combined extracts were treated with $NaHCO_3$ solution, washed with water (100 mL), brine (100 mL), dried over anhydrous $Na_2SO_4$, filtered and evaporated. The crude residue was purified by column chromatography by using ($SiO_2$) EtOAc: Pct ether (2:98) to afford (E)-ethyl 3-(2-chloro-6-(3-(trifluoromethyl)phenyl)pyridin-3-yl)acrylate (6.3 g, 67%) as yellow solid.

Step 4:

Trimethyl sulfoxonium iodide (4.6 g, 21.25 mmol) was added slowly in small portions over a period of 20 min, to a suspension of sodium hydride (850 mg, 21.25 mmol) in dry DMSO (120 mL) at RT stirred for 1 h, till the formation of clear solution. A solution of (E)-ethyl 3-(2-chloro-6-(3-(trifluoromethyl)phenyl)pyridin-3-yl)acrylate (6.3 g, 17.71 mmol) in dry DMSO (100 mL) was added slowly dropwise and stirred at RT for 30 mins. After completion, the reaction mixture was poured into ice water (100 mL), extracted with EtOAc (2×100 mL). The combined extracts were washed with ice water (2×100 mL), brine (50 mL), dried over anhydrous $Na_2SO_4$, filtered and evaporated to afford trans-ethyl 2-(2-chloro-6-(3-(trifluoromethyl)phenyl)pyridin-3-yl)cyclopropanecarboxylate (crude) (5.5 g) as reddish brown liquid. The crude was carried to next step without further purification.

Step 5:

4N NaOH solution (20 mL) was added to a solution of trans-ethyl 2-(2-chloro-6-(3-(trifluoromethyl)phenyl)pyridin-3-yl)cyclopropanecarboxylate (5.5 g, 14.90 mmol), in Methanol (50 mL) and stirred at RT for 2 h. After completion, the solvent was evaporated and the residue was diluted with water (50 mL), acidified with 4 N HCl solution, extracted with EtOAc (2×50 mL). The combined extracts were washed with water (2×50 mL), brine (50 mL), dried over anhydrous $Na_2SO_4$, filtered and evaporated to afford trans-2-(2-chloro-6-(3-(trifluoromethyl)phenyl)pyridin-3-yl)cyclopropanecarboxylic acid (4.9 g), as a yellow liquid. The crude was carried to next step without further purification.

Step 6:

Ethyl chloroformate (1.8 mL, 18.86 mmol) was added to a solution of trans-2-(2-chloro-6-(3-(trifluoromethyl)phenyl)pyridin-3-yl)cyclopropane carboxylic acid (4.9 g, 14.36 mmol), TEA (2.9 mL, 21.54 mmol) in acetone (70 mL) at −20° C. and stirred at for 1 h, then a solution of $NaN_3$ (1.86 g, 28.71 mmol), in water (10 mL) was added and stirred for 30 mins at RT. After completion, the solvent was evaporated and crude residue was dissolved in ethyl acetate (100 mL), washed with water (40 mL), dried over anhydrous $Na_2SO_4$, filtered and evaporated to afford trans-2-(2-chloro-6-(3-(trifluoromethyl)phenyl)pyridin-3-yl)cyclopropanecarbonyl azide (5 g). The crude was carried to next step without further purification.

Step 7:

A solution of trans-2-(2-chloro-6-(3-(trifluoromethyl)phenyl)pyridin-3-yl)cyclopropanecarbonyl azide (5 g, 13.66 mmol) in tert-Butanol (100 mL) was heated at 90° C. for 16 h. After completion, the solvent was evaporated residue was taken in water (100 mL), extracted with EtOAc (2×50 mL). The combined organic extracts were washed with water (50 mL), brine (50 mL), dried over anhydrous $Na_2SO_4$, filtered and evaporated. The crude residue was purified by column chromatography by using ($SiO_2$) EtOAc: Pet ether (2:98) to afford tert-butyl (trans)-2-(2-chloro-6-(3-(trifluoromethyl)phenyl)pyridin-3-yl)cyclopropylcarbamate (1.6 g, 28.5%) as a white solid.

Step 8:

HCl in dioxane (1 mL) was added to a solution of tert-butyl (trans)-2-(2-chloro-6-(3-(trifluoromethyl)phenyl)pyridin-3-yl)cyclopropylcarbamate (100 mg, 0.242 mmol) in dioxane (2 mL) at 0° C. and stirred for 3 h at RT. After completion, the solvent was evaporated, residue was triturated with $Et_2O$ and dried to afford trans-2-(2-chloro-6-(3-(trifluoromethyl)phenyl)pyridin-3-yl)cyclopropanamine hydrochloride (80 mg, 95%) as white solid.

$^1$H-NMR (400 MHz, DMSO D6) δ: 8.8-8.6 (brs, 3H), 8.4 (d, 2H), 8.2 (d, 1H), 7.85-7.78 (m, 3H), 3.05 (brs, 1H), 2.65 (brs, 1H), 1.55 (brs, 1H), 1.4 (q, 1N). MS (M+H): 313.1.

Example 77: (trans)-2-(2-(4-chlorophenyl)-6-(3-(trifluoromethyl)phenyl)pyridin-3-yl)cyclopropan-amine hydrochloride

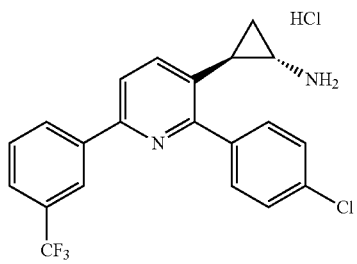 [SMILES: Cl ; N[C@H]1C[C@@H]1c1ccc(-c2cccc(C(F)(F)F)c2)nc1-c1ccc(Cl)cc1]

This compound could be synthesized following the method described for example 77 but previous to the Boc-deprotection (step 8) a Suzuki coupling (step 8') is performed to get the desired product.

Step 8':

A solution of tert-butyl (trans)-2-(2-chloro-6-(3-(trifluoromethyl)phenyl)pyridin-3-yl)cyclopropylcarbamate (150 mg, 0.364 mmol), 4-chlorophenylboronic acid (67.3 mg, 0.432 mmol) and K$_2$CO$_3$ (149 mg, 1.09 mmol) in acetonitrile: water (4:1) was degassed for 20 min. Tetrakis triphenylphosphine palladium (4.2 mg, 0.00364 mmol) was added and the reaction mixture was heated at reflux for 16 h. After completion, the reaction mixture was poured into ice water (25 mL) and extracted with EtOAc (2×25 mL). The combined extracts were washed with water (25 mL), brine (25 mL) and dried over anhydrous Na$_2$SO$_4$ filtered and evaporated. The crude residue was purified by column chromatography (SiO$_2$) using EtOAc: Pet ether (1:9) to afford tert-butyl (trans)-2-(2-(4-chlorophenyl)-6-(3-(trifluoromethyl)phenyl)pyridin-3-yl)cyclopropylcarbamate (140 mg, 79%) as white solid.

Step 9':

HCl in dioxane (2 mL) was added to a solution of tert-butyl (trans)-2-(2-(4-chlorophenyl)-6-(3-(trifluoromethyl)phenyl)pyridin-3-yl)cyclopropylcarbamate (130 mg, 0.315 mmol) in dioxane (2 mL) at 0° C. and stirred for 3 h at RT. After completion, the solvent was evaporated and the residue was triturated with Et2O to afford (trans)-2-(2-(4-chlorophenyl)-6-(3-(trifluoromethyl)phenyl)pyridin-3-yl) cyclopropanamine hydrochloride (80 mg, 70.7%) as pale yellow solid. $^1$H-NMR (400 MHz, DMSO D6) δ: 8.6-8.5 (brs, 3H), 8.45 (d, 2H), 8.1 (d, 1H), 7.7-7.8 (m, 5H), 7.6 (d, 2H), 3.1 (brs, 1H), 2.4 (brs, 1H), 1.4-1.35 (m, 2H). MS (M+H): 389.1

The following compounds could be synthesized following the method described for example 77 using the corresponding commercially available boronic acid/boronate ester.

Example 78: 4-(3-((trans)-2-aminocyclopropyl)-6-(3-(trifluoromethyl)phenyl)pyridin-2-yl)phenol hydrochloride

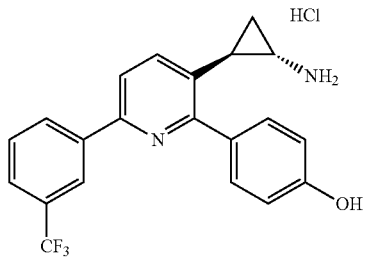 [SMILES: Cl ; N[C@H]1C[C@@H]1c1ccc(-c2cccc(C(F)(F)F)c2)nc1-c1ccc(O)cc1]

$^1$H-NMR (400 MHz, DMSO D6) δ: 8.6 (brs, 3H), 8.45 (s, 2H), 7.85-7.7 (m, 2H), 7.6 (m, 3H), 6.97 (d, 2H), 3.1 (brs, 1H), 2.5 (brs, 1H), 1.37 (m, 1H), 1.3 (q, 18). MS (M+H): 371.2.

Example 79: 4-(3-((trans)-2-aminocyclopropyl)-6-(3-(trifluoromethyl)phenyl)pyridin-2-yl)benzamide hydrochloride

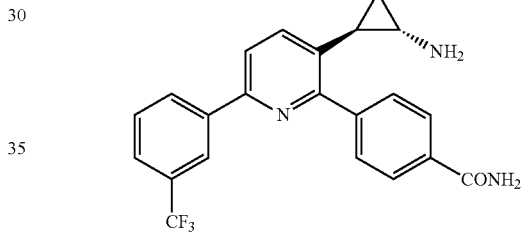

$^1$H-NMR (400 MHz, DMSO D6) δ: 8.5 (brs, 3H), 8.45 (s, 2H), 8.15 (m, 2H), 8.1 (d, 2H), 7.8-7.7 (m, 5H), 7.5 (brs, 1H), 3.1 (brs, 18), 2.45 (brs, 1H), 1.3 (m, 2H). MS (M+H): 398.1.

Example 80: (trans)-2-(2-methyl-6-(3-(trifluoromethyl)phenyl)pyridin-3-yl)cyclopropanamine hydrochloride

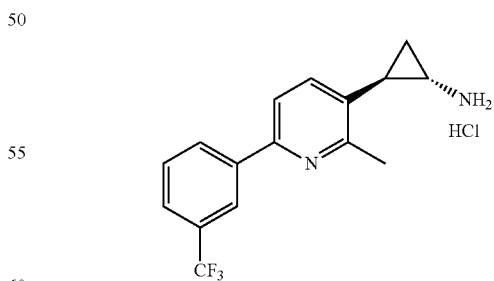

$^1$H-NMR (400 MHz, DMSO D6) δ: 8.75 (brs, 3H), 8.4 (s, 1H), 8.35 (d, 1H), 8.0 (s, 1H), 7.85 (d, 1H), 7.8-7.7 (m, 2H), 2.87 (brs, 1H), 2.8 (s, 3H), 2.65 (brs, 1H), 1.5 (m, 1H), 1.4 (q, 1H). MS (M+H): 293.1.

The following compounds can be synthesized following the methodology described in Schemes 1 and 2.

Example 81: 3-(5-((trans)-2-aminocyclopropyl)pyridin-2-yl)-5-hydroxybenzonitrile hydrochloride

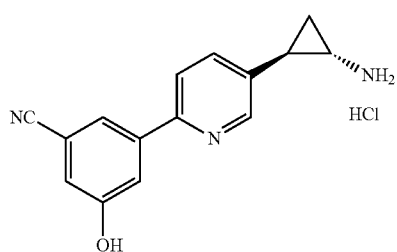 [SMILES: N#Cc1cc(O)cc(-c2ccc([C@H]3C[C@@H]3N)cn2)c1 ; Cl]

5-(5-((trans)-2-aminocyclopropyl)pyridin-2-yl)-2,3-difluorophenol hydrochloride

Example 82: (Trans)-2-(6-(3-chloro-4-fluoro-5-methoxyphenyl)pyridin-3-yl)cyclopropanamine hydrochloride

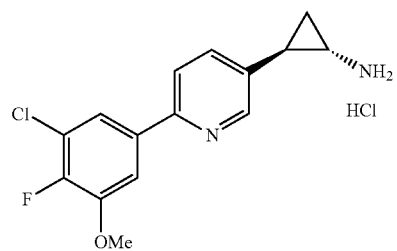 [SMILES: COc1cc(-c2ccc([C@H]3C[C@@H]3N)cn2)cc(Cl)c1F ; Cl]

Example 83: 5-(5-((trans)-2-aminocyclopropyl)pyridin-2-yl)-3-chloro-2-fluorophenol hydrochloride

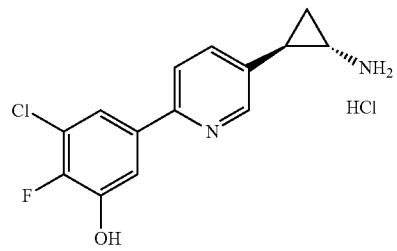 [SMILES: N[C@H]1C[C@@H]1c1ccc(-c2cc(O)c(F)c(Cl)c2)nc1 ; Cl]

Example 84: 6-(5-((trans)-2-aminocyclopropyl)pyridin-2-yl)benzofuran-2(3H)-one hydrochloride

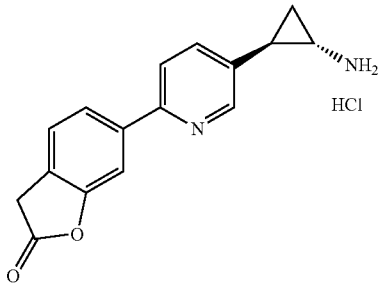 [SMILES: N[C@H]1C[C@@H]1c1ccc(-c2ccc3c(c2)OC(=O)C3)nc1 ; Cl]

Example 85: 4-(5-((trans)-2-aminocyclopropyl)pyridin-2(1H)-one hydrochloride

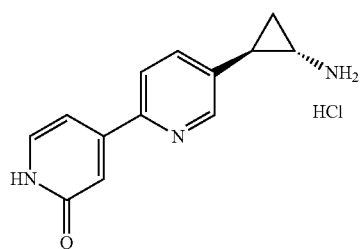 [SMILES: N[C@H]1C[C@@H]1c1ccc(-c2cc[nH]c(=O)c2)nc1 ; Cl]

Example 86: 4'-((trans)-2-aminocyclopropyl)-5-chloro-4-fluorobiphenyl-3-ol hydrochloride

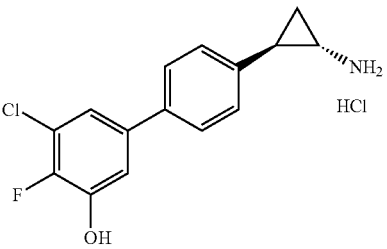 [SMILES: N[C@H]1C[C@@H]1c1ccc(-c2cc(O)c(F)c(Cl)c2)cc1 ; Cl]

Example 87: 4'-((trans)-2-aminocyclopropyl)-6-hydroxybiphenyl-3-carbonitrile hydrochloride

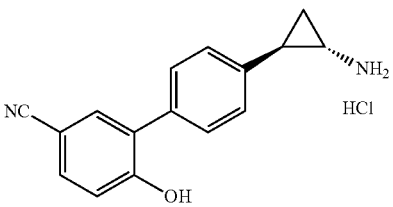 [SMILES: N#Cc1ccc(O)c(-c2ccc([C@H]3C[C@@H]3N)cc2)c1 ; Cl]

$^1$HNMR (400 MHz, DMSO-d6, D2O Exchange) δ: 7.67 (s, 1H), 7.64 (d, J=8 Hz, 1H), 7.50 (d, J=8 Hz, 2H), 7.22 (d, J=8 Hz, 2H), 7.08 (d, J=8 Hz, 1H), 2.82-2.90 (m, 1H), 2.33-2.40 (m, 18), 1.38-1.45 (m, 1H), 1.30 (q, J=7 Hz, 1H); Mass (M–H): 249.3

Example 88: N-(4'-((trans)-2-aminocyclopropyl)-6-hydroxybiphenyl-3-yl)methanesulfonamide hydrochloride

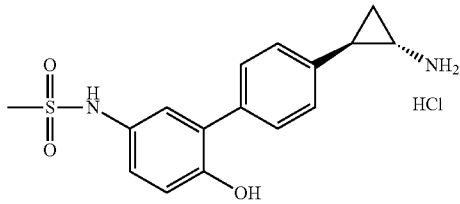 [SMILES: CS(=O)(=O)Nc1ccc(O)c(-c2ccc([C@H]3C[C@@H]3N)cc2)c1 ; Cl]

¹HNMR (400 MHz, D2O) δ: 7.53 (d, J=8 Hz, 2H), 7.31 (d, J=8 Hz, 2H), 7.20-7.28 (m, 2H), 7.06 (d, J=8 Hz, 1H), 3.10 (s, 1H), 2.94-3.04 (m, 1H), 2.48-2.58 (m, 1H), 1.48-1.58 (m, 1H), 1.44 (q, J=7 Hz, 1H); Mass (M–H): 317

Example 89: 3-(5-((trans)-2-aminocyclopropyl)pyridin-2-yl)-4-hydroxybenzonitrile hydrochloride

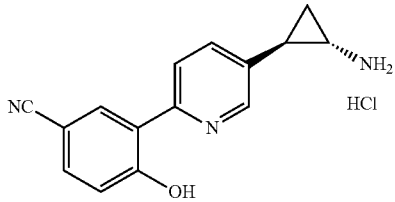 [SMILES: N#Cc1ccc(O)c(-c2ccc([C@H]3C[C@@H]3N)cn2)c1 ; Cl]

¹HNMR (400 MHz, D2O) δ: 8.45 (s, 1H), 8.03-8.13 (m, 1H), 7.92-8.02 (m, 2H), 7.66 (d, J=9 Hz, 1H), 7.03 (d, J=8 Hz, 1H), 3.02-3.10 (m, 1H), 2.56-2.64 (m, 1H), 1.57-1.67 (m, 1H), 1.45-1.56 (m, 1H); Mass (M–H): 250.0

Example 90: N-(3-(5-((trans)-2-aminocyclopropyl)pyridin-2-yl)-4-hydroxyphenyl)methanesulfonamide hydrochloride

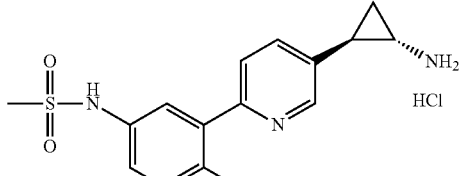

¹HNMR (400 MHz, DMSO-d6, D2O Exchange) δ: 8.60 (s, 1H), 8.06 (d, J=9 Hz, 1H), 7.95 (d, J=9 Hz, 1H), 7.67 (s, 1H), 7.24 (d, =9 Hz, 1H), 7.00 (d, J=9 Hz, 1H), 2.96-3.06 (m, 1H), 2.94 (s, 1H), 2.45-2.55 (m, 1H), 1.48-1.58 (m, 1H), 1.41 (q, J=7 Hz, 1H); Mass (M–H): 318.0

Example 91: N-(3-(5-((trans)-2-aminocyclopropyl)pyridin-2-yl)-5-(trifluoromethyl)phenyl)ethanesulfonamide hydrochloride

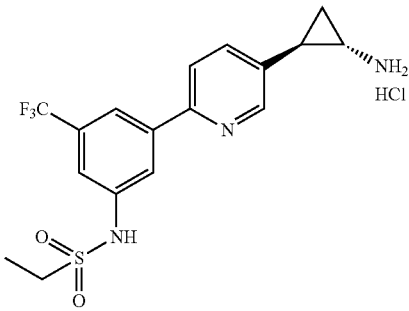 [SMILES: CCS(=O)(=O)Nc1cc(-c2ccc([C@H]3C[C@@H]3N)cn2)cc(C(F)(F)F)c1 ; Cl]

Example 92: N-(3-(5-((trans)-2-aminocyclopropyl)pyridin-2-yl)-5-(trifluoromethyl)phenyl)methanesulfonamide hydrochloride

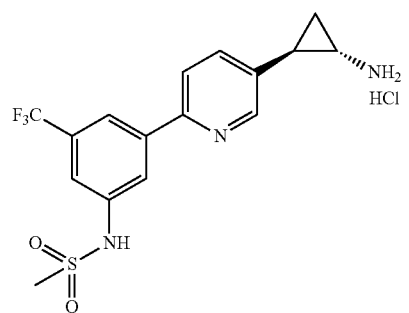 [SMILES: CS(=O)(=O)Nc1cc(-c2ccc([C@H]3C[C@@H]3N)cn2)cc(C(F)(F)F)c1 ; Cl]

Example 93: N-(3-(5-((trans)-2-aminocyclopropyl)pyridin-2-yl)-4-methoxyphenyl)methanesulfonamide hydrochloride

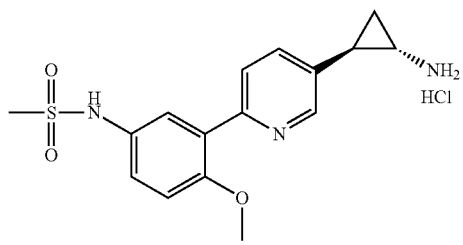 [SMILES: COc1ccc(NS(C)(=O)=O)cc1-c1ccc([C@H]2C[C@@H]2N)cn1 ; Cl]

¹HNMR (400 MHz, CD3OD) δ: 8.79 (s, 1H), 8.41 (d, J=8 Hz, 1H), 8.18 (d, J=8 Hz, 1H), 7.58 (s, 1H), 7.50 (d, J=9 Hz, 1H), 7.30 (d, J=9 Hz, 1H), 3.93 (s, 3H), 3.17-3.23 (m, 1H), 2.98 (s, 3H), 2.67-2.78 (m, 1H), 1.62-1.77 (m, 2H); Mass (M–H): 332.3

Example 94: N-(4'-((trans)-2-aminocyclopropyl)-5-chloro-[1,1'-biphenyl]-3-yl)methanesulfonamide hydrochloride

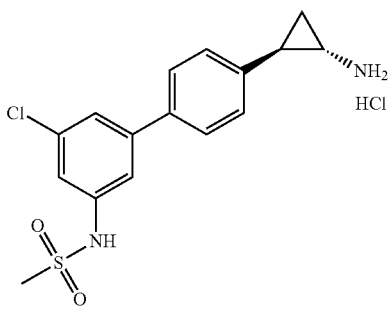 [SMILES: CS(=O)(=O)Nc1cc(Cl)cc(-c2ccc([C@H]3C[C@@H]3N)cc2)c1 ; Cl]

¹HNMR (400 MHz, D2O) δ: 7.53 (brs, 2H), 7.47 (brs, 1H), 7.32 (brs, 1H), 7.25 (brs, 3H), 3.09 (s, 3H), 2.83-2.94 (m, 1H), 2.40-2.49 (m, 1H), 1.42-1.53 (m, 1H), 1.30-1.41 (m, 1H); Mass (M−H): 335.0

Example 95: N-(3-(5-((trans)-2-aminocyclopropyl)pyridin-2-yl)-5-chlorophenyl)methanesulfonamide hydrochloride

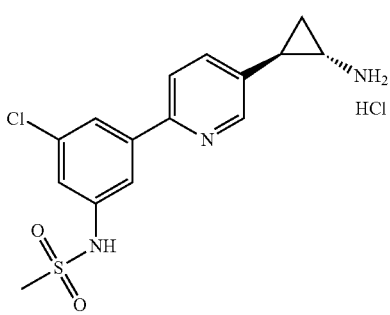 [SMILES: CS(=O)(=O)Nc1cc(Cl)cc(-c2ccc([C@H]3C[C@@H]3N)cn2)c1 ; Cl]

¹HNMR (400 MHz, D2O) δ: 8.44 (s, 1H), 8.00 (d, J=8 Hz, 1H), 7.85 (d, J=8 Hz, 1H), 7.42-7.52 (brs, 1H), 7.30-7.40 (brs, 1H), 7.22-7.30 (brs, 1H), 2.98 (s, 3H), 2.92-3.02 (m, 1H), 2.50-2.58 (m, 1H), 1.45-1.58 (m, 1H), 1.36-1.44 (m, 1H); Mass (M−H): 336.3

Example 96: N-(4'-((trans)-2-aminocyclopropyl)-4-fluoro-[1,1'-biphenyl]-3-yl)methanesulfonamide hydrochloride

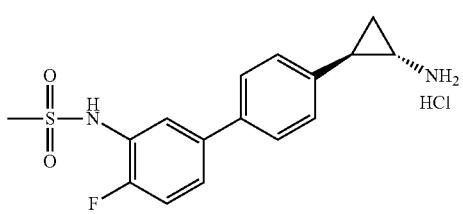 [SMILES: CS(=O)(=O)Nc1cc(-c2ccc([C@H]3C[C@@H]3N)cc2)ccc1F ; Cl]

¹HNMR (400 MHz, D2O) δ: 7.63 (d, J=8 Hz, 1H), 7.50-7.60 (m, 3H), 7.25-7.36 (m, 1H), 7.27 (d, J=8 Hz, 2H), 3.15 (s, 3H), 2.88-2.95 (m, 1H), 2.42-2.55 (m, 1H), 1.42-1.55 (m, 1H), 1.39 (q, J=7 Hz, 1H); Mass (M−H): 319.3

Example 97: N-(5-(5-((trans)-2-aminocyclopropyl)pyridin-2-yl)-2-fluorophenyl)methanesulfonamide hydrochloride

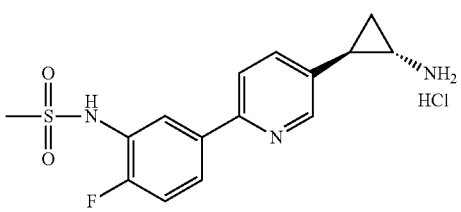 [SMILES: CS(=O)(=O)Nc1cc(-c2ccc([C@H]3C[C@@H]3N)cn2)ccc1F ; Cl]

¹HNMR (400 MHz, D2O) δ: 8.65 (s, 1H), 8.33 (d, J=8 Hz, 1H), 8.16 (d, J=8 Hz, 1H), 7.85-7.94 (brs, 1H), 7.71-7.80 (brs, 1H), 7.50 (t, J=9 Hz, 1H), 3.19 (s, 3H), 2.68-2.80 (m, 1H), 1.65-1.78 (m, 1H), 1.58-1.65 (m, 1H); Mass (M+H): 322.10

Example 98: N-(3-(5-((trans)-2-aminocyclopropyl)pyridin-2-yl)phenyl)ethanesulfonamide hydrochloride

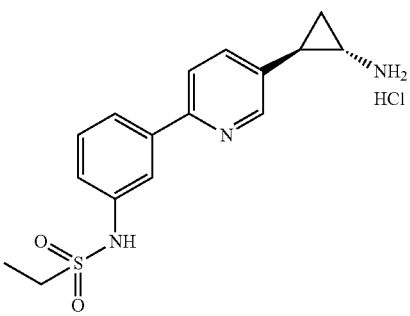 [SMILES: CCS(=O)(=O)Nc1cccc(-c2ccc([C@H]3C[C@@H]3N)cn2)c1 ; Cl]

¹HNMR (400 MHz, DMSO-d6, D2O exchange) δ: 8.61 (s, 1H), 7.93 (d, J=8 Hz, 1H), 7.88 (s, 1H), 7.80 (d, J=8 Hz, 1H), 7.72 (d, J=8 Hz, 1H), 7.50 (t, J=8 Hz, 1H), 7.32 (d, J=8 Hz, 1H), 3.15 (q, J=7 Hz, 2H), 2.90-3.00 (m, 1H), 2.46-2.56 (m, 1H), 1.48-1.58 (m, 1H), 1.42 (q, J=7 Hz, 1H), 1.23 (t, J=7 Hz, 3H); Mass (M−H): 316.3

Example 99: N-(3-(5-((trans)-2-aminocyclopropyl)pyridin-2-yl)phenyl)-4-cyanobenzenesulfonamide hydrochloride

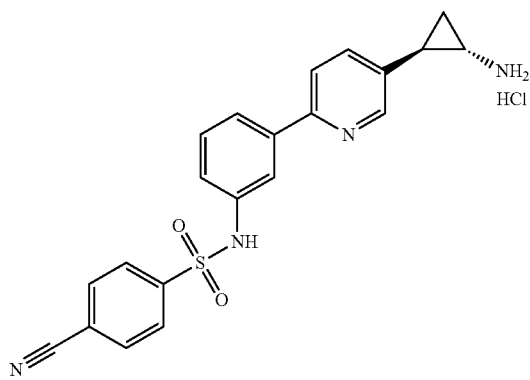 [SMILES: N#Cc1ccc(S(=O)(=O)Nc2cccc(-c3ccc([C@H]4C[C@@H]4N)cn3)c2)cc1 ; Cl]

¹HNMR (400 MHz, D2O) δ: 8.66 (s, 1H), 8.28 (d, J=8 Hz, 1H), 8.08 (d, J=8 Hz, 1H), 7.93 (s, 4H), 7.69 (d, J=6 Hz, 1H), 7.63 (s, 1H), 7.56 (t, J=8 Hz, 1H), 7.31 (d, J=8 Hz, 1H), 3.15-3.25 (m, 1H), 2.72-2.80 (m, 1H), 1.71-1.80 (m, 1H), 1.62 (q, J=7 Hz, 1H); Mass (M−H): 389.3

Example 100: N-(3-(5-((trans)-2-aminocyclopropyl)pyridin-2-yl)phenyl)-3-cyanobenzenesulfonamide hydrochloride

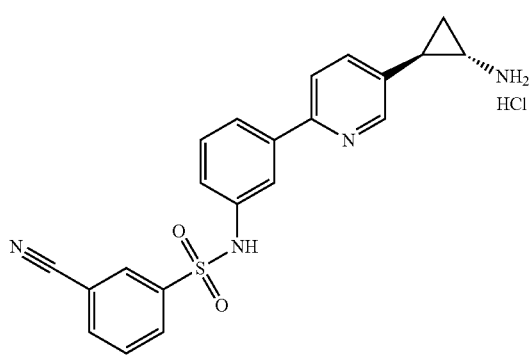 [SMILES: N#Cc1cccc(S(=O)(=O)Nc2cccc(-c3ccc([C@H]4C[C@@H]4N)cn3)c2)c1 ; Cl]

¹HNMR (400 MHz, D2O) δ: 8.58 (s, 1H), 8.18-8.26 (m, 1H), 8.11 (brs, 1H), 8.00 (d, J=8 Hz, 2H), 7.91-8.01 (m, 1H), 7.60-7.71 (m, 2H), 7.55 (s, 1H), 7.44-7.52 (m, 1H), 7.24 (brs, 1H), 3.08-3.18 (m, 1H), 2.63-2.73 (m, 1H), 1.63-1.73 (m, 1H), 1.55 (q, J=7 Hz, 1H); Mass (M−H): 389.3

Example 101: N-(3-(5-((trans)-2-aminocyclopropyl)pyridin-2-yl)phenyl)-2-cyanobenzenesulfonamide hydrochloride

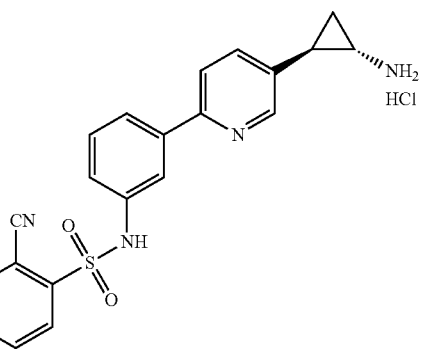

¹HNMR (400 MHz, D2O) δ: 8.59 (s, 1H), 8.20 (d, J=8 Hz, 1H), 8.08 (d, J=8 Hz, 1H), 8.01 (d, J=9 Hz, 2H), 7.89 (d, J=8 Hz, 1H), 7.83 (t, J=8 Hz, 1H), 7.75 (t, J=8 Hz, 1H), 7.62-7.68 (m, 2H), 7.48 (t, J=8 Hz, 1H), 7.20 (d, J=8 Hz, 1H), 3.08-3.16 (m, 1H), 2.64-2.72 (m, 1H), 1.63-1.74 (m, 1H), 1.55 (q, J=7 Hz, 1H); Mass (M−H): 389.3

Example 102: N-(3-(5-((trans)-2-aminocyclopropyl)pyridin-2-yl)-5-(trifluoromethyl)phenyl)-4-cyanobenzenesulfonamide hydrochloride

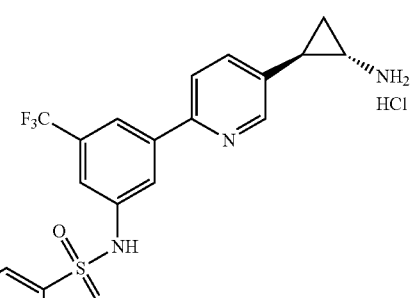

¹HNMR (400 MHz, D2O) δ: 8.59 (brs, 1H), 8.04-8.14 (m, 1H), 7.78-7.97 (m, 6H), 7.68-7.78 (m, 1H), 7.42-7.50 (m, 1H), 3.08-3.18 (m, 1H), 2.60-2.70 (m, 1H), 1.61-1.72 (m, 1H), 1.50-1.60 (m, 1H); Mass (M+H): 459.2

Example 103: N-(4'-((trans)-2-aminocyclopropyl)-[1,1'-biphenyl]-3-yl)-1,1,1-trifluoromethanesulfonamide hydrochloride

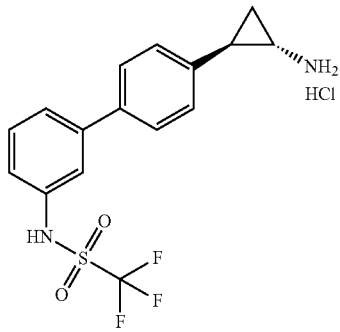 [SMILES: N[C@H]1C[C@@H]1c1ccc(-c2cccc(NS(=O)(=O)C(F)(F)F)c2)cc1 ; Cl]

¹HNMR (400 MHz, D2O) δ: 7.30-7.60 (brs, 5H), 7.10-7.30 (m, 3H), 2.80-2.92 (m, 1H), 2.38-2.48 (m, 1H), 1.40-1.50 (m, 1H), 1.22-1.40 (m, 1H); Mass (M−H): 355.3

Example 104: 4'-((trans)-2-aminocyclopropyl)-6-hydroxy-[1,1'-biphenyl]-3-carbonitrile hydrochloride

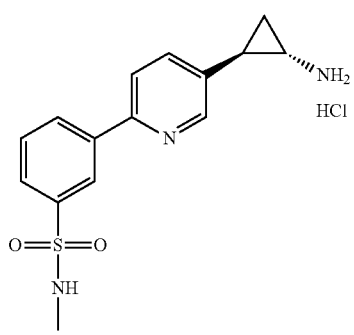 [SMILES: CNS(=O)(=O)c1cccc(-c2ccc([C@H]3C[C@@H]3N)cn2)c1 ; Cl]

¹HNMR (400 MHz, D2O) δ: 8.73 (s, 1H), 8.34 (brs, 2H), 8.23 (d, J=8 Hz, 1H), 8.17 (d, J=8 Hz, 1H), 8.13 (d, J=8 Hz, 1H), 7.92 (t, J=8 Hz, 1H), 3.18-3.28 (m, 1H), 2.74-2.84 (m, 1H), 2.64 (s, 3H), 1.72-1.82 (m, 1H), 1.65 (q, J=7 Hz, 1H); Mass (M−H): 302.3

Example 105: 4'-((trans)-2-aminocyclopropyl)-[1,1'-biphenyl]-2-ol hydrochloride

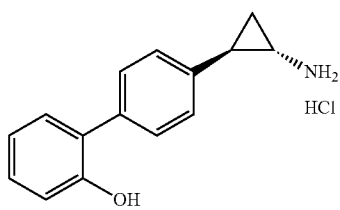 [SMILES: N[C@H]1C[C@@H]1c1ccc(-c2ccccc2O)cc1 ; Cl]

¹HNMR (400 MHz, D2O) δ: 7.46 (brs, 2H), 7.20-7.35 (m, 4H), 6.94-7.04 (m, 2H), 2.84-2.95 (m, 1H), 2.41-2.50 (m, 1H), 1.40-1.52 (m, 1H), 1.34-1.43 (m, 1H); Mass (M+H): 226.18

Example 106: 4'-((trans)-2-aminocyclopropyl)-3'-methoxy-[1,1'-biphenyl]-3-ol hydrochloride

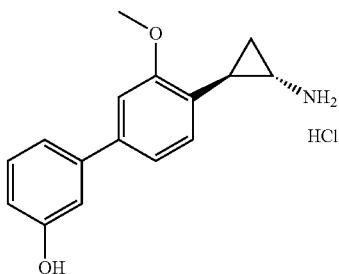 [SMILES: COc1cc(-c2cccc(O)c2)ccc1[C@H]1C[C@@H]1N ; Cl]

¹HNMR (400 MHz, D2O) δ: 7.39-7.49 (m, 1H), 7.20-7.34 (m, 3H), 7.08-7.20 (m, 2H), 6.92-7.00 (m, 1H), 3.99 (s, 3H), 2.85-2.94 (m, 1H), 2.52-2.62 (m, 1H), 1.42-1.52 (m, 1H), 1.35-1.43 (m, 1H); Mass (M+H): 256.0

The following compounds can be synthesized following the methodology described in Scheme 3.

Example 107: 3-(6-((trans)-2-aminocyclopropyl)pyridin-3-yl)phenol hydrochloride

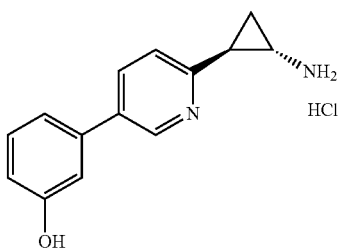 [SMILES: N[C@H]1C[C@@H]1c1ccc(-c2cccc(O)c2)cn1 ; Cl]

Example 108: (Trans)-2-(5-(3-methoxyphenyl)pyridin-2-yl)cyclopropanamine hydrochloride

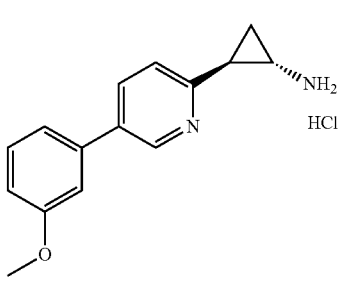 [SMILES: COc1cccc(-c2ccc([C@H]3C[C@@H]3N)nc2)c1 ; Cl]

Example 109: 4-(6-((trans)-2-aminocyclopropyl) pyridin-3-yl)phenol hydrochloride

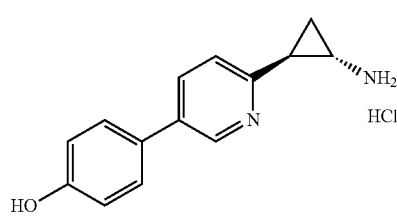 [SMILES: N[C@H]1C[C@@H]1c1ccc(-c2ccc(O)cc2)cn1 ; Cl]

Example 110: 2-(6-((trans)-2-aminocyclopropyl) pyridin-3-yl)phenol hydrochloride

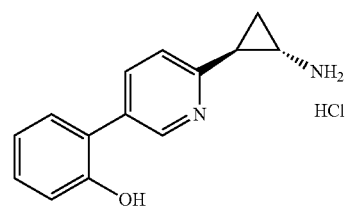 [SMILES: N[C@H]1C[C@@H]1c1ccc(-c2ccccc2O)cn1 ; Cl]

Example 111: 2-(5-((trans)-2-aminocyclopropyl) thiophen-2-yl)phenol hydrochloride

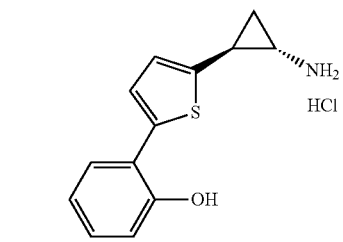 [SMILES: N[C@H]1C[C@@H]1c1ccc(-c2ccccc2O)s1 ; Cl]

Example 112: 3-(5-((trans)-2-aminocyclopropyl) thiophen-2-yl)phenol hydrochloride

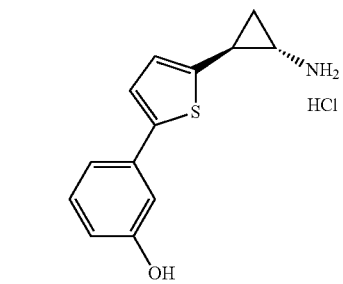 [SMILES: N[C@H]1C[C@@H]1c1ccc(-c2cccc(O)c2)s1 ; Cl]

Example 113: 3-(5-((trans)-2-aminocyclopropyl) thiophen-2-yl)phenol trihydrochloride

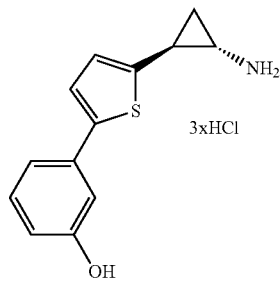 [SMILES: N[C@H]1C[C@@H]1c1ccc(-c2cccc(O)c2)s1 ; "3xHCl"]

¹HNMR (400 MHz, D2O) δ: 7.15-7.36 (m, 3H), 7.10 (brs, 1H), 6.80-6.92 (m, 2H), 2.88-2.98 (m, 1H), 2.58-2.64 (m, 1H), 1.46-1.58 (m, 1H), 1.40 (q, J=7 Hz, 1H); Mass (M+H): 232.2

Example 114: 4-(5-((trans)-2-aminocyclopropyl) thiophen-2-yl)phenol hydrochloride

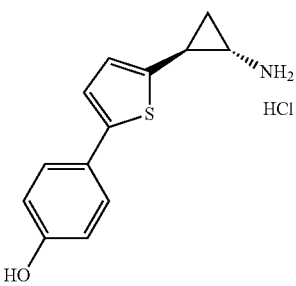 [SMILES: N[C@H]1C[C@@H]1c1ccc(-c2ccc(O)cc2)s1 ; Cl]

Example 115: 2-(5-((trans)-2-aminocyclopropyl) thiazol-2-yl)phenol hydrochloride

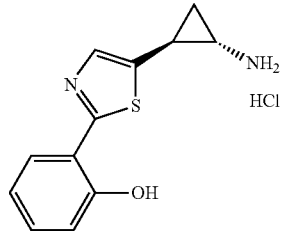 [SMILES: N[C@H]1C[C@@H]1c1cnc(-c2ccccc2O)s1 ; Cl]

Example 116: 3-(5-((trans)-2-aminocyclopropyl)thiazol-2-yl)phenol hydrochloride

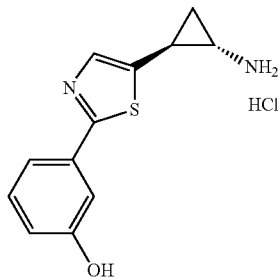 [SMILES: N[C@H]1C[C@@H]1c1cnc(-c2cccc(O)c2)s1 ; Cl]

¹HNMR (400 MHz, DMSO-d6, D2O Exchange) δ: 7.68 (s, 1H), 7.31 (s, 3H), 6.89 (brs, 1H), 2.88-2.96 (m, 1H), 2.58-2.64 (m, 1H), 1.48-1.58 (m, 1H), 1.36 (q, J=7 Hz, 1H); Mass (M+H): 233.3

Example 117: 4-(5-((trans)-2-aminocyclopropyl)thiazol-2-yl)phenol hydrochloride

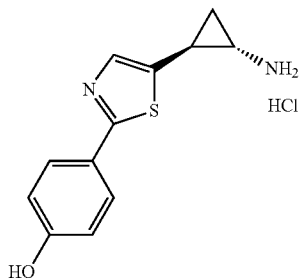 [SMILES: N[C@H]1C[C@@H]1c1cnc(-c2ccc(O)cc2)s1 ; Cl]

Example 118: 2-(2-((trans)-2-aminocyclopropyl)thiazol-5-yl)phenol hydrochloride

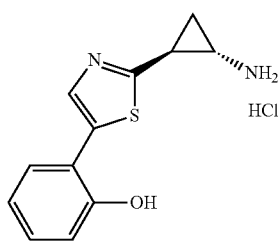 [SMILES: N[C@H]1C[C@@H]1c1ncc(-c2ccccc2O)s1 ; Cl]

Example 119: 3-(2-((trans)-2-aminocyclopropyl)thiazol-5-yl)phenol hydrochloride

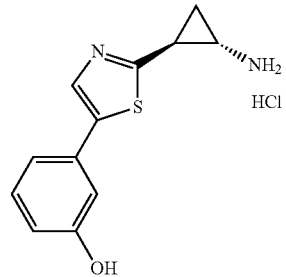 [SMILES: N[C@H]1C[C@@H]1c1ncc(-c2cccc(O)c2)s1 ; Cl]

Example 120: 2-(2-((trans)-2-aminocyclopropyl)thiazol-5-yl)phenol hydrochloride

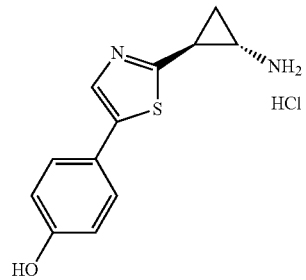 [SMILES: N[C@H]1C[C@@H]1c1ncc(-c2ccc(O)cc2)s1 ; Cl]

Example 121: 3-(2-((trans)-2-aminocyclopropyl)thiazol-5-yl)phenol hydrochloride

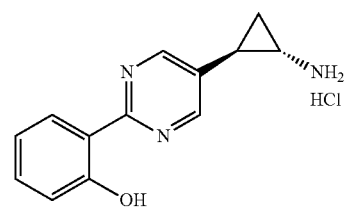 [SMILES: N[C@H]1C[C@@H]1c1cnc(-c2ccccc2O)nc1 ; Cl]

Example 122: 3-(5-((trans)-2-aminocyclopropyl)pyrimidin-2-yl)phenol hydrochloride

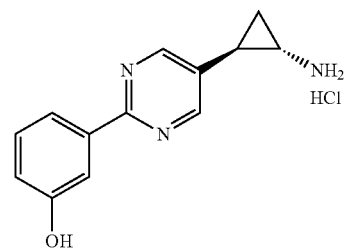 [SMILES: N[C@H]1C[C@@H]1c1cnc(-c2cccc(O)c2)nc1 ; Cl]

Example 123: 4-(5-((trans)-2-aminocyclopropyl)pyrimidin-2-yl)phenol hydrochloride

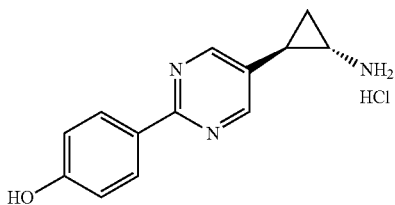 [SMILES: N[C@H]1C[C@@H]1c1cnc(-c2ccc(O)cc2)nc1 ; Cl]

Example 124: N-(3-(5-((trans)-2-aminocyclopropyl)thiazol-2-yl)phenyl)-2-cyanobenzenesulfonamide dihydrochloride

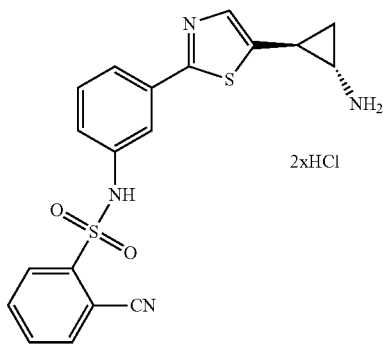 [SMILES: N#Cc1ccccc1S(=O)(=O)Nc1cccc(-c2ncc([C@H]3C[C@@H]3N)s2)c1]

$^1$HNMR (400 MHz, D2O) δ: 8.05 (d, J=8 Hz, 1H), 7.76-7.88 (m, 2H), 7.67-7.75 (m, 1H), 7.56 (s, 1H), 7.45 (brs, 2H), 7.25-7.34 (m, 1H), 7.09 (d, J=8 Hz, 1H), 2.94-3.03 (m, 1H), 2.60-2.68 (m, 1H), 1.46-1.58 (m, 1H), 1.40 (q, J=7 Hz, 1H); Mass (M−H): 395.0

Example 125: Biological Assays

The compounds of the invention can be tested for their ability to inhibit LSD1. The ability of the compounds of the invention to inhibit LSD1 can be tested as follows. Human recombinant LSD1 protein was purchased from BPS Bioscience Inc. In order to monitor LSD1 enzymatic activity and/or its inhibition rate by our inhibitor(s) of interest, di-methylated H3-K4 peptide (Millipore) was chosen as a substrate. The demethylase activity was estimated, under aerobic conditions, by measuring the release of $H_2O_2$ produced during the catalytic process, using the Amplex® Red peroxide/peroxidase-coupled assay kit (Invitrogen).

Briefly, a fixed amount of LSD1 was incubated on ice for 15 minutes, in the absence and/or in the presence of various concentrations of inhibitor (e.g., from 0 to 75 μM, depending on the inhibitor strength). Tranylcypromine (Biomol International) was used as a control for inhibition. Within the experiment, each concentration of inhibitor was tested in triplicate. After leaving the enzyme interacting with the inhibitor, 12.5 μM of di-methylated H3-K4 peptide was added to each reaction and the experiment was left for 1 hour at 37° C. in the dark. The enzymatic reactions were set up in a 50 mM sodium phosphate, pH 7.4 buffer. At the end of the incubation, Amplex® Red reagent and horseradish peroxidase (HPR) solution were added to the reaction according to the recommendations provided by the supplier (Invitrogen), and left to incubate for 30 extra minutes at room temperature in the dark. A 1 μM $H_2O_2$ solution was used as a control of the kit efficiency. The conversion of the Amplex® Red reagent to resorufin due to the presence of $H_2O_2$ in the assay, was monitored by fluorescence (excitation at 540 nm, emission at 590 nm) using a microplate reader (Infinite 200, Tecan). Arbitrary units were used to measure level of $H_2O_2$ produced in the absence and/or in the presence of inhibitor.

The maximum demethylase activity of LSD1 was obtained in the absence of inhibitor and corrected for background fluorescence in the absence of LSD1. The Ki (IC50) of each inhibitor was estimated at half of the maximum activity.

The results presented in Table I below show the results of the LSD1 inhibition studies for a number of the Example compounds. Parnate (2-trans phenylcyclopropylamine) was found to have a Ki (IC50) of from about 15 to 35 micromolar depending on the enzyme preparation. The studies show that the compounds of the invention have unexpectedly potent LSD1 inhibition.

Example 126: Biological Assays-Monoamine Oxidase Assays for Determining the Selectivity of the Compounds of the Invention for LSD1

Human recombinant monoamine oxidase proteins MAO-A and MAO-B were purchased from Sigma Aldrich. MAOs catalyze the oxidative deamination of primary, secondary and tertiary amines. In order to monitor MAO enzymatic activities and/or their inhibition rate by inhibitor(s) of interest, a fluorescent-based (inhibitor)-screening assay was set up. 3-(2-Aminophenyl)-3-oxopropanamine (kynuramine dihydrobromide, Sigma Aldrich), a non fluorescent compound was chosen as a substrate. Kynuramine is a non-specific substrate for both MAOs activities. While undergoing oxidative deamination by MAO activities, kynuramine is converted into 4-hydroxyquinoline (4-HQ), a resulting fluorescent product.

The monoamine oxidase activity was estimated by measuring the conversion of kynuramine into 4-hydroxyquinoline. Assays were conducted in 96-well black plates with clear bottom (Corning) in a final volume of 100 μL. The assay buffer was 100 mM HEPES, pH 7.5. Each experiment was performed in triplicate within the same experiment.

Briefly, a fixed amount of MAO (0.25 μg for MAO-A and 0.5 μg for MA-B) was incubated on ice for 15 minutes in the reaction buffer, in the absence and/or in the presence of various concentrations of inhibitor (e.g., from 0 to 50 μM, depending on the inhibitor strength). Tranylcypromine (Biomol International) was used as a control for inhibition. After leaving the enzyme(s) interacting with the inhibitor, 60 to 90 μM of kynuramine was added to each reaction for MAO-B and MAO-A assay respectively, and the reaction was left for 1 hour at 37° C. in the dark. The oxidative deamination of the substrate was stopped by adding 50 μL (v/v) of NaOH 2N. The conversion of kynuramine to 4-hydroxyquinoline, was monitored by fluorescence (excitation at 320 nm, emission at 360 nm) using a microplate reader (Infinite 200, Tecan). Arbitrary units were used to measure levels of fluorescence produced in the absence and/or in the presence of inhibitor.

The maximum of oxidative deamination activity was obtained by measuring the amount of 4-hydroxyquinoline formed from kynuramine deamination in the absence of inhibitor and corrected for background fluorescence in the absence of MAO enzymes. The Ki (IC50) of each inhibitor was determined at Vmax/2.

TABLE 1

Summary of Data from MAO-A, MAO-B, and LSD1 Inhibition Studies

| Example No. | MAO-A (Ki) | MAO-B (Ki) | LSD1 (Ki) |
| --- | --- | --- | --- |
| 1 | I | I | II |
| 2 | I | II | II |
| 3 | I | I | II |
| 4 | I | I | III |
| 5 | I | II | II |
| 6 | I | II | II |
| 7 | I | II | II |
| 8 | I | II | II |
| 9 | I | III | II |
| 10 | I | I | II |
| 11 | I | I | II |
| 12 | I | I | II |
| 13 | I | I | III |
| 14 | I | I | II |
| 15 | I | I | II |
| 16 | I | I | II |
| 17 | I | I | III |
| 18 | I | I | I |
| 19 | I | I | II |
| 20 | I | I | III |
| 21 | I | I | III |
| 22 | I | I | II |
| 23 | I | I | III |
| 24 | I | I | III |
| 25 | I | I | III |
| 26 | I | I | II |
| 29 | I | I | III |
| 30 | I | I | II |
| 31 | I | I | III |
| 34 | I | I | II |
| 36 | I | I | I |
| 37 | I | I | I |
| 38 | I | I | II |
| 39 | I | I | II |
| 40 | I | I | II |
| 41 | I | I | II |
| 42 | I | I | II |
| 43 | I | I | II |
| 44 | I | I | II |
| 45 | I | I | II |
| 46 | I | I | III |
| 47 | I | I | II |
| 48 | I | I | III |
| 49 | I | I | II |
| 50 | I | I | II |
| 51 | I | I | II |
| 52 | I | I | II |
| 53 | I | I | III |
| 54 | I | I | II |
| 55 | I | I | II |
| 56 | I | I | III |
| 57 | I | I | II |
| 58 | I | I | II |
| 59 | nd | I | III |
| 60 | I | I | II-III |
| 61 | I | I | I |
| 62 | I | I | II |
| 63 | I | I | III |
| 63 | I | I | III |
| 64 | I | I | III |
| 65 | I | I | III |
| 66 | I | I | III |
| 67 | I | I | III |
| 68 | I | I | III |
| 69 | I | I | III |
| 70 | I | I | III |
| 71 | I | I | II |
| 72 | I | I | II |
| 73 | I | I | II-III |
| 74 | I | I | II-III |
| 75 | I | I | III |
| 76 | I | I | II |
| 77 | I | I | I |
| 78 | I | I | I |
| 79 | I | I | I |
| 80 | I | I | II |
| 87 | II | I | II |
| 88 | I | I | III |
| 89 | II | I | III |
| 90 | I | I | III |
| 93 | I | I | II |
| 94 | II | II | III |
| 95 | II | I | III |
| 96 | II | I | III |
| 97 | I | I | II |
| 98 | I | I | III |
| 99 | II | I | III |
| 100 | II | I | III |
| 101 | I | I | III |
| 102 | I | I | III |
| 103 | nd | nd | II |
| 104 | II | I | II |
| 105 | I | nd | II |
| 106 | II | I | II |
| 113 | II | II | III |
| 116 | III | I | III |
| 124 | I | I | III |

The ranges for the Ki value reported in Table I are for MAO-A, MAO-B and LSDI-I=between 1 μM and 40 μM; II=between 0.1 μM and 1 μM; III between 0.001 μM and 0.1 μM. "nd" means "not determined".

Generally compounds of Examples were found to have Ki (IC50) values for MAO-A and MAO-B greater than the LSD1 Ki values, whereas LSD1 Ki values were generally lower than 0.5 μM.

Thus the compounds of the invention are unexpectedly potent LSD1 inhibitors and unexpectedly selective for LSD1 as compared to MAO-A and MAO-B, or the compounds are dual inhibitors of LSD and MAO-B.

Some compounds of the Examples have been tested for antiproliferative/cytotoxic activity and been found to have activity in the micromolar to low micromolar range against cancer cell lines including HCT-116.

Previous reports of LSD1 have found that it is involved in cell proliferation and growth. Some studies have implicated LSD1 as a therapeutic target for cancer. Huang et al. (2007) *PNAS* 104:8023-8028 found that polyamine inhibitors of LSD1 modestly cause the reexpression of genes aberrantly silenced in cancer cells and particularly colorectal cancer (Huang et al. *Clin Cancer Res*. (2009) December 1; 15(23): 7217-28. Epub 2009 November 24. PMID: 19934284). Scoumanne et al. ((2007) *J. Biol. Chem. May* 25; 282(21): 15471-5) found that deficiency in LSD1 leads to a partial cell cycle arrest in G2/M and sensitizes cells to growth suppression induced by DNA damage. Kahl et al. ((2006) *Cancer Res*. 66(23):11341-7.) found that LSD1 expression is correlated with prostate cancer aggressiveness. Metzger et al. reported that LSD1 modulation by siRNA and pargyline regulates androgen receptor (AR) and may have therapeutic potential in cancers where AR plays a role, like prostate, testis, and brain cancers. Lee et al. ((2006) *Chem. Biol.* 13:563-567) reported that tranylcypromine derepresses Egr-1 gene expression in some cancer lines. A body of evidence is accumulating that Egr-1 is a tumor suppressor gene in many contexts (see e.g., Calogero et al. (2004) *Cancer Cell International* 4:1 exogenous expression of EGR-1 resulted in growth arrest and eventual cell death in primary cancer cell lines; Lucerna et al. (2006) *Cancer Research* 66, 6708-6713 show that sustained expression of Egr-1 causes antiangiogeneic effects and inhibits tumor growth in some models; Ferraro et al. ((2005) *J. Clin. Oncol.* March 20; 23(9):1921-6) reported that Egr-1 is downregulated in lung cancer patients with a higher risk of recurrence and may be more resistant to therapy. Thus, increasing Egr-1 expression via inhibition of LSD1 is a therapeutic approach for some cancers. Recent studies have also implicated LSD1 in brain cancer (Schulte et al. (2009) *Cancer Res.* March 1; 69(5):2065-71). Other studies have implicated LSD1 in breast cancer (Lims et al. Carcinogenesis. PMID: 20042638).

Thus, a body of evidence has implicated LSD1 in a number of cancers, which suggests that LSD1 is a therapeutic target for cancer. The instant inventors have discovered a class of LSD1 inhibitors that can be used to treat diseases where LSD1 is implicated as a therapeutic target like cancer. Accordingly, the phenylcyclopropylamine compounds of the invention can be used to treat such diseases.

Recent studies have also implicated LSD1 in viral infection and reactivation. In particular it was shown that pharmacological inhibitors of LSD1 like parnate and siRNA knock down of LSD1 caused reduced viral infectivity and reduced reactivation after latency (Liang et al. (2009) *Nat. Med.* 15:1312-1317). Therefore it is believed that the compounds of the invention can be used for treating or preventing viral infection. Furthermore, it is believed that the compounds of the invention can treat or prevent viral reactivation after latency.

Thus, without wishing to be bound by theory, the inventors have identified a new class of substituted heterocyclyl-cyclopropylamines, phenylcyclopropylamines, and pyridinylcyclopropanamine containing LSD1 inhibitors with unexpected potency and selectivity for LSD1 a biologically relevant target in oncology and other diseases and/or LSD1/MAO-B.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

The invention claimed is:

1. A compound of Formula (I) or an enantiomer, a diastereomer, or a mixture thereof, or a pharmaceutically acceptable salt or solvate thereof:

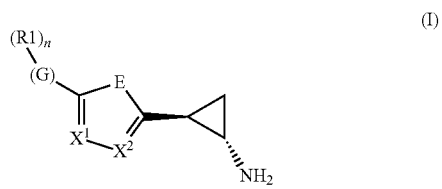

wherein:
E is —$X^3$=$X^4$—, and $X^1$, $X^2$, $X^3$ and $X^4$ are independently C(R2);
(G) is an aryl or heterocyclyl group;
each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acetyl, and carboxyl;
each (R2) is independently chosen from H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, and carboxyl, wherein each (R2) group has 1, 2, or 3 independently chosen optional substituents or two (R2) groups can be taken together to form a heterocyclyl or aryl group having 1, 2, or 3 independently chosen optional substituents, wherein said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, and carbamate;
each L1 is independently alkylene or heteroalkylene; and
n is 0, 1, 2, 3, 4 or 5;
with the proviso that the compound of Formula (I) is not:
(1S,2R)-2-([1,1'-biphenyl]-4-yl)cyclopropanamine, (1 S,2R)-2-(4'-chloro-[1,1'biphenyl]-4-yl)cyclopropanamine, (1 S,2R)-2-(3-chloro-4-(trifluoromethyl)-[1,1'-biphenyl]-4-yl)cyclopropanamine, 2-(3,4',5-trichloro-[1,1'-biphenyl]-4-yl)cyclopropanamine, 2-(3,3',4',5-tetrachloro[1,1'-biphenyl]-4-yl)cyclopropanamine, 2-(3,3',4'-trichloro-[1,1'-biphenyl]-4-yl)cyclopropanamine, or 2-(3,5-dichloro-4'-methyl-[1,1'-biphenyl]-4-yl)cyclopropanamine.

2. The compound of claim 1 wherein said compound is a compound of Formula (II) or an enantiomer, a diastereomer, or a mixture thereof, or a pharmaceutically acceptable salt or solvate thereof:

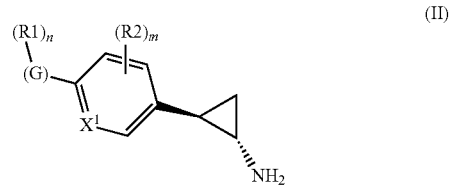

wherein:
$X^1$ is CH;
(G) is an aryl or heterocyclyl group;
each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acetyl, and carboxyl;

each (R2) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, and carboxyl, wherein each (R2) group has 1, 2, or 3 optional substituents, wherein said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, and carbamate;

each L1 is independently alkylene or heteroalkylene;

m is 0, 1, 2 or 3; and n is 0, 1, 2, 3, 4 or 5, provided that n and m are chosen independently such that n+m is greater than zero when (G) is an aryl;

with the proviso that the compound of Formula (II) is not: (1S,2R)-2-(4'-chloro-[1,1'-biphenyl]-4-yl)cyclopropanamine, (1 S,2R)-2-(3-chloro-4'-(trifluoromethyl)-[1,1'-biphenyl]-4-yl)cyclopropanamine, 2-(3,4',5-trichloro-[1,1'-biphenyl]-4-yl) cyclopropanamine, 2-(3,3',4',5-tetrachloro-[1,1'-biphenyl]-4-yl)cyclopropanamine, 2-(3,3',4'-trichloro-[1,1'-biphenyl]-4-yl)cyclopropanamine, or 2-(3,5-dichloro-4'-methyl-[1,1'-biphenyl]-4-yl)cyclopropanamine.

3. The compound of claim 1 wherein (G) is a heterocyclyl.

4. The compound of claim 1 wherein (G) is phenyl.

5. The compound of claim 1 wherein (G) is a phenyl, thienyl, benzothienyl, indolyl, indolinyl, indolinonyl, pyridinyl, pyridinonyl, benzofuranyl, benzofuranonyl, indazolyl, or carbazolyl group.

6. The compound of claim 1 wherein each (R1) is independently chosen from alkyl, amino, amido, nitro, —F, haloalkoxy, cyano, sulfonyl, sulfonamide, and hydroxyl.

7. The compound of claim 1 wherein each (R1) is independently chosen from —F, —CN, —CH$_3$, —OH, —C(=O)NH$_2$, —NH—CO—CH$_3$, —NH—SO$_2$—CH$_3$, —NH—SO$_2$—CH$_2$—CH$_3$, —NH—SO$_2$—CH(CH$_3$)—CH$_3$, —NH—SO$_2$-(C$_6$H$_5$), —NH—SO$_2$-(C$_6$H$_4$)—CN, —NHSO$_2$CF$_3$, and —S(=O)$_2$NHCH$_3$.

8. The compound of claim 1 wherein each (R2) is —H.

9. The compound of claim 1 wherein n is 1, 2, or 3.

10. The compound of claim 1 wherein the compound of formula (I) is:
4'-((trans)-2-aminocyclopropyl)biphenyl-4-ol;
4'-((trans)-2-aminocyclopropyl)biphenyl-3-ol;
4'-((trans)-2-aminocyclopropyl)-4-fluorobiphenyl-3-ol;
4'-((trans)-2-aminocyclopropyl)-5-chlorobiphenyl-3-ol;
4'-((trans)-2-aminocyclopropyl)-5-chloro-4-fluorobiphenyl-3-ol;
N-(4'-((trans)-2-aminocyclopropyl)biphenyl-3-yl)benzenesulfonamide;
N-(4'-((trans)-2-aminocyclopropyl)biphenyl-3-yl)propane-2-sulfonamide;
N-(4'-((trans)-2-aminocyclopropyl)biphenyl-3-yl)methanesulfonamide;
N-(4'-((trans)-2-aminocyclopropyl)biphenyl-2-yl)methanesulfonamide;
4'-((trans)-2-aminocyclopropyl)-6-methoxybiphenyl-3-carbonitrile;
N-(4'-((trans)-2-aminocyclopropyl)-6-methoxybiphenyl-3-yl)methanesulfonamide;
4'-((trans)-2-aminocyclopropyl)-6-hydroxybiphenyl-3-carbonitrile;
N-(4'-((trans)-2-aminocyclopropyl)-6-hydroxybiphenyl-3-yl)methanesulfonamide;
N-(4'-((trans)-2-aminocyclopropyl)-5-chloro-[1,1'-biphenyl]-3-yl)methanesulfonamide;
N-(4'-((trans)-2-aminocyclopropyl)-4-fluoro-[1,1'-biphenyl]-3-yl)methanesulfonamide;
N-(4'-((trans)-2-aminocyclopropyl)-[1,1'-biphenyl]-3-yl)-1,1,1-trifluoromethanesulfonamide;
4'-((trans)-2-aminocyclopropyl)-6-hydroxy-[1,1'-biphenyl]-3-carbonitrile;
4'-((trans)-2-aminocyclopropyl)-[1,1'-biphenyl]-2-ol; and
4'-((trans)-2-aminocyclopropyl)-3'-methoxy-[1,1'-biphenyl]-3-ol;
or
a pharmaceutically acceptable salt or solvate thereof.

11. The compound of claim 4 wherein each (R1) is independently chosen from alkyl, amino, amido, nitro, —F, haloalkoxy, cyano, sulfonyl, sulfonamide, and hydroxyl.

12. The compound of claim 5 wherein each (R1) is independently chosen from alkyl, amino, amido, nitro, —F, haloalkoxy, cyano, sulfonyl, sulfonamide, and hydroxyl.

13. The compound of claim 4 wherein each (R1) is independently chosen from —F, —CN, —CH$_3$, —OH, —C(=O)NH$_2$, —NH—CO—CH$_3$, —NH—SO$_2$—CH$_3$, —NH—SO$_2$—CH$_2$—CH$_3$, —NH—SO$_2$—CH(CH$_3$)—CH$_3$, —NH—SO$_2$—(C$_6$H$_5$), —NH—SO$_2$—(C$_6$H$_4$)—CN, —NHSO$_2$CF$_3$, and —S(=O)$_2$NHCH$_3$.

14. A pharmaceutical composition comprising a compound of Formula (I) or an enantiomer, a diastereomer, or a mixture thereof, or a pharmaceutically acceptable salt or solvate thereof:

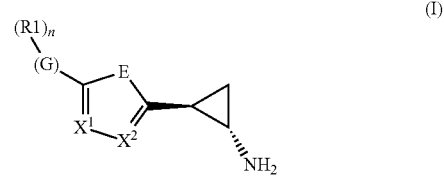

(I)

wherein:
E is —X$^3$=X$^4$—, and X$^2$, X$^3$ and X$^4$ are independently C(R2);
(G) is an aryl or heterocyclyl group;
each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acetyl, and carboxyl;
each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, and carboxyl, wherein each (R2) group has 1, 2, or 3 independently chosen optional substituents or two (R2) groups can be taken together to form a heterocyclyl or aryl group having 1, 2, or 3 independently chosen optional substituents, wherein said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, and carbamate;

each L1 is independently alkylene or heteroalkylene; and n is 0, 1, 2, 3, 4 or 5;

and a pharmaceutically acceptable carrier.

15. The pharmaceutical composition of claim 14, wherein the compound of formula (I) is:

4'-((trans)-2-aminocyclopropyl)biphenyl-4-ol;
4'-((trans)-2-aminocyclopropyl)biphenyl-3-ol;
4'-((trans)-2-aminocyclopropyl)-4-fluorobiphenyl-3-ol;
4'-((trans)-2-aminocyclopropyl)-5-chlorobiphenyl-3-ol;
4'-((trans)-2-aminocyclopropyl)-5-chloro-4-fluorobiphenyl-3-ol;
N-(4'-((trans)-2-aminocyclopropyl)biphenyl-3-yl)benzenesulfonamide;
N-(4'-((trans)-2-aminocyclopropyl)biphenyl-3-yl)propane-2-sulfonamide;
N-(4'-((trans)-2-aminocyclopropyl)biphenyl-3-yl)methanesulfonamide;
N-(4'-((trans)-2-aminocyclopropyl)biphenyl-2-yl)methanesulfonamide;
4'-((trans)-2-aminocyclopropyl)-6-methoxybiphenyl-3-carbonitrile;
N-(4'-((trans)-2-aminocyclopropyl)-6-methoxybiphenyl-3-yl)methanesulfonamide;
4'-((trans)-2-aminocyclopropyl)-6-hydroxybiphenyl-3-carbonitrile;
N-(4'-((trans)-2-aminocyclopropyl)-6-hydroxybiphenyl-3-yl)methanesulfonamide;
N-(4'-((trans)-2-aminocyclopropyl)-5-chloro-[1,1'-biphenyl]-3-yl)methanesulfonamide;
N-(4'-((trans)-2-aminocyclopropyl)-4-fluoro-[1,1'-biphenyl]-3-yl)methanesulfonamide;
N-(4'-((trans)-2-aminocyclopropyl)-[1,1'-biphenyl]-3-yl)-1,1,1-trifluoromethanesulfonamide;
4'-((trans)-2-aminocyclopropyl)-6-hydroxy-[1,1'-biphenyl]-3-carbonitrile;
4'-((trans)-2-aminocyclopropyl)-[1,1'-biphenyl]-2-ol; and
4'-((trans)-2-aminocyclopropyl)-3'-methoxy-[1,1'-biphenyl]-3-ol; or a pharmaceutically acceptable salt or solvate thereof.

16. The pharmaceutical composition of claim 14 wherein (G) is a phenyl, thienyl, benzothienyl, indolyl, indolinyl, indolinonyl, pyridinyl, pyridinonyl, benzofuranyl, benzofuranonyl, indazolyl, or carbazolyl group.

17. The pharmaceutical composition of claim 14 wherein (G) is phenyl.

18. The pharmaceutical composition of claim 14 wherein each (R2) is —H.

19. The pharmaceutical composition of claim 16 wherein each (R1) is independently chosen from alkyl, amino, amido, nitro, —F, haloalkoxy, cyano, sulfonyl, sulfonamide, and hydroxyl.

20. The pharmaceutical composition of claim 17 wherein each (R1) is independently chosen from alkyl, amino, amido, nitro, —F, haloalkoxy, cyano, sulfonyl, sulfonamide, and hydroxyl.

* * * * *